US010157261B2

United States Patent
Disney et al.

(10) Patent No.: US 10,157,261 B2
(45) Date of Patent: Dec. 18, 2018

(54) TRANSCRIPTOME-WIDE DESIGN OF SELECTIVE, BIOACTIVE SMALL MOLECULES TARGETING RNA

(71) Applicant: The Scripps Research Institute, La Jolla, CA (US)

(72) Inventors: Matthew D. Disney, Jupiter, FL (US); Sai Velagapudi, Jupiter, FL (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 14/911,032

(22) PCT Filed: Aug. 8, 2014

(86) PCT No.: PCT/US2014/050399
§ 371 (c)(1),
(2) Date: Feb. 9, 2016

(87) PCT Pub. No.: WO2015/021415
PCT Pub. Date: Feb. 12, 2015

(65) Prior Publication Data
US 2016/0188791 A1 Jun. 30, 2016

Related U.S. Application Data

(60) Provisional application No. 61/864,081, filed on Aug. 9, 2013.

(51) Int. Cl.
| | | |
|---|---|---|
| G06F 19/16 | (2011.01) | |
| C07D 235/18 | (2006.01) | |
| C07D 403/14 | (2006.01) | |
| C07H 15/04 | (2006.01) | |
| C07D 235/20 | (2006.01) | |
| C07H 15/234 | (2006.01) | |
| G01N 33/53 | (2006.01) | |
| G06F 19/22 | (2011.01) | |

(52) U.S. Cl.
CPC .......... *G06F 19/16* (2013.01); *C07D 235/18* (2013.01); *C07D 235/20* (2013.01); *C07D 403/14* (2013.01); *C07H 15/04* (2013.01); *C07H 15/234* (2013.01); *G01N 33/5308* (2013.01); *G06F 19/22* (2013.01); *G01N 2500/04* (2013.01)

(58) Field of Classification Search
None
See application file for complete search history.

(56) References Cited

FOREIGN PATENT DOCUMENTS

| WO | WO2008/103489 A2 | * | 8/2008 | ............ G01N 33/00 |
|---|---|---|---|---|
| WO | WO-2008/103489 A2 | | 8/2008 | |
| WO | WO-2013/019469 A1 | | 2/2013 | |
| WO | WO-2015/021415 A1 | | 2/2015 | |

OTHER PUBLICATIONS

Velagapudi et al, J. Am. Chem. Soc., 2011, 133, 10111-10118.*
Setny, "Search for novel aminoglycosides by combining fragment-based virtual screening and 3D-QSAR scoring," Journal of chemical information and modeling, vol. 49(2), p. 390-400, 2009.*
"International Application Serial No. PCT/US2014/050399, International Search Report dated Dec. 9, 2014", 7 pgs.
"International Application Serial No. PCT/US2014/050399, Invitation to Pay Additional Fees and Partial Search Report dated Oct. 16, 2014", 7 pgs.
"International Application Serial No. PCT/US2014/050399, Written Opinion dated Dec. 9, 2014", 7 pgs.
Childs-Disney, J. L., et al., "A Small Molecule Microarray Program Platform to Select RNA Internal Loop-Ligand Interactions", ACS Chemical Biology, 2(11), (2007), 745-754.
Disney, M. D., et al., "Two-Dimensional Combinational Screening Identifies Specific Aminoglycoside-RNA Internet Loop Partners", J. Am. Chem. Soc., 130, (2008), 11185-11194.
Guan, Lirui, et al., "Recent Advances in Developing Small Molecules Targeting RNA", ACS Chemical Biology, vol. 7, No. 1,, (Jan. 20, 2012), 73-86.
Velagapudi, S. P., et al., "Structure-Activity Relationships through Sequencing (StARTS) Defines Optimal and Suboptimal RNA Motif Targets for Small Molecules", Angew. Chem. Int. Ed., 49, (2010), 3816-3818.
Velagapudi, Sai Pradeep, et al., "Defining the RNA Internal Loops Preferred by Benzimidazole Derivatives via 2D Combinational Screening and Computational Analysis", J. Am. Chem. Soc., 133 (26):10111-10118, (Jul. 6, 2011), 10111-10118.

* cited by examiner

*Primary Examiner* — G Steven Vanni
(74) *Attorney, Agent, or Firm* — Geoffrey K. Cooper; Thomas Fitting

(57) ABSTRACT

Methods and computer systems are described herein for identifying small molecules that bind to selected RNA structural features (e.g., to RNA secondary structures). Also described are compounds and compositions that modulate RNA function and/or activity.

22 Claims, 57 Drawing Sheets

Specification includes a Sequence Listing.

RNA motif-small molecule database

6 ▽     7 ★

8 ⬡     9 ◇ miR-96:
5'UUUGGCACUAGCACAUUUUUGCU miR-182:
5'UUUGGCAAUGGUAGAACUCACACU miR-183:
5'UAUGGCACUGGUAGAAUUCACU

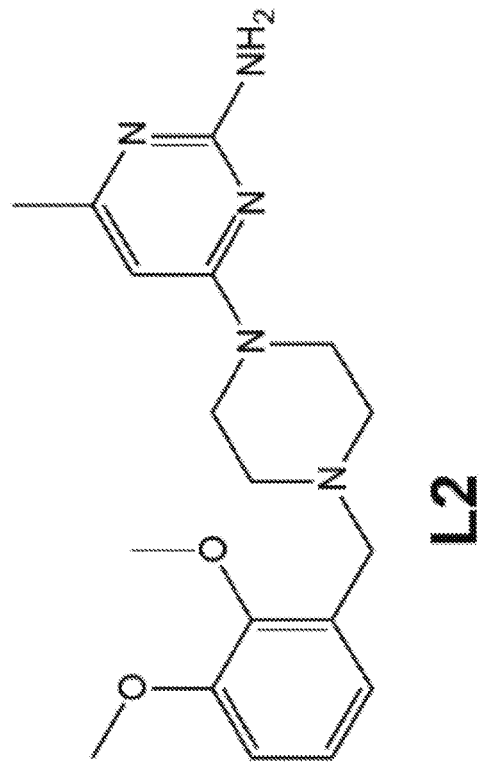
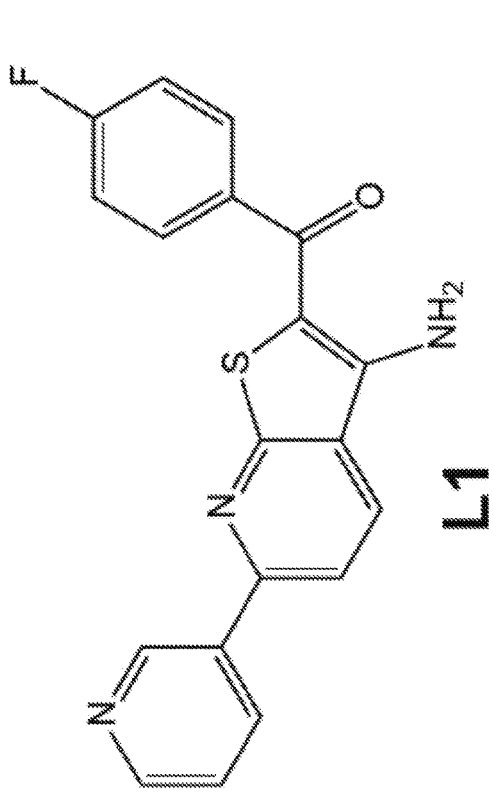
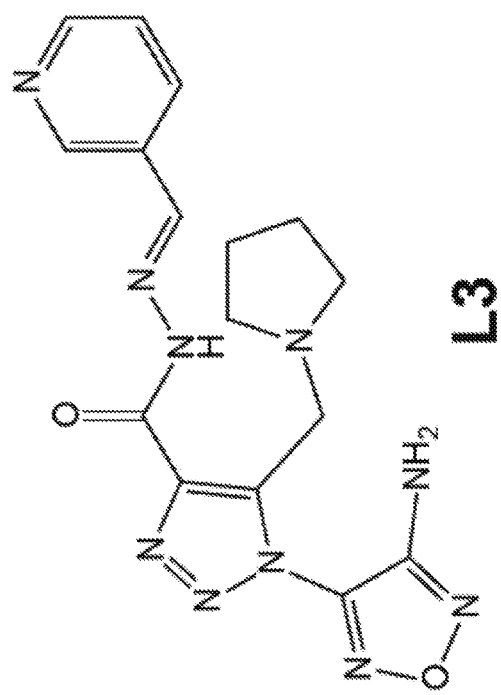
Fig. 12A-1

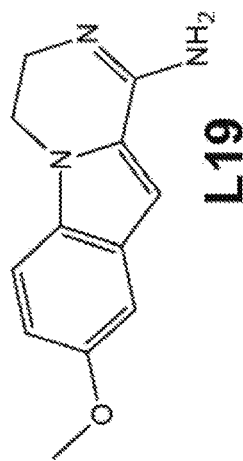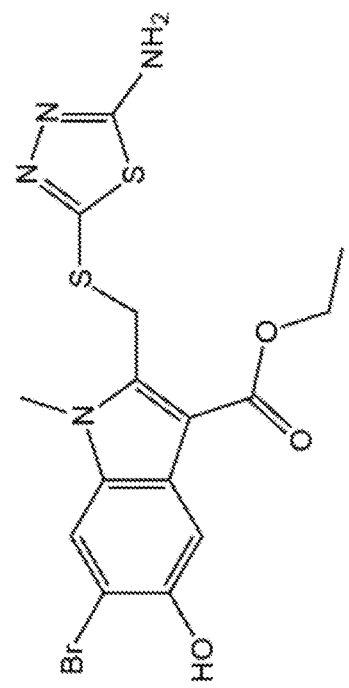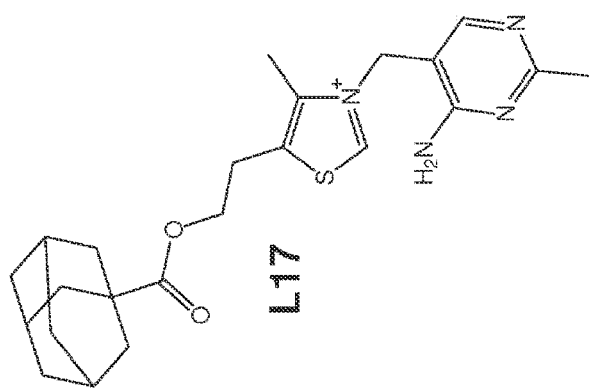
Fig. 12A-6

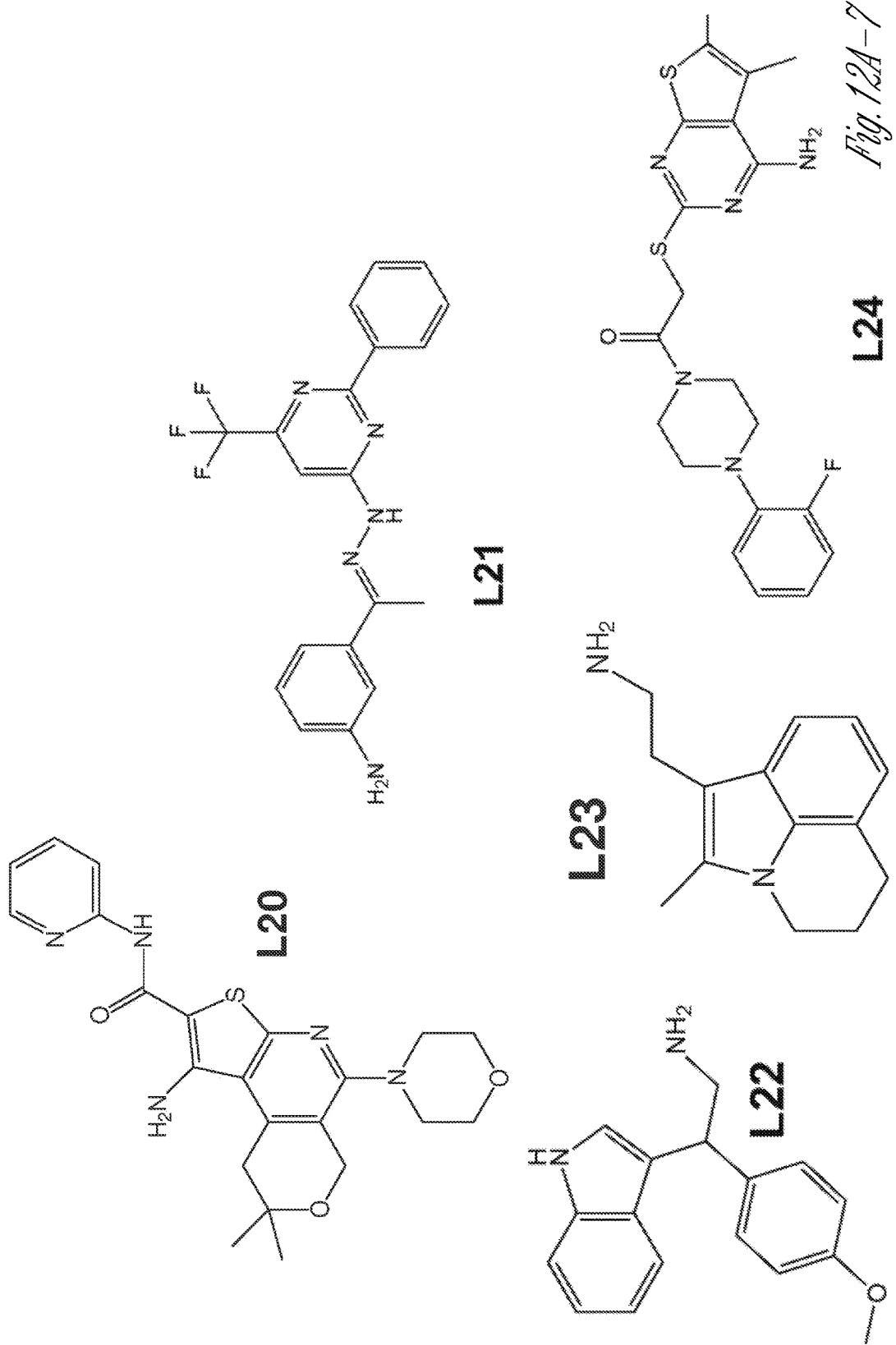

TRANSCRIPTOME-WIDE DESIGN OF SELECTIVE, BIOACTIVE SMALL MOLECULES TARGETING RNA

CROSS-REFERENCE TO RELATED APPLICATIONS

This application is a U.S. national stage application filed under 35 U.S.C. § 371 from International Application Serial No. PCT/US2014/050399, which was filed Aug. 8, 2014, and published as WO 2015/021415 on Feb. 12, 2015, and which claims the benefit of priority to U.S. Provisional Patent Application Serial No. 61/864,081, entitled "Transcriptome-Wide Design of Selective, Bioactive Small Molecules Targeting RNA," filed Aug. 9, 2013, which applications and publication are incorporated by reference as if reproduced herein and made a part hereof in their entirety, and the benefit of priority of each of which is claimed herein.

GOVERNMENT FUNDING

This invention was made with Government support under Grant Number R01GM097455 awarded by the National Institutes of Health. The United States Government has certain rights in the invention.

BACKGROUND OF THE INVENTION

RNA has essential cellular functions and is a highly desirable target for small molecule modulators of function. Developing bioactive compounds that target RNA is challenging, however, due to the perception that RNA is "undruggable" (Guan & Disney, ASC Chem Biol 7: 73-86 (2012); Thomas & Hergenrother, Chem Rev 108: 1171-1224 (2008)). The lack of success in this area can be traced to a fundamental lack of understanding about the RNA secondary structural motifs that are the preferred binding sites of small molecules and about the types of small molecules that bind RNA motifs with high affinity and specificity. If small molecules could be reliably designed to target RNA, more effective therapeutic agents might be designed, much like studies of antibacterial agent binding to the ribosome were helpful for elucidating the intricacies of the translational machinery (Yoshizawa et al., Science 285: 1722-25 (1999): Carter et al., Nature 407: 340-348. (2000)).

SUMMARY

The methods and computer systems described herein can solve many of the problems of designing small molecules that can effectively target RNA molecules.

One aspect of the invention is therefore a method for identifying a compound that binds to an RNA, comprising comparing a query dataset of RNA secondary structures from the RNA, with a dataset of identified bound RNA motif-small molecule pairs, to thereby identify a compound that binds to the RNA.

Another aspect of the invention is a computer system for identifying a molecule that binds to an RNA comprising: one or more computer processors and storage configured to compare a structured query dataset describing RNA secondary structures of the RNA, and a structured dataset of identified RNA motif-small molecule pairs, to thereby identify a molecule that binds to the RNA.

A further aspect of the invention is a compound with any of the following structures:

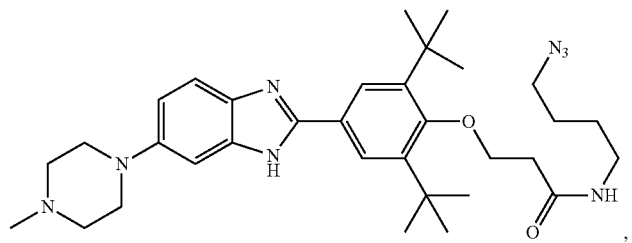

1

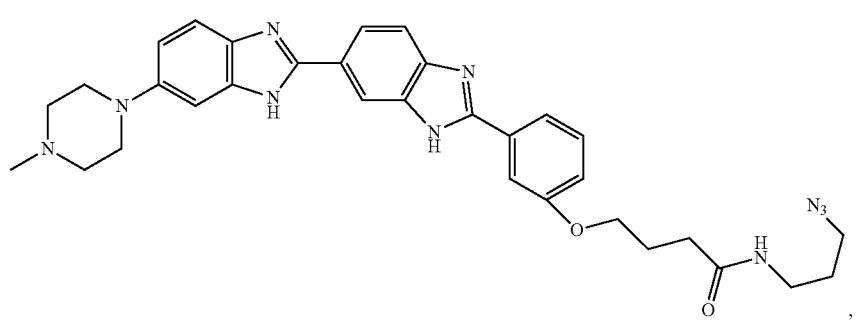

2

3
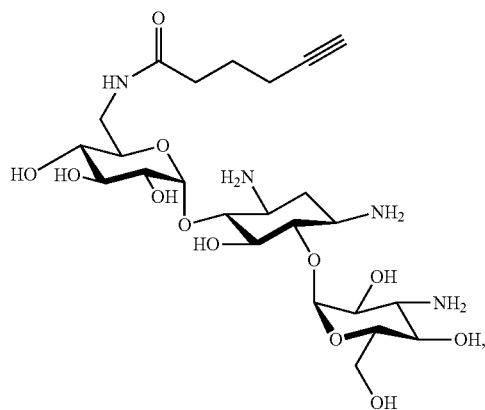
4
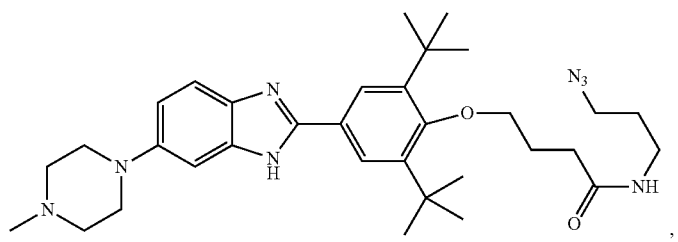
5
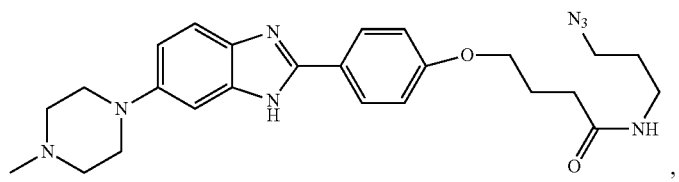
BSH-n-H
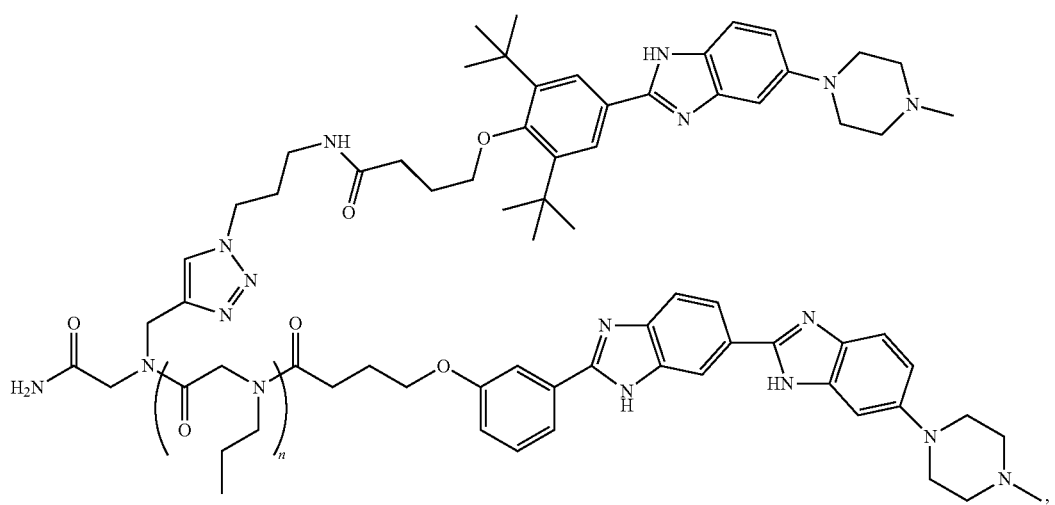

-continued
BSH-1-H
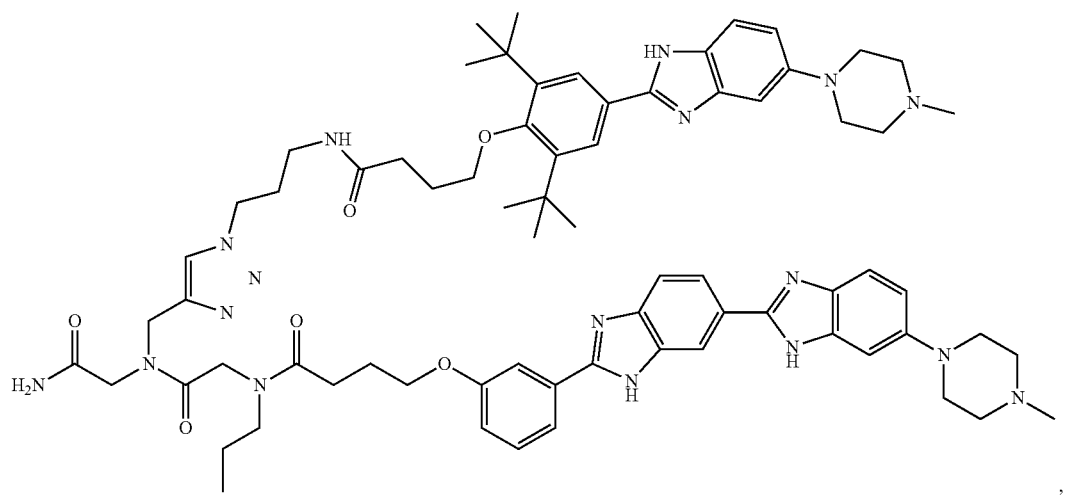
,
BSH-2-H
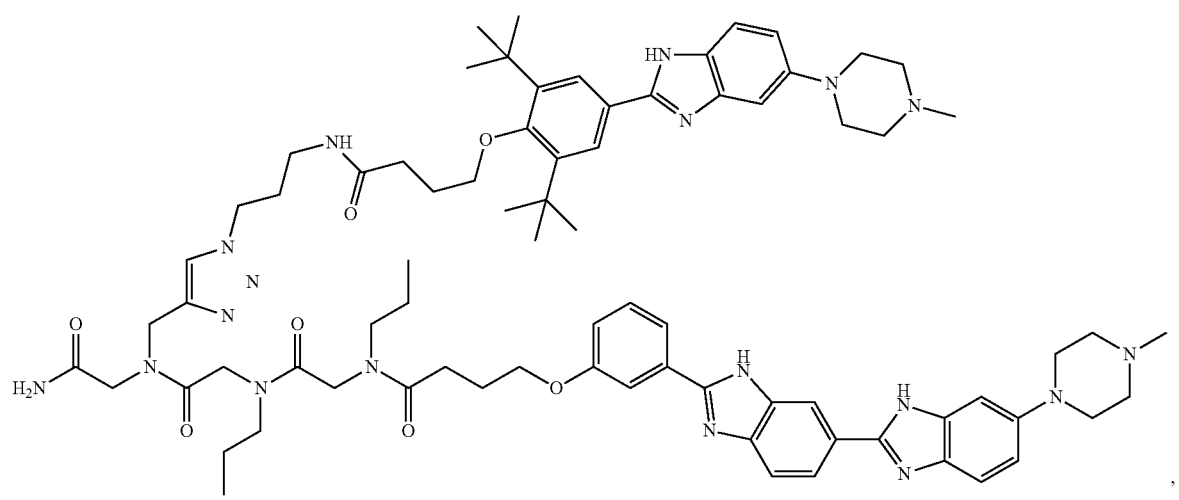
,

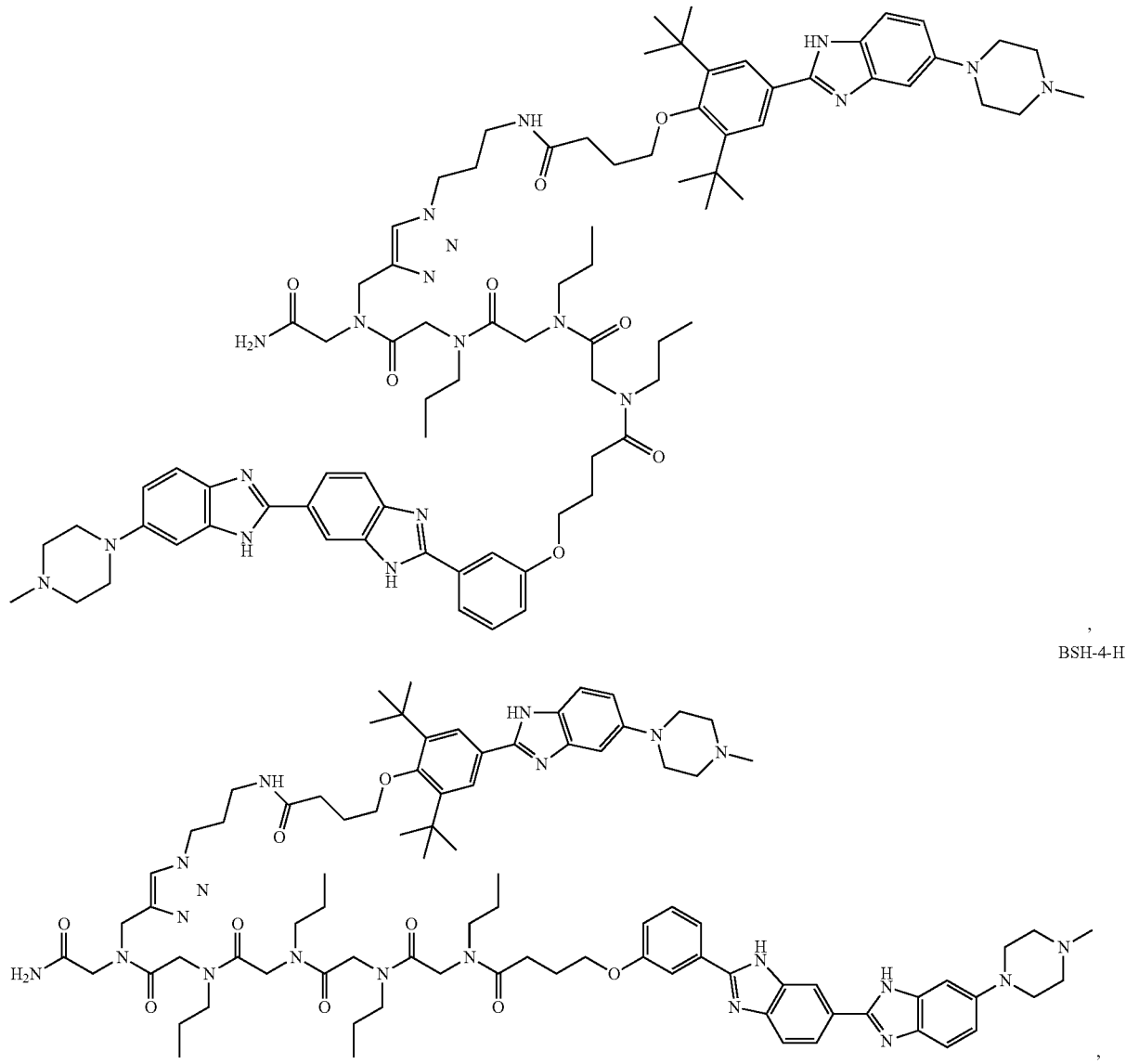

and any combination thereof, where n is an integer of 1 to 10. In some instances, n is an integer of 1 to 8, or 1 to 6, or 1 to 5.

Compositions of various compounds and methods of using the compounds to modulate microRNA function are described herein.

Thus, another aspect of the invention is a method of modulating microRNA function or activity comprising, contacting the microRNA with any of the compounds described herein or a composition including any of the compounds described herein.

A further aspect of the invention is a method of treating cancer in a subject, comprising administering to the subject any of the compounds described herein (including combinations thereof) or a composition including one or more of the compounds described herein.

DESCRIPTION OF THE FIGURES

FIG. 3A schematically illustrates a database of information on RNA motif—small molecule binding pairs. FIG. 3B illustrates the inforna process. Sequences of all miRNA precursors in the human transcriptome were downloaded from miRBase (Griffiths-Jones et al., *Nucleic Acids Res.* 36, D154-158 (2008)) and their secondary structures were predicted via RNAstructure (Mathews et al., *Proc. Natl. Acad. Sci. U.S.A.* 101, 7287-7292 (2004)). Inforna then extracted the secondary structural elements from each query RNA and compared those secondary structures to a database of RNA motif-small molecule interactions identified by two-dimensional combinatorial screening (2DCS). FIGS. 3C and 3D illustrate the results of inforna mining of miRNA precursor-small molecule interactions. FIG. 3C is a plot of the miRNA precursors for which a small molecule was predicted to bind Dicer or Drosha enzymatic processing sites as a function of the small molecule's Fitness Score. Higher Fitness Scores indicate a higher affinity interaction. FIG. 3D shows the structures of small molecules 1, 2, 3, and 4 that bind to processing sites in miRNA precursors. Compound 5 is structurally similar to compound 1 and was employed in various assays. FIG. 3E shows the structures of the other small molecules indicated in FIG. 3C, including compound 6 with chemical name 6'-N-5-hexynoate neamine (upside down triangle); compound 7 with chemical name 5-O-(2-azidoethyl)-neamine (star); compound 8 with chemical name 6'-azido-tobramycin (hexagon); and compound 9 with chemical name 5'-azidoneomycin B (diamond).

FIG. 4A illustrates StARTS analysis by showing fitness plots for various compounds predicted to bind miRNA. The StARTS analysis for compounds 1 (circles), 2 (squares), and 3 (triangles) and all potential miRNA targets is shown. In each case, the compound inhibits biogenesis of its predicted miRNA target (FIG. 5B). FIG. 4B illustrates StARTS analysis for compounds 1 (circles), 2 (squares), and 4 (X) and all potential miRNA targets. The analysis indicates that only compound 1 is expected to bind the miR-96 precursor with high affinity and selectivity. Compounds 2 and 4 are not predicted by this analysis to bind the miR-96 precursor. FIG. 4C shows secondary structures of RNAs to which the affinities of small molecules were measured. The 5'UUU/3'AUA secondary structure (with sequence GGGA-GAGGGUUUAA UUUUACGAAAGUAAUAUUG-GAUCCGCAAGG; SEQ ID NO:8) contains the loop and closing base pairs present near the processing site of pre-microRNA-96. The 5'CGAUUU/3'GGUAUA secondary structure (with sequence GGGAGAGGGUUUAAUC-CGAUUUUACGAAA GUAAUAUGGGAUUGGAUC-CGCAAGG: SEQ ID NO:9) is an expanded region of the miR-96 precursor near the Drosha processing site (which contains two internal loops separated by two base pairs). The 5'GUA/3'UCU secondary structure (with sequence GGGA-GAGGGUUUAAUGGUAGUACGAAA GUACUCU-CAUUGGAUCCGCAAGG; SEQ ID NO:10) is the targetable loop in the miR-449c precursor. FIG. 4D shows a representative binding curve for 1-Fl and 5'UUU/3'AUA. FIG. 4E shows a representative binding curve for 1-Fl and 5'-CGAUUU/3'GGUAUA. FIG. 4F shows a representative binding curve for 1-Fl to C1. FIG. 4G shows a representative binding curve for 2-Fl and 5'UUU/3'AUA. FIG. 4H shows a representative binding curve for 4-Fl and 5'UUU/3'AUA. FIG. 4H shows a representative binding curve for 5-Fl and 5'UUU/3'AUA. FIG. 4J illustrates that compounds 2, 4, and 5 (which are chemically similar to 1) do not affect miR-96, miR-182, or miR-183 expression as determined by qRT-PCR. MCF7 cells were treated with 40 µM of the different compounds for 20 h. Total RNA was then isolated and subjected to qRT-PCR.

FIG. 5A shows the secondary structures of the miRNA precursors studied, where the miR-96 precursor has SEQ ID NO:11; the miR-182 precursor has SEQ ID NO:12; the miR-183 precursor has SEQ ID NO:13; and the miR-210 precursor has SEQ ID NO:14. Compounds 1, 2, and 3 bind the regions indicated with boxes in miR-96, miR-182, and miR-210 precursors, respectively. Note that miR-96, miR-182, and miR-183 are transcribed as a cluster. FIG. 5B graphically illustrates the relative expression of microRNA-96 (right bar), microRNA-182 (middle bar), microRNA-183 (right bar), when various concentrations of compound 1 or compound 3 are incubated with MCF7 cells. The left graph graphically illustrates the relative expression of microRNA-210 when various concentrations of compound 2 are incubated with MCF7 cells. As shown, the designer compounds modulate biogenesis of the microRNAs to varying extents and with varying selectivities. FIG. 5C shows that oligonucleotide targeting of miR-96 is not as selective as 1. The sequences of the mature miRNAs that were studied are shown to the left. The miR-96 has sequence UUUGGCACUAGCACAUUUUUGCU (SEQ ID NO: 15). The miR-182 has sequence UUUGGCAAUGGUAGAA-CUCACACU (SEQ ID NO:16). The miR-183 has sequence UAUGGCACUGGUAGAAUUCACU (SEQ ID NO:17). The underlined regions indicate designed oligonucleotide binding sites; mismatches are within boxes. The graph to the right graphically illustrates quantitative RNA levels of miR-96, miR-182, and miR-183 after treatment with an LNA oligonucleotide targeting miR-96. As illustrated the LNA oligonucleotides are unable to discriminate between miR-96 and miR-182 at any concentration tested. In contrast, compound 1 selectively silences miR-96 (FIG. 5B). The symbol "*" indicates p-value <0.05 while "**" indicates p-value <0.01 as determined by a two-tailed student t-test.

FIG. 6A graphically illustrates the effect of compounds 1, 2, 4 or 5 on FOXO1 expression as assessed by a luciferase model system, which is negatively regulated by miR-96. The compounds inhibit miR-96 maturation in MCF7 cells and increase luciferase activity in a dose dependent fashion (dark bars). For example, compound 1 (40 µM) increases luciferase activity by ~2.2-fold. No effect on luciferase expression is observed when the miR-96 seed region is mutated such that it is unresponsive to microRNA-96 (light bars). In contrast, compounds 2, 4, and 5 have no effect on luciferase expression. FIG. 6B graphically illustrates that compound 1 increases endogenous FOXO1 protein expression as determined by western blot (inset). FIG. 6C graphically illustrates that compound 1 induces apoptosis as determined by TUNEL and Annexin V/PI assays (see also FIG. 8) by increasing FOXO1 expression. As illustrated, compound 1 stimulates apoptosis when MCF7 cells are treated with 40

μM compound 1, while compounds 2, 4, and 5 do not (also at 40 μM) stimulate apoptosis. FIG. 6D graphically illustrates the effect of different concentrations of compound 1 on the percentage of cells expressing Annexin (top section of each bar), the percentage of healthy cells (second section from the top of each bar), the percentage of cells expressing Annexin and staining with propidium iodide (the third section from the bottom of each bar), and the percentage of cells stained with propidium iodide alone (the bottom section of each bar). Propidium iodide staining is an indicator of cell death. FIG. 6E confirms that compound 1 induces apoptosis via increasing expression of FOXO1. Small interfering RNA (siRNA) was used to knock down expression of FOXO1. If the expression of another protein is affected by compound 1, then treatment should still induce apoptosis. The ability of compound 1 to induce apoptosis is reduced by 75% upon FOXO1 siRNA treatment. Thus, the compound 1 mode of action is via inhibition of premicroRNA-96 maturation and concomitant induction of FOXO1 expression. The symbol "**" indicates p-value <0.01 as determined by a two-tailed student t-test.

FIG. 7A is a Fitness Plot for compound 1 in which potential off-targets are indicated. Large shaded circles indicate Drosha sites; large clear circles indicate Dicer sites. FIG. 7B illustrates that amongst 149 microRNAs, only the production of mature miR-96 is significantly affected by compound 1. Symbols above the curve represent microRNAs that are activated; and symbols below the curve represent micrRNAs that are inhibited by compound 1. These studies demonstrate the selectivity of the small molecule for the intended target and pathway.

FIG. 8A shows a flow cytometric quadrant analysis of Annexin V/Propidium Iodide stained MCF7 cells, treated or untreated with compound 1, showing that the percentage of cells in quadrant 3 increase to about 66.4% when the concentration of compound 1 increases to 40 μM. FIG. 8B graphically illustrates quantification of the Annexin V/Propidium Iodide stained cell flow cytometric analysis, showing that the percentage of cells that are stained by Annexin V only (top section of each bar). The number of cells stained with AnnexinV increases as the concentration of compound 1 increases, while the concentration of healthy cells (second section from the top of each bar) decreases. The number of cells that are stained with both Annexin V and Propidium Iodide also increases as the concentration of compound 1 increases (third section from the top of each bar). Cells stained only by Propidium Iodide (an indicator of cell death) tend to decrease as the concentration of compound 1 increases (bottom section of each bar). The symbol "**" indicates p<0.01 as determined by a two-tailed student t-test.

FIG. 9A shows the structure of pre-microRNA-96 (SEQ ID NO: 231) and representative autoradiograms illustrating that G6, U8, U9, and U10 of GGG-pre-microRNA-96 are protected from RNase III and T1 cleavage by compound 1. The GGG-pre-microRNA-96 was radioactively labeled and incubated with RNase III in the presence of 0, 1, and 10 μM of compound 1 (indicated by the triangle, with the larger concentration at the larger end of the triangle). "L" indicates a hydrolysis ladder; "Control RNA" is untreated with nuclease or compound; and "S1" indicates GGG-pre-microRNA-96 cleaved with S1 nuclease (cleaves single stranded regions). Circles indicate nucleotides that are protected from cleavage, within or adjacent to the internal loop predicted by inforna to bind compound 1. FIG. 9B shows a representative gel autoradiogram illustrating that compound 1 inhibits Drosha cleavage in vitro (left) with quantification of the data in the graph to the right. FIG. 9C graphically illustrates that compound 1 inhibits Drosha processing of pri-miR-96 in vivo. Cells were treated with compound 1 followed by extraction of total RNA, which was subjected to qRT-PCR. An increase in the amount of pri-miR-96 (rightmost bar) was observed with concomitant decreases in expression of pre-miR-96 (middle bar) and mature miR-96 (leftmost bar). The symbol "**" indicates p<0.01 as determined by a two-tailed student t-test.

FIG. 11A1-11A2 show the structures of compounds used for studying binding affinity. FIG. 11B shows the synthetic method used for making fluorescent compound 5-Fl.

FIG. 12A1-A8 show the structures of compounds screened for inhibiting the biogenesis of miR-96 using the luciferase model system. FIG. 12B graphically illustrates the results of the luciferase assay for each compound. None of these compounds is able to increase luciferase production indicating that they do not inhibit miR-96 biogenesis.

FIG. 13A is schematic diagram of the RNA motif-small molecule interactions in the system that has been constructed. The system can be used to guide the rational design of small molecules that target an RNA of interest. FIG. 13B is a schematic of data flow for the search engine/algorithm that queries the database of RNA motif-small molecule interactions.

FIG. 14A is diagram of a method showing that the Compare and Identify process (e.g., inforna) can receive information from various datasets and provide an output of RNA and small molecule pairs that will likely bind with specificity. FIG. 14B is a diagram that a Prediction Process (such as StARTS) can be included, for example, to further refine the inform output and provide an output of RNA and small molecule pairs with a greater likelihood of binding specificity.

FIG. 16A is a schematic diagram of a process for designing small dimer molecules that and that target precursor miRNA-96 (SEQ ID NO:11). The dimers contain compound 1 (circular symbol) and a new molecule (H, diamond shaped molecule) linked together. Inform was used to identify the H small molecules that can pair with compound 1 to target a Drosha processing site and an adjacent internal loop in the miRNA-96 hairpin precursor (SEQ ID NO:11). Optimal designer dimers were 400-fold more potent than the monomeric compounds that bind the Drosha processing site. FIG. 16B shows the general structure of the designed peptoid dimer library, where the circular symbol is used to designate the compound 1 half of the dimer, and the diamond shaped symbol is used to designate the generic compound H half of the dimer molecule. FIG. 16C shows the structure of the optimal dimer, BSH-2-H, which was active at 50 nM as a modulator of cellular microRNA-96 hairpin precursor biogenesis.

FIG. 20A graphically illustrates the effects of 50 nM peptoid dimers on apoptosis in MDA MB 231 cells (a triple negative breast cancer cell line) after incubation for 72 hours. As shown, peptoid dimers BSH-2-H and BSH-4-H induce apoptosis to a varying extent as determined by an Annexin V/PI assay. BSH-2-H induces apoptosis in about 75% cells while BSH-4-H induces apoptosis in about 40% cells. The amount of apoptosis is indicated by the clear, top section of each bar. FIG. 20B graphically illustrates the effects of 50 nM peptoid dimers on apoptosis in MCF10A (healthy breast cells) after incubation for 72 hours. None of the designer peptoid dimers induce significant apoptosis in MCF10A, healthy human breast cells under conditions where apoptosis is induced in MDA MB 231. As illustrated, only small amounts of apoptosis are observable, as indicated by the clear, top section of each bar. FIG. 20C graphically illustrates the effects of 50 nM dimer BSH-2-H on apoptosis in MDA MB 231 cancer cells as compared to healthy human breast MCF10A cells after incubation for 72 hours. As illustrated, BSH-2-H induces apoptosis (clear, top section of each bar) in at least 70% of MDA MB 231 cancer cells, but has little to no effect on healthy breast cancer cells.

DETAILED DESCRIPTION

A method is described herein called inforna that provides a streamlined approach for designing bioactive small molecules that target RNA sequence secondary structures (e.g., structural motifs). A myriad of genomic and functional studies are rapidly providing information about disease-associated genes, including non-coding RNAs (Kramer & Cohen, Nat. Rev. Drug Discov. 3, 965-972 (2004). The inforna methods provide an expedited route to identify small molecules that target the RNA product of those genes. The inforna methods not only speed up drug discovery, but also more accurately identify drug candidates that have a higher likelihood of having useful activity. For example, as described in more detail below, use of the inforna methods identified multiple bioactive compounds from only a small dataset of RNA motif-small molecule interactions.

The inforna methods provided herein utilize and compare datasets of information, providing an output of which RNA structural secondary structures will likely bind to which small molecule. Those datasets include (a) a dataset of RNA secondary structures to be queried; and (b) a dataset of identified RNA motif-small molecule interactions (e.g., as identified by two-dimensional combinatorial screening (2DCS)). In general, the term "motif" refers to an RNA structure that has already been identified. The term "secondary structure" is a more general term referring to the structures that can form when an RNA molecule folds back on itself.

The output of RNA sequences and secondary structures that will likely bind to a small molecule can be further analyzed by other prediction processes and by chemical and biological assays (e.g., binding assays). For example, a StARTS statistical method can be used to further refine predictions. The StARTS method predicts the affinities and selectivities of RNA motif-small molecule interactions by comparing the rate of occurrence of small structural features (a guanine adjacent to an adenine, for example) in selected RNA motifs to its rate of occurrence in the entire RNA library. The StARTS method therefore facilitates identification of which RNA secondary structures and motifs are most unique or distinctive in populations of RNA molecules.

Figure 13A:
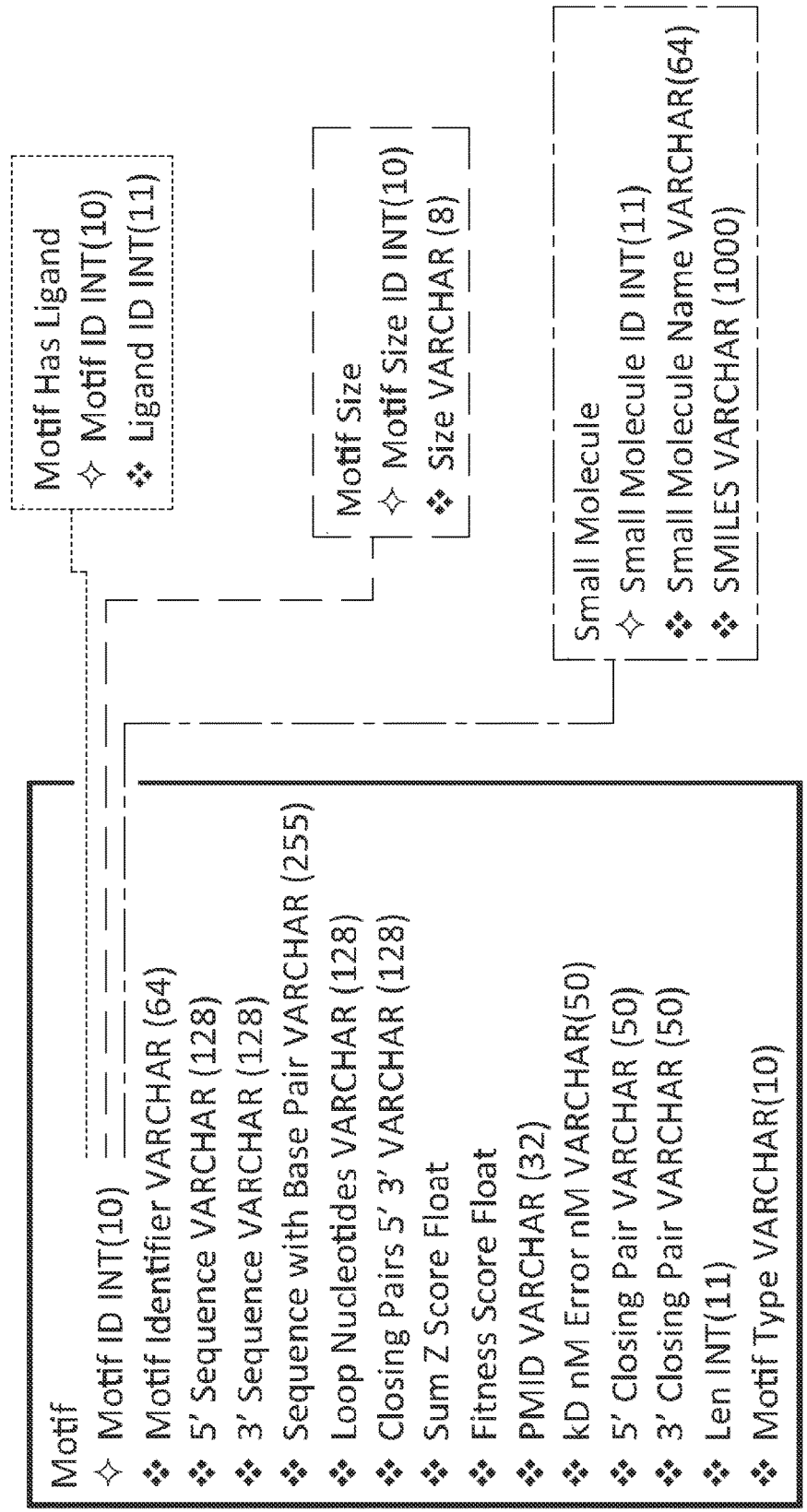
FIG. 13A-13B shows schematic diagrams illustrating aspects of the methods described herein.
Figure 13B:
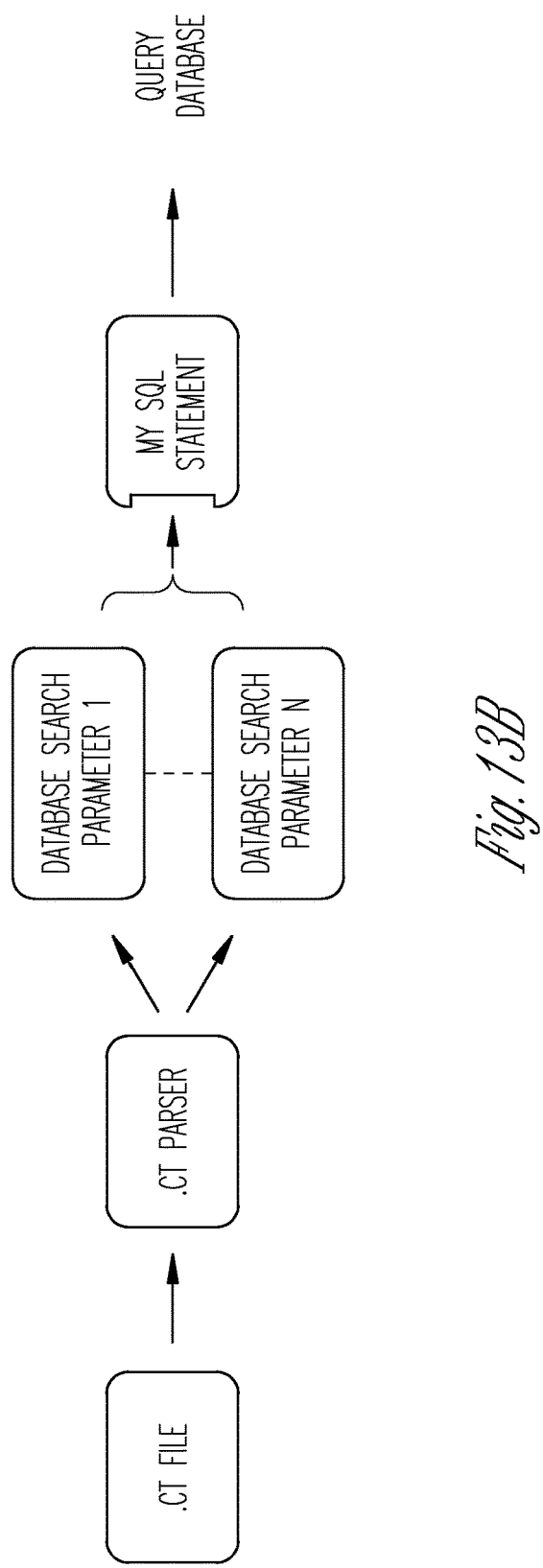
Figure 14A:
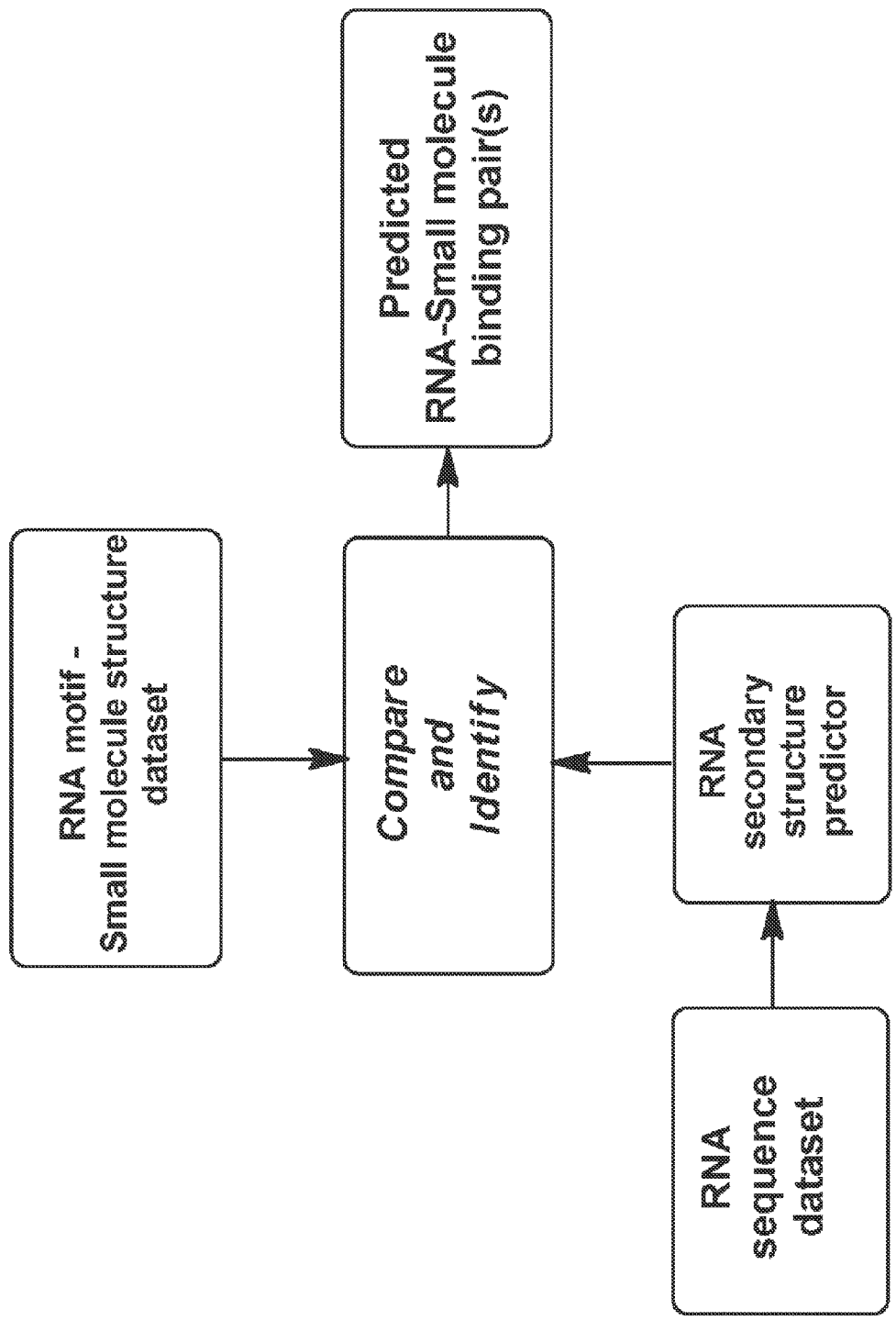
FIG. 14A-14B are schematic diagram illustrating a method for identifying likely RNA targets for small molecules and the small molecules that bind those RNA targets.
Figure 14B:
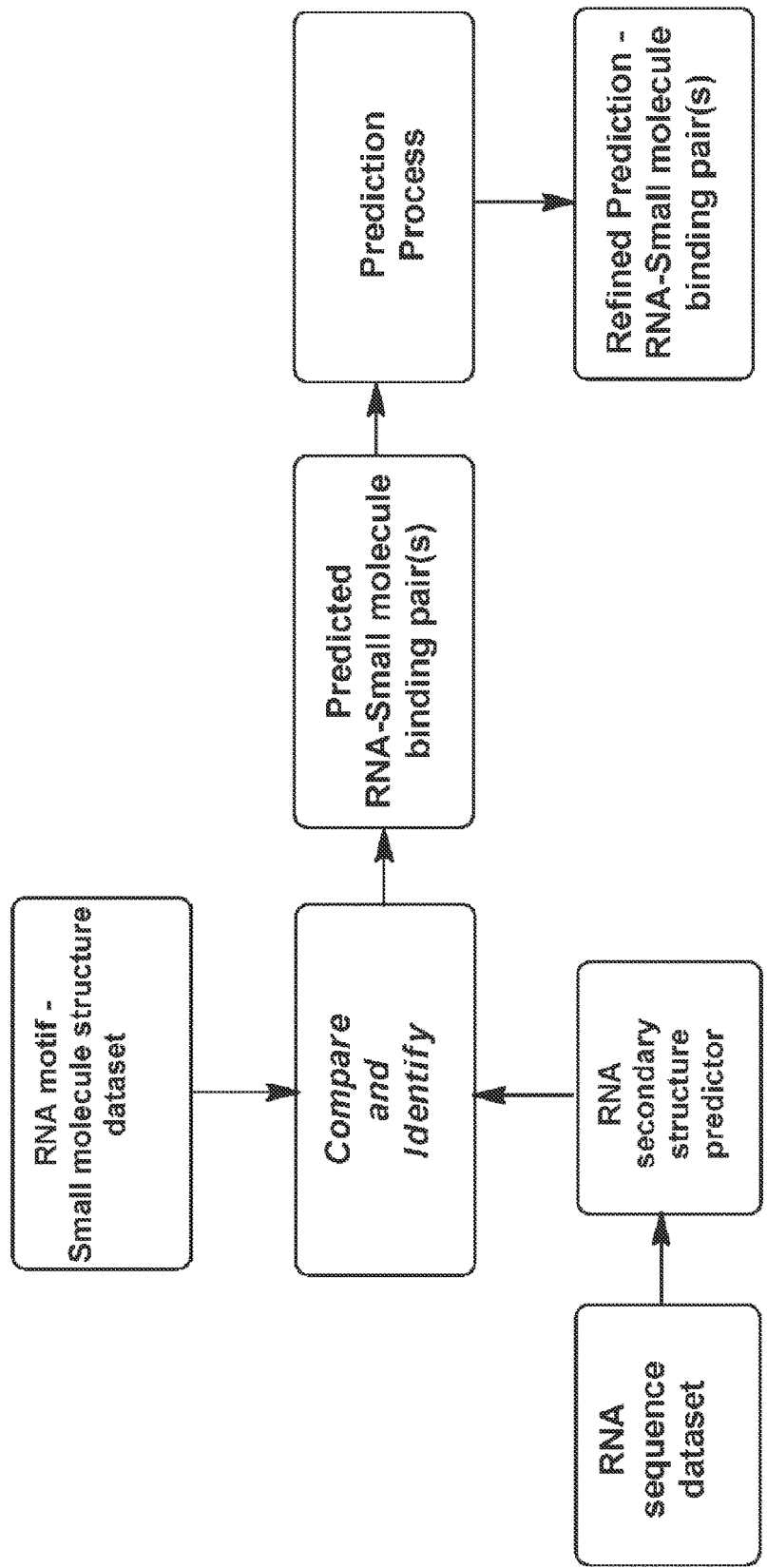

For example, FIGS. 13-14 are schematic diagrams illustrating how datasets and analyses can be performed. The method step and datasets that can be employed are described in more detail below.

A dataset of RNA secondary structures to be queried can be generated from one or more RNA sequences alone. For example, RNA secondary structures can be identified as the lowest free energy secondary structures formed by an RNA as it folds back upon itself to form double-stranded regions as well as single-stranded loops and mismatched 'bubbles' in the double-stranded regions. Such low free energy secondary structures can be predicted by programs such as RNAstructure (Mathews et al., *Proc. Natl. Acad. Sci. U.S.A* 101, 7287-7292 (2004); Mathews et al., *J. Mol. Biol.* 288, 911-940 (1999), which are specifically incorporated by reference herein in their entireties).

Figure 1:
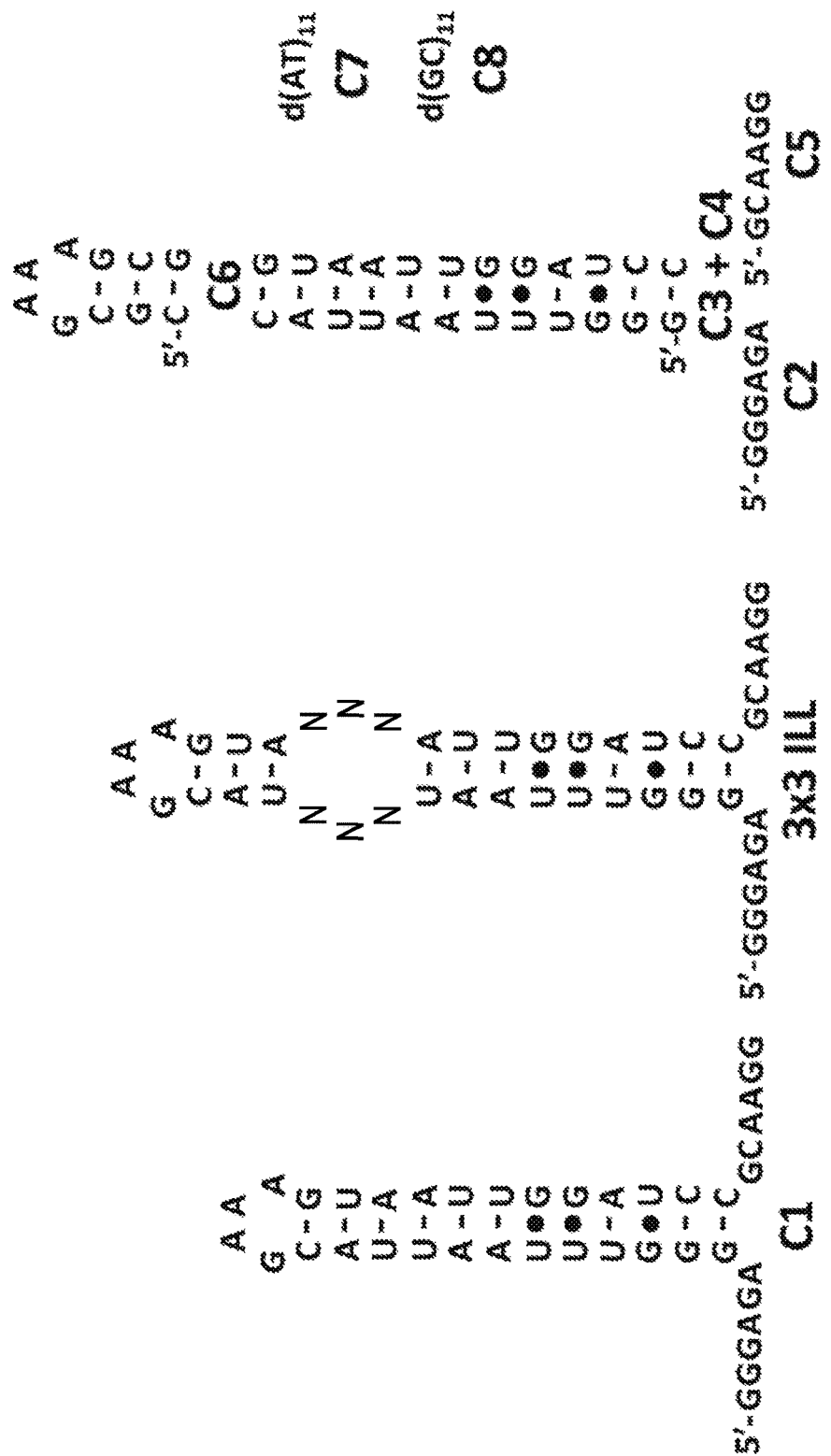
FIG. 1 shows secondary structures of the RNA hairpin cassette C1 (GGGAGAGGGUUUAAUUAC-GAAAGUAAUUGGAUCCGCAAGG, SEQ ID NO:1) used as a framework for displaying the 3×3 nucleotide internal loop library (3×3 ILL; GGGA-GAGGGUUUAAUNNNUACGAAAGUANNN AUUG-GAUCCGCAAGG; SEQ ID NO:2) of motifs. The RNA competitor oligonucleotides C2 (GGGAGA), C3 (GGGUUUAAUUAC; SEQ ID NO:3), C4 (GUAAUUG-GAUCC; SEQ ID NO:4), C5 (GCAAGG), and C6 (CGC-GAAAGCG; SEQ ID NO:5) are also shown. The deoxyoligonucleotides C7 deoxy(AT)$_{11}$ (SEQ ID NO:6) and C8 deoxy(GC)$_{11}$ (SEQ ID NO:7) were used to prevent nonspecific interactions with DNA.

The regions of secondary structure that are more likely to bind small molecules are openings in double-stranded regions ('internal loops'), single-stranded ends of RNA molecules, and other single-stranded regions. For example, FIG. 1 illustrates some types of loops and 'bubbles' (internal loops) in various RNA secondary structure motifs. The secondary structures and motifs can also include regions of double-stranded RNA, though in some embodiments these regions of double-stranded secondary structure are excluded from the datasets because they may be less likely to bind a small molecule with specificity.

A listing of one or many selected RNA sequences can be evaluated so that a dataset of RNA secondary structures is provided. For example, the query dataset of RNA secondary structures can include one or more RNA secondary structures from just one RNA of particular interest, which could be a target for drug design. The dataset can therefore include each RNA secondary structure within the selected RNA. In other situations, the query dataset of RNA secondary structures can be generated from a family of RNA species having related functions, or from a series of RNA species (e.g., those thought to be involved in the onset, maintenance or progression of disease). For example, the query dataset of RNA secondary structures can be from just one RNA molecule, or from 1-5 RNA molecules, or from 1-10 RNA molecules, or from 1-50 RNA molecules, or from 1-100 RNA molecules, or from 1-500 RNA molecules, or from 1-1000 RNA molecules, or from 1-5000 RNA molecules, or from 1-10,000 RNA molecules. The query dataset of RNA secondary structures can also, for example, include structures from just one RNA molecule, or from 2-5 RNA molecules, or from 2-10 RNA molecules, or from 5-50 RNA molecules, or from 10-100 RNA molecules, or from 20-500 RNA molecules, or from 100-1000 RNA molecules, or from 5000-5000 RNA molecules, or from 100-10,000 RNA molecules.

In some instances, the methods described herein can employ an RNA motif library, or can employ an RNA motif library as a query dataset. For example, the RNA motif library can be an RNA internal loop library whose members differ from one another (i) in the identity of the bases in the RNA internal loop and/or (ii) in the identity of the base pairs adjacent to the RNA internal loop (the so-called loop closing base pairs). The RNA motif library can be, for example, a symmetric internal loop library, an asymmetric internal loop library, a 1×1 internal loop library, a 1×2 internal loop library, a 1×3 internal loop library, a 2×2 internal loop library, a 2×3 internal loop library, a 2×4 internal loop library, a 3×3 internal loop library, a 3×4 internal loop library, a 4×4 internal loop library, a 4×5 internal loop library, a 5×5 internal loop library, a 1 base bulge library, a 2 base bulge library, a 3 base bulge library, a 4 base bulge library, a 5 base bulge library, a 4 base hairpin loop library, a 5 base hairpin loop library, a 6 base hairpin loop library, a 7 base hairpin loop library, an 8 base hairpin loop library, a 9 base hairpin loop library, a 10 base hairpin loop library, a multibranch loop library, a pseudoknot library, etc. Combinations of these and other RNA motif libraries can be used or evaluated. For example, the RNA motif library can have two or more internal or terminal loops, bulges, stems, hairpins, or other structural elements.

For completeness, it may be desirable to employ or evaluate an RNA motif library that includes all possible combinations of bases (e.g., an 3×3 internal loop library containing 1600 different 3×3 internal loops). The members of the RNA motif library can further include (i.e., in addition to the variable RNA motif region) RNA regions that do not vary from member to member (e.g., invariant stem regions, invariant hairpin loop regions, etc.). Suitable RNA motif libraries can be prepared by conventional transcription techniques (e.g., those employing T7 RNA polymerase, as described, for example, in Milligan et al., "Synthesis of Small RNAs Using T7 RNA Polymerase," Methods Enzymol., 180:51-62 (1989), which is hereby incorporated by reference) from DNA templates, such as DNA templates that are commercially available from Integrated DNA Technologies (Coralville, Iowa)).

The Examples illustrate analyses of numerous human microRNAs (miRNAs). MicroRNAs have important functional roles in the regulation of transcription and translation. By using the methods described herein small molecules can be identified that can modulate the function of such microRNAs. However, the methods are also useful for modulating the function of other types of RNA, such as pri-miRNA, mRNA, tRNA and rRNA. The RNA molecules that are evaluated can be small or large.

The complete sequence of each query RNA molecule can be provided in the dataset of RNA secondary structures, or the complete sequence of each query RNA molecule can be linked to its query RNA secondary structures so that the source of the secondary structures within the query dataset can be identified.

The dataset of identified RNA motif-small molecule interactions is distinct from the dataset of RNA secondary structures to be queried. The dataset of RNA motif-small molecule interactions is a dataset of the RNA motifs and the molecules that are known to bind to those RNA motifs. Such a dataset can be generated by the two-dimensional combinatorial screening (2DCS) procedures that have previously been developed by the inventors (see, e.g., U.S. Patent Application Publication 20080188377 by Disney & Childs-Disney; Childs-Disney et al., *ACS Chem. Biol.* 2, 745-754 (2007); Disney et al., *J. Am. Chem. Soc.* 130, 11185-11194 (2008), each of which is specifically incorporated by reference herein in its entirety).

Figure 2:
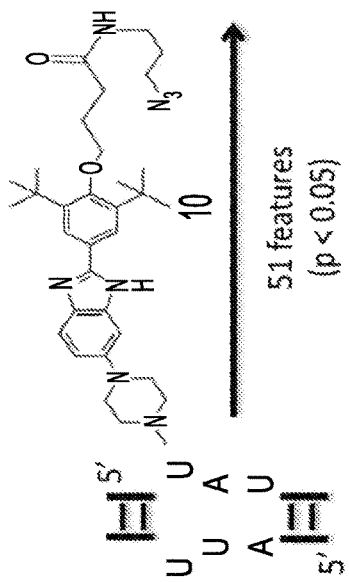
FIG. 2 is a schematic diagram and a chart for calculation of ΣZ-scores for the miR-96 internal loop and compound 1. There are 51 different motifs shown in the chart. The Z score for each motif is shown below the sequence of the motif. The highest Z score (8.24) is in the top leftmost box of this chart, and the sum of Z scores for these 51 motifs is 228.

The 2DCS method involves probing a library of compounds with a library of RNA motifs, and then identifying which RNA motifs bind to which compounds. Thus wet experimentation and physical manipulation is performed on the small molecules and the library of RNS motifs. The library of RNA motifs employed for 2DCS can include a synthetic RNA framework with at least one defined structural region (e.g., one or more double-stranded 'stem' regions of known sequence), and one variable region (e.g., a single stranded loop, or a single stranded 'bubble' of variable sequence that can be a nonhybridized section RNA flanked by doubled stranded RNA segments). For example, the library of RNA motifs can be a 3×3 nucleotide RNA internal loop library, where the defined regions of the 3×3 ILL RNA molecule are shown in FIG. 1 along with two segments of variable sequence, and where each variable segment is three nucleotides long (N—N—N). FIG. 2 shows the library of three-nucleotide RNA motif combinations that was used in some of the experiments described herein. In another example, the library of RNA motifs can have more than one variable segment or more than one pair of variable segments.

For the 2DCS method, the library of compounds can be immobilized onto a microarray so that the address of each compound is known. The array of compounds can be embedded within a gel (e.g., agarose or polyacrylamide) to facilitate localization and processing of small molecule-RNA motif binding pairs. A mix of RNA molecules, including an entire library of RNA motifs, optionally with any desired control RNAs, and/or competitor oligonucleotides is incubated with each compound in the array. After incubation under conditions that allow binding, RNA molecules bound by the compounds are separately harvested, amplified, and sequenced.

For example, in 2DCS experiments described herein, a small molecule library was conjugated onto an agarose microarray surface. The small molecule microarray was then probed with a library of small RNA motifs likely to be found as components of RNAs of interest. For example, the 3×3 ILL RNA with a variable internal loop that is shown in FIG. 1 was used as a platform for presenting the library of small RNA motifs shown in FIG. 2. Incubation of the compounds with the library of RNA motifs can be performed in the presence of competitor oligonucleotides such as the C2-C8 oligonucleotides (FIG. 1) to ensure that only small molecules bound to the randomized region of the 3×3 ILL RNA will be retained, while small molecules that might bind to regions common to all library members instead bind to the C2-C8 oligonucleotides. (See, Childs-Disney et al., *ACS Chem. Biol.* 2, 745-754 (2007); Disney et al., *J. Am. Chem. Soc.* 130, 11185-11194 (2008), the contents of which are specifically incorporated herein by reference in their entireties.)

RNAs bound by the immobilized compounds are separately harvested, amplified, and sequenced. The RNA motifs in the bound RNAs are identified and the dataset of identified RNA motif-small molecule interactions is prepared by listing the small molecules and the RNA motif(s) that are bound by the small molecule(s). The dataset can include primary and secondary structural information for each RNA motif as well as structural information for each small molecule (e.g., name, chemical formula, chemical structure, three-dimensional structure, and the like).

StARTS is a statistical approach that can be paired with inforna to further evaluate the binding affinity of RNA secondary structures for the small molecule partner(s) identified by inforna. StARTS identifies features in RNA motifs that positively and negatively contribute to binding (see, Velagapudi et al., *Angew. Chem. Int. Ed. Engl.* 49, 3816-3818 (2010); Velagapudi et al., *J. Am. Chem. Soc.* 133, 10111-10118 (2011); Paul et al., *Nucleic Acids Res.* 37 (17): 5894-5907 (2009), each of which is incorporated by reference herein in its entirety).

In the StARTS approach, sequences of one or more RNA secondary structures identified as binding a small molecule are compiled, and the occurrence rate of each sequence feature in the RNA secondary structures is compared to the occurrence rate of that feature in a larger population of RNA motifs. A sequence feature is any short RNA sequence (for example, a 5'GC step) that may or may not be different from the sequence features that are present in a larger population of RNA sequences. However, the sequence features are those sequences that are present in the population of RNA secondary structures that bind to a small molecule. By comparing these two populations, the relative enrichment for a specific feature in RNA secondary structure for binding to a small molecule can be computed. Thus, the StARTS method identifies which sequence features are more prevalent in a selected population of RNA sequences than in a larger population of RNA sequences.

The more distinctive sequence features are assigned a statistical significance, or a Z-score and a corresponding two-tailed p-value. The Z scores can be determined by statistical analysis using a RNA Privileged Space Predictor (RNA-PSP) program that determines which features occur in the selected RNA secondary structures with greater than 95% confidence (see, Paul et al., *Nucleic Acids Res.* 37 (17): 5894-5907 (2009), which is incorporated herein by reference in its entirety). The confidence intervals are associated with a Z-score, where a larger value corresponds to a higher confidence level. Each RNA secondary structure can have multiple features that contribute to it being different from a larger population of RNA motifs and a sum of the Z-scores for all features in an RNA secondary structure can be computed ($\Sigma Z$) as an indicator of the total structural distinctiveness of an RNA motif.

To complete the StARTS analysis, the Z-scores can then plotted against the measured binding affinities of the RNA secondary structure for a compound, and this relationship can be fitted to an inverse first-order equation, which allows prediction of the affinity of a compound for a RNA library member.

The computer program RNA-PSP has previously been developed by the inventors to address the need for fast and accurate statistical analysis of selected RNAs. RNA-PSP was developed on a Microsoft Visual Basic 2008 platform, and allows direct input of sequence files from any selection. The inputted sequence file is then analyzed to extract the sequences of the variable region for each selected library member. For the automated extraction of selected sequences, users specify the constant and the variable regions of the library, allowing RNA-PSP to sort through a sequencing file and identify embedded RNAs from the selection. See, Paul et al., *Nuc. Acids Res.* 37 (17): 5894-5907 (2009). Once the selected structures are extracted by the program, it generates all possible combinations of sequences from the original library and stores the results. For example, in the 3×3 nucleotide hairpin library shown in FIG. 2 there are just 51 boxes in the table, but 4096 possible motifs because each three-nucleotide sequence shown in the table has at least one variable nucleotide.

RNA-PSP ranks the most statistically significant feature for the various RNA motif sequences by performing a Z-test that generates Z-scores using Equations (I) and (II):

$$\varphi = \frac{n_1 p_1 + n_2 p_2}{n_1 + n_2} \qquad \mathrm{I}$$

$$Z_{obs} = \frac{(p_1 - p_2)}{\sqrt{\varphi(1-\varphi)\left(\left(\frac{1}{n_1}\right)+\left(\frac{1}{n_2}\right)\right)}} \qquad \mathrm{II}$$

where
$n_1$ is the size of Population 1 (e.g., the selected RNA secondary structure(s)),
$n_2$ is the size of Population 2 (e.g., a library of RNA motifs),
p1 is the observed proportion of Population 1 displaying the feature, and p2 is the observed proportion for Population 2 displaying the feature.

The output of RNA-PSP is a $Z_{obs}$ score, and a corresponding two-tailed p-value is assigned to reflect a confidence level that a structural feature is distinct from those in the population as a whole. Z scores are the $Z_{obs}$ scores with greater than 95% confidence limits. The table in FIG. 2 shows the output of RNA-PSP analysis for the indicated 51 features (Z-scores).

Population 1 can be any selected subset of RNA sequences, such as the output from an inforna analysis, or a subset of the inforna output, such as one or more RNA secondary structures that are predicted to bind a small molecule, or appear to contribute to binding of a small molecule by wet testing. A family or genus of related RNA sequences or motifs that share some structural features is typically evaluated to assess whether the common structural features contribute to binding with a small molecule. For example, Population 1 could include all the sequences defined by the generic loop structure in the first box in the table shown in FIG. 2. This box defines a genus of RNA structures because there is a first three-nucleotide segment (5'ANU) and a second three-nucleotide (5'UNU) in that loop, where each of these three-nucleotide segments has a variable nucleotide that can be any of four ribonucleotides (A, C, G, U). So the first box in the table shown in FIG. 2 describes a genus of loops—not just one. Population 2 in this example could be all the 4096 possible sequences in the FIG. 2 table. Alternatively, population 1 could be all of sequences in the FIG. 2 table that bind a specific small molecule, as assessed by inforna, while population 2 could be all sequences in FIG. 2, or all microRNA sequences.

The genus of secondary structures or motifs (e.g., loops) can have a multitude of different sequence features, and a multitude of different Z scores. When a given genus contains the sequence with the highest Z score, that high scoring sequence and that genus could be good target for binding a small molecule. However, each sequence within the genus of sequences (those described by the first box in FIG. 2) also shares common structural features with all of the other sequences in the genus. Hence, a sum of all Z scores ($\Sigma Z$) for all the sequence features in genus of sequences can be a more useful indicator of the potential of a structural motif for specific binding to a small molecule.

The affinity of a small molecule for the various RNA library members can be illuminated when Z scores are plotted against the measured binding affinities and this plot is fitted to an inverse first-order equation. Such a graph can be used to predict the affinity of the small molecule for any RNA library member (see, e.g., Velagapudi et al., *Angew. Chem. Int. Ed. Engl.* 49, 3816-3818 (2010); Velagapudi et al., *J. Am. Chem. Soc.* 133, 10111-10118 (2011)). The combination of statistical and experimental evaluation makes StARTS a valuable tool for clarifying which of the secondary structures identified by inforna are the best drug targets.

StARTS therefore predicts the affinities and selectivities of RNA-small molecule interactions by comparing the rate of occurrence of a feature in selected RNA motifs (a guanine adjacent to an adenine, for example) to its rate of occurrence in the entire RNA library. The confidence that a selected feature did not occur randomly is assigned a Z-score and a corresponding two-tailed p-value. Only features that are statistically significant ($p<0.05$ or $>95\%$ confidence) are considered. The analysis identifies features that contribute positively (positive Z-score) and negatively (negative Z-score) to binding, facilitating prediction of which RNAs bind and which RNAs do not.

FIG. 13 is schematic diagram of a system for analysis of RNA motif-small molecule interactions that has been constructed. The system can be used to guide the rational design of small molecules that target an RNA of interest. The small molecules are referred to as ligands in FIG. 13. The system can draw upon a dataset of all RNA motif-small molecule interactions identified by 2DCS or by other methods. Such an RNA motif-ligand dataset can be stored within the system along with the inforna program, or the RNA motif-small molecule dataset can be maintained independently of the inforna program and accessed or used as input for inform when desired.

The system can include a number of entries. For example, each entry can be assigned the following parameters, which can be present in various tables that are linked for facile searching: (i) a unique ligand (small molecule) identifier; (ii) a unique RNA secondary structure or motif identifier; (iii) the RNA secondary structure or motif type; (iv) the RNA secondary structure or motif size; (v) the RNA secondary structure or motif sequence; (vi) the closing base pair(s) of the RNA; (vii) the Fitness Score for the RNA secondary structure or motif (which indicates the overall fitness of the RNA motif-small molecule interactions and is highly correlated to the binding affinity); (viii) the dissociation constant, $K_d$, of the RNA motif-small molecule pair if measured; and, (ix) other notes including, for example, the PubMed identification reference number of the RNA molecules that are the source of the secondary structures(s) and motif(s).

FIG. 13 refers to ID INT, which creates a column "id" that will automatically increment each time a new entry is added to the table. The term VARCHAR (#) indicates that a variable-length string of text can be listed, where "#" indicates the maximum number of characters with the string.

The Motif table shown at the left in FIG. 13A has a number of components. The Motif ID (Motif Identifier) in the Motif table assigns each RNA motif a numerical identifier. The current dataset has about 1500 RNA motif-small molecule partners. The Motif Identifier VARCHAR assigns each motif a name.

In FIG. 13A, the Motif Table defines the entire sequence of the RNA motif including:

5' Sequence: the 5' sequence of the RNA motif with closing base pair

3' Sequence: the 3' sequence of the RNA motif with closing base pair

Sequence with Base Pair: the entire sequence of the RNA motif and the closing base pairs Loop Nucleotides: the sequences of each RNA motif excluding closing base pairs Closing Pairs (5', 3'): sequence of the 5' and 3' closing base pairs.

The Small Molecule table to the right in FIG. 13A identifies the name of small molecule (also referred to as a ligand) to which the RNA motif binds.

The Motif Size INT component in the Motif Size table of FIG. 13A links to the Motif table to autopopulate the table and assign a unique identifier to each row; this creates a column "id" that will automatically increment each time a new entry is added to the table.

The Small Molecule ID INT in the table to right in FIG. 13A links to the Motif table to autopopulate the table, creating a column "id" that will automatically increment each time a new entry is added to the table.

The Fitness Score Float in the Motif table to left in FIG. 13A is the fitness of an RNA motif for binding a specific small molecule (ligand). The Binding constant (Kd nM error nm) in the Motif table of FIG. 13A is the binding affinity or $IC_{50}$ if determined, and can be shown in the output. The PMID (VARCHAR) is the PubMed Identification number of the RNA that is the source of the motif(s).

The Motif Size table on the right side of FIG. 13 is linked to the Motif Table. The Motif Size table includes a Motif Size ID INT function that creates a column "id" that will automatically increment each time a new entry is added to the table. As explained above, VARCHAR (#) represents variable-length strings of text where "#" indicates the maximum number of characters with the string. Each motif type is represented by a numerical identifier within the Motif Size Id, and this identifier is annotated within this table. The "motif size" can have different functional forms. For example, for hairpins and bulges, the motif size is simply a number that indicates the number of nucleotides in the loop. The functional form for internal loops is "A×B" where A indicates the number of 5' unpaired nucleotides and B indicates the number of 3' unpaired nucleotides. The functional form for the motif size of a multi-branch loop can have multiple forms such as "A×B×C" or "A×B×C×D", indicating a 3- or 4-way junction, respectively.

The Small Molecule Table shown at the right in FIG. 13A also has a number of components. The Small Molecule table is linked to the Motif Table as illustrated in FIG. 13A. The id INT creates a column "id" that will automatically increment each time a new entry is added to the table. The Small Molecule ID in the Small Molecule Table assigns a numerical identifier to each small molecule starting from 1. The current database has 24 small molecules (see, e.g., FIG. 12). The Small Molecule Name is the name assigned to each small molecule to identify it. SMILES, or simplified molecular-input line-entry system, is text that describes the small molecule's structure. SMILES text can be input into various programs to reconstitute the ligand's structure. There can be a separate folder of the structures with files (e.g., JPEG files) that can be output for each search.

The Motif Has Ligand Table shown at the right in FIG. 13A also has a number of components. The Motif Has Ligand table is linked to the Motif Table as shown in FIG. 13. The Motif Has Ligand Table correlates the Motif ID with a Small Molecule ID. The ID INT creates a column "id" that will automatically increment each time a new entry is added to the table. The small molecule id is a numerical identifier assigned to each small molecule starting from 1. The current database has 24 small molecules. The Motif ID is a numerical identifier for each motif type, which is annotated in the Motif Table.

FIG. 13B is a schematic diagram illustrating one example of a search engine's flow of data during the methods describes herein. The inforna software accepts a .CT file (a simple text file that describes the secondary structure of an RNA) with two search options: search loop nucleotides WITHOUT closing base pairs and search loop nucleotides WITH closing base pairs. The user can select a .CT file or a zip file that contains multiple .CT files. After choosing the .CT file and submitting the Search option, the process first calls a function to parse the .CT file. This function applies a parsing algorithm, which creates a database search parameter. Once the .CT file parsing function is completed another search parameter is created depending on the selected search option. When these functions are completed another function converts these search parameters into a structured query language (SQL) statement used to query the database. This SQL statement consists of the fields in the database that are being queried, the tables within the database that contain the queried fields, and the search criteria, which filters the result set based on the user's selected options.

Each record in the database is assigned a unique Motif ID, Motif Identifier, Motif Type, Motif Size, Closing Base Pair, Sum Z-score for the motif, which indicates statistical significance and is highly correlated to affinity, Fitness Score, Dissociation Constant ($K_d$) if measured and the PMID publication reference ID. There are two defined functions in the system that are used in parsing the CT files. Depending on the search criteria the system will either return no matches or a set of records that match the search criteria. This record set can then be passed to the user interface where it is processed further to apply any format changes. Once this is complete this record set populates the user interface grid. The values are displayed in the following order: CT Filename, Compound Structure which is an image visualizing the SMILES field, Query Motif, Motif in Target RNA, Loop Nucleotides, Fitness Score, Loop Identifier, Dissociation Constant ($K_d$) if measured and the PMID publication reference link. Since the search results can be rather large, a 200 row limit is applied to reduce the load of the server and the lag between search submissions. If the user wishes to view all the records, an export to excel option is available. This option is not limited by the number of records.

Thus, the inforna process generates an output after dataset comparison(s)/queries, where the output can include the structure of the RNA molecule(s) queried (e.g., as a .ct file), the structure of the small molecule(s) that bind to an identified motif in the queried RNA including a link to the corresponding SMILES file, the motif(s) within the RNA motif-small molecule dataset that is similar to or exactly matches motif(s) in the queried RNA that binds the small molecule, the motif(s) in the queried RNA that is predicted to bind a small molecule ligand, the (loop) nucleotides in the motif(s) from the queried RNA, the Fitness Score of each newly discovered small molecule-RNA motif pair, a Binding constant ($K_d$ or $IC_{50}$), a Loop Identifier for the motif in the database that is similar to or exactly matches motif(s) in the queried RNA (as referred to in publications), and the PubMed identification where the motif in the database is reported.

The functions or algorithms described herein may be implemented in software or a combination of software and human implemented procedures, for example. The software may consist of computer executable instructions stored on computer readable media such as memory or other type of storage devices. Further, such functions correspond to modules, which are software, hardware, firmware or any combination thereof. Multiple functions may be performed in one or more modules as desired, and the embodiments described are merely examples. The software may be executed on a digital signal processor, ASIC, microprocessor, or other type of processor operating on a computer system, such as a personal computer, server or other computer system. In one embodiment, multiple such computer systems are utilized in a distributed network to implement multiple analyses, draw upon information from distributed sources, or facilitate transaction based usage. An object-oriented, service-oriented, or other architecture may be used to implement such functions and communicate between the multiple systems and components.

For example, the computer may operate in a networked environment using a communication connection to connect to one or more remote computers, such as database servers. The remote computer may include a personal computer (PC), server, router, network PC, a peer device or other common network node, or the like. The communication connection may include a Local Area Network (LAN), a Wide Area Network (WAN) or other networks.

Datasets of information can be in different forms and from different sources. For example, datasets can be stored and updated in the form of computer-accessible storage. Computer-accessible storage includes random access memory (RAM), read only memory (ROM), erasable programmable read-only memory (EPROM) & electrically erasable programmable read-only memory (EEPROM), flash memory or other memory technologies, compact disc read-only memory (CD ROM), Digital Versatile Disks (DVD) or other optical disk storage, magnetic cassettes, magnetic tape, magnetic disk storage or other magnetic storage devices, or any other medium capable of storing computer-readable instructions.

Computer-readable instructions (e.g., for inforna) can be stored on a computer-readable medium and can be executable by a processing unit of the computer. A hard drive, CD-ROM, and RAM are some examples of articles including a non-transitory computer-readable medium. For example, a computer program linked to, or including, the inforna programs can be capable of providing a generic technique to perform an access control check for data access and/or for doing an operation on one of the servers in a component object model (COM) based system, or can be included on a CD-ROM and loaded from the CD-ROM to a hard drive. The computer-readable instructions allow computer to provide generic access controls in a COM based computer network system having multiple users and servers.

A system bus can be any of several types of bus structures including a memory bus or memory controller, a peripheral bus, and a local bus using any of a variety of bus architectures. The system memory can also be referred to as simply the memory, and, in some embodiments, includes read-only memory (ROM) and random-access memory (RAM). A basic input/output system (BIOS) program, containing the basic routines that help to transfer information between elements within the computer, such as during start-up, may be stored in ROM. A computer that includes the inforna process can further include a hard disk drive for reading from and writing to a hard disk, a magnetic disk drive for reading from or writing to a removable magnetic disk, and an optical disk drive for reading from or writing to a removable optical disk such as a CD ROM or other optical media.

Such a hard disk drive, magnetic disk drive, and optical disk drive can couple with a hard disk drive interface, a magnetic disk drive interface, and an optical disk drive interface, respectively. The drives and their associated computer-readable media provide non-volatile storage of computer-readable instructions, data structures, program modules and other data for the computer. It should be appreciated by those skilled in the art that any type of computer-readable media which can store data that is accessible by a computer, such as magnetic cassettes, flash memory cards, digital video disks, Bernoulli cartridges, random access memories (RAMs), read only memories (ROMs), redundant arrays of independent disks (e.g., RAID storage devices) and the like, can be used in the exemplary operating environment.

A plurality of program modules can be stored on the hard disk, magnetic disk, optical disk, ROM, or RAM, including an operating system, one or more application programs, other program modules, and program data. Programming for implementing one or more processes or method described herein may be resident on any one or number of these computer-readable media.

A user may enter commands and information into computer through input devices such as a keyboard and pointing device. Other input devices (not shown) can include a microphone, touch screen, joystick, game pad, satellite dish, scanner, or the like. These other input devices are often connected to the processing unit through a serial port interface that is coupled to the system bus, but can be connected by other interfaces, such as a parallel port, game port, or a universal serial bus (USB). A monitor or other type of display device can also be connected to the system bus via an interface, such as a video adapter. The monitor can display a graphical user interface for the user, and may include a touchscreen, allowing user interactions to select functions and enter data. In addition to a monitor, computers typically include other peripheral output devices, such as speakers and printers.

The computer may operate in a networked environment using logical connections to one or more remote computers or servers, such as remote computer. These logical connections are achieved by a communication device coupled to or a part of the computer; the invention is not limited to a particular type of communications device. Such a remote computer can be another computer, a server, a router, a network PC, a client, a peer device or other common network node, and typically includes many or all of the elements described above relative to the computer. The logical connections include a local area network (LAN) and/or a wide area network (WAN). Such networking environments are commonplace in office networks, enterprise-wide computer networks, intranets and the internet, which are all types of networks.

When used in a LAN-networking environment, the computer can be connected to the LAN through a network interface or adapter, which is one type of communications device. In some embodiments, when used in a WAN-networking environment, the computer typically includes a modem (another type of communications device) or any other type of communications device, e.g., a wireless transceiver, for establishing communications over the wide-area network, such as the internet. Such a modem, which may be internal or external, is connected to the system bus via the serial port interface. In a networked environment, program modules depicted relative to the computer can be stored in the remote memory storage device of remote computer, or server. It is appreciated that the network connections described are exemplary and other means of, and communications devices for, establishing a communications link between the computers may be used including hybrid fiber-coax connections, T1-T3 lines, DSL's, OC-3 and/or OC-12, TCP/IP, microwave, wireless application protocol, and any other electronic media through any suitable switches, routers, outlets and power lines, as the same are known and understood by one of ordinary skill in the art.

Electronic Apparatus and System

Example embodiments may therefore be implemented in digital electronic circuitry, or in computer hardware, firmware, software, or in combinations of them. Example embodiments may be implemented using a computer program product, for example, a computer program tangibly embodied in an information carrier, for example, in a machine-readable medium for execution by, or to control the operation of, data processing apparatus, for example, a programmable processor, a computer, or multiple computers.

A computer program can be written in any form of programming language, including compiled or interpreted languages, and it can be deployed in any form, including as a stand-alone program or as a module, subroutine, or other unit suitable for use in a computing environment. A computer program can be deployed to be executed on one computer or on multiple computers at one site or distributed across multiple sites and interconnected by a communication network.

In example embodiments, operations may be performed by one or more programmable processors executing a computer program to perform functions by operating on input data and generating output. Method operations can also be performed by, and apparatus of example embodiments may be implemented as, special purpose logic circuitry (e.g., a FPGA or an ASIC).

The computing system can include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that both hardware and software architectures merit consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice. Below are set out hardware (e.g., machine) and software architectures that may be deployed, in various example embodiments.

Example Machine Architecture and Machine-Readable Medium

Figure 15:
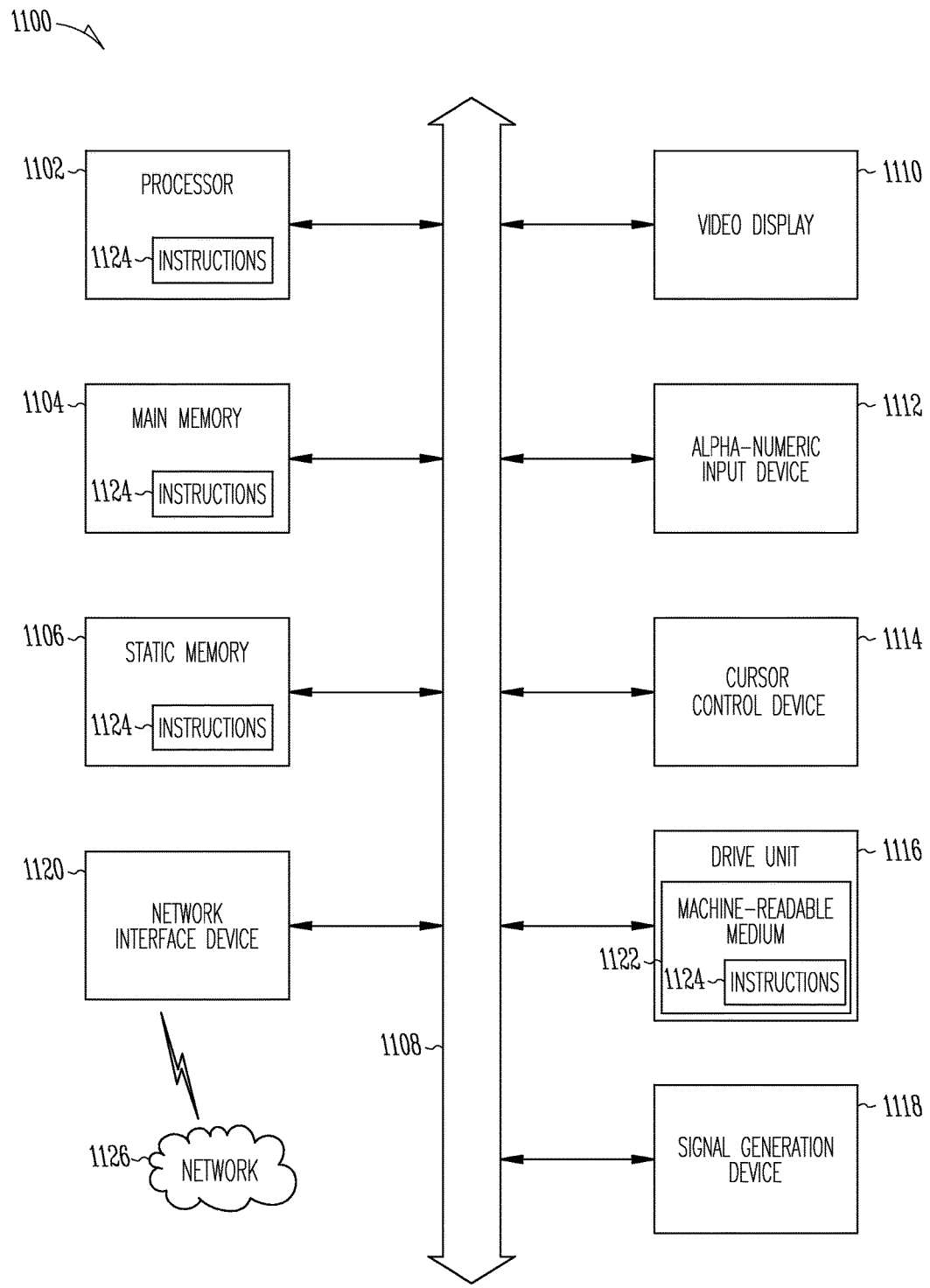
FIG. 15 is a block diagram of a machine in the example form of a computer system.

FIG. 15 is a block diagram of machine in the example form of a computer system 1100 within which there may be executed instructions 1124 for causing the machine to perform any one or more of the methodologies discussed herein. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a PDA, a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1100 includes a processor 1102 (e.g., a central processing unit (CPU), a graphics processing unit (GPU) or both), a main memory 1104 and a static memory 1106, which communicate with each other via a bus 1108. The computer system 1100 may further include a video display unit 1110 (e.g., a liquid crystal display (LCD) or a cathode ray tube (CRT)). The computer system 1100 also includes an alphanumeric input device 1112 (e.g., a keyboard), a cursor control device 1114 (e.g., a user interface (UI) navigation device or computer mouse), a disk drive unit 1116, a signal generation device 1118 (e.g., a speaker) and a network interface device 1120.

Machine Readable Medium

The disk drive unit 1116 includes a machine-readable medium 1122 on which is stored one or more sets of data structures and instructions 1124 (e.g., software) embodying or used by any one or more of the methodologies or functions described herein. The instructions 1124 may also reside, completely or at least partially, within the main memory 1104, static memory 1106, and/or within the processor 1102 during execution thereof by the computer system 1100, the main memory 1104 and the processor 1102 also constituting machine-readable media.

While the machine-readable medium 1122 is shown in an example embodiment to be a single medium, the term "machine-readable medium" may include a single medium or multiple media (e.g., a centralized or distributed database, and/or associated caches and servers) that store the one or more instructions 1124 or data structures. The term "machine-readable medium" shall also be taken to include any tangible medium that is capable of storing, encoding or carrying instructions for execution by the machine and that cause the machine to perform any one or more of the methodologies of the embodiments of the present invention, or that is capable of storing, encoding or carrying data structures used by or associated with such instructions. The term "machine-readable medium" shall accordingly be taken to include, but not be limited to, solid-state memories, and optical and magnetic media. Specific examples of machine-readable media include non-volatile memory, including by way of example, semiconductor memory devices (e.g., Erasable Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks. A "machine-readable storage medium" shall also include devices that may be interpreted as transitory, such as register memory, processor cache, and RAM, among others. The definitions provided herein of machine-readable medium and machine-readable storage medium are applicable even if the machine-readable medium is further characterized as being "non-transitory." For example, any addition of "non-transitory," such as non-transitory machine-readable storage medium, is intended to continue to encompass register memory, processor cache and RAM, among other memory devices.

Transmission Medium

The instructions 1124 may further be transmitted or received over a communications network 1126 using a transmission medium. The instructions 1124 may be transmitted using the network interface device 1120 and any one of a number of well-known transfer protocols (e.g., HTTP). Examples of communication networks include a LAN, a WAN, the Internet, mobile telephone networks, Plain Old Telephone (POTS) networks, and wireless data networks (e.g., Wi-Fi and WiMax networks). The term "transmission medium" shall be taken to include any intangible medium that is capable of storing, encoding or carrying instructions for execution by the machine, and includes digital or analog communications signals or other intangible media to facilitate communication of such software.

Methods of Treatment

As illustrated herein, the methods of the invention can identify compounds that modulate the function of RNA. For example, several compounds were identified that modulate microRNA function, including compounds 1, 2, and 3 (see, FIGS. 3 and 5; Example 4). Thus, compound 1 reduces the expression level of miR-96 by 90% at 40 µM; compound 2 reduces the formation of miR-210 by 60% at 500 nM; and compound 3 reduces the production of miR-182 by 40% at 200 µM In another example, a dimeric compound referred to herein as the BSH-2-H exhibited significant selectivity for an RNA that contains two loop sites. The BSH-2-H dimeric molecule also had greater than 30-fold higher affinity for the two-site RNA than did monomeric compounds that make up BSH-2-H. Compound 1 constitutes one half of the BSH-2-H molecule, while the other half was a molecule identified by experiments described in Example 10. Incubation of the BSH-2-H compound with MCF7 cells led to significant reduction in the production of the mature microRNA-96 at 50 nM concentration, while also inhibiting production of the pre-microRNA-96 and boosting production of the pri-microRNA-96. In addition, the BSH-2-H compound at 50 nM concentration induced apoptosis in about 75% of MDA MB 231 breast cancer cells, but did not adversely affect healthy breast cells at similar concentrations.

One aspect of the invention is a method of treatment in a subject in need thereof that includes administering to the mammal a compound identified by the methods described herein to thereby treat the subject. Any of the compounds described herein can be used in such methods. For example, the methods can include administering any of the following compounds to a mammal.

1

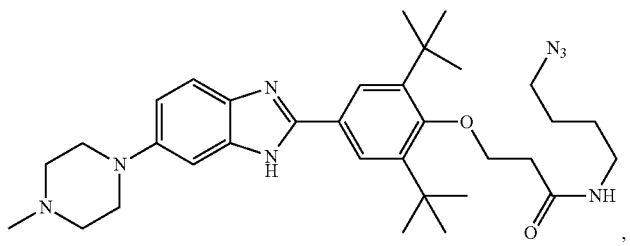

2

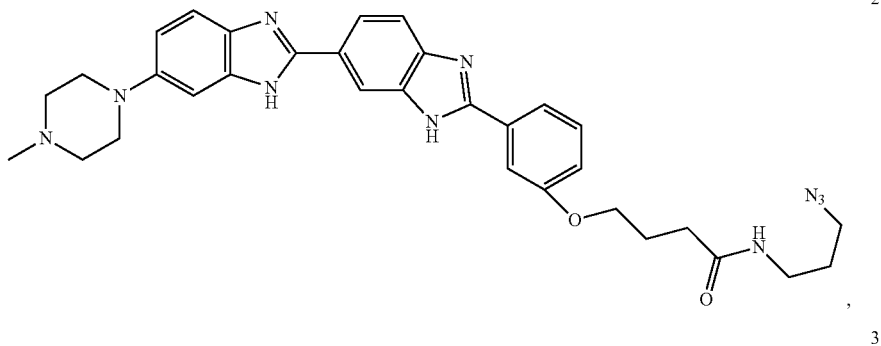

3

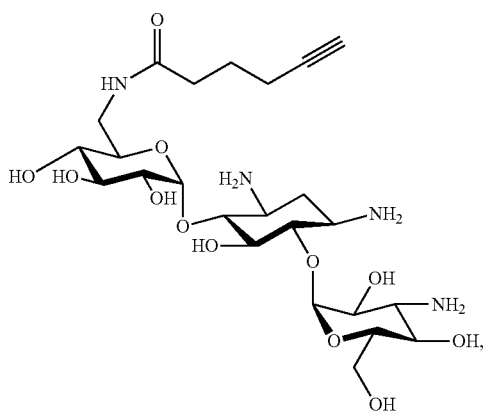

4

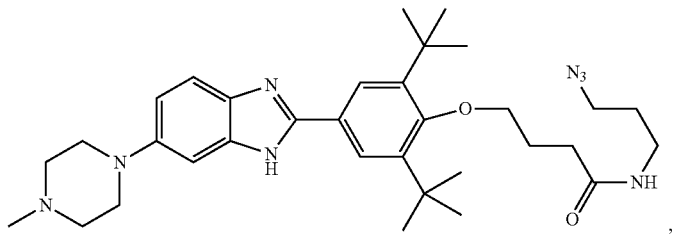

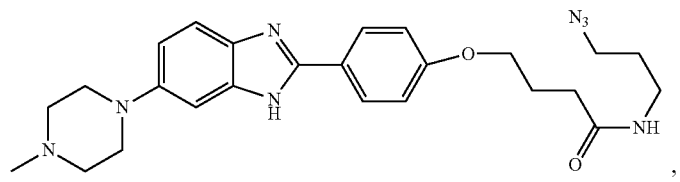
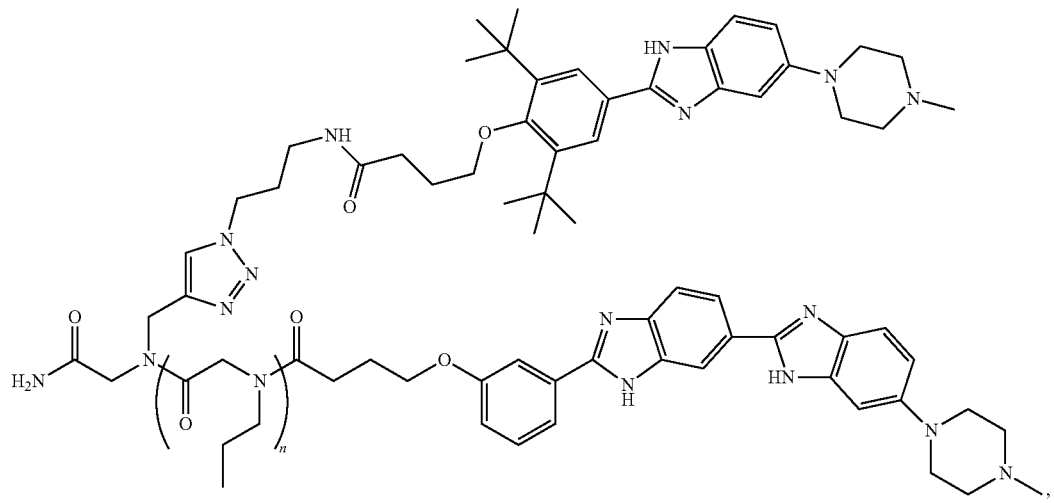
BSH-n-H
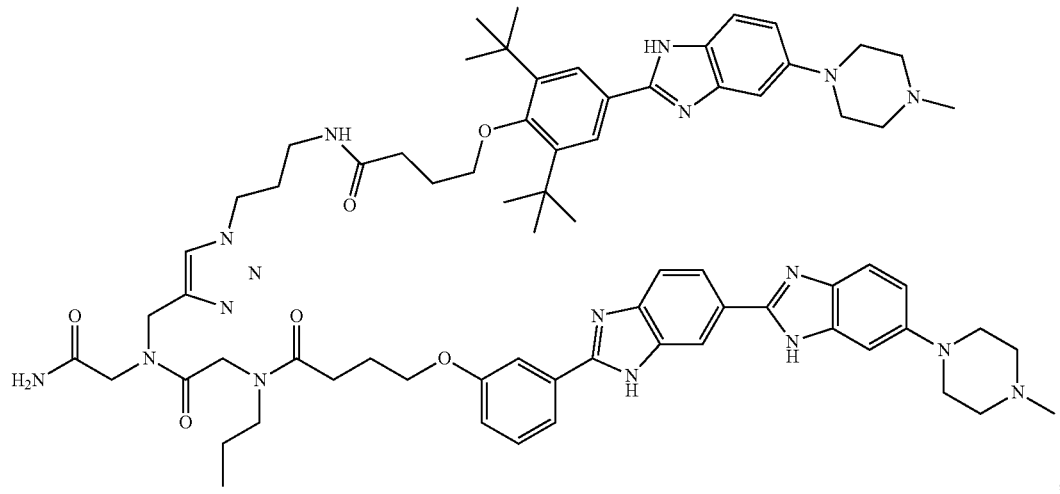
BSH-1-H

BSH-2-H
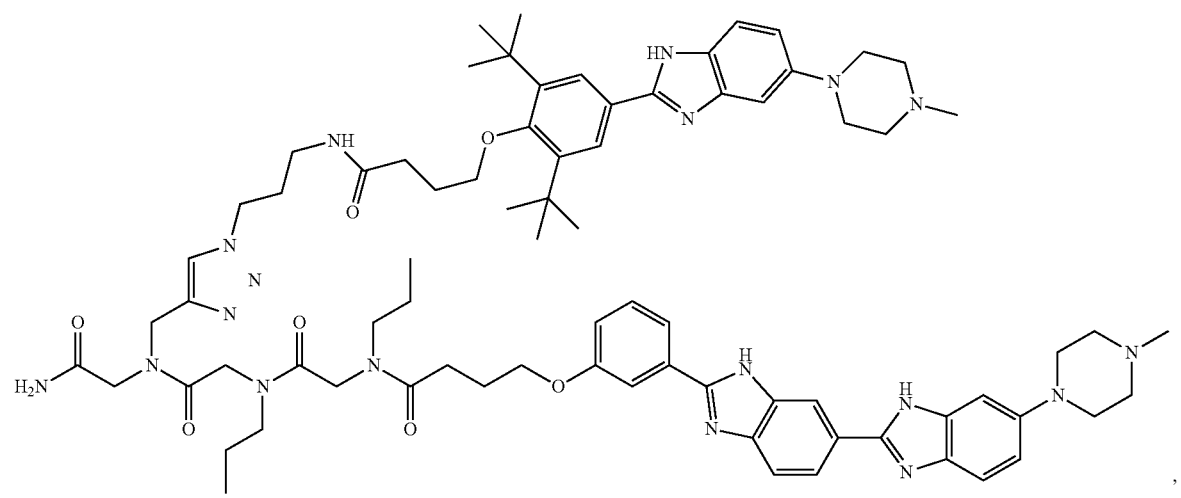
BSH-3-H
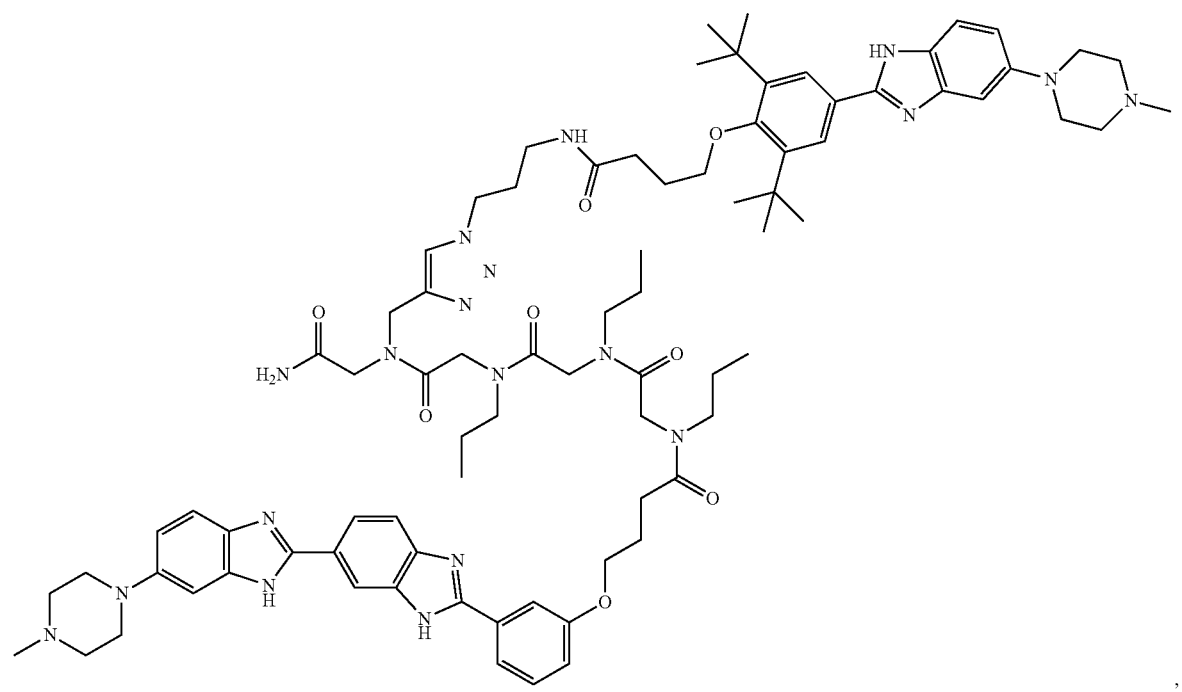

-continued

BSH-4-H

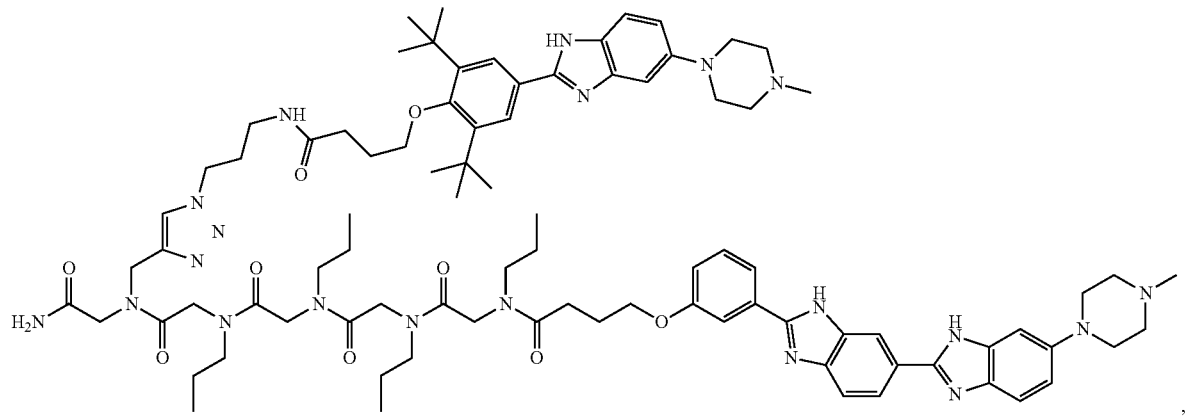

and any combination thereof, wherein n is any integer of 1 to 10.

Figure 6A:
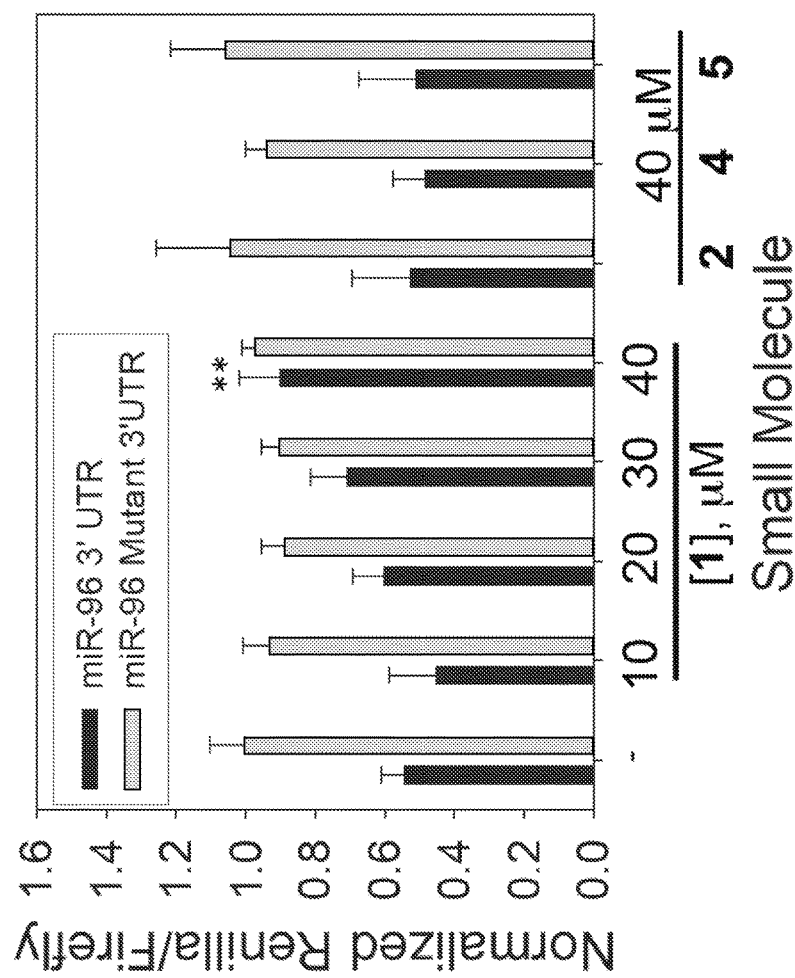
FIG. 6A-6E illustrate the effects of small molecules on the downstream targets of miR-96.

As illustrated herein, compounds described herein can increase apoptosis. For example, compounds 1, BSH-2-H and BSH-4-H induce apoptosis by modulation of the miR-96-FOXO1 regulation pathway in breast cancer cells (MCF7 or MDA MB 231 breast cancer cells). As shown in FIG. 6E, addition of compound 1 dramatically increases the percentage of TUNEL-positive MCF7 cells by at least 10-fold. As shown in FIG. 20, the BSH-4-H compound induces apoptosis in about 40% of breast cancer cells while the BSH-2-H compound induces apoptosis in about 75% of breast cancer cells.

In some embodiments, compounds identified by the methods described herein can increase apoptosis by at least 10%, or 20%, or 40%, or 50%, or 70%, or 75%, or 100%, or 150%, or 200%, or 300%, or 400%, or 500%, or 700%, or 1000%. Some compounds can increase apoptosis by at least 2-fold, or 3-fold, of 4-fold, or 5-fold, or 6-fold, or 7-fold, or 8-fold, or 9-fold, or by at least 10-fold.

The methods and compositions described herein can be used to treat a variety of cancers and tumors, for example, leukemia, sarcoma, osteosarcoma, lymphomas, melanoma, glioma, pheochromocytoma, hepatoma, ovarian cancer, skin cancer, testicular cancer, gastric cancer, pancreatic cancer, renal cancer, breast cancer, prostate cancer, colorectal cancer, cancer of head and neck, brain cancer, esophageal cancer, bladder cancer, adrenal cortical cancer, lung cancer, bronchus cancer, endometrial cancer, nasopharyngeal cancer, cervical or liver cancer, and cancer at an unknown primary site.

Compositions

The invention also relates to compositions containing one or more small molecules, including any small molecule identified by the methods described herein. The compositions of the invention can be pharmaceutical compositions. In some embodiments, the compositions can include a pharmaceutically acceptable carrier. By "pharmaceutically acceptable" it is meant a carrier, diluent, excipient, and/or salt that is compatible with the other ingredients of the formulation, and is not deleterious to the recipient thereof.

The small molecule(s) included in the compositions can be any of the compounds disclosed herein, as well as any compound identified by the methods described herein. Examples include any of the following compounds:

1

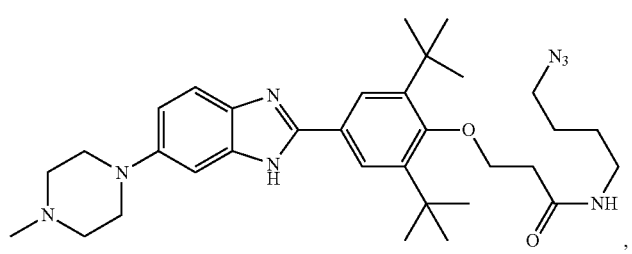

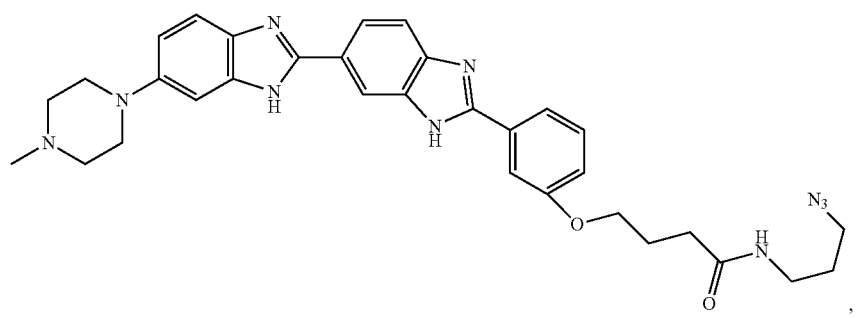
2
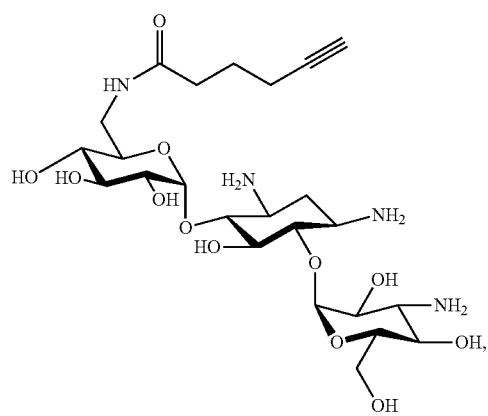
3
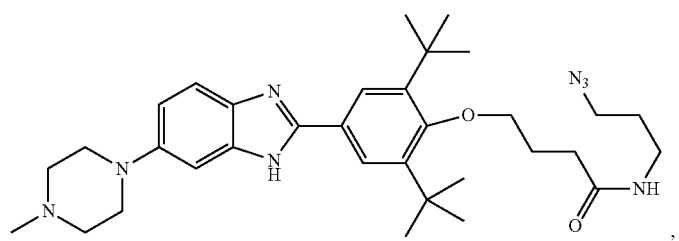
4
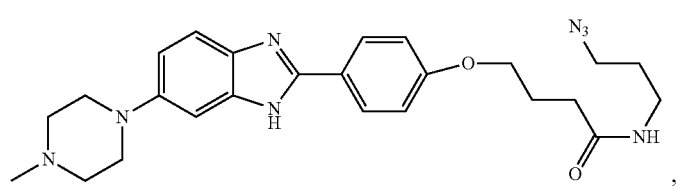
5

-continued
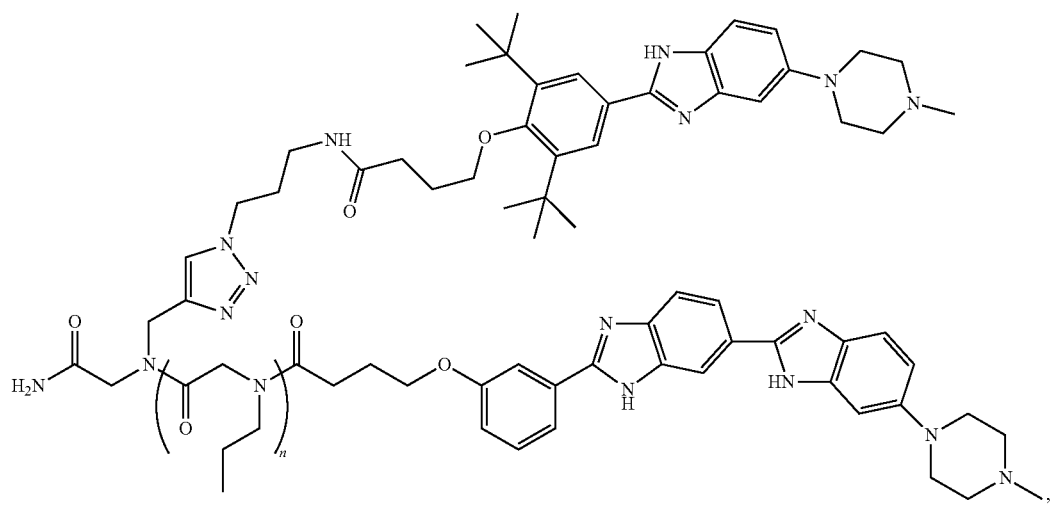
BSH-n-H
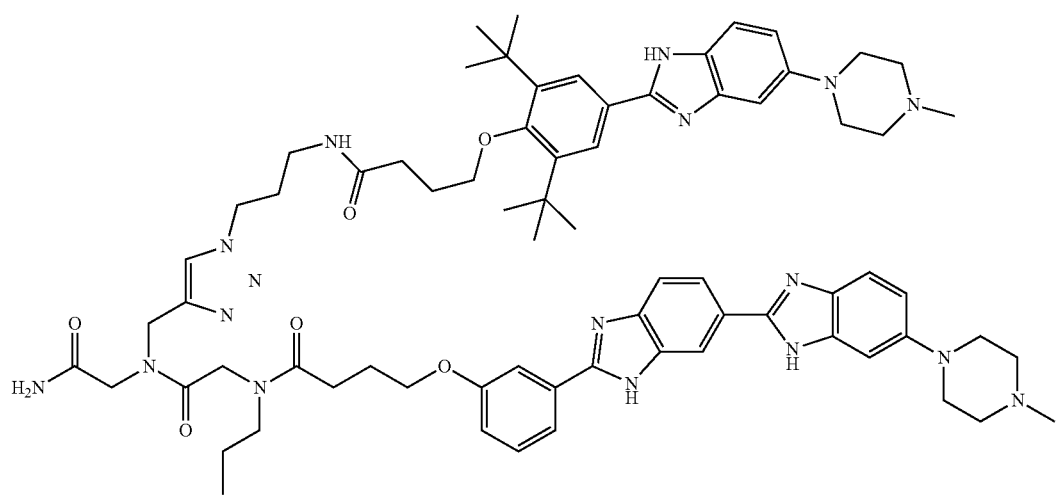
BSH-1-H
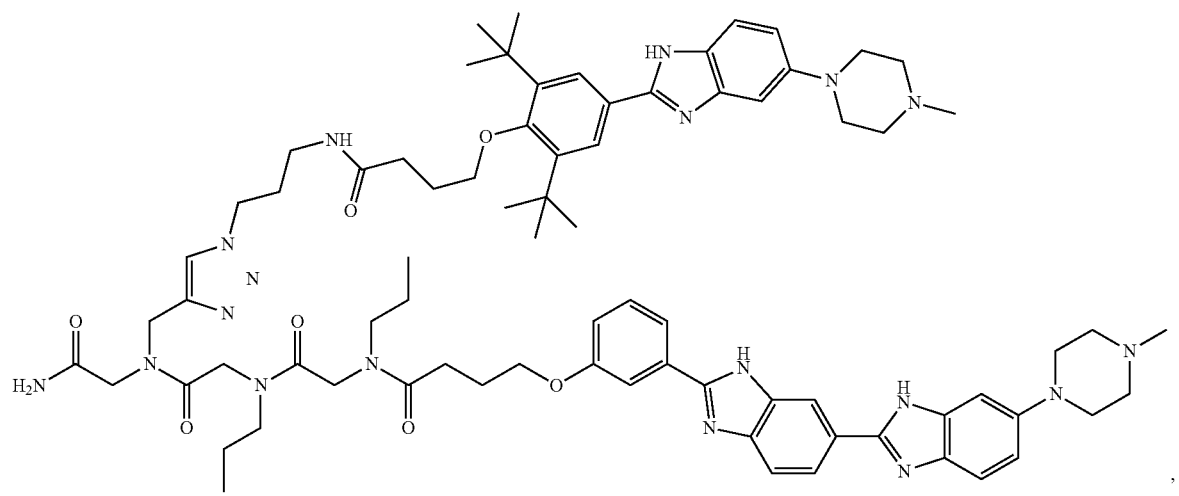
BSH-2-H

-continued

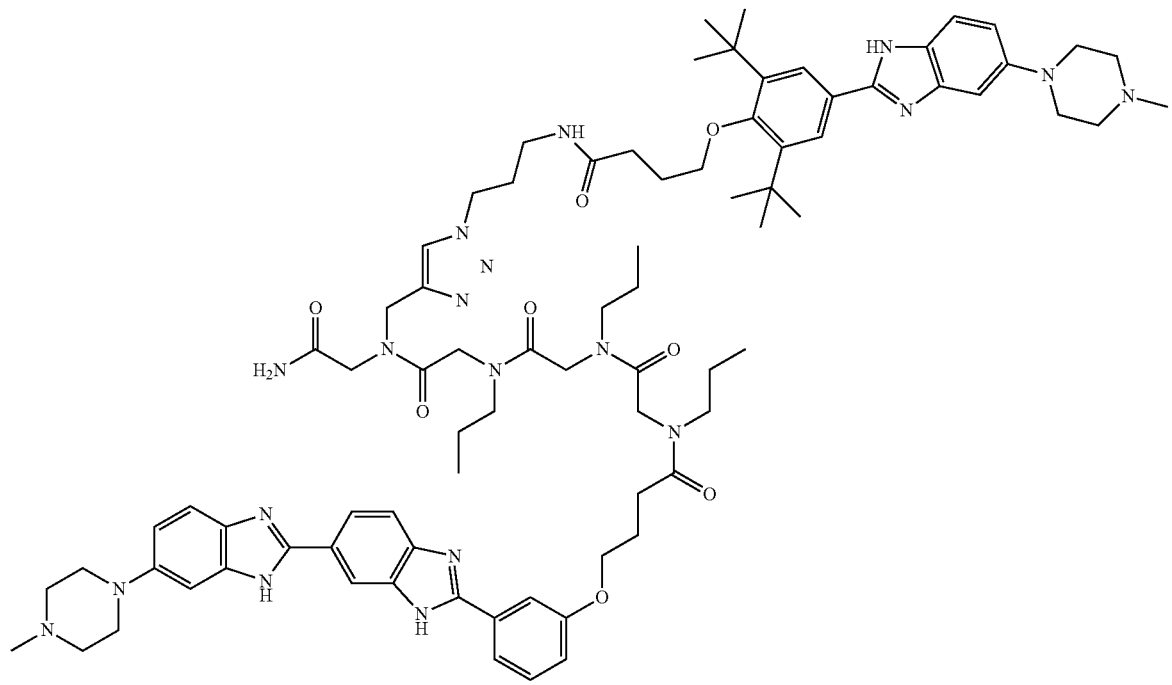

BSH-3-H

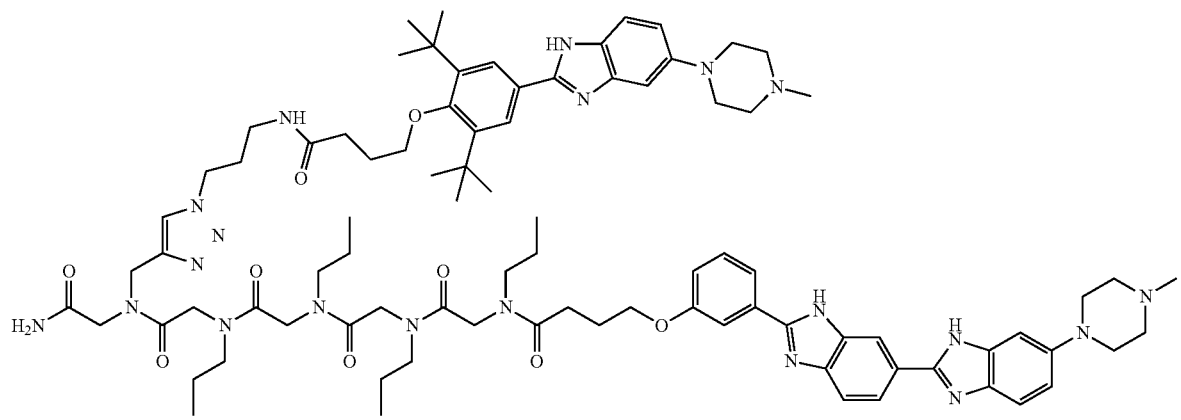

BSH-4-H and any combination thereof, where n is an integer of 1 to 10.

In some embodiments, the small molecules are administered in a "therapeutically effective amount." Such a therapeutically effective amount is an amount sufficient to obtain the desired physiological effect, e.g., treatment of a condition, disorder, disease and the like or reduction in symptoms of the condition, disorder, disease and the like. For example, the therapeutic agents can be administered to treat a condition, disorder, or disease such as cancer, viral infection, bacterial infection and/or microbial infection.

To achieve the desired effect(s), a small molecule or a combination thereof, may be administered as single or divided dosages. For example, one or more of the small molecules can be administered in dosages of at least about 0.001 mg/kg to about 500 to 750 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight, although other dosages may provide beneficial results. The amount administered will vary depending on various factors including, but not limited to, the molecule, polypeptide, antibody or nucleic acid chosen for administration, the disease, the weight, the physical condition, the health, and the age of the mammal. Such factors can be readily determined by the clinician employing animal models or other test systems that are available in the art.

Administration of the small molecules as therapeutic agents in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration of the small molecules and compositions of the invention may be essentially continuous over a preselected period of time or may be in a series of spaced doses. Both local and systemic administration is contemplated.

To prepare the composition, the small molecules (and other agents if desired) are synthesized or otherwise obtained, purified as necessary or desired. These small molecules (and other agents if desired) can be suspended in a pharmaceutically acceptable carrier and/or lyophilized or otherwise stabilized. These small molecules (and selected agents if any) can be adjusted to an appropriate concentration, and optionally combined with other agents. The absolute weight of a given small molecule (and other optional agents) included in a unit dose can vary widely. For example, about 0.01 to about 2 g, or about 0.1 to about 500 mg, of at least one small molecule can be administered. Alternatively, the unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

Daily doses of the small molecules of the invention can vary as well. Such daily doses can range, for example, from about 0.1 g/day to about 50 g/day, from about 0.1 g/day to about 25 g/day, from about 0.1 g/day to about 12 g/day, from about 0.5 g/day to about 8 g/day, from about 0.5 g/day to about 4 g/day, and from about 0.5 g/day to about 2 g/day.

It will be appreciated that the amount of small molecules for use in treatment will vary not only with the particular carrier selected but also with the route of administration, the nature of the condition being treated and the age and condition of the patient. Ultimately the attendant health care provider may determine proper dosage. In addition, a pharmaceutical composition may be formulated as a single unit dosage form.

Thus, one or more suitable unit dosage forms comprising the small molecules can be administered by a variety of routes including parenteral (including subcutaneous, intravenous, intramuscular and intraperitoneal), oral, rectal, dermal, transdermal, intrathoracic, intrapulmonary and intranasal (respiratory) routes. The small molecules can also be formulated for sustained release (for example, using microencapsulation, see WO 94/07529, and U.S. Pat. No. 4,962,091). The formulations may, where appropriate, be conveniently presented in discrete unit dosage forms and may be prepared by any of the methods well known to the pharmaceutical arts. Such methods may include the step of mixing the therapeutic agent with liquid carriers, solid matrices, semi-solid carriers, finely divided solid carriers or combinations thereof, and then, if necessary, introducing or shaping the product into the desired delivery system.

The compositions of the invention may be prepared in many forms that include aqueous solutions, suspensions, tablets, hard or soft gelatin capsules, and liposomes and other slow-release formulations, such as shaped polymeric gels. However, administration of small molecules can also involve parenteral or local administration in an aqueous solution or sustained release vehicle.

Liquid pharmaceutical compositions may be in the form of, for example, aqueous or oily suspensions, solutions, emulsions, syrups or elixirs, dry powders for constitution with water or other suitable vehicle before use. Such liquid pharmaceutical compositions may contain conventional additives such as suspending agents, emulsifying agents, non-aqueous vehicles (which may include edible oils), or preservatives.

A compound or small molecule can be formulated for parenteral administration (e.g., by injection, for example, bolus injection or continuous infusion) and may be presented in unit dosage form in ampoules, prefilled syringes, small volume infusion containers or multi-dose containers with an added preservative. The pharmaceutical compositions may take such forms as suspensions, solutions, or emulsions in oily or aqueous vehicles, and may contain formulatory agents such as suspending, stabilizing and/or dispersing agents. Suitable carriers include saline solution and other materials commonly used in the art.

The compositions can also contain other ingredients such as chemotherapeutic agents, anti-viral agents, antibacterial agents, antimicrobial agents and/or preservatives. Examples of additional therapeutic agents that may be used include, but are not limited to: alkylating agents, such as nitrogen mustards, alkyl sulfonates, nitro soureas, ethylenimines, and triazenes; antimetabolites, such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids, estrogens/antiestrogens, androgens/antiandrogens, progestins, and luteinizing hormone-releasing hormone anatagonists, octreotide acetate; microtubule-disruptor agents, such as ecteinascidins or their analogs and derivatives; microtubule-stabilizing agents such as paclitaxel (Taxol®), docetaxel (Taxotere®), and epothilones A-F or their analogs or derivatives; plant-derived products, such as *vinca* alkaloids, epipodophyllotoxins, taxanes; and topoisomerase inhibitors; prenyl-protein transferase inhibitors; and miscellaneous agents such as, hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators, and monoclonal antibodies. The compounds of the invention may also be used in conjunction with radiation therapy.

Definitions

The terms "small molecule" and "compound" have the same meaning and are used interchangeably.

"Nucleic acid", as used herein, is meant to refer to RNA and DNA. "RNA", as used herein, is meant to refer to ribonucleic acid molecules and oligomers. "DNA", as used herein, is meant to refer to deoxyribonucleic acid molecules and oligomers.

"RNA motif", as used herein, is meant to refer to a targetable internal loop, hairpin loop, bulge, or other targetable nucleic acid structural motifs, for example, as described in Batey et al., "Tertiary Motifs in RNA Structure and Folding," *Angew. Chem. Int. Ed.,* 38:2326-2343 (1999), which is hereby incorporated by reference. Examples of RNA motifs include symmetric internal loops, asymmetric internal loops, 1×1 internal loops, 1×2 internal loops, 1×3 internal loops, 2×2 internal loops, 2×3 internal loops, 2×4 internal loops, 3×3 internal loops, 3×4 internal loops, 4×4 internal loops, 4×5 internal loops, 5×5 internal loops, 1 base bulges, 2 base bulges, 3 base bulges, 4 base bulges, 5 base bulges, 4 base hairpin loops, 5 base hairpin loops, 6 base hairpin loops, 7 base hairpin loops, 8 base hairpin loops, 9 base hairpin loops, 10 base hairpin loops, multibranch loops, pseudoknots, etc. RNA motifs have known structures.

"Interacts", as used herein, is mean to refer to binding or other stabilized association between a small molecule and an RNA motif. The association can be thermodynamically stabilized or kinetically stabilized or both, and the interaction can be the result of covalent bonding, hydrogen bonding, van der Waals interactions, electrostatic interactions, or combinations of these and/or other types of interactions.

The following non-limiting Examples describe some of the experiments performed in developing and validating aspects of the invention.

EXAMPLE 1

Materials and Methods

This Example describes some of the materials and methods used in developing the invention.

StARTS Analysis

The inventors have previously developed a selection-based strategy referred to as Two-Dimensional Combinatorial Screening (2DCS; Childs-Disney et al., *ACS Chem. Biol.* 2, 745-754 (2007); Disney et al., *J. Am. Chem. Soc.* 130, 11185-11194 (2008)) as well as a method to statistically analyze selection data called Structure-Activity Relationships Through Sequencing (StARTS) to identify and annotate (score) RNA motif-small molecule interactions (Velagapudi et al., *Angew. Chem. Int. Ed. Engl.* 49, 3816-3818 (2010); Velagapudi et al., *J. Am. Chem. Soc.* 133, 10111-10118 (2011), the contents of which are specifically incorporated herein by reference in their entireties).

For 2DCS, a small molecule library is conjugated onto an agarose microarray surface. The microarray is then probed for binding to a library of small RNA motifs likely to be found as components of larger cellular RNAs, for example, the 3×3 ILL RNA motif shown in FIG. 1. Incubation is completed in the presence of competitor oligonucleotides such as the C2-C8 oligonucleotides (FIG. 1) to ensure that small molecules bind to the randomized region (the region with two series of 'N' nucleotides in the 3×3 ILL RNA motif shown in FIG. 1), and not regions common to all library members. (See, Childs-Disney et al., *ACS Chem. Biol.* 2, 745-754 (2007); Disney et al., J. Am. Chem. Soc. 130, 11185-11194 (2008), the contents of which are specifically incorporated herein by reference in their entireties.) FIG. 2 shows the randomized three-nucleotide (N) sequences that can be in the 3×3 ILL RNA motif shown in FIG. 1. Bound RNAs are harvested, amplified, and sequenced. Sequences of selected RNAs are analyzed via StARTS.

StARTS is a statistical approach that identifies features in RNA motifs that positively and negatively contribute to binding (Velagapudi et al., *Angew. Chem. Int. Ed. Engl.* 49, 3816-3818 (2010); Velagapudi et al., *J. Am. Chem. Soc.* 133, 10111-10118 (2011). StARTS predicts the affinities and selectivities of RNA-small molecule interactions by comparing the rate of occurrence of a feature in selected RNA motifs (a guanine adjacent to an adenine, for example) to its rate of occurrence in the entire RNA library. The confidence that a selected feature did not occur randomly is assigned a Z-score and a corresponding two-tailed p-value (Velagapudi et at, *Angew. Chem. Int. Ed. Engl.* 49, 3816-3818 (2010); Velagapudi et al., *J. Am. Chem. Soc.* 133, 10111-10118 (2011). Only features that are statistically significant ($p \leq 0.05$ or $\geq 95\%$ confidence) are considered. This analysis identifies features that contribute positively (positive Z-score) and negatively (negative Z-score) to binding, allowing prediction of which RNAs bind and which RNAs do not. Each RNA motif has many statistically significant features. Therefore, the Z-scores for each feature are summed to afford a $\Sigma Z$-score (FIG. 2).

By combining statistical parameters from StARTS with experimentally determined binding affinities, the affinity and selectivity of every RNA motif displayed in a library can be predicted. The selectivity of a selected RNA for different small molecules can be predicted by comparing its $\Sigma Z$-score for one small molecule to its $\Sigma Z$-score for another. For example, an RNA that has a large $\Sigma Z$-score for small molecule A and a small $\Sigma Z$-score for small molecule B is selective for small molecule A. Fitness Scores are normalized to the RNA motif with the highest $\Sigma Z$-score.

A database of RNA motif-small molecule interactions and their corresponding StARTS analyses were used to identify lead small molecules that may modulate the function of microRNAs. The current version of the database of RNA motif-small molecule interactions consists of 794 RNA motifs and 11 small molecules.

All human precursor miRNAs (1,048) were downloaded from miRBase (v. 16) (Griffiths-Jones et al., *Nucleic Acids Res.* 34, D140-144 (2006); Griffiths-Jones et al., *Nucleic Acids Res.* 36, D154-158 (2008)), and their secondary structures were predicted using the free energy minimization program RNAstructure (Mathews et al., *Proc. Natl. Acad. Sci. U.S.A.* 101, 7287-7292 (2004)). Note that secondary structure prediction is considered structure determination for microRNAs (Ambros et al., *RNA* 9, 277-279 (2003)). Inforna parsed the secondary structural motifs and compared them to the database of RNA motif-small molecule interactions. A total of 1,668 RNA motif-small molecule hits were obtained. Of those hits, 26 motifs are internal loops located in either Drosha or Dicer processing sites of miRNAs that are implicated in disease and that have been validated for modulation of the disease by oligonucleotides. Only RNA motifs that are in processing sites (by Drosha or Dicer) of miRNAs associated with diseases are listed. Inforna provided an output of the targetable motifs in each RNA, and the corresponding small molecules that bind those RNAs. A subset of the results is provided in Table 1, where column 1 represents the serial number of the microRNA hits (1-22), column 4 (labeled "Small") identifies the small molecule by number (1-9), column 6 is the Pubmed reference for the microRNA disease association, column 7 (labeled "Up or Down") shows whether the microRNA is up-regulated or down-regulated in the disease indicated in column 5. The numbers "4" and "6" in the last two rows of Table 1 indicate that are two small molecules "4" and "6" that target pre-miR-885.

TABLE 1

Hits obtained from searching the RNA motifs in miRBase (v. 16) for overlap with the database of RNA motif-small molecule interactions using inforna.

| microRNA | Loop | Small | Disease | PubMed ID | Up or Down |
|---|---|---|---|---|---|
| 1 pre-miR-34c | 5'GCU/<br>3'CCA | 6 | pancreatic cancer | 19714243 | Down |
|  |  |  | Parkinson's disease | 21558425 | Down |

TABLE 1-continued

Hits obtained from searching the RNA motifs in miRBase (v. 16) for overlap with the database of RNA motif-small molecule interactions using inforna.

| microRNA | Loop | Small | Disease | PubMed ID | Up or Down |
|---|---|---|---|---|---|
| | | | Alzheimer's disease | 21946562 | Down |
| | | | melanoma | 22102694 | Down |
| | | | breast cancer | 22074923 | Down |
| 2 pre-miR-92a-2 | 5'CCU/ 3'GUG | 6 | lymphoma | 21383985 | Down |
| | | | hepatocellular carcinoma | 16331254 | Up |
| | | | glioblastoma | 22895567 | Up |
| | | | colorectal neoplasm | 21826996 | Up |
| 3 pre-miR-96 | 5'UUU/ 3'AUA | 1 | breast neoplasm | 19574223 | Up |
| | | | breast neoplasm | 21203424 | Up |
| | | | urinary bladder neoplasm | 21166959 | Up |
| | | | hepatocellular neoplasm | 22160187 | Up |
| | | | prostatic neoplasm | 22045813 | Up |
| | | | colorectal neoplasm | 22844381 | Up |
| 4 pre-miR-130b | 5'UAC/ 3'ACG | 6 | stomach neoplasms | 20176475 | Up |
| | | | chronic myeloid leukemia | 21638198 | Up |
| 5 pre-miR-181c | 5'GAG/ 3'C_C (bulge) | 9 | acute myeloid leukemia | 22251480 | Up |
| 6 pre-miR-182 | 5'UUUU/ 3'AUCA | 3 | melanoma | 19188590 | Up |
| | | | prostatic neoplasms | 19267923 | Up |
| | | | glioma | 20406893 | Up |
| | | | breast neoplasm | 19574223 | Up |
| | | | acute leukemia | 20227111 | Up |
| | | | endometrial neoplasm | 20028871 | Up |
| | | | lung cancer | 21904633 | Up |
| | | | prostatic neoplasm | 22045813 | Up |
| | | | ovarian neoplasm | 22322863 | Up |

TABLE 1-continued

Hits obtained from searching the RNA motifs in miRBase (v. 16) for overlap with the database of RNA motif-small molecule interactions using inforna.

| microRNA | Loop | Small | Disease | PubMed ID | Up or Down |
|---|---|---|---|---|---|
| 7 pre-miR-210 | 5'ACU/<br>3'UCA | 2 | ischemic heart disease | 20837903 | Up |
| | | 7 | renal carcinoma | 21465485 | Up |
| 8 pre-miR-301a | 5'UAC/<br>3'ACG | 6 | pancreatic cancer | 22628193 | Up |
| | | | colorectal cancer | 23393589 | Up |
| 9 pre-miR-301b | 5'UCU/<br>3'AAA | 1 | breast cancer | 21393507 | Up |
| 10 pre-miR-320c | 5'UCU/<br>3'AAA | 1 | breast cancer | 21393507 | Up |
| 11 pre-miR-320d-1 | 5'UCU/<br>3'AAA | 1 | breast cancer | 21393507 | Up |
| | | | Kaposi's sarcoma | 23418466 | Down |
| 12 pre-miR-378 | 5'GGC/<br>3'CGG | 8 | stomach neoplasms | 19175831 | Down |
| | | | leukemia | 19022373 | Down |
| | | | melanoma | 20529253 | Down |
| | | | neoplasms (Myc regulator) | 21242960 | Up/Down |
| | | | non-small cell lung cancer | 22052152 | Up |
| | | | colorectal neoplasm | 22469014 | Down |
| 13 pre-miR-433 | 5'UUA/<br>3'ACU | 1 | Parkinson's disease | 18252210 | Up |
| 14 pre-miR-449c | 5'GUA/<br>3'UCU | 1 | stomach neoplasm | 21418558 | Down |
| 15 pre-miR-515-1 | 5'UUC/<br>3'GCG | 7 | squamous cell neoplasm | 21244772 | Up |
| 16 pre-miR-515-2 | 5'UCA/<br>3'AUU | 4 | squamous cell neoplasm | 21244772 | Up |
| | | 7 | stomach neoplasm | 22112324 | Up |
| 17 pre-miR-517c | 5'CCC/<br>3'GUG | 6 | hepatocellular carcinoma | 22027761 | Up |
| | | 9 | | | |
| 18 pre-miR-518e | 5'CCC/<br>3'GUG | 9 | melanoma | 20529253 | Down |
| 19 pre-miR-519d | 5'CCC/<br>3'GUG | 9 | breast neoplasm | 20331864 | Up |
| | | | hepatocellular neoplasm | 21524841 | Down |
| | | | hepatocellular neoplasm | 22262409 | Up |

TABLE 1-continued

Hits obtained from searching the RNA motifs in miRBase (v. 16) for overlap with the database of RNA motif-small molecule interactions using inforna.

| | microRNA | Loop | Small | Disease | PubMed ID | Up or Down |
|---|---|---|---|---|---|---|
| 20 | pre-miR-525 | 5'CUC/<br>3'GCG | 9 | hepatocellular carcinoma | 22362728 | Up |
| 21 | pre-miR-661 | 5'AGG/<br>3'UGC | 6 | breast neoplasm | 20543867 | Up |
| | | | | stomach neoplasm | 22112324 | Down |
| 22 | pre-miR-885 | 5'UCU/<br>3'AUA | 4 | squamous cell neoplasm | 22071691 | Down |
| | | | 6 | | | |

Figure 3A:
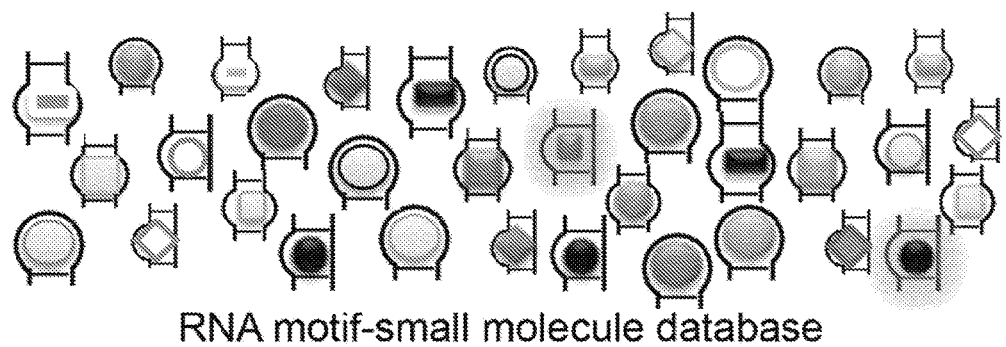
FIG. 3A-3E illustrates the inforna approach to design small molecules that target RNA as applied to human microRNA (miRNA) precursors.
Figure 3B:
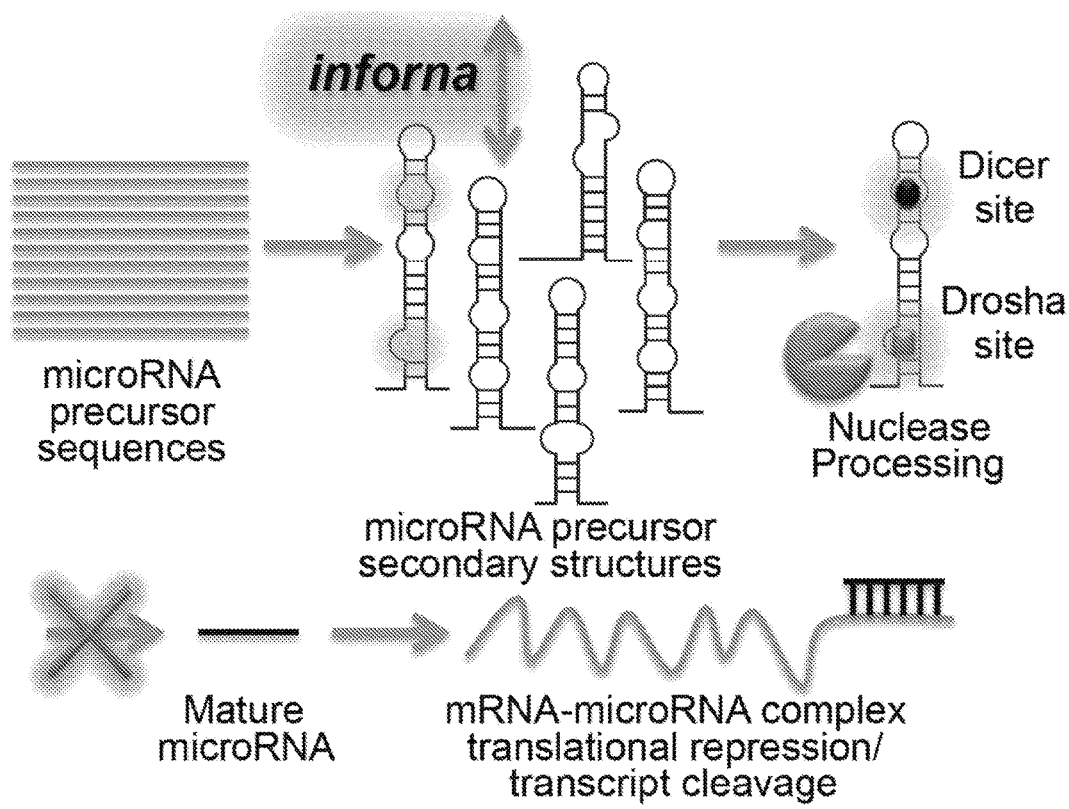
Figure 3C:
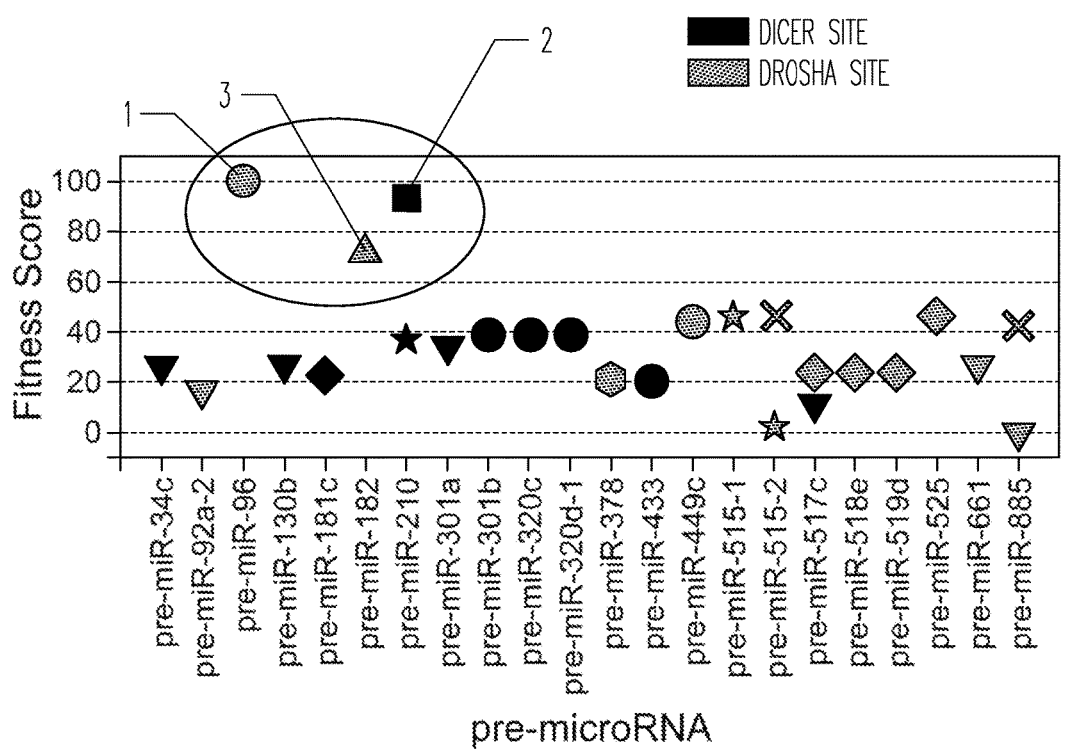
Figure 3D:
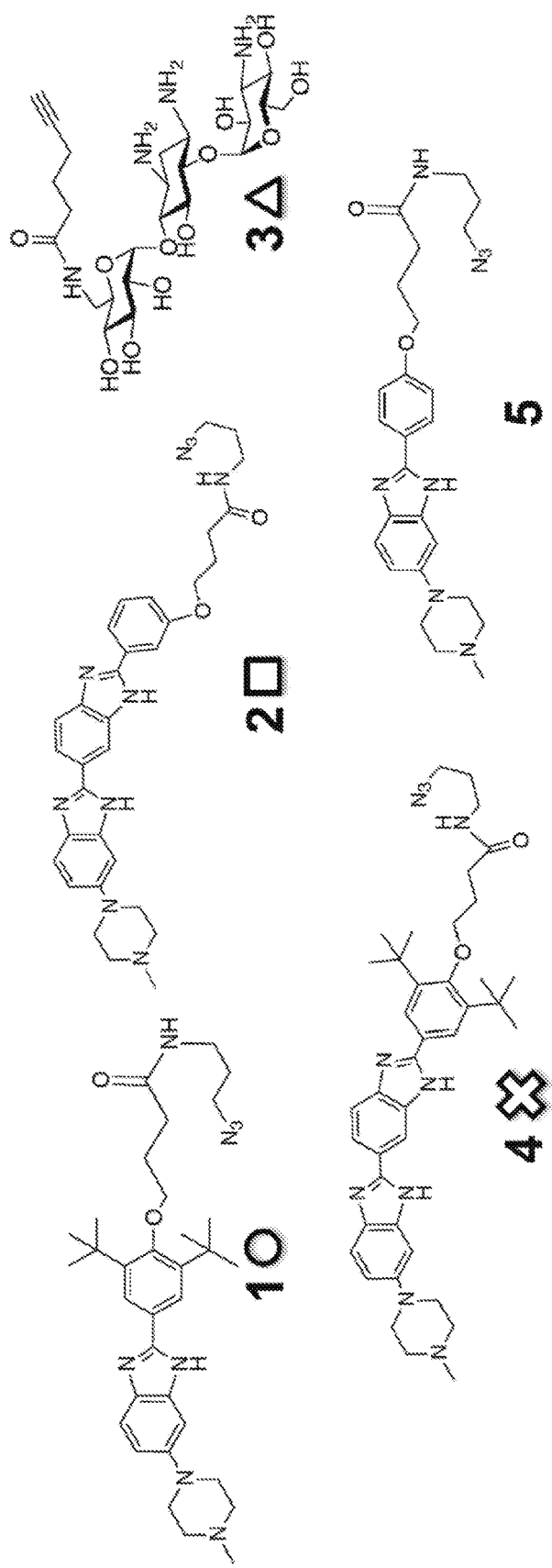
Figure 3E:
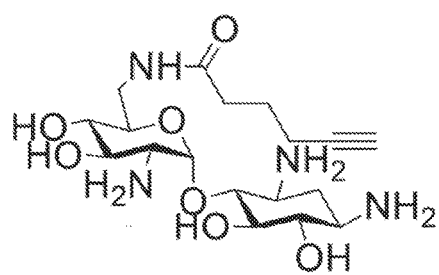
Figure 3E:
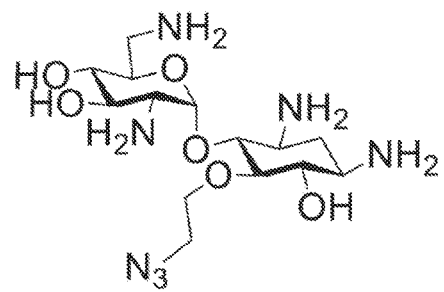
Figure 3E:
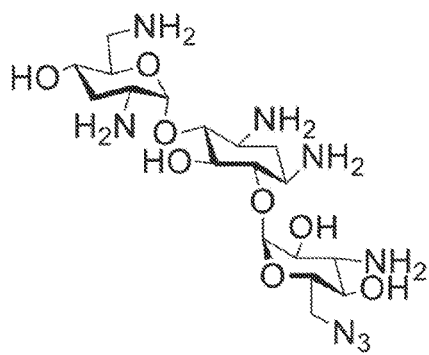
Figure 3E:
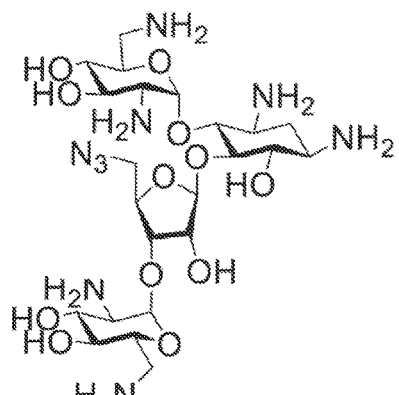

StARTS analyses were used to determine the fitness of a small molecule for binding the RNA target of interest identified as output by inforna (Table 1; FIG. 3C-3D). Based on these analyses, three pre-microRNA targets were selected: pre-microRNA-96 (binds 1), pre-microRNA-210 (binds 2), and pre-microRNA-182 (binds 3). All other potential pre-microRNA targets have low $\Sigma$Z-scores indicating that they bind weakly to the corresponding small molecule (FIGS. 3C and 3E). Thus, small molecules 6-9 would likely bind more tightly to other cellular RNAs and would not be specific for the microRNA motifs to which they are paired in Table 1.

Compound 1 was predicted by inforna to bind other pre-microRNAs, including pre-microRNA-301b, 320c, 320d-1, 433 and 449c, which may indicate that the compound is non-selective. However, StARTS analysis predicts that 1 binds the targetable loop in pre-microRNA-449c with low affinity (FIG. 4A-4B), which was confirmed by measuring affinity in solution FIG. 4D-4I). Taken together with in vivo data shown in FIGS. 5-7, StARTS accurately predicts RNA targets that will or will not bind and the potential selectivity of a small molecule.

A number of compounds were evaluated as described herein including, for example, compounds 1, 2, 3, 4 and 5 shown below:

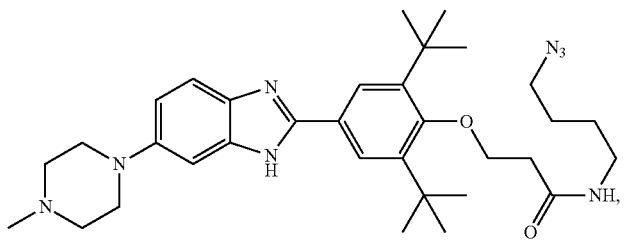

1

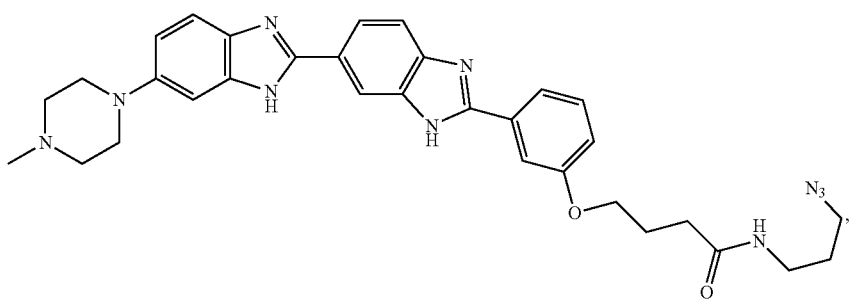

2

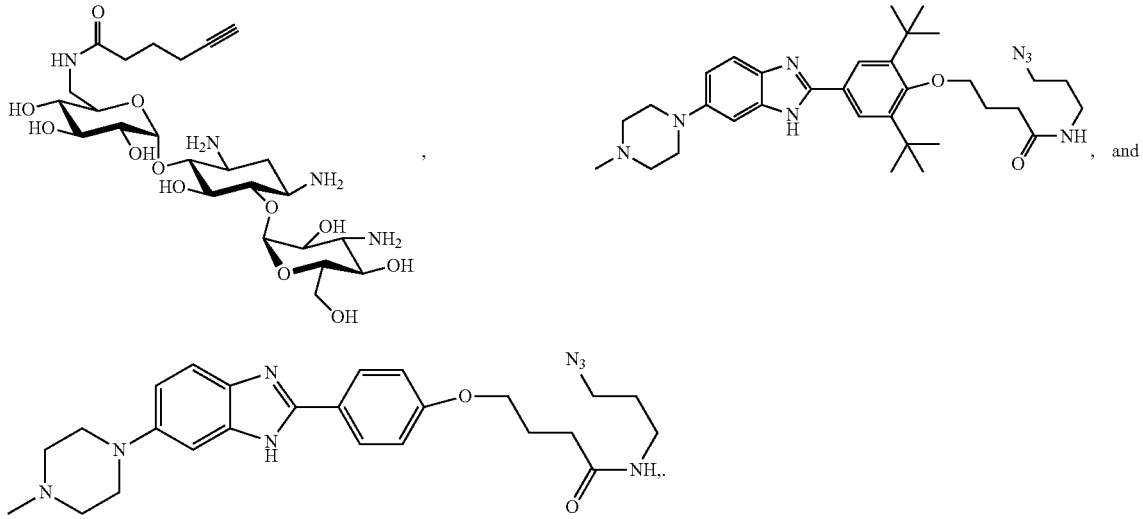

While compounds 1, 2, 4 and 5 share some structural features, the structure of compound 3 is quite different from the others shown above.

Figure 4A:
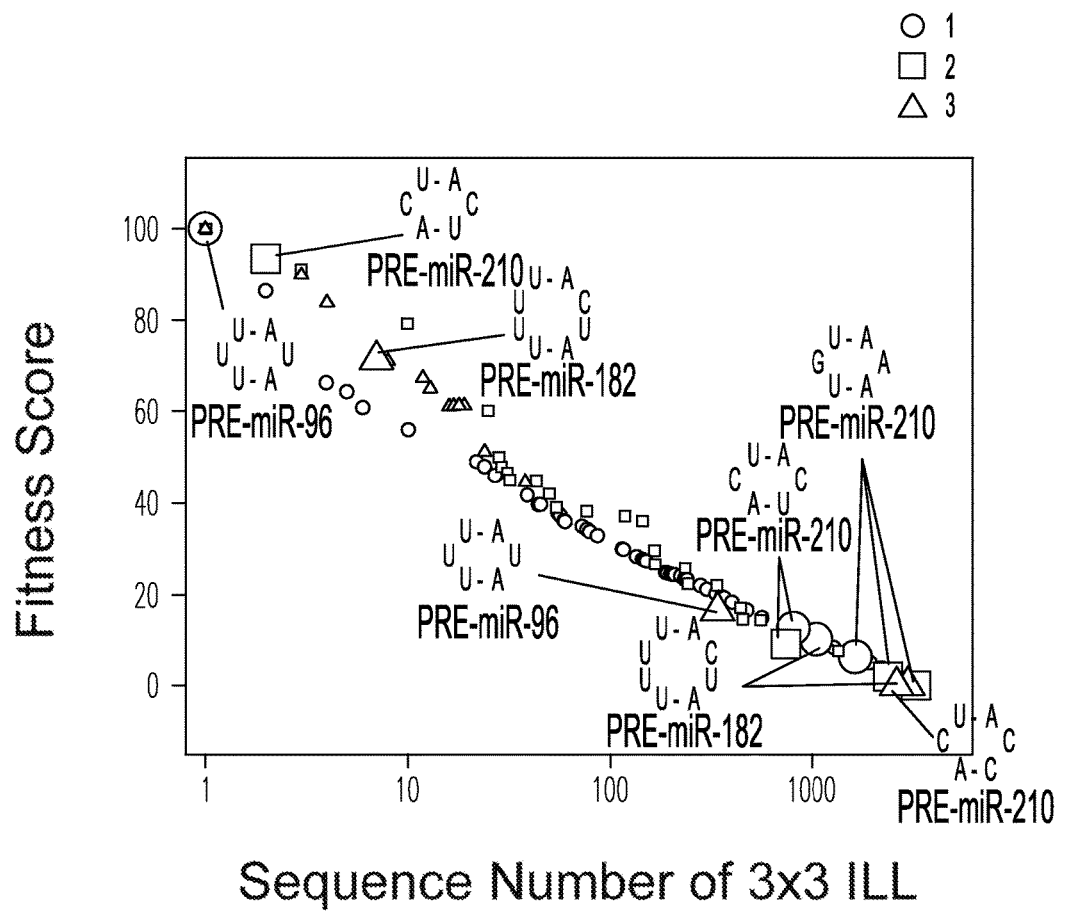
FIG. 4A-4J illustrates StARTS analysis for compounds and miRNA targets by showing fitness plots, RNA secondary structures and representative binding curves.
Figure 4B:
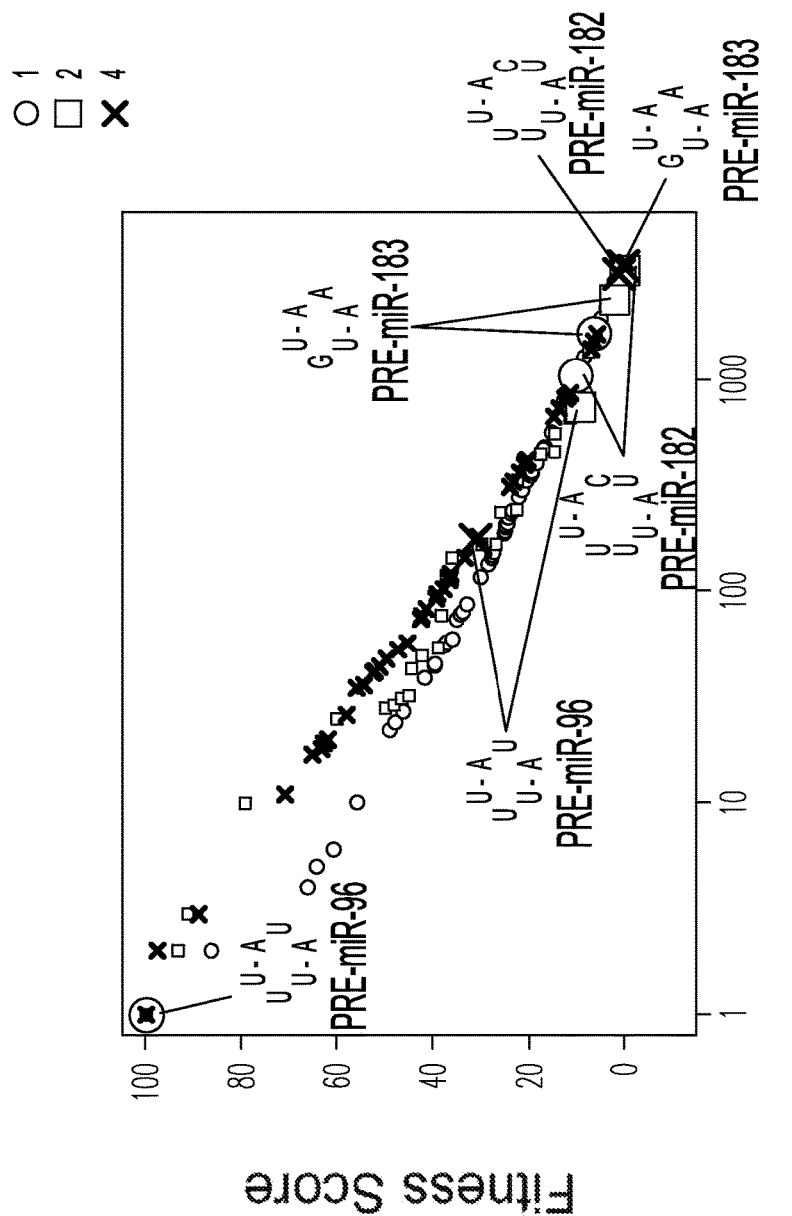
Figure 4C:
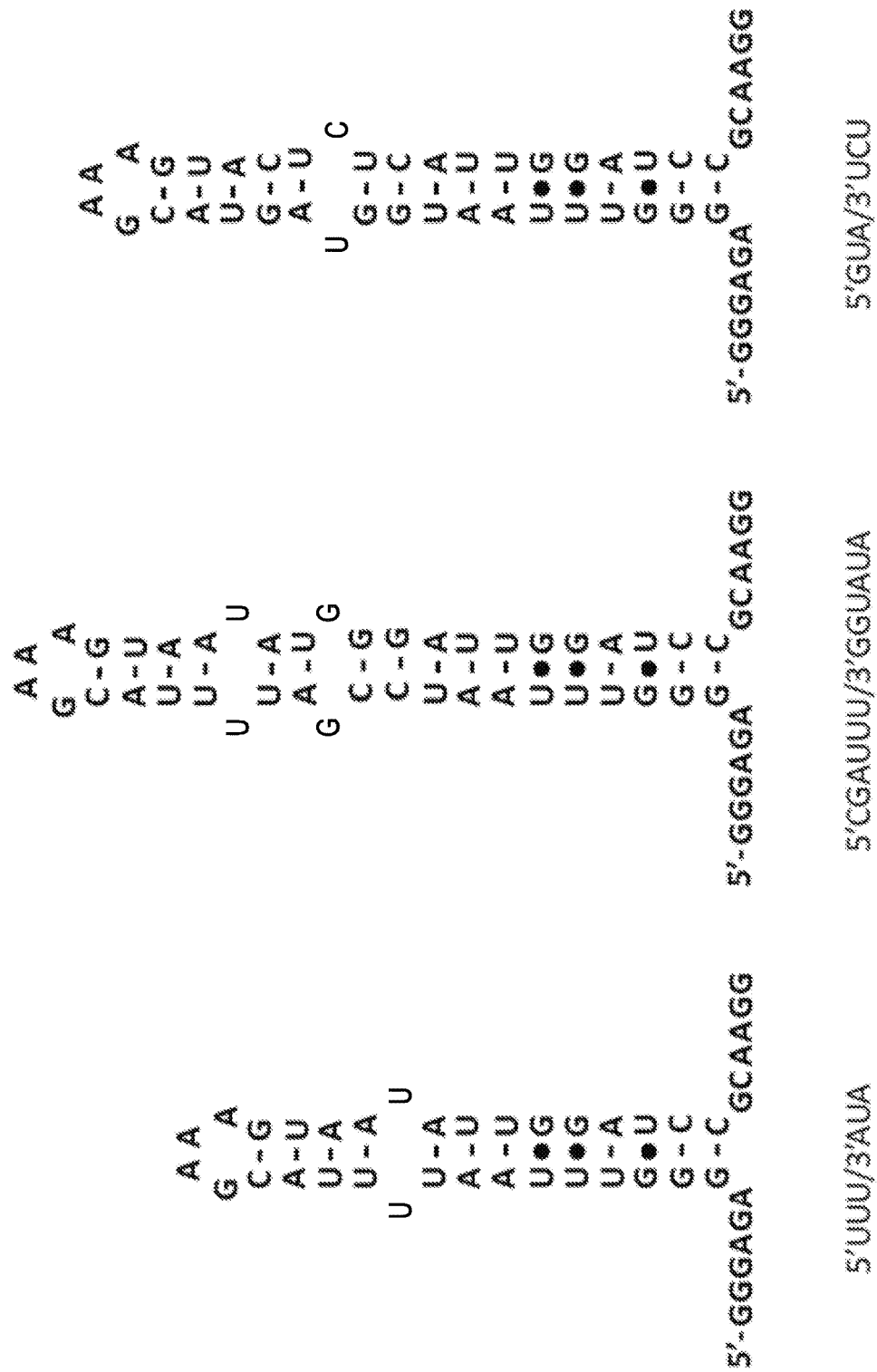
Figure 4D:
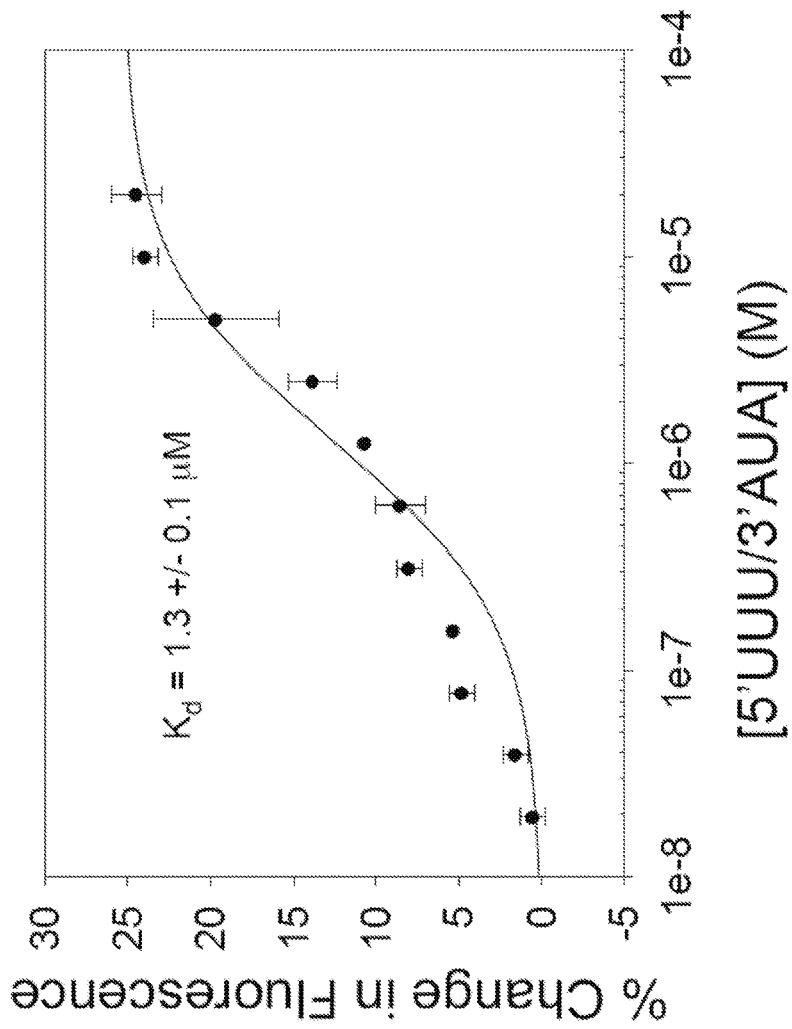
Figure 4E:
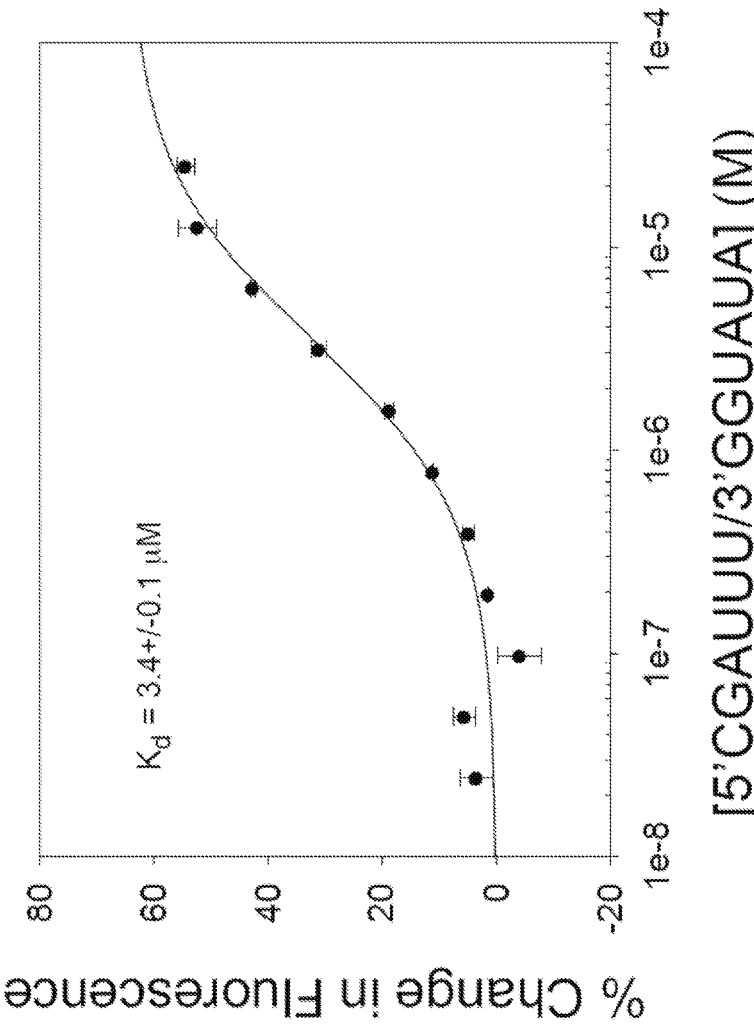
Figure 4F:
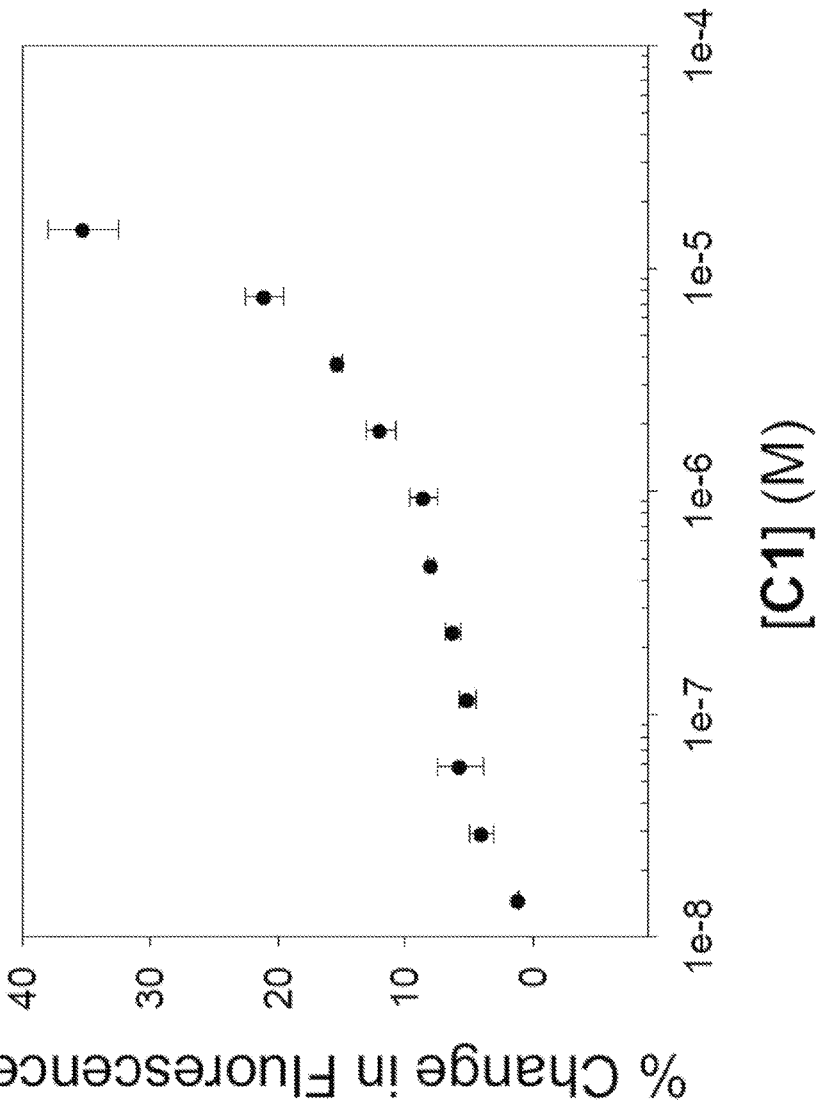
Figure 4G:
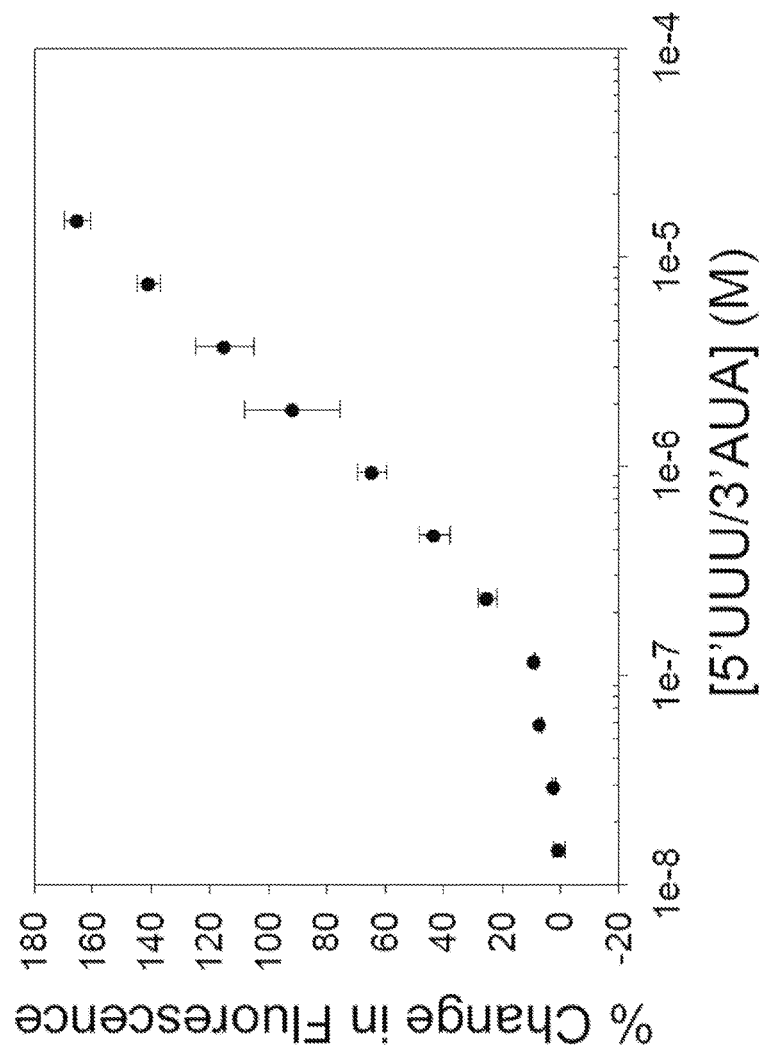
Figure 4H:
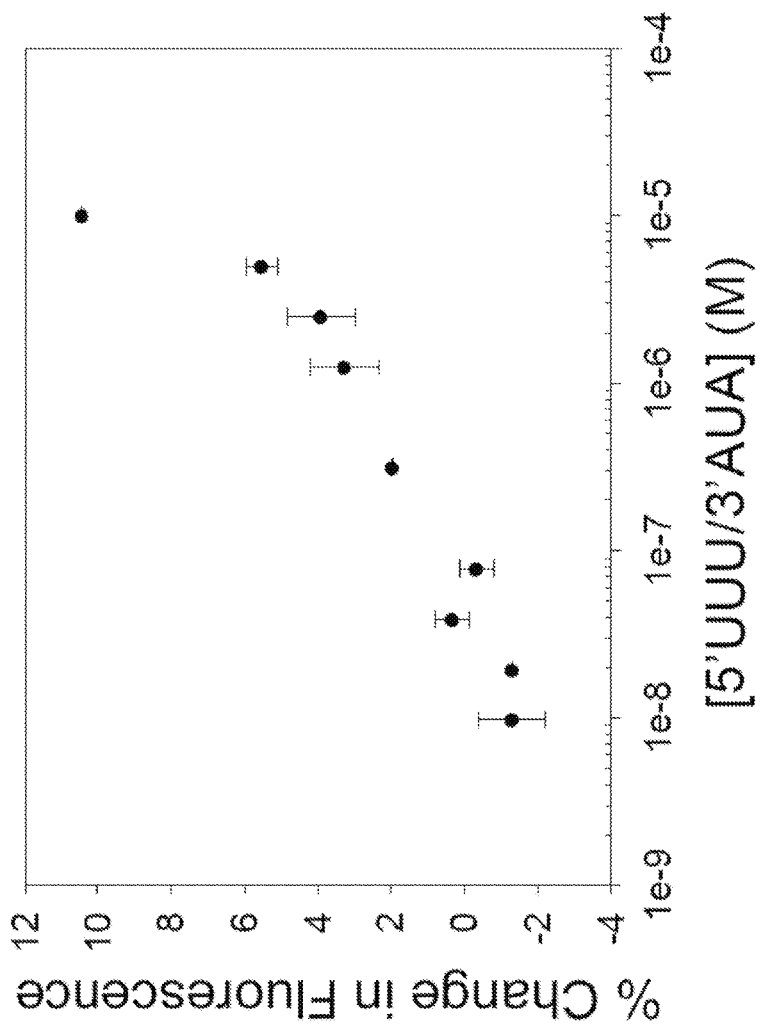
Figure 4I:
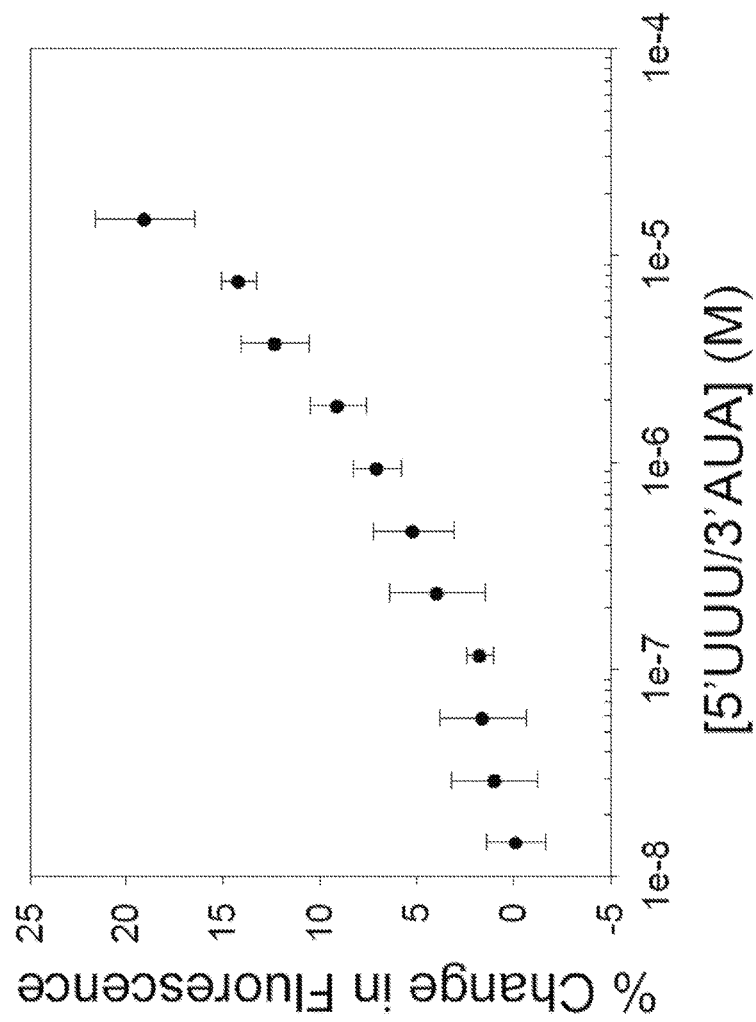

2DCS selection was completed for three compounds that are chemically similar to compound 1: compounds 2, 4, and 5 (Velagapudi et al., *J. Am. Chem. Soc.* 133, 10111-10118 (2011). Visual inspection suggests that 2 and 4 might bind RNA with higher affinity than 1 because of their larger surface areas that could stack on RNA bases and because of the presence of additional hydrogen bond donors and acceptors. However, StARTS analysis predicts that 2 and 4 bind weakly to the targetable loop in the miR-96 precursor, which is in excellent agreement with the in vivo data (FIG. 4A-4B). (Note that a 2DCS selection was attempted for compound 5; however, RNAs could not be selected due to its weak affinity (id.).)

DNA Templates and PCR Amplification

The RNA motifs (internal loops) used in these studies were embedded into a hairpin cassette, C1 (FIG. 1). The corresponding DNA templates (purchased from Integrated DNA Technologies (IDT) and used without further purification) were PCR amplified in 1×PCR Buffer (10 mM Tris, pH 9.0, 50 mM KCl, and 0.1% (v/v) Triton X-100), 2 µM forward primer: 5'-GGCCGGATCCTAATACGACTCAC-TATAGGGAGAGGGTTTAAT (SEQ ID NO:18), 2 µM reverse primer: 5'-CCTTGCGGATCCAAT (SEQ ID NO:19), 4.25 mM MgCl$_2$, 330 µM dNTPs, and 1 µL of Taq DNA polymerase in a 50 µL reaction. The cycling conditions used for PCR were 95° C. for 30 s, 50° C. for 30 s, and 72° C. for 1 min.

The miR-96 precursor used in nuclease protection assays was modified to contain a 5'-GGG overhang to facilitate transcription using T7 RNA polymerase, or GGG-pre-microRNA-96. There was no change in the lowest free energy secondary structure predicted by RNAstructure (Mathews et al., *Proc. Natl. Acad. Sci. U.S.A* 101, 7287-7292 (2004)), and nuclease protection assays confirm that the predicted structure is adopted in solution (FIG. 9). The DNA template for GGG-pre-microRNA-96 was PCR amplified as described above except the primers were: 5'-GGCCGGATC-CTAATACGACTCACTATA GGGTGGCCGATTTTGGC (SEQ ID NO:20, forward) and 5'-TTTCCC ATATTGGCA (SEQ ID NO:21, reverse) and the cycling conditions were 95° C. for 30 s, 55° C. for 30 s, and 72° C. for 1 min. The DNA templates used for PCR to produce double stranded DNAs suitable for transcription were:

C1:
(SEQ ID NO: 1)
5'-GGGAGAGGGTTTAATTACGAAAGTAATTGGATCCGCAAGG;

5'UUU/3'AUA:
(SEQ ID NO: 8)
5'-GGGAGAGGGTTTAATTTTACGAAAGTAATATTGGATCCGCAAGG;

5'CGAUUU/3'GGUAUA:
(SEQ ID NO: 9)
5'-GGGAGAGGGTTTAATCCGATTTTACGAAAGTAATATGGGATTGGA
TCCGCAAGG;
and

GGG-pre-microRNA-96:
(SEQ ID NO: 22)
5'GGGTGGCCGATTTTGGCACTAGCACATTTTTGCTTGTGTCTCTCCGC
TCTGAGCAATCATGTGCAGTGCCAATATGGGAAA.

RNA Transcription

RNA oligonucleotides were in vitro transcribed by T7 RNA polymerase in 1× Transcription Buffer (40 mM Tris HCl, pH 8.1, 1 mM spermidine, 0.001% (v/v) Triton X-100 and 10 mM DTT) (McKenna et al., *Nat. Protoc.* 2, 3270-3277 (2007)) containing 2.25 mM of each rNTP and 5 mM MgCl$_2$ at 37° C. overnight. The transcribed RNAs were purified on a denaturing 15% polyacrylamide gel and isolated as previously described by Childs-Disney et al., *ACS Chem. Biol.* 2, 745-754 (2007). Concentrations were determined by absorbance at 260 nm and the corresponding extinction coefficient. Extinction coefficients were calculated using the HyTher server (Peyret et al., *Biochemistry* 38, 3468-3477 (1999); SantaLucia et al., *Proc. Natl. Acad. Sci. U.S.A* 95, 1460-1465 (1998)), which uses parameters based on the extinction coefficients of RNA nearest neighbors (Puglisi & Tinoco, *Methods Enzymol.* 180, 304-325 (1989)).

Binding Affinity Measurements

Dissociation constants were determined using an in solution, fluorescence-based assay (Disney et al., *J. Am. Chem. Soc.* 130, 11185-11194 (2008)). The RNA of interest was folded in 1× Assay Buffer (8 mM $Na_2HPO_4$, pH 7.0, 190 mM NaCl, 1 mM EDTA and 40 µg/mL BSA) by heating at 60° C. for 5 min and slowly cooling to room temperature. A selected fluorescently labeled compound was added to a final concentration of 50 nM for compounds 1-Fl, 4-Fl, and 5-Fl or 500 nM for compound 2. Serial dilutions (1:2) were then completed in 1× Assay Buffer supplemented with 50 nM of compounds 1-Fl, 4-Fl, or 5-Fl or 500 nM of 2. The solutions were incubated for 30 min at room temperature and then transferred to a 96-well plate and fluorescence intensity measured. The change in fluorescence intensity as a function of RNA concentration was fit to the following equation (Wang & Rando, *Chem. Biol.* 2, 281-290. (1995)):

$$I = I_0 + 0.5\Delta\varepsilon(([FL]_0 + [RNA]_0 + K_t) - (([FL]_0 + [RNA]_0 + K_t)^2 - 4[FL]_0[RNA]_0)^{0.5})$$

where I and $I_0$ are the observed fluorescence intensity in the presence and absence of RNA respectively, $\Delta\varepsilon$ is the difference between the fluorescence intensity in the absence of RNA and in the presence of infinite RNA concentration, $[FL]_0$ and $[RNA]_0$ are the concentrations of small molecule and RNA, respectively, and $K_t$ is the dissociation constant.

The targetable loops (motifs) were embedded into C1 (FIG. 1) so that affinity measurements could be completed. The secondary structures of the RNAs as predicted by RNAstructure (Mathews et al., *Proc. Natl. Acad. Sci. U.S.A.* 101, 7287-7292 (2004).) and representative binding curves are shown in (FIG. 4D-4I).

Nuclease Protection Assays

GGG-pre-microRNA-96 was 5'end labeled with $^{32}P$ as previously described by Disney et al. (*Biochemistry* 39, 14269-14278 (2000)).

For double stranded-RNA specific endoribonuclease cleavage the RNA was folded in 1× Reaction Buffer (Ambion) by heating at 60° C. for 5 min and slowly cooling to room temperature. Double stranded-RNA specific endoribonuclease (*Escherichia coli* RNase III; Ambion) was then added to a final concentration of 0.15 units/µL followed by addition of serially diluted concentrations of compound 1. The solution was incubated at 37° C. for 2 h, and the cleavage products were separated on a denaturing 15% polyacrylamide gel.

For RNase T1 Cleavage, the RNA was folded in either 1×RNA Sequencing Buffer (Ambion; denaturing conditions) or in 1×RNA Structure Buffer (Ambion; native conditions) by incubating it at 55° C. for 10 min followed by slowly cooling to room temperature. RNase T1 was added to a final concentration of 0.1 units/µL followed by addition of serially diluted concentrations of 1. The solution was incubated at room temperature for 15 min, and the cleaved products were separated on a denaturing 15% polyacrylamide gel.

Preparation of Cell Extracts Containing Drosha

Drosha is a Class 2 RNase III enzyme that initiates the processing of microRNA (miRNA), or short RNA molecules naturally expressed by cells.

HEK 293T cells were maintained in DMEM supplemented with 10% FBS in a T-75 flask. After cells reached 70% confluence, they were transfected with Drosha-cmyc51, obtained from Addgene (Addgene plasmid 10828) using Lipofectamine 2000 (Invitrogen) per the manufacturer's protocol. Approximately 48 h post-transfection, the cells were collected by scrapping them in 1 mL ice-cold 1×DPBS followed by centrifugation at 6000 rpm for 5 min at 4° C.

The cells were resuspended in 500 µL of 1× Lysis Buffer (20 mM Tris HCl, pH 8.0, 100 mM KCl and 0.2 mM EDTA) and sonicated for 30 seconds. Cellular debris was pelleted by centrifugation (12000 rpm for 15 min at 4° C.), and the supernatant containing Drosha was transferred to a new tube.

Inhibition of Drosha Cleavage In Vitro

The cDNA template for pri-miRNA-96 was PCR amplified from MCF7 genomic DNA using the following primers: forward primer: 5'GGCCGAATTCTAATACGACTCAC-TATAGGC ACCAGTGCCATCTGCTT (SEQ ID NO:23); and reverse primer: 5'-CGCAGCTGCGGGTCCT (SEQ ID NO: 232). The forward primer contains a T7 promoter that was employed to produce pri-miR-96 via run-off transcription as described herein. Internally labeled pri-miR-96 was transcribed using $\alpha$-$^{32}P$ ATP and purified using a denaturing 10% polyacrylamide gel. In order to determine if compound 1 inhibits Drosha cleavage in vitro, 2 µL of $^{32}P$-labeled pri-miR-96 (approx. 10,000 counts) and 40 µM of compound 1 were incubated in 6.4 mM $MgCl_2$ (30 µL total volume) at room temperature for 10 min. (Untreated controls included 0.04% DMSO, the same concentration as in treated samples). Then, 1 µL of the Drosha-cmyc lysate was added, and the samples were incubated at 37° C. for 3 h. The reactions were quenched by phenol-chloroform extraction followed by ethanol precipitation. The resulting pellet was dissolved in 10 µL of 2× Gel Loading Buffer (8 M urea, 50 mM EDTA, 0.05% (w/v) bromphenol blue, 0.05% (w/v) xylene cyanol), and the reaction products were separated on a denaturing 10% acrylamide gel.

Cell Culture

Cells (e.g., from the MCF7 breast cancer cell line) were cultured in Dulbecco's modified eagle medium/F12 (DMEM/F12) supplemented with 10% FBS (complete growth medium) at 37° C. and 5% $CO_2$.

Plasmids

Luciferase constructs are those describe by Guttilla & White (*J. Biol. Chem.* 284, 23204-23216 (2009)).

RNA Isolation and Quantitative Real Time Polymerase Chain Reaction (qRT-PCR) of miRNAs MCF7 cells were cultured in either 6-well or 12-well plates, and total RNA was extracted using TRIzol LS reagent (Ambion) per the manufacturer's protocol. Approximately 200 ng of total RNA was used in reverse transcription (RT) reactions, which were completed using a Taqman Micro-RNA RT Kit (Applied Biosystems) or a miScript II RT kit (Qiagen) per the manufacturer's protocol. qRT-PCR was performed on a 7900HT Fast Real Time PCR System (Applied Biosystem) using Taqman Universal PCR Master Mix or power SYBR green master mix (Applied Biosystems). All primer sets for mature miRNAs were purchased from Applied Biosystems. The expression level of mature miRNAs was normalized to U6 small nuclear RNA.

Pri-, pre-, and mature miR-96 RT-PCR products were analyzed on a denaturing 10% polyacrylamide gel stained with ethidium bromide. Expression levels were normalized to GAPDH. The primers used for pre- and pri-miR-96 and GAPDH were purchased from IDT and have the sequences shown in Table 2.

TABLE 2

Sequences of forward primers used for an SYBR qRT-PCR system to profile the effect of compound 1 on other miRNAs and the sequence of the universal reverse primer. Also listed are forward and reverse primers for pri-miR-96, pre-miR-96, and GAPDH.

| MicroRNA | Primer Sequence | SEQ ID NO: |
|---|---|---|
| hsa-miR-212 | TAACAGTCTCCAGTCACGGCC | 24 |
| hsa-miR-346 | TGTCTGCCCGCATGCCTGCCTCT | 25 |
| hsa-miR-194 | TGTAACAGCAACTCCATGTGGA | 26 |
| hsa-miR-196b | TAGGTAGTTTCCTGTTGTTGGG | 27 |
| hsa-miR-196a | TAGGTAGTTTCATGTTGTTGGG | 28 |
| hsa-miR-106b | TAAAGTGCTGACAGTGCAGAT | 29 |
| hsa-miR-210 | CTGTGCGTGTGACAGCGGCTGA | 30 |
| hsa-miR-214 | ACAGCAGGCACAGACAGGCAGT | 31 |
| hsa-miR-17 | CAAAGTGCTTACAGTGCAGGTAG | 32 |
| hsa-miR-514 | ATTGACACTTCTGTGAGTAGA | 33 |
| hsa-miR-29c | TAGCACCATTTGAAATCGGTTA | 34 |
| hsa-miR-410 | AATATAACACAGATGGCCTGT | 35 |
| hsa-miR-198 | GGTCCAGAGGGGAGATAGGTTC | 36 |
| hsa-let-7i | TGAGGTAGTAGTTTGTGCTGTT | 37 |
| hsa-miR-188-5p | CATCCCTTGCATGGTGGAGGG | 38 |
| hsa-miR-92a | TATTGCACTTGTCCCGGCCTGT | 39 |
| hsa-miR-126 | TCGTACCGTGAGTAATAATGCG | 40 |
| hsa-miR-181c | AACATTCAACCTGTCGGTGAGT | 41 |
| hsa-miR-30b | TGTAAACATCCTACACTCAGCT | 42 |
| hsa-miR-183 | TATGGCACTGGTAGAATTCACT | 43 |
| hsa-miR-30c | TGTAAACATCCTACACTCTCAGC | 44 |
| hsa-miR-421 | ATCAACAGACATTAATTGGGCGC | 45 |
| hsa-miR-193b | AACTGGCCCTCAAAGTCCCGCT | 46 |
| hsa-miR-651 | TTTAGGATAAGCTTGACTTTTG | 47 |
| hsa-miR-15a | TAGCAGCACATAATGGTTTGTG | 48 |
| hsa-miR-301b | CAGTGCAATGATATTGTCAAAGC | 49 |
| hsa-miR-18b | TAAGGTGCATCTAGTGCAGTTAG | 50 |
| hsa-miR-15b | TAGCAGCACATCATGGTTTACA | 51 |
| hsa-miR-10a | TACCCTGTAGATCCGAATTTGTG | 52 |
| hsa-miR-26b | TTCAAGTAATTCAGGATAGGT | 53 |
| hsa-let-7a | TGAGGTAGTAGGTTGTATAGTT | 54 |
| hsa-miR-506 | TAAGGCACCCTTCTGAGTAGA | 55 |
| hsa-let-7g | TGAGGTAGTAGTTTGTACAGTT | 56 |
| hsa-miR-25 | CATTGCACTTGTCTCGGTCTGA | 57 |
| hsa-miR-433 | ATCATGATGGGCTCCTCGGTGT | 58 |
| hsa-miR-144 | TACAGTATAGATGATGTACT | 59 |
| hsa-miR-32 | TATTGCACATTACTAAGTTGCA | 60 |
| hsa-miR-200c | TAATACTGCCGGGTAATGATGGA | 61 |
| hsa-miR-29a | TAGCACCATCTGAAATCGGTTA | 62 |
| hsa-miR-497 | CAGCAGCACACTGTGGTTTGT | 63 |
| hsa-miR-548b-3p | CAAGAACCTCAGTTGCTTTTGT | 64 |
| hsa-miR-24 | TGGCTCAGTTCAGCAGGAACAG | 65 |
| hsa-miR-187 | TCGTGTCTTGTGTTGCAGCCGG | 66 |
| hsa-miR-18a | TAAGGTGCATCTAGTGCAGATAG | 67 |
| hsa-miR-222 | AGCTACATCTGGCTACTGGGT | 68 |
| hsa-miR-9 | TCTTTGGTTATCTAGCTGTATGA | 69 |
| hsa-miR-125b | TCCCTGAGACCCTAACTTGTGA | 70 |
| hsa-miR-365 | TAATGCCCCTAAAAATCCTTAT | 71 |
| hsa-miR-10b | TACCCTGTAGAACCGAATTTGTG | 72 |
| hsa-let-7c | TGAGGTAGTAGGTTGTATGGTT | 73 |
| hsa-miR-185 | TGGAGAGAAAGGCAGTTCCTGA | 74 |
| hsa-miR-648 | AAGTGTGCAGGGCACTGGT | 75 |
| hsa-miR-206 | TGGAATGTAAGGAAGTGTGTGG | 76 |
| hsa-miR-124 | TAAGGCACGCGGTGAATGCC | 77 |
| hsa-miR-132 | TAACAGTCTACAGCCATGGTCG | 78 |
| hsa-miR-519b-5p | CTCTAGAGGGAAGCGCTTTCTG | 79 |
| hsa-miR-148b | TCAGTGCATCACAGAACTTTGT | 80 |
| hsa-miR-125a-5p | TCCCTGAGACCCTTTAACCTGTGA | 81 |
| hsa-miR-20b | CAAAGTGCTCATAGTGCAGGTAG | 82 |
| hsa-miR-512-3p | AAGTGCTGTCATAGCTGAGGTC | 83 |
| hsa-miR-186 | CAAAGAATTCTCCTTTTGGGCT | 84 |
| hsa-miR-149 | TCTGGCTCCGTGTCTTCACTCCC | 85 |
| hsa-miR-622 | ACAGTCTGCTGAGGTTGGAGC | 86 |
| hsa-miR-429 | TAATACTGTCTGGTAAAACCGT | 87 |
| hsa-miR-23a | ATCACATTGCCAGGGATTTCC | 88 |
| hsa-miR-485-3p | GTCATACACGGCTCTCCTCTCT | 89 |
| hsa-miR-19b | TGTGCAAATCCATGCAAAACTGA | 90 |
| hsa-miR-141 | TAACACTGTCTGGTAAAGATGG | 91 |
| hsa-miR-103 | AGCAGCATTGTACAGGGCTATGA | 92 |

TABLE 2-continued

Sequences of forward primers used for an SYBR qRT-PCR system to profile the effect of compound 1 on other miRNAs and the sequence of the universal reverse primer. Also listed are forward and reverse primers for pri-miR-96, pre-miR-96, and GAPDH.

| MicroRNA | Primer Sequence | SEQ ID NO: |
|---|---|---|
| hsa-miR-96 | TTTGGCACTAGCACATTTTTGCT | 93 |
| hsa-miR-23b | ATCACATTGCCAGGGATTACC | 94 |
| hsa-miR-152 | TCAGTGCATGACAGAACTTGG | 95 |
| hsa-miR-610 | TGAGCTAAATGTGTGCTGGGA | 96 |
| hsa-miR-203 | GTGAAATGTTTAGGACCACTAG | 97 |
| hsa-miR-127-3p | TCGGATCCGTCTGAGCTTGGCT | 98 |
| hsa-miR-134 | TGTGACTGGTTGACCAGAGGGG | 99 |
| hsa-let-7f | TGAGGTAGTAGATTGTATAGTT | 100 |
| hsa-miR-122 | TGGAGTGTGACAATGGTGTTTG | 101 |
| hsa-miR-142-3p | TGTAGTGTTTCCTACTTTATGGA | 102 |
| hsa-miR-34a | TGGCAGTGTCTTAGCTGGTTGT | 103 |
| hsa-miR-24 | TGGCTCAGTTCAGCAGGAACAG | 104 |
| hsa-miR-187 | TCGTGTCTTGTGTTGCAGCCGG | 105 |
| hsa-miR-18a | TAAGGTGCATCTAGTGCAGATAG | 106 |
| hsa-miR-222 | AGCTACATCTGGCTACTGGGT | 107 |
| hsa-miR-9 | TCTTTGGTTATCTAGCTGTATGA | 108 |
| hsa-miR-125b | TCCCTGAGACCCTAACTTGTGA | 109 |
| hsa-miR-365 | TAATGCCCCTAAAAATCCTTAT | 110 |
| hsa-miR-10b | TACCCTGTAGAACCGAATTTGTG | 111 |
| hsa-let-7c | TGAGGTAGTAGGTTGTATGGTT | 112 |
| hsa-miR-185 | TGGAGAGAAAGGCAGTTCCTGA | 113 |
| hsa-miR-648 | AAGTGTGCAGGGCACTGGT | 114 |
| hsa-miR-206 | TGGAATGTAAGGAAGTGTGTGG | 115 |
| hsa-miR-124 | TAAGGCACGCGGTGAATGCC | 116 |
| hsa-miR-132 | TAACAGTCTACAGCCATGGTCG | 117 |
| hsa-miR-519b-5p | CTCTAGAGGGAAGCGCTTTCTG | 118 |
| hsa-miR-148b | TCAGTGCATCACAGAACTTTGT | 119 |
| hsa-miR-125a-5p | TCCCTGAGACCCTTTAACCTGTGA | 120 |
| hsa-miR-20b | CAAAGTGCTCATAGTGCAGGTAG | 121 |
| hsa-miR-512-3p | AAGTGCTGTCATAGCTGAGGTC | 122 |
| hsa-miR-186 | CAAAGAATTCTCCTTTTGGGCT | 123 |
| hsa-miR-149 | TCTGGCTCCGTGTCTTCACTCCC | 124 |
| hsa-miR-622 | ACAGTCTGCTGAGGTTGGAGC | 125 |
| hsa-miR-429 | TAATACTGTCTGGTAAAACCGT | 126 |
| hsa-miR-23a | ATCACATTGCCAGGGATTTCC | 127 |
| hsa-miR-485-3p | GTCATACACGGCTCTCCTCTCT | 128 |
| hsa-miR-19b | TGTGCAAATCCATGCAAAACTGA | 129 |
| hsa-miR-141 | TAACACTGTCTGGTAAAGATGG | 130 |
| hsa-miR-103 | AGCAGCATTGTACAGGGCTATGA | 131 |
| hsa-miR-96 | TTTGGCACTAGCACATTTTTGCT | 132 |
| hsa-miR-23b | ATCACATTGCCAGGGATTACC | 133 |
| hsa-miR-152 | TCAGTGCATGACAGAACTTGG | 134 |
| hsa-miR-610 | TGAGCTAAATGTGTGCTGGGA | 135 |
| hsa-miR-203 | GTGAAATGTTTAGGACCACTAG | 136 |
| hsa-miR-127-3p | TCGGATCCGTCTGAGCTTGGCT | 137 |
| hsa-miR-134 | TGTGACTGGTTGACCAGAGGGG | 138 |
| hsa-let-7f | TGAGGTAGTAGATTGTATAGTT | 139 |
| hsa-miR-122 | TGGAGTGTGACAATGGTGTTTG | 140 |
| hsa-miR-142-3p | TGTAGTGTTTCCTACTTTATGGA | 141 |
| hsa-miR-34a | TGGCAGTGTCTTAGCTGGTTGT | 142 |
| hsa-miR-19a | TGTGCAAATCTATGCAAAACTGA | 143 |
| hsa-miR-130b | CAGTGCAATGATGAAAGGGCAT | 144 |
| hsa-miR-128a | TCACAGTGAACCGGTCTCTTT | 145 |
| hsa-miR-182 | TTTGGCAATGGTAGAACTCACACT | 146 |
| hsa-miR-135b | TATGGCTTTTCATTCCTATGTGA | 147 |
| hsa-miR-34c-5p | AGGCAGTGTAGTTAGCTGATTGC | 148 |
| hsa-miR-1 | TGGAATGTAAAGAAGTATGTAT | 149 |
| hsa-miR-143 | TGAGATGAAGCACTGTAGCTC | 150 |
| hsa-miR-338-3p | TCCAGCATCAGTGATTTTGTTG | 151 |
| hsa-miR-138 | AGCTGGTGTTGTGAATCAGGCCG | 152 |
| hsa-miR-27a | TTCACAGTGGCTAAGTTCCGC | 153 |
| hsa-miR-27b | TTCACAGTGGCTAAGTTCTGC | 154 |
| hsa-miR-320 | AAAAGCTGGGTTGAGAGGGCGA | 155 |
| hsa-miR-16 | TAGCAGCACGTAAATATTGGCG | 156 |
| hsa-miR-100 | AACCCGTAGATCCGAACTTGTG | 157 |
| hsa-miR-140-3p | TACCACAGGGTAGAACCACGG | 158 |
| hsa-miR-590-5p | GAGCTTATTCATAAAAGTGCAG | 159 |
| hsa-miR-135a | TATGGCTTTTTATTCCTATGTGA | 160 |
| hsa-miR-378 | ACTGGACTTGGAGTCAGAAGG | 161 |

TABLE 2-continued

Sequences of forward primers used for an SYBR qRT-PCR system to profile the effect of compound 1 on other miRNAs and the sequence of the universal reverse primer. Also listed are forward and reverse primers for pri-miR-96, pre-miR-96, and GAPDH.

| MicroRNA | Primer Sequence | SEQ ID NO: |
|---|---|---|
| hsa-miR-139-5p | TCTACAGTGCACGTGTCTCCAG | 162 |
| hsa-miR-331-5p | CTAGGTATGGTCCCAGGGATCC | 163 |
| hsa-miR-342-3p | TCTCACACAGAAATCGCACCCGT | 164 |
| hsa-miR-99a | AACCCGTAGATCCGATCTTGTG | 165 |
| hsa-miR-517a | ATCGTGCATCCCTTTAGAGTGT | 166 |
| hsa-miR-489 | GTGACATCACATATACGGCAGC | 167 |
| hsa-miR-20a | TAAAGTGCTTATAGTGCAGGTAG | 168 |
| hsa-miR-218 | TTGTGCTTGATCTAACCATGT | 169 |
| hsa-miR-101 | TACAGTACTGTGATAACTGAA | 170 |
| hsa-miR-205 | TCCTTCATTCCACCGGAGTCTG | 171 |
| hsa-miR-98 | TGAGGTAGTAAGTTGTATTGTT | 172 |
| hsa-let-7b | TGAGGTAGTAGGTTGTGTGGTT | 173 |
| hsa-miR-181b | AACATTCATTGCTGTCGGTGGGT | 174 |
| hsa-miR-30a | TGTAAACATCCTCGACTGGAAG | 175 |
| hsa-miR-21 | TAGCTTATCAGACTGATGTTGA | 176 |
| hsa-miR-140-5p | CAGTGGTTTTACCCTATGGTAG | 177 |
| hsa-miR-302a | TAAGTGCTTCCATGTTTTGGTGA | 178 |
| hsa-miR-29b | TAGCACCATTTGAAATCAGTGTT | 179 |
| hsa-miR-590-3p | TAATTTTATGTATAAGCTAGT | 180 |
| hsa-let-7d | AGAGGTAGTAGGTTGCATAGTT | 181 |
| hsa-miR-519c-3p | AAAGTGCATCTTTTTAGAGGAT | 182 |
| hsa-miR-181a | AACATTCAACGCTGTCGGTGAGT | 183 |
| hsa-miR-181d | AACATTCATTGTTGTCGGTGGGT | 184 |
| hsa-miR-301a | CAGTGCAATAGTATTGTCAAAGC | 185 |
| hsa-miR-150 | TCTCCCAACCCTTGTACCAGTG | 186 |
| hsa-miR-298 | AGCAGAAGCAGGGAGGTTCTCCCA | 187 |
| hsa-miR-137 | TTATTGCTTAAGAATACGCGTAG | 188 |
| hsa-miR-127-5p | CTGAAGCTCAGAGGGCTCTGAT | 189 |
| hsa-miR-133a | TTTGGTCCCCTTCAACCAGCTGAA | 190 |
| hsa-miR-153 | TTGCATAGTCACAAAAGTGATC | 191 |
| hsa-miR-193a-3p | AACTGGCCTACAAAGTCCCAGTAA | 192 |
| hsa-miR-216a | TAATCTCAGCTGGCAACTGTGAAA | 193 |
| hsa-miR-217 | TACTGCATCAGGAACTGATTGGAAA | 194 |
| hsa-miR-224 | CAAGTCACTAGTGGTTCCGTT | 195 |
| hsa-miR-199a-5p | CCCAGTGTTCAGGCTACCTGTTC | 196 |
| hsa-miR-200a | TAACACTGTCTGGTAACGATGTAA | 197 |
| hsa-miR-302a* | TAAACGTGGATGTACTTGCT | 198 |
| hsa-miR-326 | TGGGCCCTTCCTCCAGAA | 199 |
| hsa-miR-33b | GTGCATTGCTGTTGCATTGC | 200 |
| hsa-miR-139-3p | GGAGACGCGGCCCTGTTGGAGT | 201 |
| hsa-miR-451 | CCGTTACCATTACTGAGTTAA | 202 |
| hsa-miR-324-3p | ACTGCCCCAGGTGCTGCTGG | 203 |
| hsa-miR-509-3-5p | GGGTACTGCAGACGTGGCAATCATG | 204 |
| hsa-miR-483-3p | TCACTCCTCTCCTCCCGTCTT | 205 |
| hsa-miR-146b-3p | CTGTGGACTCAGTTCTGGAA | 206 |
| hsa-miR-34b | AATCACTAACTCCACTGCCATC | 207 |
| hsa-miR-371-5p | CAAACTGTGGGGGCACTAA | 208 |
| hsa-miR-488* | CCCAGATAATGGCACT | 209 |
| hsa-miR-513a-3p | TTTCACCTTTCTGAGAAGGA A | 210 |
| hsa-miR-513b | TTCACAAGGAGGTGTCATTTAT | 211 |
| hsa-miR-449b | GCCAGCAGGCAGTGTATTGTTAGCTGGC | 212 |
| hsa-miR-486-5p | TCCTGTACTGAGCTGCCCCGAG | 213 |
| hsa-miR-1246 | AATGGATTTTTGGAGCAGG | 214 |
| hsa-miR-1245 | AAGTGATCTAAAGGCCTACAT | 215 |
| SNORD48 | CCCCAGGTAACTCTTGAGTGT | 216 |
| SNORD47 | TAATGATATCACTGTAAAACC | 217 |
| SNORD44 | ATGCTGACTGAACATGAAGGTC | 218 |
| RNU6 | ACACGCAAATTCGTGAAGCGTTC | 219 |
| Universal Reverse | GAATCGAGCACCAGTTACGC | 220 |
| Pre-miRNA-96-F | ATTTTGGCACTAGCACATTTTTGCT | 221 |
| Pre-miRNA-96-R | CCATATTGGCACTGCACATGATT | 222 |
| Pri-miRN A-96-F | AGAGAGCCCGCACCAGT | 223 |
| Pri-miRN A-96-R | CTTGAGGAGGAGCAGGCT | 224 |
| GAPDH-F | AAGGTGAAGGTCGGAGTCAA | 225 |
| GAPDH-R | AATGAAGGGGTCATTGATGG | 226 |

Transcriptome-wide Profiling of Mature MicroRNAs by qRT-PCR

MCF7 cells were cultured and total RNA was extracted as described above. Approximately 1 µg of total RNA was used in RT reactions, which were completed using miScript II RT kit (Qiagen) per the manufacturer's protocol. qRT-PCR was performed using power SYBR green master mix (Applied Biosystems) on a 7900HT Fast Real Time PCR System. All forward primers were purchased from Life Technologies while the universal reverse primer was purchased from IDT (Table 2). Expression levels were normalized using RNU6, SNORD44, SNORD47 and SNORD48.

Dual Luciferase Assay

MCF7 cells were grown in 96-well plates to ~80% confluency in complete growth medium. The cells were transiently transfected with 100 ng of plasmid encoding either the miR-96 3' UTR target or a mutated 3' UTR target using Lipofectamine 2000 per the manufacturer's protocol. Approximately 5 h post transfection, the small molecule of interest was added in complete growth medium, and the cells were incubated for another 20 h. Luciferase activity was then measured using a Dual Glo Luciferase Assay System (Promega) per the manufacturer's protocol. The values reported are the average of at least three measurements, and errors are the corresponding standard deviations.

Western Blotting

MCF7 cells were grown in 6-well plates to ~80% confluency in complete growth medium. The cells were then incubated with 40 µM of 1 for 20 h. Total protein was extracted using M-PER Mammalian Protein Extraction Reagent (Pierce Biotechnology) using the manufacturer's protocol. Extracted total protein was quantified using a Micro BCA Protein Assay Kit (Pierce Biotechnology). Approximately 40 µg of total protein was resolved on an 8% SDS-polyacrylamide gel, and then transferred to a PVDF membrane. The membrane was briefly washed with 1× Tris-buffered saline (TBS), and then blocked in 5% milk in 1×TBST (1×TBS containing 0.1% Tween-20) for 1 h at room temperature. The membrane was then incubated in 1:1000 FOXO1 primary antibodies (Cell Signaling Technology) in 1×TBST containing 3% BSA overnight at 4° C. The membrane was washed with 1×TBST and incubated with 1:2000 anti-rabbit IgG horseradish-peroxidase secondary antibody conjugate (Cell Signaling Technology) in 1×TBS for 1 h at room temperature. After washing with 1×TBST, protein expression was quantified using SuperSignal West Pico Chemiluminescent Substrate (Pierce Biotechnology) per the manufacturer's protocol. The membrane was then stripped using 1× Stripping Buffer (200 mM glycine, pH 2.2 and 0.1% SDS) followed by washing in 1×TBS. The membrane was blocked and probed for GAPDH following the same procedure described above using 1:2000 GAPDH primary antibodies (Abcam). Image J software from the National Institutes of Health was used to quantify band intensities.

siRNA Treatment

ON-TARGETplus SMARTpool FOXO1 siRNA and ONTARGETplus GAPD Control Pool were purchased from Dharmacon (Thermo Scientific) and were used at a final concentration of 100 nM. MCF7 cells were reverse transfected in a 6-well plate using Lipofectamine RNAiMAX reagent (Invitrogen) per the manufacturer's protocol.

APO BrdU TUNEL Assay

MCF7 cells were grown in 6-well plates to 70-80% confluency. For experiments in which RNAi was used to knock down FOXO1 or GAPDH expression, the cells were first transfected as described above. Cells were treated with small molecules for 20 h followed by completion of an APO BrdU TUNEL assay (Molecular Probes) per the manufacturer's protocol. Flow cytometry was performed using a BD LSRII instrument (BD Biosciences). At least 10,000 events were used for analysis.

Annexin V/PI Assays

Annexin V staining was used as an indicator of apoptosis. In normal cells phosphatidylserine is located on the cytoplasmic surface of cell membrane. In apoptotic cells, phosphatidylserine is translocated to the outer leaflet of plasma membrane. Such tranlocation exposes phosphadidylserine, so that it can be stained by Annexin V, which has high affinity for phosphatidylserine.

MCF7 cells were grown in 6-well plates to 70-80% confluency. The cells were incubated with 40 µM of compound 1 for 20 h and then detached from the surface using accutase. They were washed twice each with ice cold 1×DPBS and 1× Annexin Binding Buffer (50 mM Hepes (pH 7.4), 700 mM NaCl and 12.5 mM $CaCl_2$). The cells were resuspended in 100 µL 1× Annexin Binding Buffer, and then 5 ?IL Annexin V-APC (eBioscience) were added. The solution was incubated for 10 min at room temperature followed by washing with 1× Annexin Binding Buffer. The cells were then stained with 1 µg/mL propidium iodide in 300 ?IL of 1× Annexin Binding Buffer for 15 min at room temperature. Flow cytometry was performed using a BD LSRII instrument (BD Biosciences). At least 10,000 events were used for analysis.

Cellular Permeability

Figure 10A:
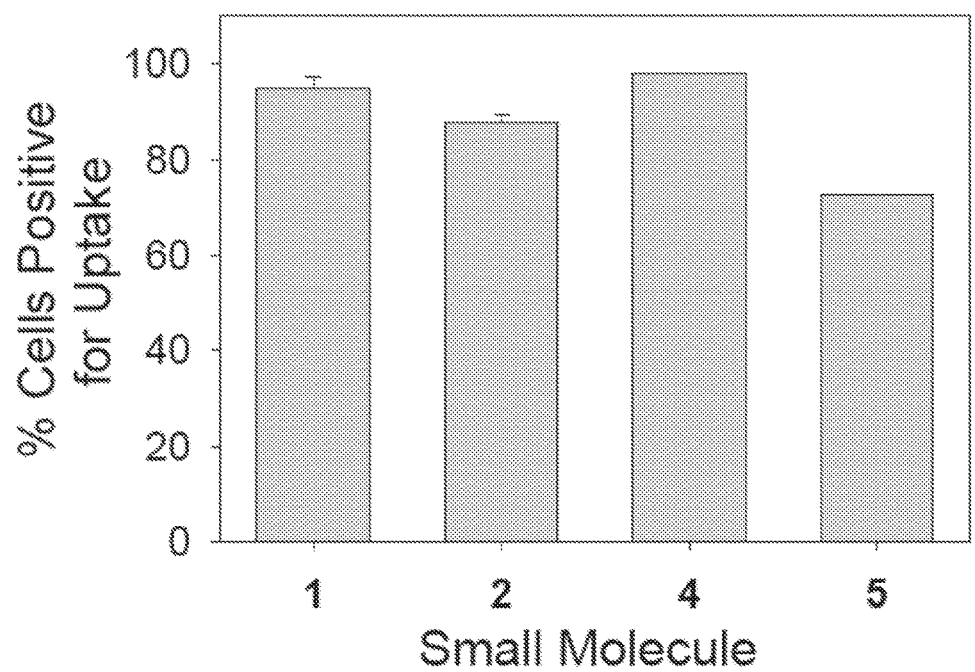
FIG. 10A illustrates the cellular permeability of compounds 1, 2, 4, and 5 in MCF7 cells. Cells were treated with 10 μM of small molecule for 20 h.
Figure 10B:
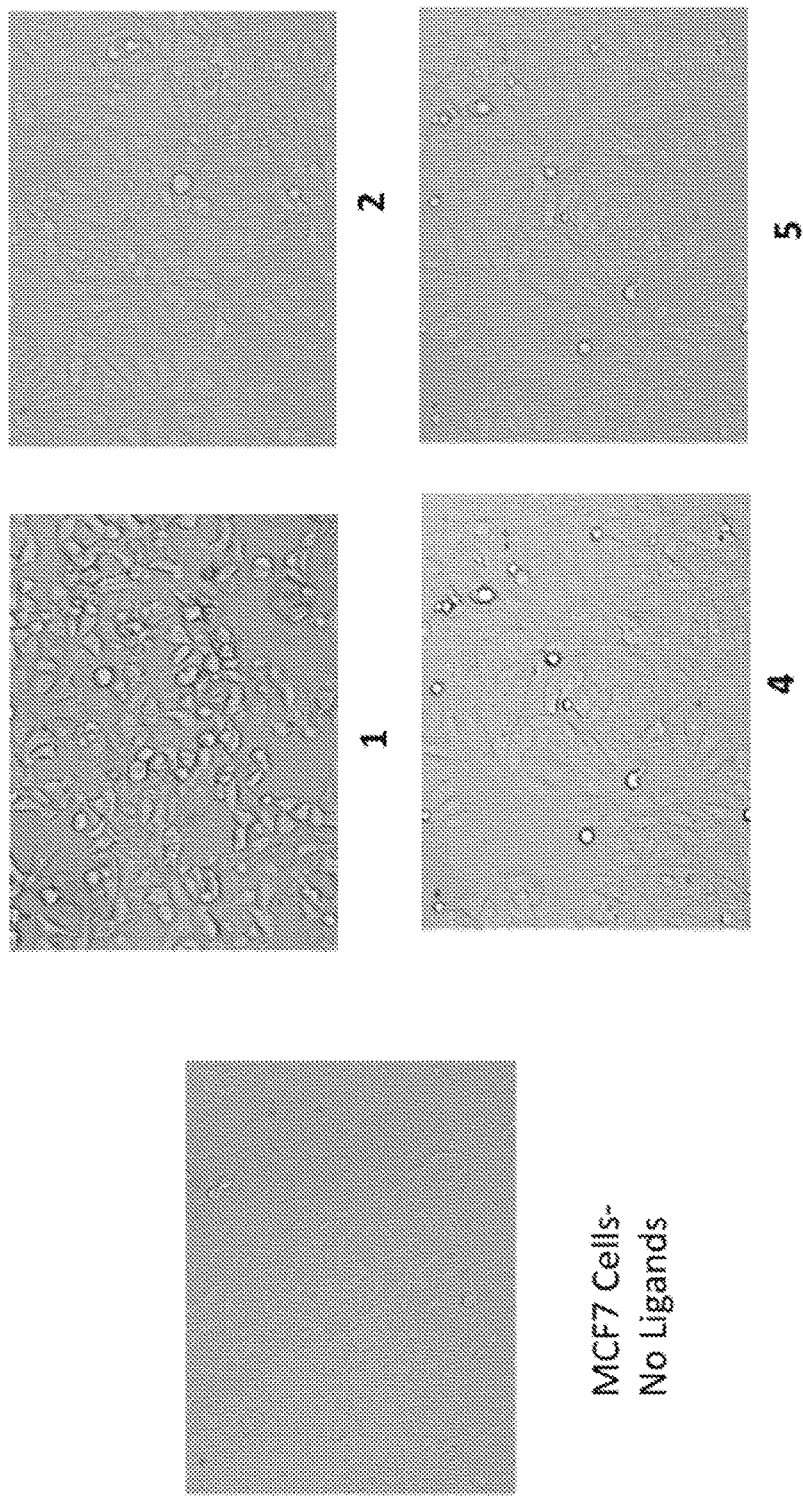
FIG. 10B provides images of cells after treatment with 40 μM of the indicated compounds 1, 2, 4, or 5. Images were acquired at 20× magnification.

MCF7 cells were grown in 6-well plates to ~80% confluency in complete growth medium. Then, 10 µM of the indicated small molecule was added, and the cells were incubated for 20 h. The cells were trypsinized from the plate, washed twice with 1×DPBS, and stained with 1 µg/mL PI for 30 min on ice. Cellular permeability was quantified by flow cytometry using a BD LSRII flow cytometer (BD Biosciences) and Hoechst filters. At least 10,000 events were used for analyses (FIG. 10).

Assessment of Cellular Morphology

MCF7 cells were grown in 6-well plates to ~80% confluency in complete growth medium. Then, 40 µM of the indicated small molecule was added to the well, and the cells were incubated for 20 h. The cells were imaged using an Olympus IX71 microscope (FIG. 10).

Synthesis of 1, 2, 4, 5 and their Fluorescein Conjugates

Compounds 1, 2, 4 and 5 and the fluorescein conjugates of 1 and 4 (1-Fl and 4-Fl, respectively (FIG. 11) were synthesized as previously described by Velagapudi et g. (*J. Am. Chem. Soc.* 133, 10111-10118 (2011)). Compounds 1-Fl, 4-Fl, and 5-Fl were used to measure binding affinities; compound 2 was used directly to measure affinities without fluorescein conjugation.

Synthesis of 5-Fl

Figures 1, 11A:
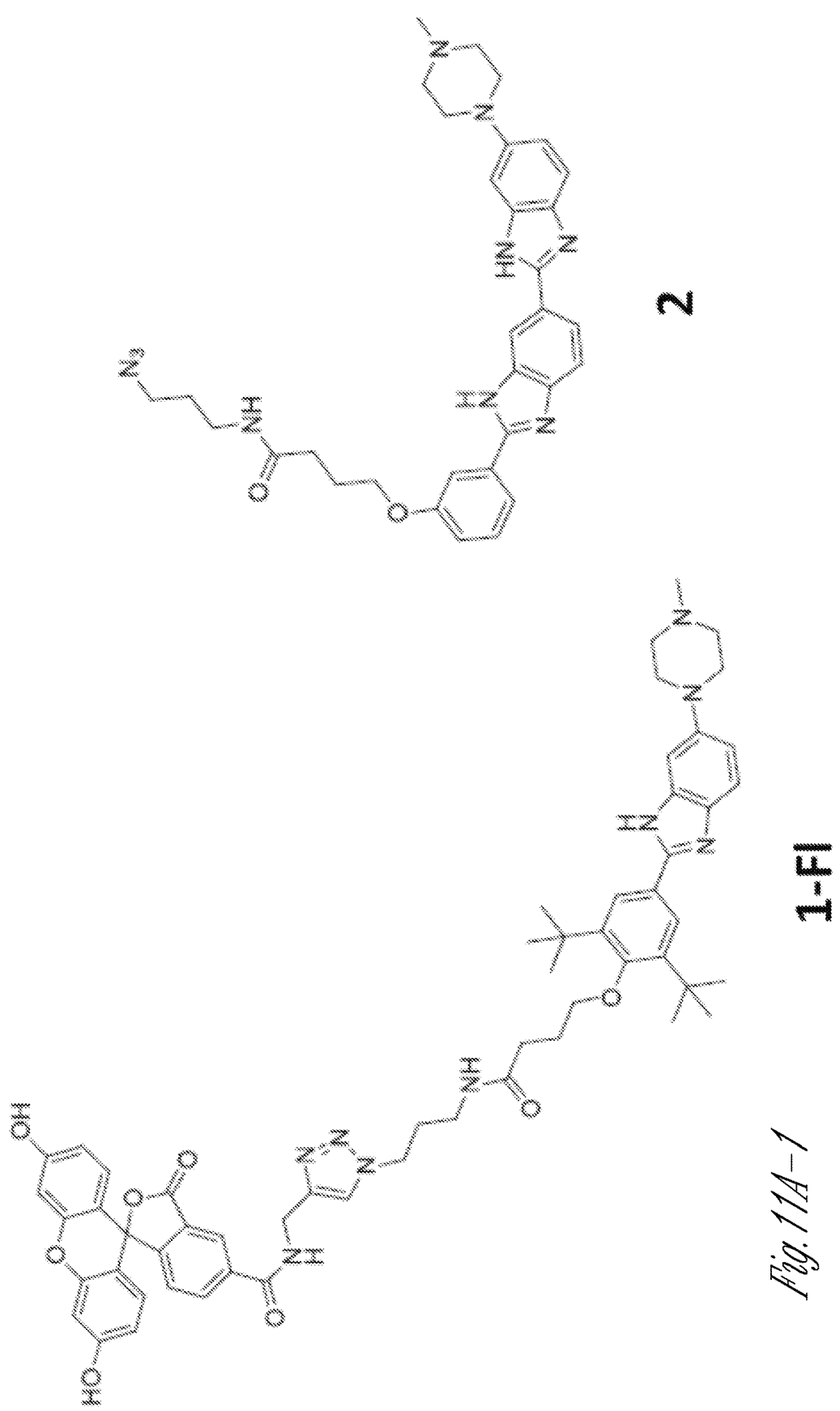
FIG. 11A-11B shows compounds used in the microRNA binding assays described in the Examples.
Figures 2, 11A:
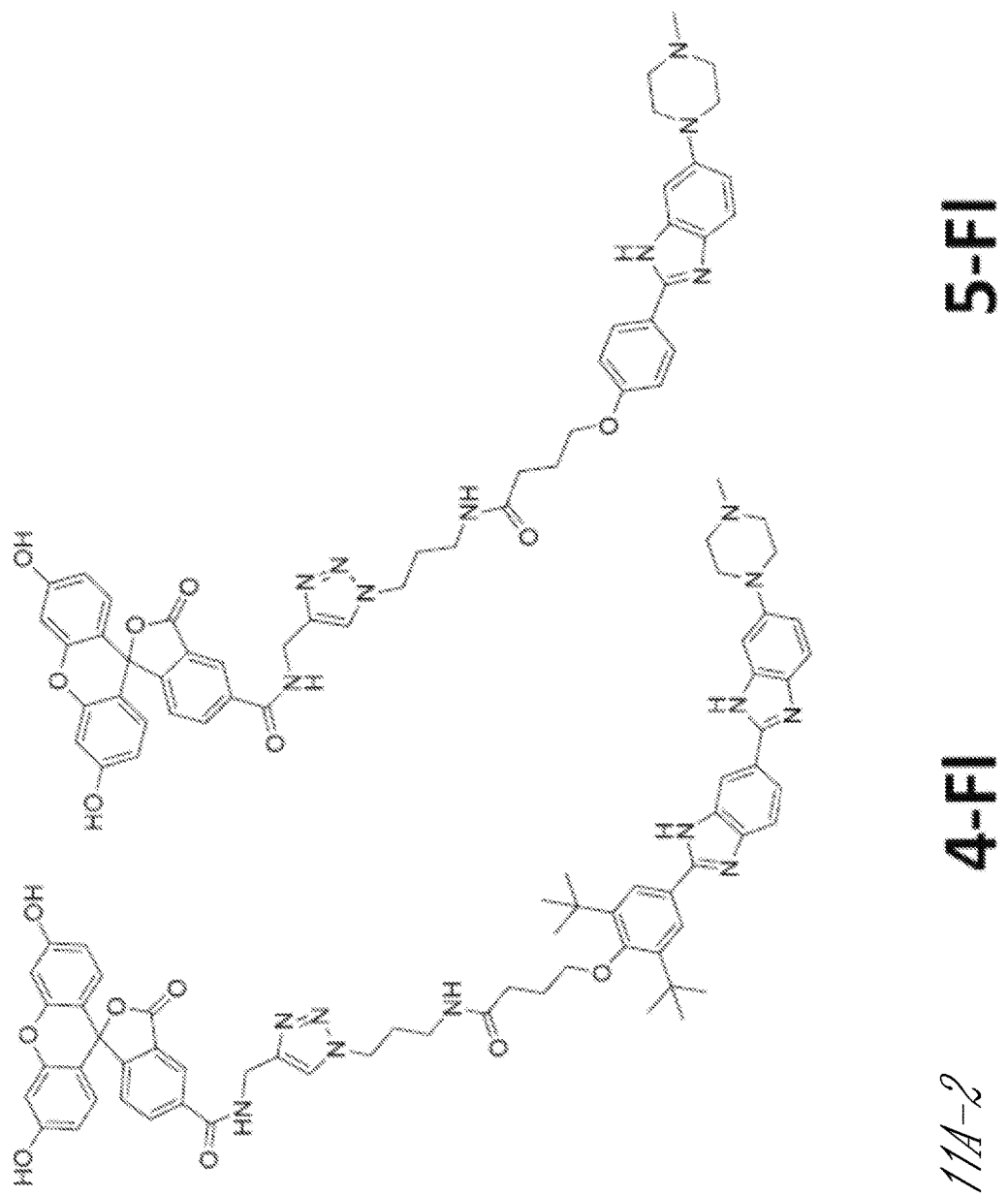
Figure 11B:
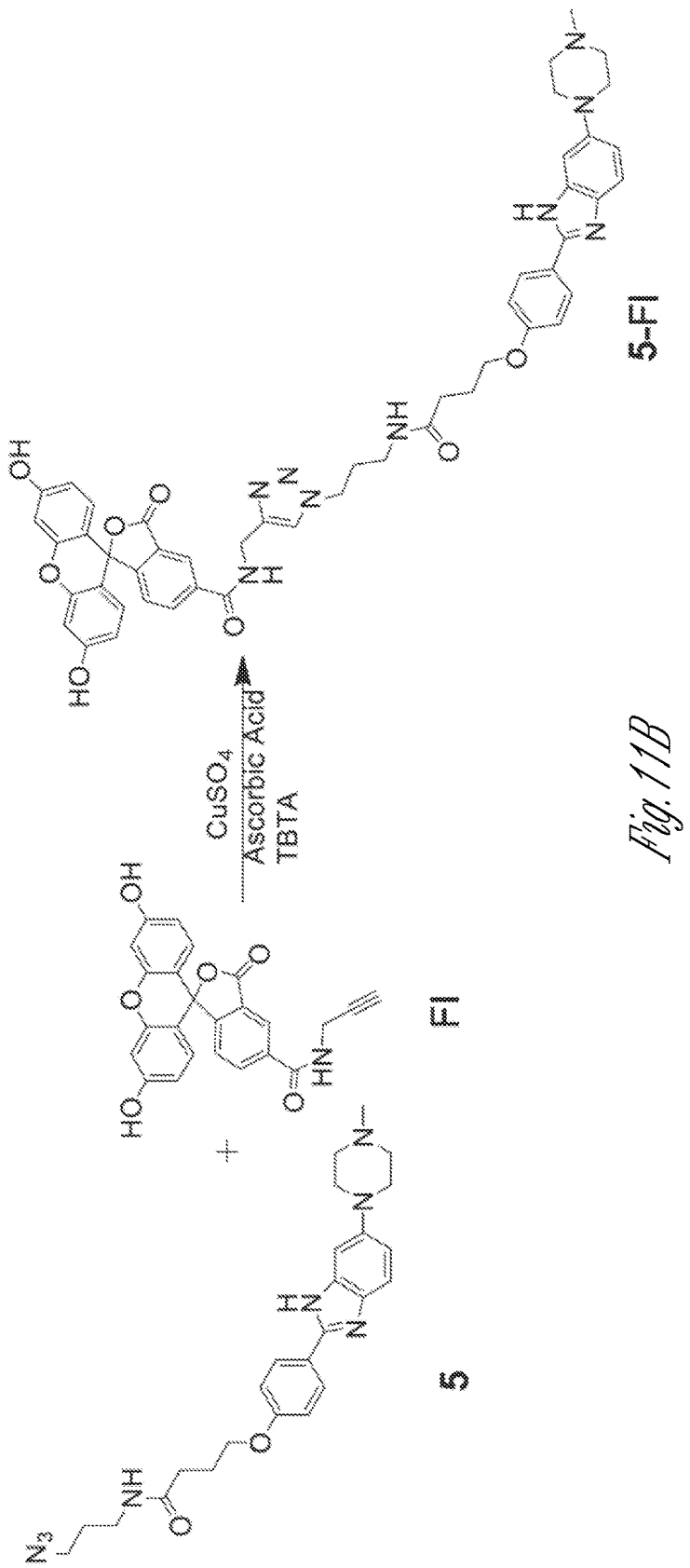

The synthetic scheme for making compound 5-Fl is shown in FIG. 11. A sample of 3.4 µmol N-(2-propynyl) 5-fluoresceincarboxamide in methanol was added to a solution containing 10 µmol compound 5, 34 µmol $CuSO_4$, 72 µmol freshly dissolved ascorbic acid, and 0.3 µmol TBTA. The final volume was brought to 1.5 mL with methanol. The reaction mixture was transferred to a microwave reaction vessel, a magnetic stir bar was added, and the flask was sealed with a Teflon septum and aluminum crimp top. The reaction vessel was placed in an Emrys™ Optimizer system (Biotage), and the reaction was maintained at 110° C. for 4 h with stirring. The crude reaction mixture was purified by reverse phase HPLC using a linear gradient of 20% to 100% solvent B in solvent A over 60 min. Solvent A was 0.1% (v/v) TFA in water while B was 0.1% (v/v) TFA in methanol. The purity of the product was evaluated on a Waters Symmetry® C18 5 µm 4.6×150 mm column using a Waters 1525 binary HPLC pump equipped with a Waters 2487 dual λ absorbance detector system. Separations were completed at room temperature using a 1 mL/min flow rate and a linear gradient of 0% to 100% solvent B in solvent A over 50 min Absorbance was monitored at 220 and 254 nm. $t_R$=35 min; isolated yield=70% (determined by absorbance at 496 nm in 1×PBS, pH 7.4, using an extinction coefficient of 45000 $M^{-1}cm^{-1}$). HRMS, calculated mass: 890.3580 (M+H$^+$); observed mass: 890.3590 (M+H$^+$).

EXAMPLE 2

Compounds Identified for 22 Disease-Related miRNA Precursors

This Example describes development of an approach to identify lead small molecules that inhibit microRNA biogenesis, where the compounds are identified solely from the RNA sequences.

In order to develop a computational approach to design small molecules that bind RNA from sequence, an algorithm was developed to parse RNA secondary structures into motifs. These motifs are then compared to our database of RNA motif-small molecule interactions to identify overlap (FIG. 3A-3B). The output is the targetable RNA structural motifs and the corresponding lead small molecules for an RNA of interest. Lead compounds can then be tested for modulating biological function.

The computational approach was validated using microRNAs (miRNAs), a class of RNAs that regulate many biological processes. MicroRNAs are transcribed as precursors that are processed into 21-25 nucleotide RNAs that negatively regulate gene expression through translational repression or cleavage of a target mRNA (FIG. 3B) (see, e.g., Bartel, Cell 136, 215-233 (2009) for a description of microRNA target recognition and regulatory functions).

The goal of these studies was to use inforna to identify a small molecule that binds a precursor miRNA and inhibits its maturation (see FIG. 3A-3B for a schematic diagram of the inforna process). The sequences of all known precursor miRNAs in the human transcriptome (Griffith-Jones et al., Nucleic Acids Res. 36, D154-158 (2008)) were downloaded and modeled into secondary structures (Mathews et al., Proc. Natl. Acad. Sci. U.S.A. 101, 7287-7292 (2004)). Precursor miRNAs fold into small hairpin secondary structures (FIG. 3B) that are accurately predicted from sequence (Ambros et al., RNA 9, 277-279 (2003). The entire set of secondary structures was then parsed by inforna, which generates an output of the targetable motifs in each RNA and the corresponding small molecules that bind to those motifs. By mining all precursor miRNAs in the human transcriptome for overlap with the RNA motif-small molecule database, inforna probed more than 5,400,000 potential interactions (the motifs contained in 1,048 miRNA precursors (about 6,850) with 792 RNA motif-small molecule interactions housed in the inventors' database). In this study, the inventors required that the targetable motif and its closing base pairs were exact matches for motifs in the database. Previously, it has been shown that the identity of internal loop closing pairs can dramatically affect loop structure and thus recognition by a small molecule (Wu & Turner, Biochemistry 35, 9677-9689 (1996); SantaLucia & Turner, Biochemistry 32, 12612-12623 (1993)).

Next, the inventors refined the lead interactions based on the following criteria:
(i) the targetable motif must be in a Drosha or Dicer processing site, which are cleaved to produce pre-miRNAs and mature miRNAs, respectively. Processing is required for the mature, active miRNA to be produced (Bartel, Cell 116, 281-297 (2004)); and
(ii) the miRNA must be causative of disease.

In order to be validated as a miRNA upregulated in disease, phenotype reversal with oligonucleotides (i.e., antagomirs) was previously established (Krutzfeldt et al., Nature 438, 685-689 (2005); Ebert & Sharp, RNA 16, 2043-2050 (2010); Obad et al., Nat. Genet. 43, 371-378 (2011). For miRNAs under-expressed in a disease, validation was previously established by adding the miRNA to cells and observing improvement of disease-associated defects. In summary, lead small molecules were identified for twenty-two (22) different miRNA precursors that are causative of diseases including prostate, breast, ovarian, and pancreatic cancers, Parkinson's disease, and Alzheimer's disease (FIGS. 3C-3E, and Table 1).

EXAMPLE 3

StARTS Analysis of Lead Compounds

This Example describes Structure-Activity Relationships Through Sequencing (StARTS) to computationally probe the fitness of miRNA precursor-small molecule interactions.

StARTS analysis of hit compounds was used to assess the fitness of each small molecule lead for binding the corresponding RNA motif in the precursor miRNA target (Velagapudi et al., Angew. Chem. Int. Ed. Engl. 49, 3816-3818 (2010); Velagapudi et al., J. Am. Chem. Soc. 133, 10111-10118 (2011); see also Example 1). FIG. 2 shows the potential randomized (N) sequences that can be in the 3×3 ILL RNA motif shown in FIG. 1, while FIG. 3C graphically illustrates that the Fitness Scores for the different compounds varies depending upon to which miRNA they are interacting.

Briefly, StARTS determines the fitness of a small molecule binder by assigning statistical significance for each feature in a motif (such as a GC step) that contributes positively or negatively to binding. Statistical significance is expressed as a Z-score; the Z-scores are summed to afford a ΣZ-score for each motif (FIG. 3). ΣZ-scores accurately predict affinity and selectivity of a small molecule for all members of an RNA library (such as a 3×3 nucleotide internal loop library, which has 4,096 members (FIGS. 1-2) with affinity positively correlating with ΣZ-score. A fitness score is calculated by normalizing the ΣZ-score to the highest ΣZ-score from the StARTS analysis. For example, a Fitness Score of 100 indicates that a given RNA motif-small molecule interaction is the highest affinity RNA motif(s) that binds to a given small molecule from a library of RNA motifs. Likewise, a Fitness Score of 80 means that an RNA-small molecule interaction is 80% as fit as the optimal interaction (Fitness Score=100).

Figure 5A:
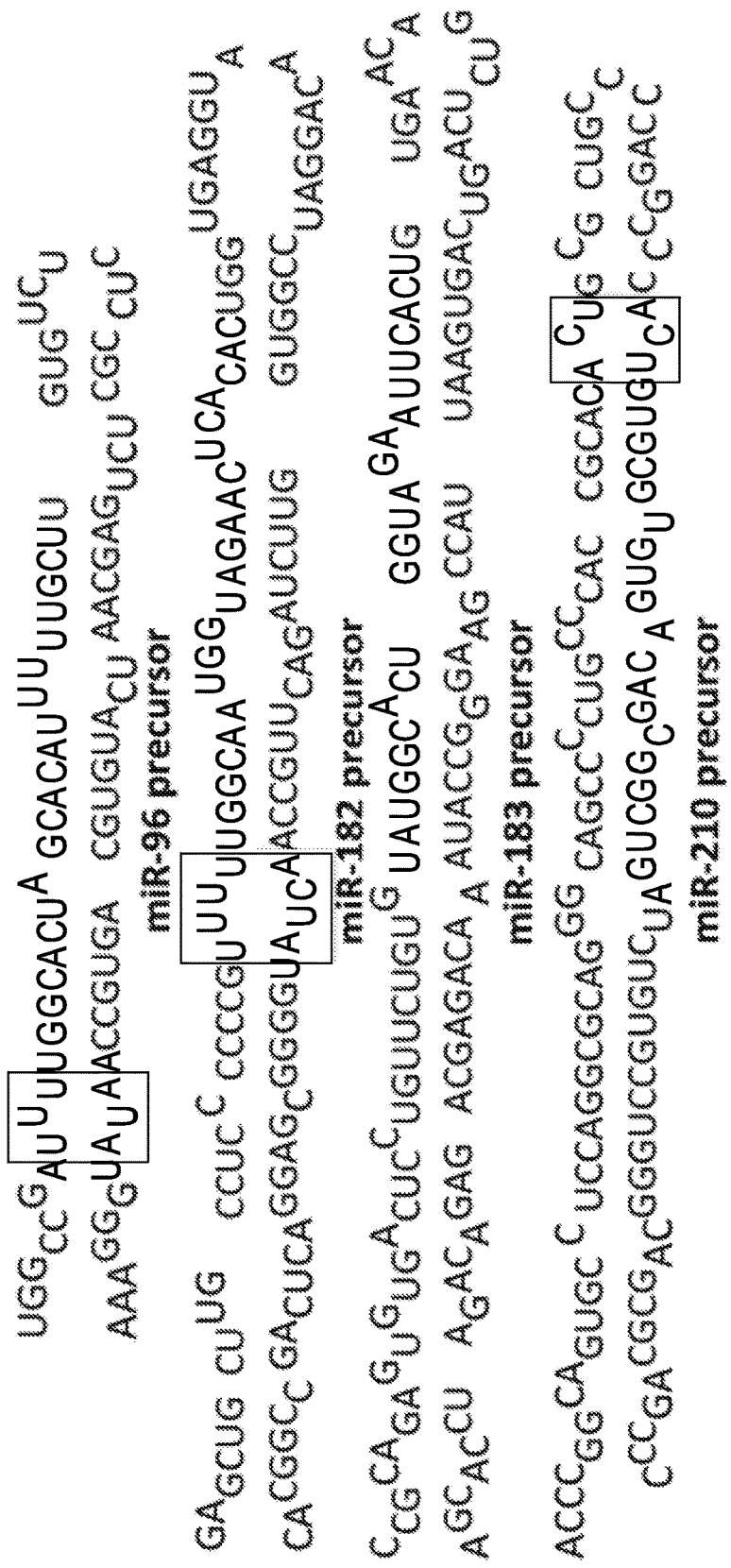
FIG. 5A-5C illustrate that designer small molecules that target miRNA precursors identified via inforna are bioactive and selective. These compounds selectively inhibit biogenesis of its target precursor miRNA by MCF7 cells in a dose-dependent fashion.

StARTS analysis determined that the fittest interactions were: compound 1 with the miR-96 precursor (Fitness Score=100), compound 2 with the miR-210 precursor (Fitness Score=95), and compound 3 with miR-182 precursor (fitness score=75) (FIGS. 3C, 3D, 5A). It should be noted that the affinities and selectivities of these RNA motif-small molecule interactions and their Fitness Scores were measured in previous studies (Disney et al., J. Am. Chem. Soc. 130, 11185-11194 (2008); Velagapudi et al, J. Am. Chem. Soc. 133, 10111-10118 (2011)). Because of high fitness of these interactions, compounds 1-3 were tested for inhibiting microRNA biogenesis in primary cells lines in which the microRNAs are highly expressed and cause disease-associated phenotypes. Specifically, compounds 1 and 3 were tested in MCF7 breast cancer cell line (Guttilla & White, J. Biol. Chem. 284, 23204-23216 (2009)) while compound 2 was tested in ACHN renal cancer cell line (Redova et al., *Tumour Biol.* 34, 481-491 (2013)). The other lead interactions identified in FIG. 3C could also be leveraged to design bioactive molecules targeting other miRNA precursors. The lower fitness scores of these interactions relative to those selected for follow-up suggest that they may require optimization, which could be accomplished by modular assembly approaches (Childs-Disney et al., *ACS Chem. Biol.* 7, 856-862 (2012); Pilch et al., *Proc. Natl. Acad. Sci. U.S.A* 93, 8306-8311 (1996); Pushechnikov et al., *J. Am. Chem. Soc.* 131, 9767-9779 (2009); Lee et al., *ACS Chem. Biol.* 4, 345-355 (2009)) or chemical similarity searching (Parkesh et al., *J. Am. Chem. Soc.* 134, 4731-4742 (2012); Kumar et al., *ACS Chem. Biol.* 7, 496-505 (2012); Pinto et al., *J. Med. Chem.* 51, 7205-7215 (2008); Disney et al., *ACS Chem. Biol.* 7, 1711-1718 (2012); Luzhkov et al., *Bioorg. Med. Chem.* 15, 7795-7802 (2007)).

EXAMPLE 4

Figure 5B:
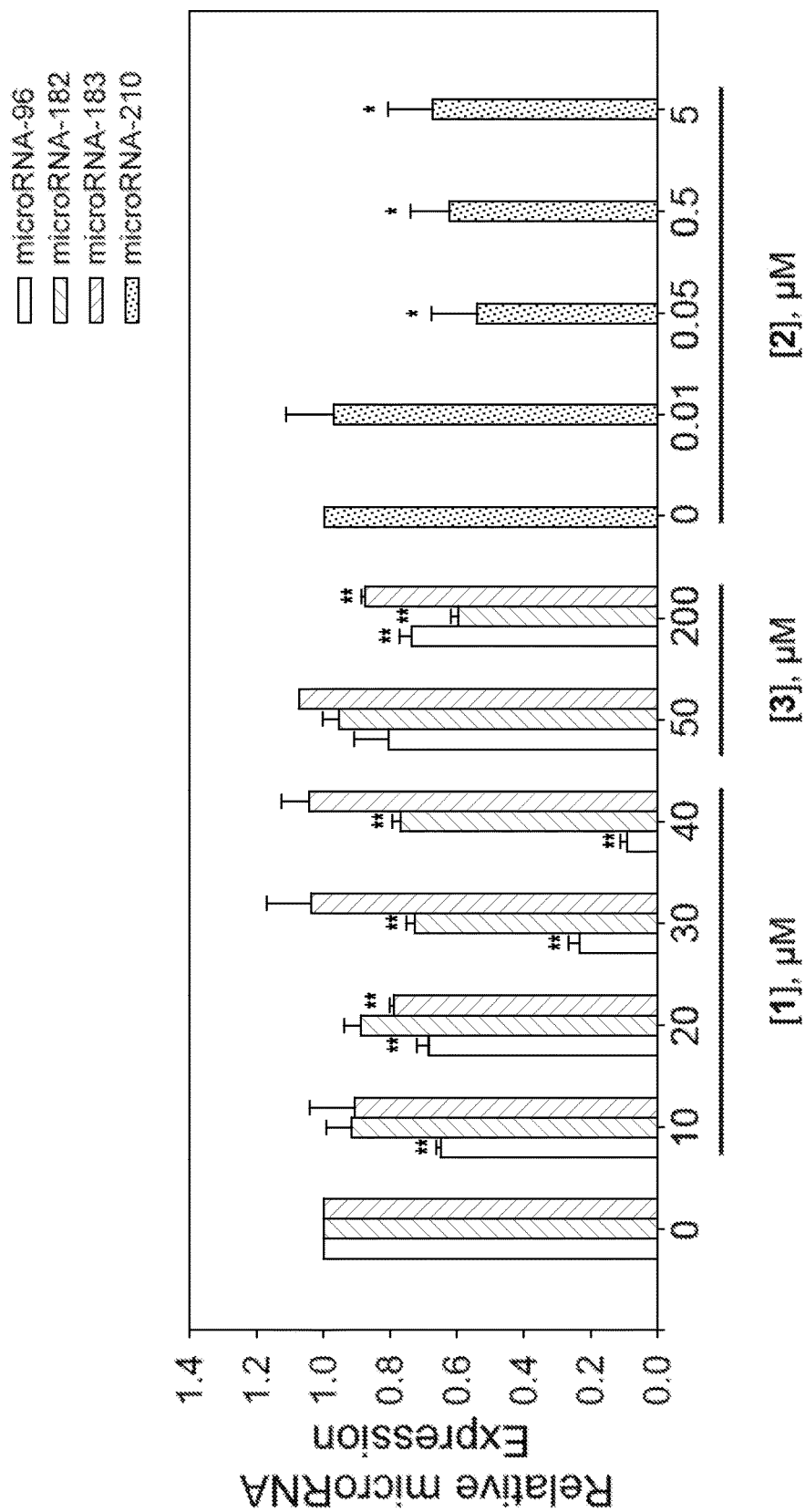

Bioactivity and Selectivity of Compounds Predicted to Target microRNA Precursors by inforna This Example illustrates the bioactivity and selectivity of the small molecules predicted to target microRNA precursors by inforna. Initially, compounds 1, 2, and 3 were tested for inhibiting production of the mature miRNA from their target precursors in primary cell lines by quantitative real time RT-PCR (FIGS. 5A-5B). Each compound inhibits biogenesis of its target precursor miRNA, although to varying extents (FIG. 5B): compound 1 reduces the expression level of miR-96 by 90% at 40 μM; compound 2 reduces the formation of miR-210 by 60% at 500 nM; and compound 3 reduces the production of miR-182 by 40% at 200 μM.

Treatment of primary cells with higher concentrations of compound 2 leads to reduced potency, perhaps due to a lack of selectivity at these elevated concentrations. These differences in bioactivity could be due to differences in affinity, selectivity, permeability, and cellular localization. Importantly, these studies demonstrate that small molecules targeting either Dicer (compound 2) or Drosha (compounds 1 and 3) sites in precursor miRNAs can inhibit biogenesis in cell culture. Importantly, these data show that bioactive small molecules targeting RNA can be designed from only sequence in a transcriptome-wide manner without target bias.

Interestingly, miR-96, -182, and -183 precursors (FIG. 5A) are transcribed as a single transcript (Xu et al., *J. Biol. Chem.* 282, 25053-25066 (2007)). Thus, biogenesis of one microRNA can serve as an internal control for the others. Therefore, compound 1 (which targets precursor miR-96) and compound 3 (which targets precursor miR-182) were studied for decreasing production of the other two microRNAs in the MCF7 cell line by qRT-PCR. Although compound 3 decreases production of the desired target, miR-182, by about 40% when cells are dosed with 200 μM compound, a less, but significant, effect was observed on miR-96 expression that indicates sub-optimal selectivity (FIG. 5B). In contrast, compound 1 efficiently and selectively silences production of miR-96 at 40 μM while not affecting miR-182 or -183 (FIG. 5B). Thus, compound 1 provides a higher knock down of the target microRNA than compounds 2 and 3 and is more selective than 3.

Figure 5C:
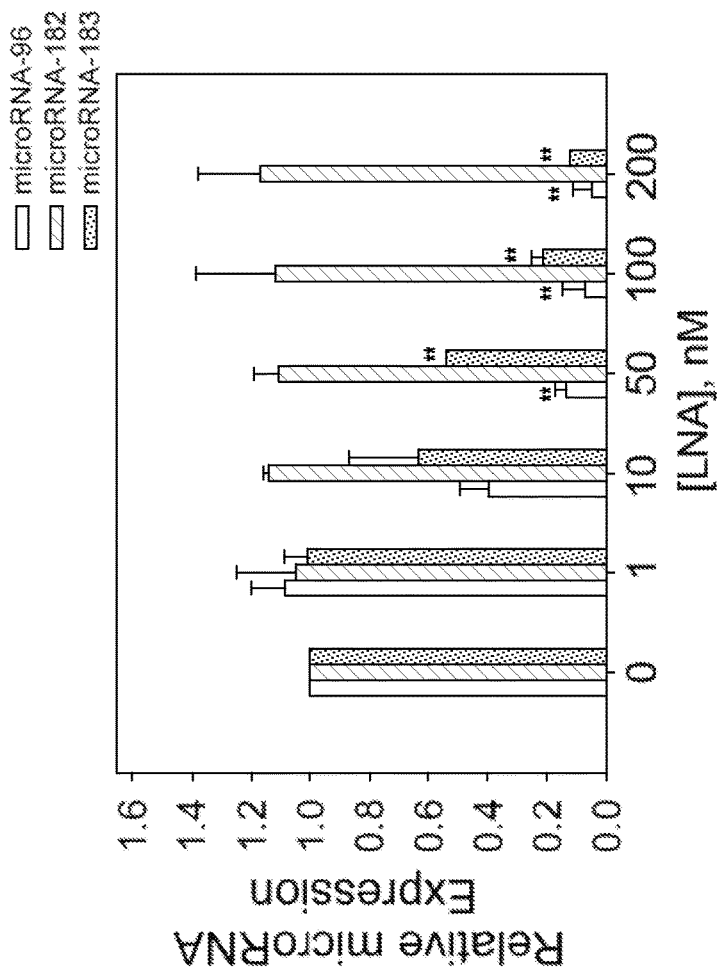
Figure 5C:
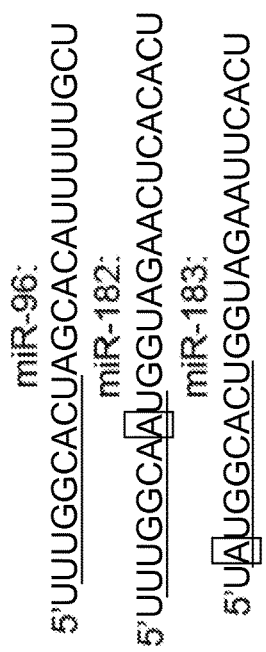
Figure 9A:
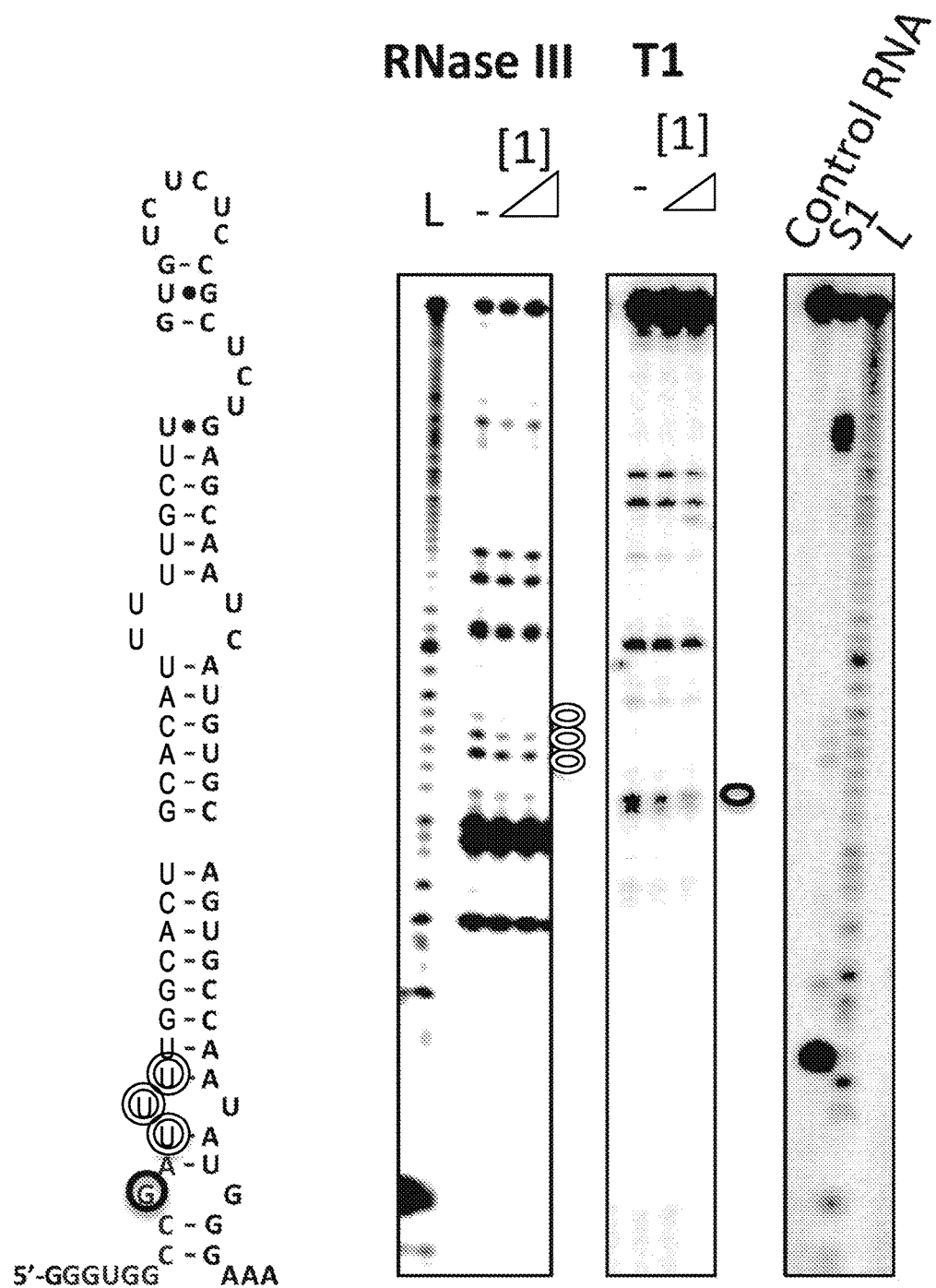
FIG. 9A-9C illustrates that compound 1 binds the Drosha processing site and inhibits microRNA maturation in vitro and in vivo.
Figure 9B:
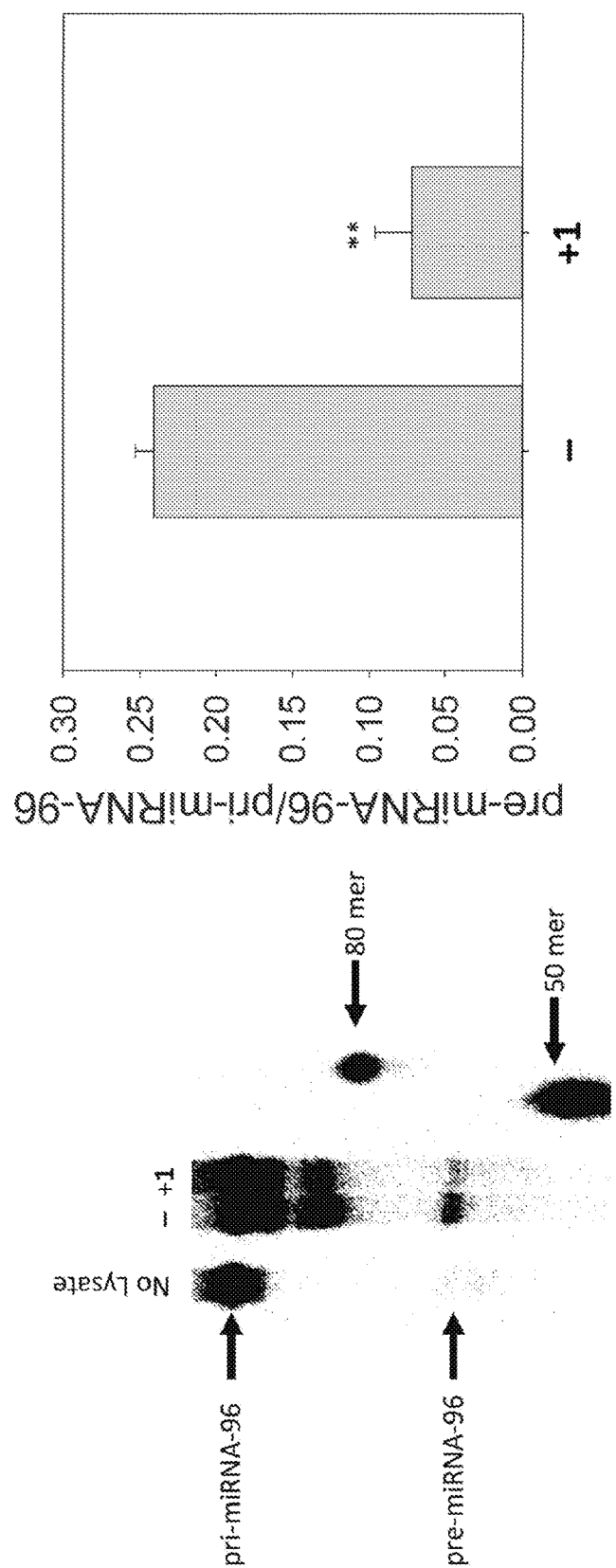
Figure 9C:
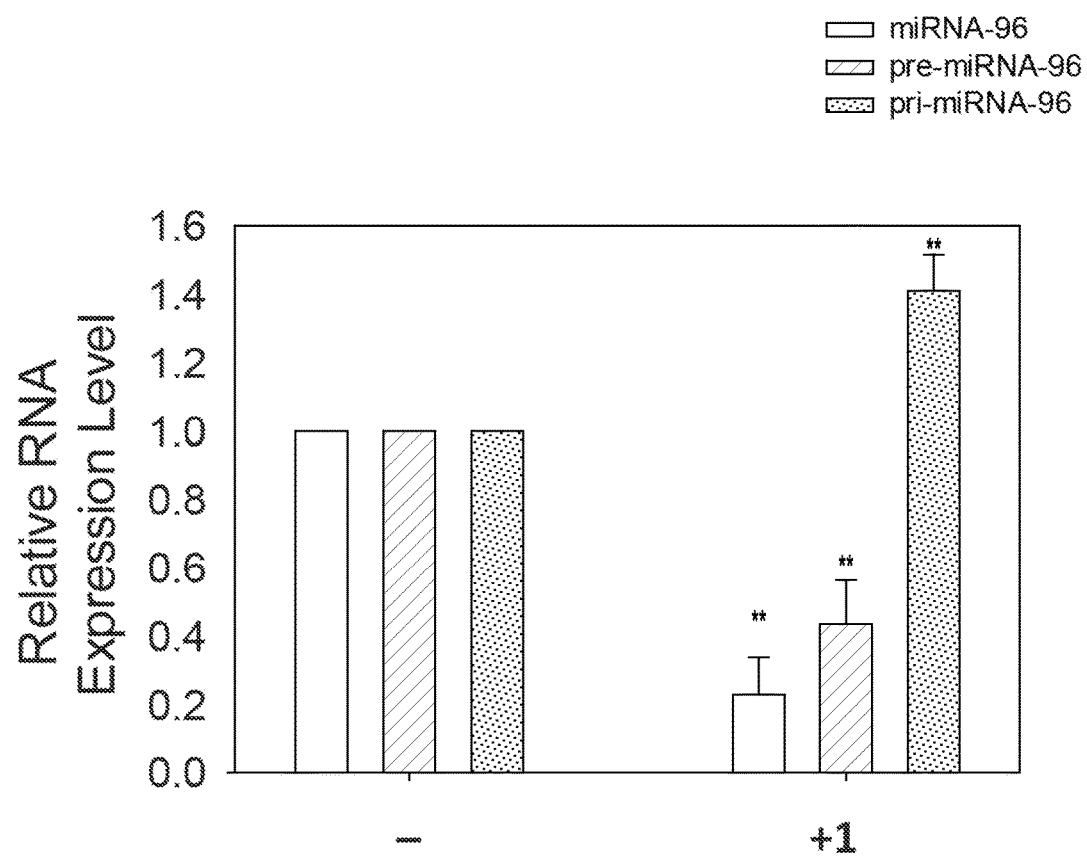

To confirm that the binding site of compound 1 in the miR-96 precursor was accurately predicted by inforna, the inventors completed nuclease protection assays. These studies confirm that compound 1 binds to the Drosha processing site (FIG. 9A). Moreover, compound 1 inhibits Drosha cleavage of pri-miR-96 in vitro (FIG. 9B) and in vivo, as evidenced by an increase in the amount of pri-miRNA and a reduction in pre- and mature miRNAs in treated cells, as expected if compound 1 binds to the Drosha site (FIG. 9C). Next, the inventors compared the selectivity of compound 1 to a locked nucleotide acid (LNA) oligonucleotide that is complementary to nucleotides 2-9 in microRNA-96's seed region (FIG. 5C). The LNA oligonucleotide directed at miR-96 was studied for silencing miR-96, miR-182, and miR-183; miR-182:LNA and miR-183:LNA complexes each contain a single mismatch. Interestingly, the LNA only modestly discriminates between miR-96 and miR-183 at all concentrations tested (1-200 nM) (FIG. 5C). At 50 nM concentration, the LNA silences about 90% of miR-96 expression and ~50% of miR-183 expression. Non-selective effects of oligonucleotides on silencing specific miRNAs have been previously observed (Stenvang et al., *Silence* 3, 1 (2012)). In contrast, at a concentration of compound 1 that silences 90% of miR-96 expression, microRNA-182 is affected by only 15% and microRNA-183 is unaffected (FIG. 5C). Taken together, small molecules targeting the secondary structure of precursor miRNAs can be more selective modulators of function than oligonucleotides that target RNA sequence perhaps due to energetic degeneracy in targeting sequence (even with mismatches) that does not occur when targeting structure with a small molecule. Another important advantage of small molecules is their cellular permeability, a property not innate to oligonucleotides.

EXAMPLE 5

The Downstream Effects of Compound 1

This Example illustrates the effect of compound 1 on the downstream targets of miR-96. MicroRNA-96 is upregulated in cancer and is linked to oncogenic transformation by silencing of FOXO1 (Forkhead box protein 01) through translational repression (Guttilla & White, *J. Biol. Chem.* 284, 23204-23216 (2009); Xie, et al., *Blood* 119, 3503-3511 (2012)). FOXO transcription factors function as regulators of cell cycle progression, including apoptosis (Dansen & Burgering, *Trends Cell Biol.* 18, 421-429 (2008)).

Compound 1 was tested for its ability to increase expression of FOXO1 protein using a luciferase model system. A target sequence fully complementary to miR-96 was inserted downstream of the Renilla luciferase gene (Guttila et al. *J. Biol. Chem.* 284, 23204-23216 (2009)). A small molecule that inhibits maturation of miR-96 will increase luciferase expression. MCF7 cells were transfected with a plasmid that express the luciferase model system, followed by treatment with 1. In agreement with decreased miR-96 production observed in qRT-PCR experiments (FIG. 5C), compound 1 stimulates production of luciferase, indicating inhibition of miR-96 maturation (FIG. 6A). Specifically, compound 1 increases production of luciferase by about 2.2-fold when cells are treated with 40 μM of compound. Importantly, compound 1 does not affect production of luciferase when a plasmid encoding a FOXO1 3' UTR that is unresponsive to miR-96 is used, confirming that miR-96, and not the FOXO1 UTR, is compound 1's target (FIG. 6A).

Figure 6B:
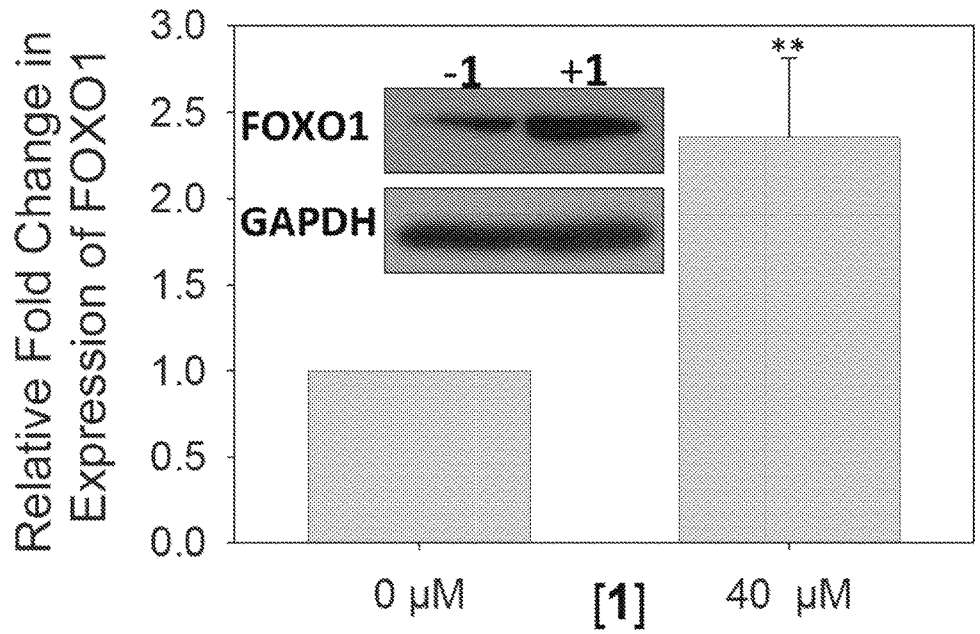
Figure 6C:
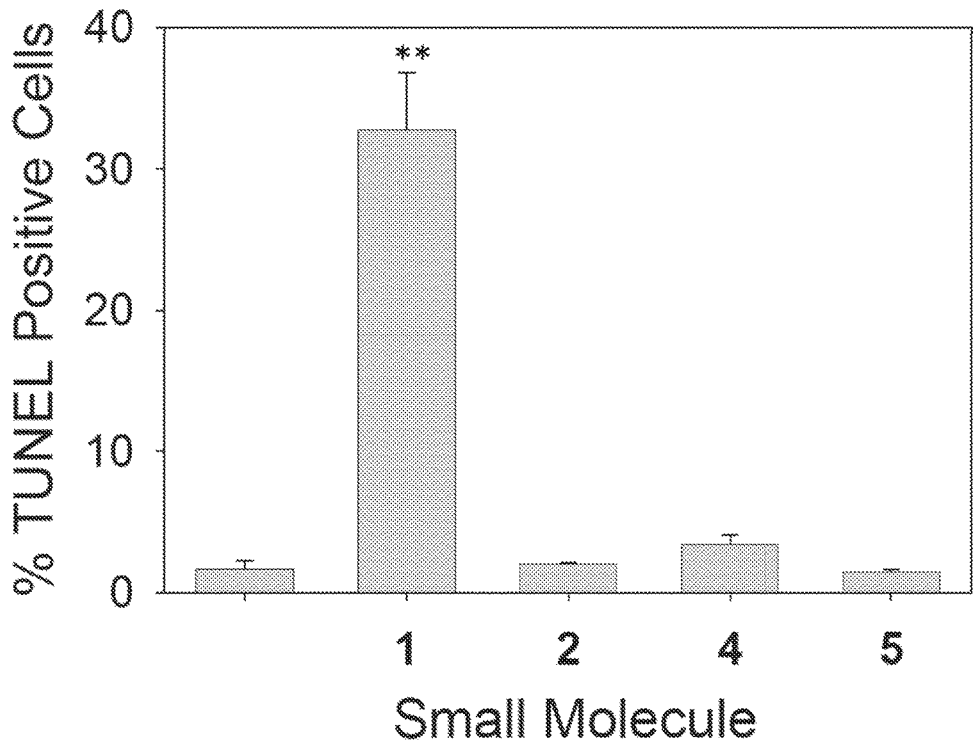
Figure 6D:
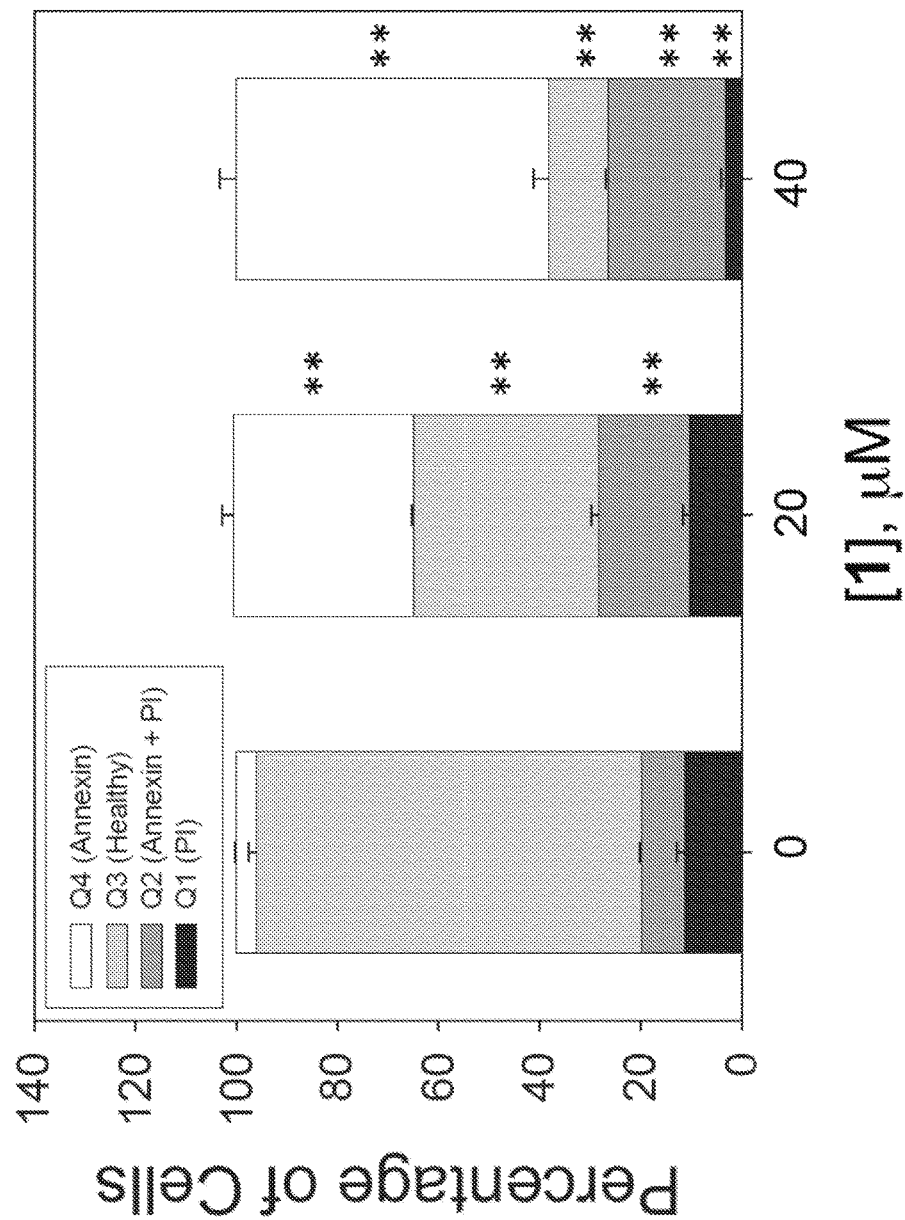
Figure 6E:
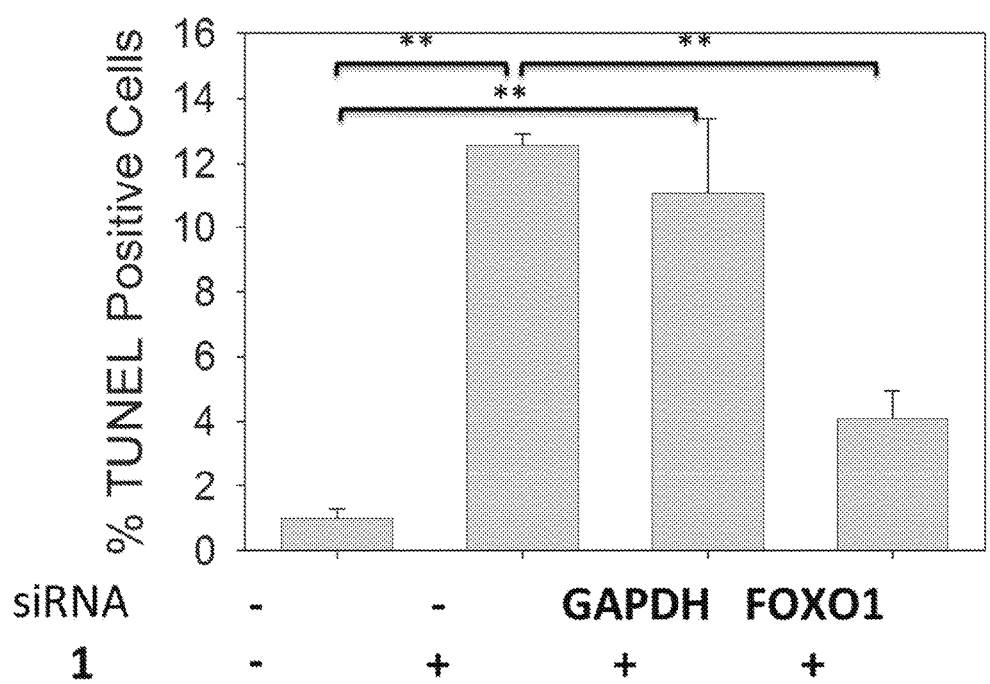
Figure 8A:
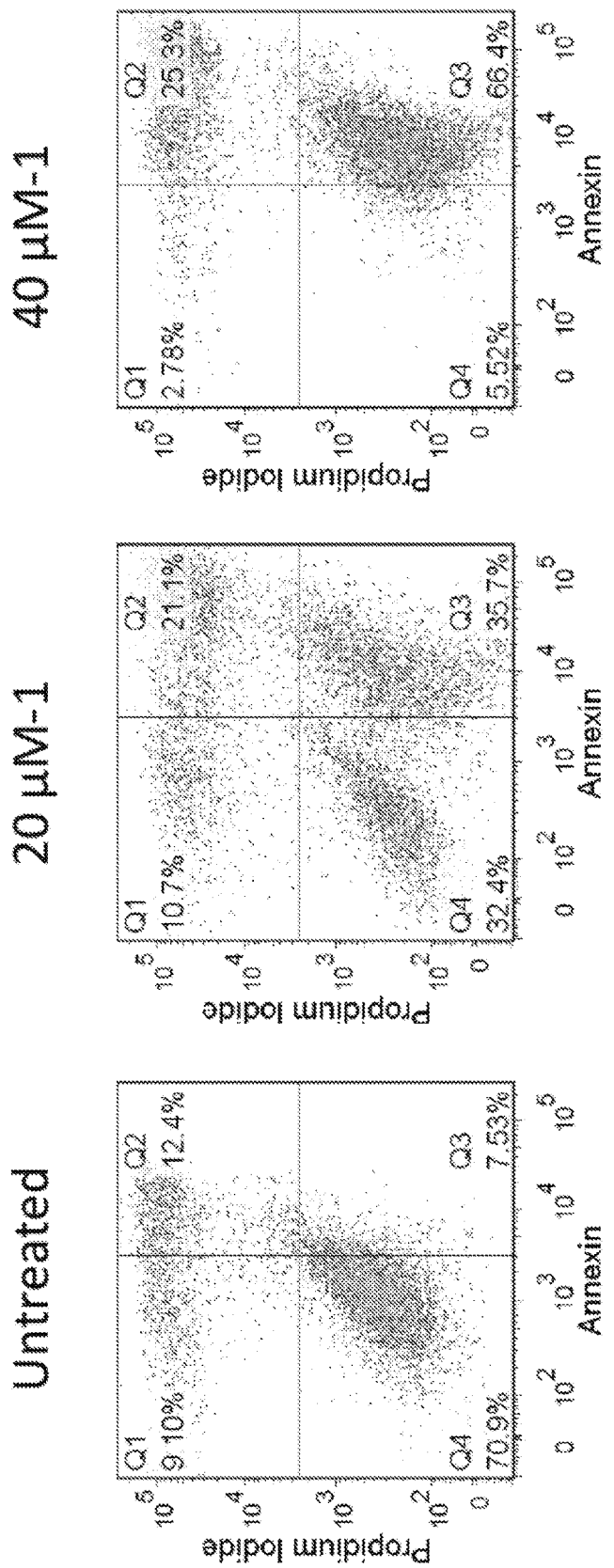
FIG. 8A-8B illustrate that Annexin V/Propidium Iodide staining and TUNEL assays confirm that compound 1 induces apoptosis and not necrosis. Annexin is an early marker for apoptosis. Propidium Iodide staining is an indicator of cell death.
Figure 8B:
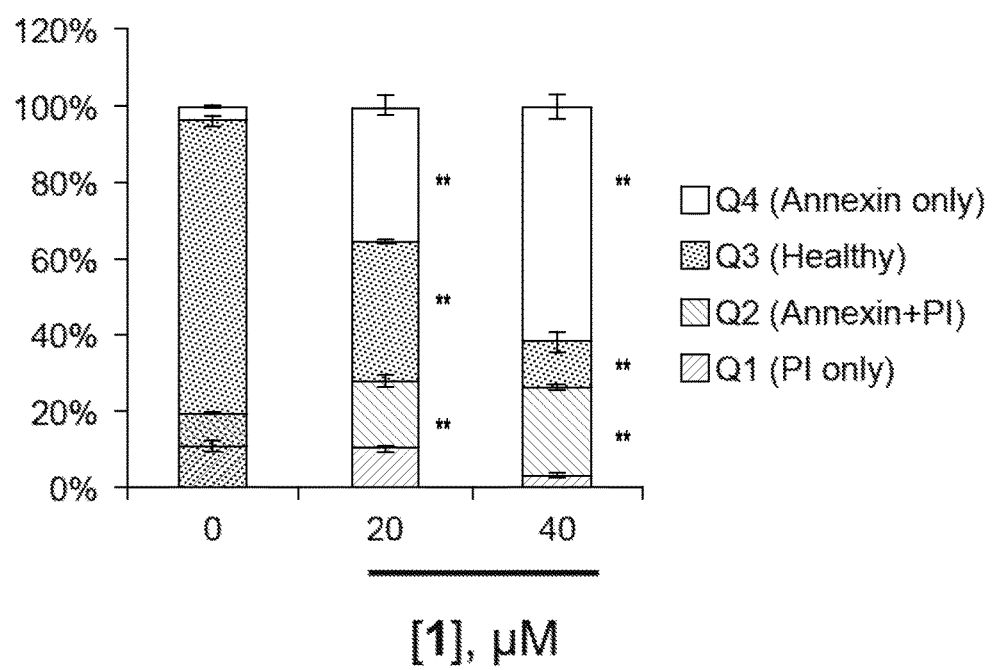

Next, the inventors tested compound 1 for its ability to increase endogenous levels of FOXO1 protein by Western blotting (FIG. 6B). When MCF7 cells were treated with 40 μM of compound 1, an approximate 2.5-fold increase in FOXO1 protein levels was observed, which is consistent with luciferase experiments. No effect was observed on the expression of a GAPDH control (FIG. 6B). FOXO1 upregulation stimulates apoptosis (Huang & Tindall, *Future Oncol.* 2, 83-89. (2006) 37). Therefore, the inventors determined if compound 1 stimulates late apoptosis via a TUNEL assay. When MCF7 cells are treated with 40 µM of compound 1, approximately 40% of the cells are TUNEL positive (FIG. 6C). As a secondary test of apoptosis, Annexin V/Propidium I assays were employed as they can distinguish necrosis from early apoptosis. As expected, these studies show that compound 1 stimulates early apoptosis, not global cell death via necrosis (FIG. 6C; FIG. 8A-8B).

EXAMPLE 6

Compound 1 can Stimulate Apoptosis

This Example illustrates that compound 1 induces apoptosis by modulation of the miR-96-FOXO1 regulation pathway.

As shown in FIG. 6E, addition of compound 1 dramatically increases the percentage of TUNEL-positive cells (note that the second bar is much higher than the first bar). If compound 1 induces apoptosis by selectively targeting miR-96, then removal of FOXO1 should affect apoptosis. FOXO1 expression was knocked down via siRNA (FIG. 6E) to illustrate the effects of reduced FOXO1 expression on apoptosis. As shown, knockdown of FOXO1 expression increases the percentage of TUNEL-positive cells, indicating that FOXO1 knockdown also increases or induces apoptosis. When FOXO1 siRNA is applied to cells that are then treated with compound 1, a 70% reduction in apoptosis is observed compared to cells transfected with an siRNA against GAPDH (control) and treated with compound 1 (FIG. 6E). It is not surprising that using an siRNA to ablate FOXO1 mRNA from cells does not completely eliminate the apoptotic effect of compound 1 because miRNAs can target many different mRNAs, and can silence different mRNAs simultaneously (Lewis et al., *Cell* 120, 15-20 (2005)). These studies, however, demonstrate that the miR-96-FOXO1 mRNA pathway is regulated by compound 1, illustrating that compound 1 is a specific inducer of apoptosis. This selectivity is traced to modulation of an oncogene rather than non-specifically affecting cellular function. Most anticancer therapeutics, such as cis-platin and chlorambucil, target biomolecules non-specifically, giving rise to side effects (Wolkenberg & Boger, *Chem. Rev.* 102, 2477-2495 (2002)).

EXAMPLE 7

Compound 1 Selectivity for MicroRNA-96

Figure 7A:
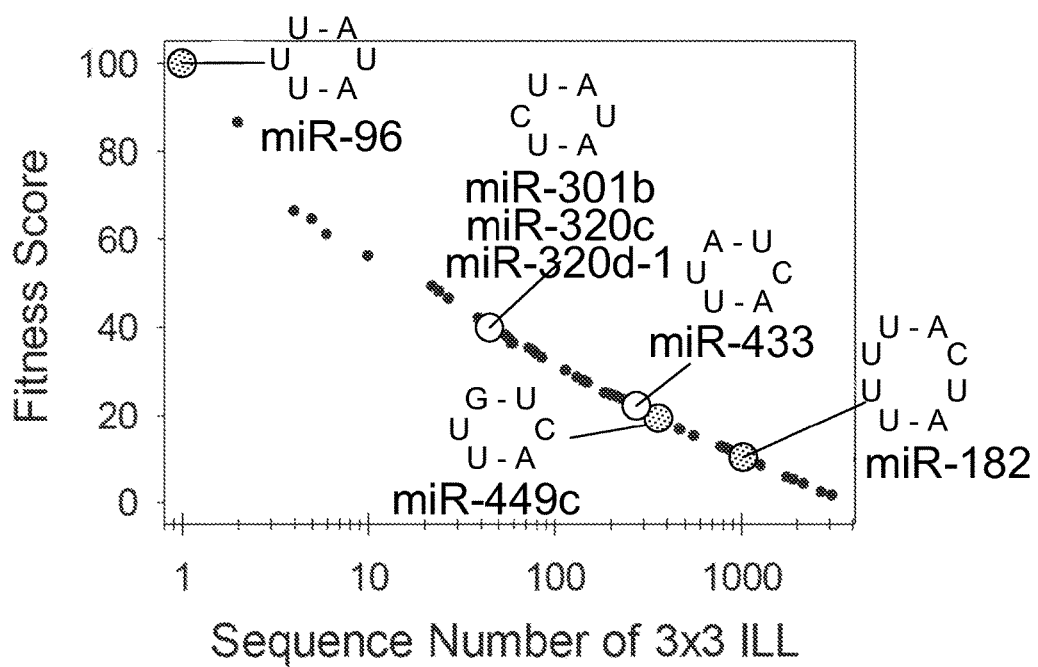
FIG. 7A-7B graphically illustrates how disease-associated microRNAs are affected by addition of 40 μM of compound 1.

Compound 1 was predicted to bind Dicer and Drosha processing sites in miRNA precursors other than the miR-96 precursor. However, these predicted Dicer and Drosha interactions appear to be less fit than that between compound 1 and the miR-96 precursor (FIG. 7A).

Figure 7B:
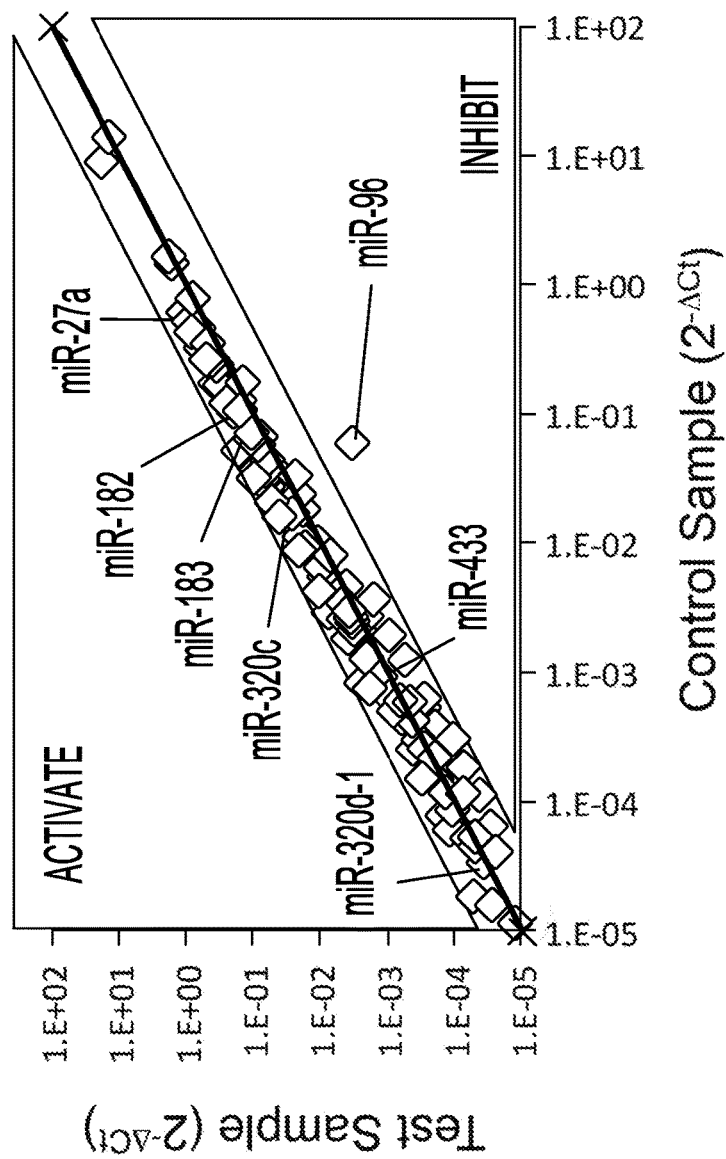

Therefore, the selectivity of compound 1 for modulating expression of 149 disease-associated and highly abundant miRNAs (Tables 1 and 2) was assessed via qRT-PCR (FIG. 7B). As shown in FIG. 7, the only miRNA that is significantly affected by compound 1 is miR-96.

These studies confirm the selectivity of compound 1 for the designed target on a transcriptome-wide level. Thus, it appears that compound 1 provides an unparalleled level of selectivity for a small molecule that modulates RNA function and has selectivity that can go beyond that observed with some miRNA-targeting oligonucleotides, as evidenced by the studies in FIG. 5C.

EXAMPLE 8

Comparison of Inforna to Traditional Medicinal Chemistry Approaches

Figures 2, 12A:
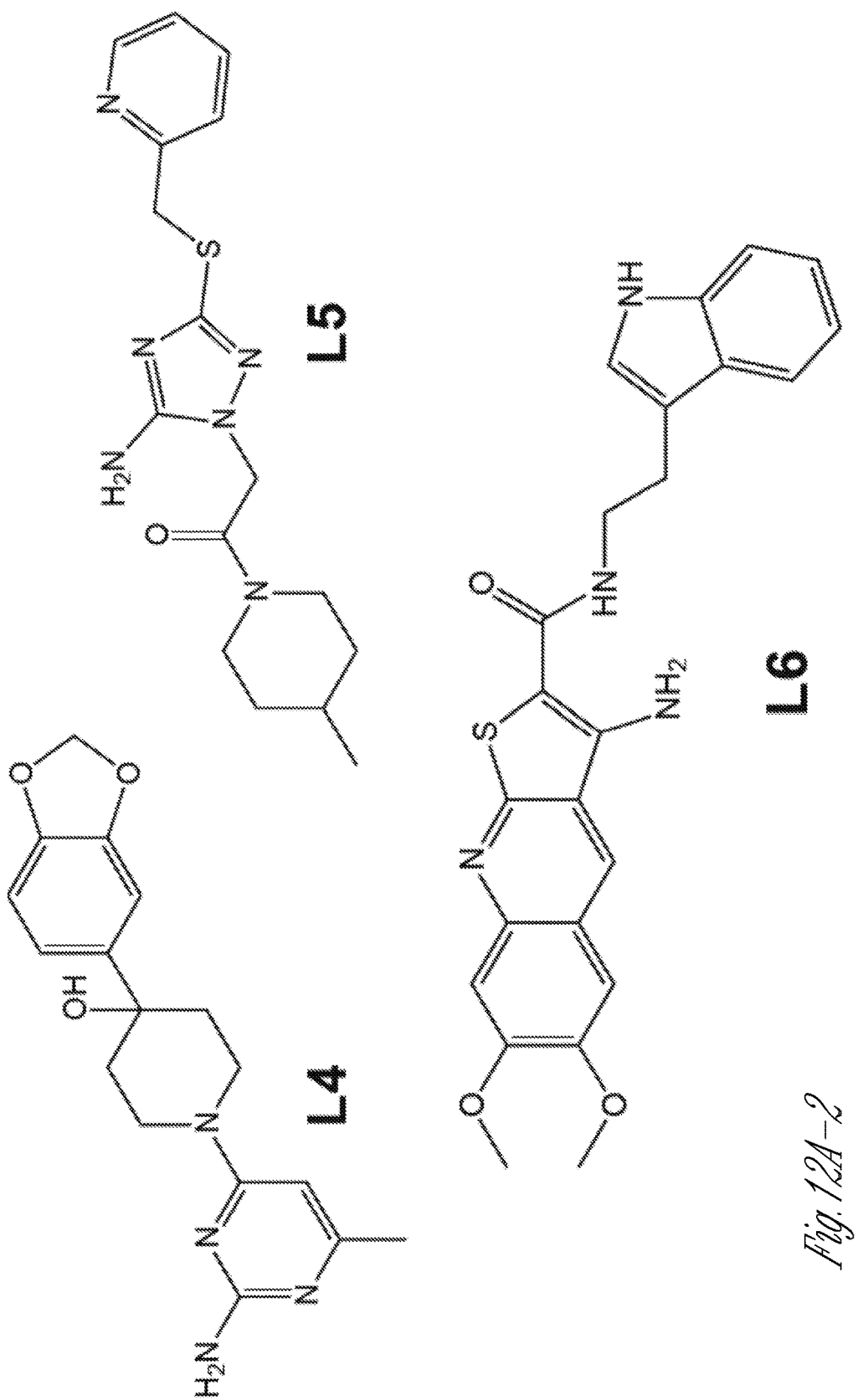
FIG. 12A-12B shows the structures of compounds and results of a luciferase assay for assessing whether the compounds inhibit miR-96 biogenesis.

The luciferase model system described above provides a robust assay to test other small molecules for modulating the miR-96-FOXO1 pathway. This system was therefore used to compare the design of small molecules via inforna to the more traditional medicinal chemistry approaches—screening and lead optimization via the synthesis of compound derivatives. First, a previously constructed library of small molecules was tested that are biased for binding RNA (28 total compounds; FIG. 12A) (Tran & Disney, *Nat. Commun.* 3, 1125 (2012)). None of the compounds stimulated luciferase production at 40 µM (FIG. 12B), indicating that: (i) the compounds are not bioactive; (ii) screening compounds is less effective than designing compounds with inforna even when the chemical library is biased for binding RNA; and (iii) miRNA-FOXO1 pathway is not easily drugable.

Figures 3, 12A:
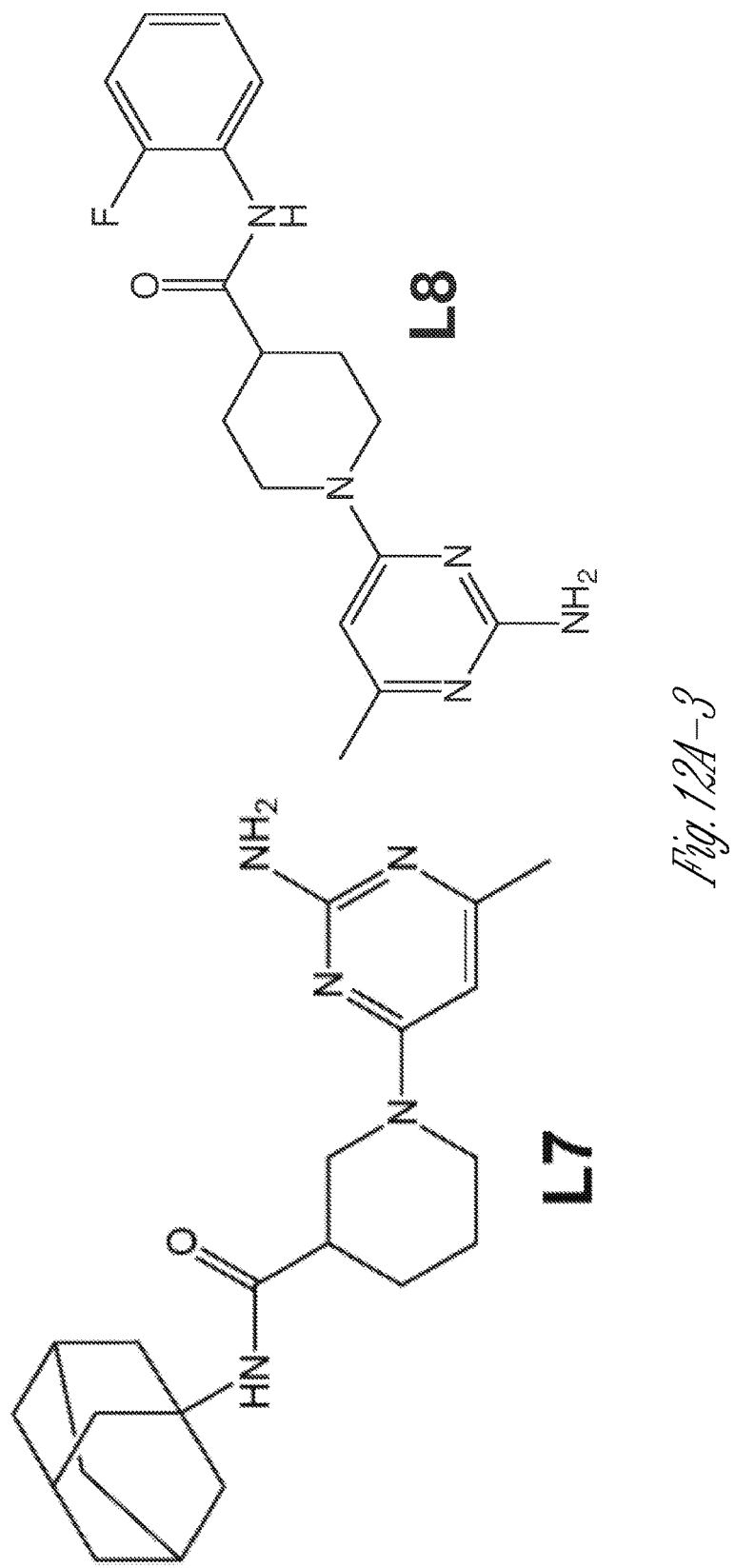
Figures 4, 12A:
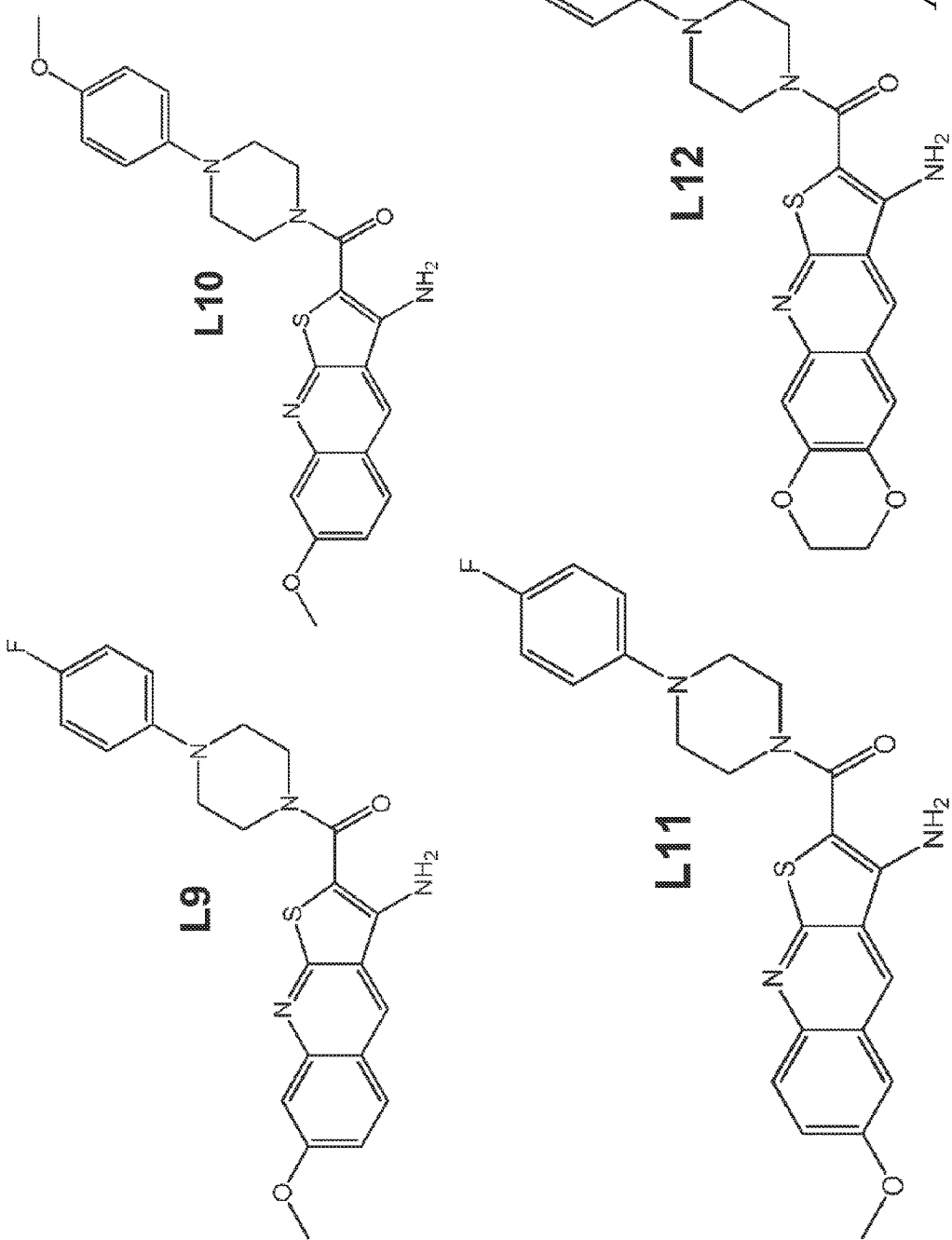
Figures 5, 12A:
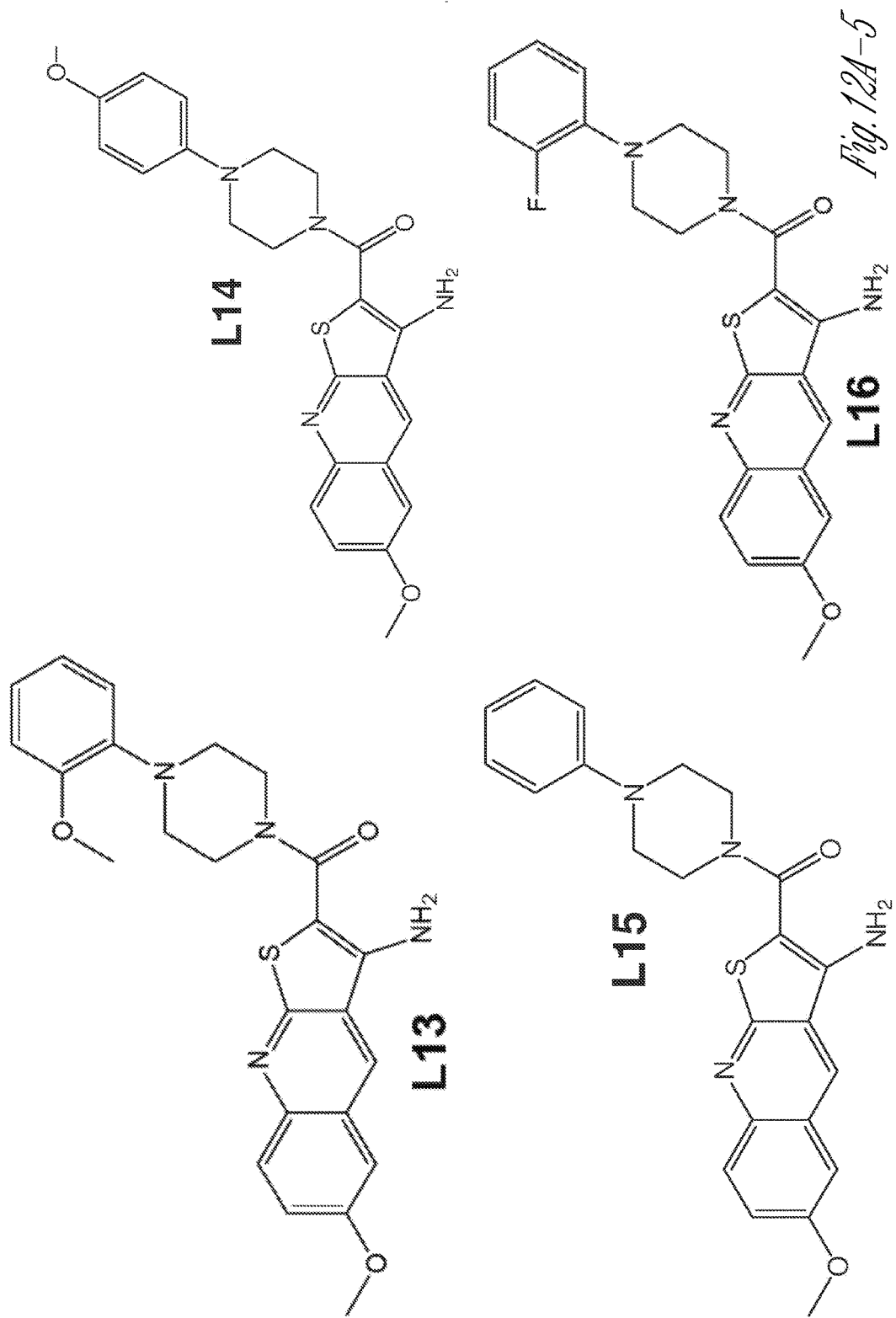
Figure 12A:
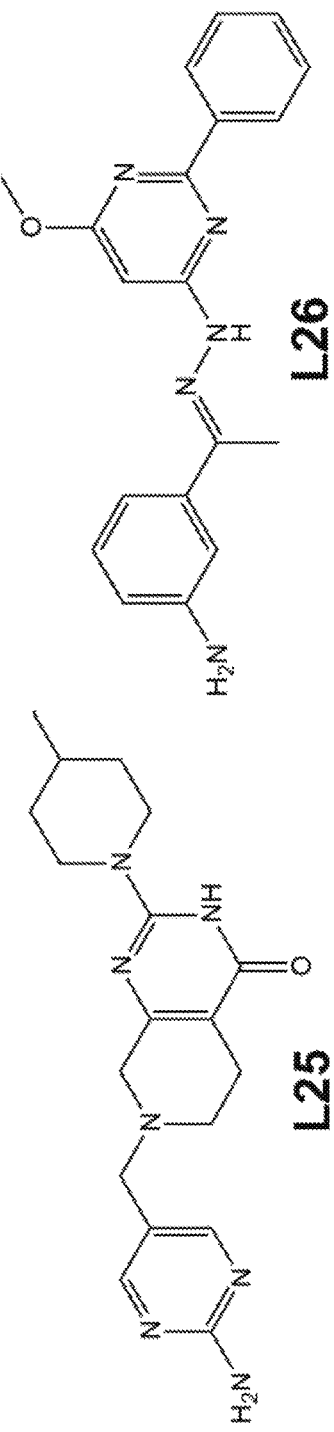
Figure 8:
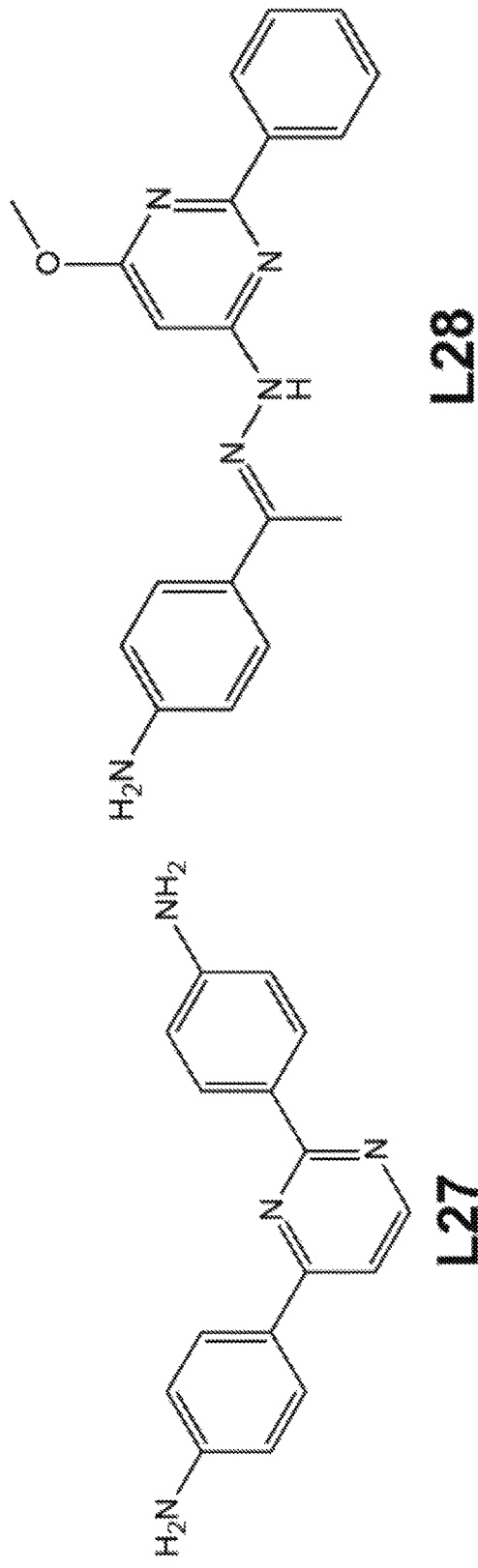
Figure 12B:
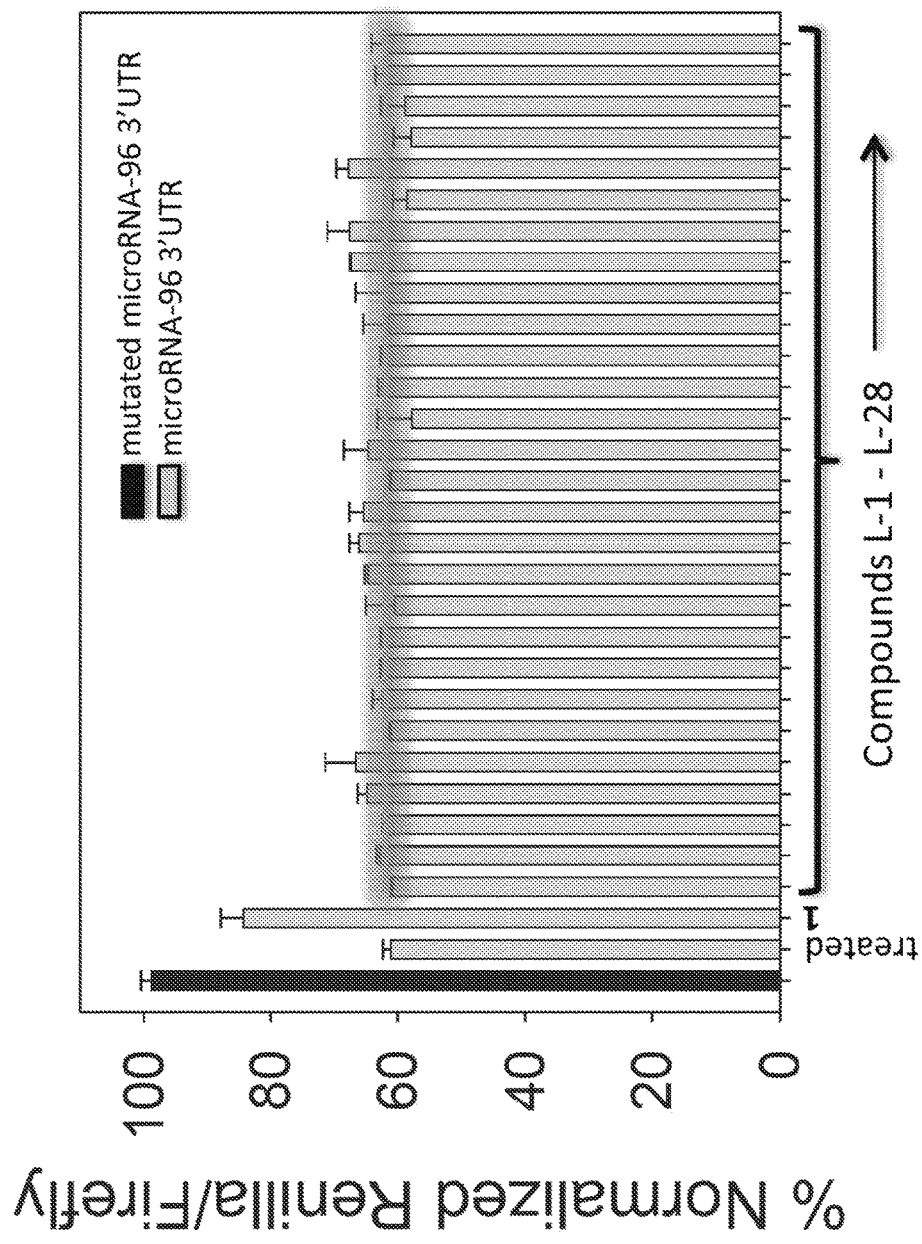

A commonly employed method for drug optimization is the synthesis of compound derivatives, i.e., chemically similar small molecules. We therefore tested three compounds that are chemically similar to 1, compounds 2, 4, and 5 (FIG. 3D), as determined by their shape Tanimoto coefficients (Hawkins et al., *J. Med. Chem.* 50, 74-82 (2007). Shape Tanimoto coefficients quantitatively determine the three dimensional similarity of two compounds; values range from 0 (no similarity) to 1 (complete similarity) (id.). The shape Tanimoto coefficients for compounds 2, 4, and 5 as compared to 1 are 0.94, 0.89, and 0.80, respectively, illustrating quantitative similarity between these compounds. Although all four compounds are based on a benzimidazole scaffold, visual inspection of structure suggests that compounds 2 and 5 might bind RNA with higher affinity than compound 1 because of the larger surface area and additional hydrogen bond donors and acceptors. Each of these factors suggests that these compounds could modulate miR-96 maturation. Despite their similarities, compounds 2, 4, and 5 have very different Fitness plots for binding to the target site of 1 in the miR-96 precursor (FIG. 4). In fact, inforna predicts that none of the compounds should bind avidly. A lack of binding affinity of these compounds for the miR-96 precursor was experimentally confirmed as shown in FIG. 4C-4I.

Figure 4J:
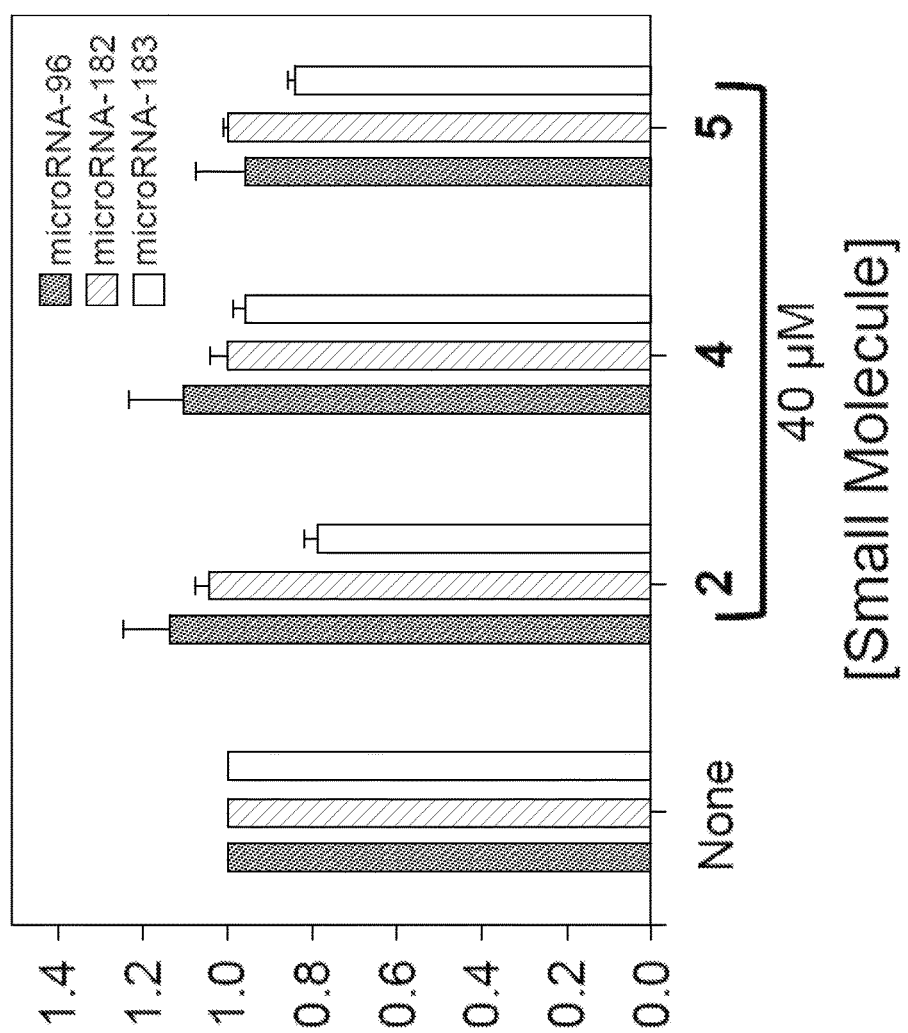

The activities of compounds 2, 4, and 5 were studied in the MCF7 cell line. The compounds are inactive at 40 µM concentration in all assays: (i) they do not affect miR-96 expression levels (FIG. 4J); (ii) they do not stimulate luciferase production in the microRNA-96-FOXO1 model system (FIG. 6A); and (iii) they do not induce apoptosis (FIG. 6C). The inactivity of 2, 4, and 5 is not due to differences in cellular permeability (FIG. 10). Thus, 2DCS, StARTS, and inforna provide reliable identification of small molecules that are capable and incapable of targeting RNAs, and these predictions are more accurate than standard medicinal chemistry approaches such as screening and chemical similarity searching. Moreover, inforna's hit rate is superior to high throughput screening and faster than computational approaches such as structure-based design and docking. For example, an important study used small molecule docking into an RNA dynamic ensemble to identify compounds that bind to HIV TAR RNA and modulate function (Stelzer et al., *Nat. Chem. Biol.* 7, 553-559 (2011)). However, the inventors have demonstrated that inforna enables reliable design of bioactive small molecules from sequence alone and without having to complete often laborious structural or docking studies.

EXAMPLE 9

Inforna Process

This Example describes computational aspects of the inforna process.

Many RNA motif-small molecule interactions have been identified by using a small molecule library-versus-RNA library screening platform developed by the inventors and their co-workers—presently about 1,500. Computational tools are generally needed to effectively assemble and process this information so that RNA molecules (especially larger, cellular RNAs) can become effective drug targets. To enable the facile programmatic searching of these interactions against a target RNA, the inventors constructed a dataset of RNA motif-small molecule interactions and inforna, which can be a web-based front end for searching the database.

Description of the Database

A schema of the database is shown in FIG. 13A. The database contains a list of all RNA motif-small molecule interactions identified by 2DCS or by other methods. Each entry is assigned the following parameters, which comprise four tables that are linked for facile searching: (i) a unique small molecule identifier; (ii) a unique motif identifier; (iii) the motif type; (iv) the motif size; (v) the motif sequence; (vi) the closing base pair(s); (vii) the Fitness Score for the motif (indicates the overall fitness of the RNA motif-small molecule interactions and is highly correlated to affinity); (viii) the dissociation constant, $K_d$, if measured; and, (ix) other notes including the PubMed identification publication reference numbers.

Motif Table:
id INT creates a column "id" that will automatically increment each time a new entry is added to the table.
VARCHAR (#) indicates variable-length strings of text where "#" indicates the maximum number of characters with the string.
DOUBLE is an approximate numeric data type that may consist of an integer, fraction, or both and indicates that the contents of the column are numeric in nature.
(i) Motif Identifier: each RNA motif is assigned a numerical identifier. The current database has ~1500 RNA motif-small molecule partners.
(ii) Motif ID: each motif is assigned a number.
(iii) Sequence with Closing Pairs: entire sequence of the RNA motif
  5' Sequence: the 5' sequence of the RNA motif with the closing base pair
  3' Sequence: the 3' sequence of the RNA motif with the closing base pair
  Sequence with Base Pair: the entire sequence of the RNA motif and the closing base pairs
  Loop Nucleotides: sequence of RNA motif excluding closing base pairs
  Closing Pairs (5',3'): sequence of the 5' and 3' closing base pairs
(iv) Small Molecule ID: name of small molecule (also referred to as a ligand) that the RNA motif binds (v) Size INT: links to the Motif Type & Size table to autopopulate the table and assign a unique identifier to each row; creates a column "id" that will automatically increment each time a new entry is added to the table.
(vi) Motif Type: each motif type (hairpin, 3×3 nucleotide internal loop, etc.) is assigned a unique numerical identifier.
(vii) Fitness Score: represents the fitness of the RNA motif for binding the small molecule (small molecule).
(viii) Len: indicates the length (integer values only) of the randomized region, or loop nucleotides.
(viii) Kd nM error nm: binding affinity (dissociation constant; $K_d$) or $IC_{50}$ if determined is shown in the output
(x) PMID: PubMed ID Motif Size Table. The Motif Size table is linked to the Motif Table as shown in FIG. 13A.
id INT creates a column "id" that will automatically increment each time a new entry is added to the table.
VARCHAR (#) indicates variable-length strings of text where "#" indicates the maximum number of characters with the string.
(i) Motif Size ID: each motif type is represented with a numerical identifier, which is annotated within this table. The "motif size" can have different functional forms. For example, for hairpins and bulges, the motif size is simply a number that indicates the number of nucleotides in the loop. The functional form for internal loops is "A×B" where A indicates the number of 5' unpaired nucleotides and B indicates the number of 3' unpaired nucleotides. The functional form for the motif size of a multibranch loop can have multiple forms such as "A×B×C" or "A×B×C×D", indicating a 3- or 4-way junction, respectively.

Small Molecule Table. The Small Molecule table is linked to the Motif Table as shown in FIG. 13A.
id INT creates a column "id" that will automatically increment each time a new entry is added to the table.
VARCHAR (#) indicates
(i) Small Molecule ID: a numerical identifier assigned to each small molecule starting from 1. The current database has 24 small molecules.
(ii) Small Molecule Name: name assigned to each small molecule to identify it.
(iii) SMILES: SMILES, or simplified molecular-input line-entry system, is text that describes the small molecule's structure. SMILES text can be input into various programs to reconstitute the small molecule's structure. There is separate folder of the structures with JPEG files that are output for each search.

Motif Has Ligand Table. The Motif Has Ligand table is linked to the Motif Table as shown in FIG. 13A. This table correlates the motif ID with small molecule ID.
id INT creates a column "id" that will automatically increment each time a new entry is added to the table.
VARCHAR (#) indicates variable-length strings of text where "#" indicates the maximum number of characters with the string.
(i) Small Molecule ID: a numerical identifier assigned to each small molecule starting from 1. The current database has 24 small molecules.
(ii) Motif ID: each motif type is represented with a numerical identifier, which is annotated in the Motif table.

Description of the Algorithm/Search Engine

A schematic of the search engine's flow of data is shown in FIG. 13B. The inforna software accepts a .CT file (a simple text file that describes the secondary structure of an RNA) with two search options: search loop nucleotides WITHOUT closing base pairs and search loop nucleotides WITH closing base pairs. The user is allowed to select a .CT file or a zip file that contains multiple .CT files. After choosing the .CT file and submitting the Search option, the application first calls a function to parse the .CT file. This function applies a parsing algorithm, which creates a database search parameter. Once the .CT file parsing function is completed another search parameter is created depending on the selected search option. When these functions are completed another function converts these search parameters into a SQL statement used to query the database. This SQL statement consists of the fields in the database that are being queried, the tables within the database that contain the queried fields, and the search criteria, which filters the result set based on the user's selected options.

Each record in the database is assigned a unique Motif ID, Motif Identifier, Motif Type, Motif Size, Closing Base Pair, Sum Z-score for the motif, which indicates statistical significance and is highly correlated to affinity, Fitness Score, Dissociation Constant (KO if measured and the PMID publication reference ID. There are two defined functions in the database that are used in parsing the CT files. Depending on the search criteria the database will either return no matches or a set of records that match the search criteria. This record set is now passed to the user interface where it is processed further to apply any format changes. Once this is complete this record set populates the user interface grid. The values are displayed in the following order: CT Filename, Compound Structure which is an image visualizing the SMILES field, Query Motif, Motif in Target RNA, Loop Nucleotides, Fitness Score, Loop Identifier, Dissociation Constant ($K_d$) if measured and the PMID publication reference link (FIG. 3). Since the search results can be rather large, a 200 row limit is applied to reduce the load of the server and the lag between search submissions. If the user wishes to view all the records, an export to excel option is available. This option is not limited to searches with over 200 records returned.

Output of a Database Query. The output of a database query includes (FIG. 3):
- the structure of the RNA that was queried (as a .ct file)
- structure of the small molecule that binds a motif in the queried RNA. The associated SMILES text is available by clicking on the structure of the small molecule.
- motif within the database that is similar to or exactly matches motif(s) in the queried RNA that binds the small molecule
- motif in the queried RNA that is predicted to bind the small molecule small molecule
- loop nucleotides in motif from the queried RNA
- Fitness Score
- Loop Identifier
- Dissociation Constant ($K_d$ or $IC_{50}$)
- PMID that is linked to the database at ncbi.nlm.nih.gov/pubmed/.

EXAMPLE 10

Designer Small Molecules that Target the Precursor to microRNA-96 and Trigger Apoptosis Selectively in Breast Cancer Cell Lines This Example describes the identification of small molecules that can target dimer loops in the secondary structures of RNA molecules, and the ability of such small molecules to reduce microRNA-96 levels and trigger apoptosis in cancer cells Materials and Methods Chemicals: Fmoc protected rink amide resin, diisopropylcarbodiimide (DIC) and 1-Hydroxy-7-azabenztriazole (HOAT), were purchased from Advanced ChemTech. 1-Ethyl-3-(3-dimethylaminopropyl) carbodiimide (EDC), Propylamine and Bromoacetic acid were purchased from Acros Organics. Propargylamine was purchased from Combi-Blocks. N,N Dimethylformamide (DMF), Dichloromethane and Methanol (ACS grade and HPLC grade) were purchased from Fisher Scientific. Dry N,N Dimethylformamide (dDMF) was purchased from EMD. N,N-Diisopropropylethylamine (DIEA) and trifluoroacetic acid (TFA) were purchased from Alfa Aesar. Piperidine was purchased from Sigma-Aldrich.

Mass Spectra: Mass spectra was recorded on a 4800 plus MALDI TOF/TOF analyzer.

Preparative HPLC: Peptoids were purified using either a reverse phase Atlantis Prep T3 C18 5 μM column or a Sunfire Prep C18 5 μM 19×150 mm column. HPLC separations were completed using a Waters 1525 Binary HPLC Pump equipped with a Waters 2487 Dual Absorbance Detector system. A linear gradient from 20% to 100% B in A over 60 min and a flow rate of 5 mL/min were employed. (A: water+0.1% (v/v) TFA; B: methanol+0.1% (v/v) TFA.)

Analytical HPLC: The purity was evaluated on a reverse phase Waters Symmetry C18 5 μm 4.6×150 mm column at room temperature. A flow rate of 1 mL/min and a linear gradient of 0% to 100% B in A over 60 min were applied. Absorbance was monitored at 220 and 345 nm.

General Protocol for Peptoid Synthesis: Peptoids were synthesized via standard resin-supported oligomerization protocol[1]. Fmoc-protected rink amide resin (200 mg, 138 μmol) with a substitution level of 0.69 mmol/g was allowed to swell for 5 min each in DCM and DMF with shaking. The resin was deprotected with 20% piperidine in DMF (3 mL, 2×20 min) at room temperature.

Coupling Step: The resin was then washed with DMF (3×5 min) Bromoacetic acid was coupled to the resin bound amine in the presence of 5 equivalents of bromoacetic acid and 5 equivalents of DIC in 3 mL dDMF. The reaction mixture was heated in a Panasonic microwave at 10% power (70 watts) (2×30 s). The resin was then washed with dDMF (3×5 min)

Displacement Step: (a) Introduction of click counterpart: The resin was then treated with 10 equivalents of propargylamine (1.38 mmol, 88 μL) in 3 mL of DMF in a Panasonic microwave at 10% power (70 watts) (1×30 s) and shaken at room temperature for 2 h. (b) Chain extension with spacer (propylamine): Coupling with Bromoacetic acid was repeated after the introduction of propargylamine. The resin was then treated with 10 equivalents of propylamine (1.38 mmol, 113 μL) in 3 mL of DMF in a Panasonic microwave at 10% power (70 watts) (1×30 s) and shaken at room temperature for 20 min. The resin was then washed with dDMF and reaction with propylamine was repeated one more time. Step (b) was repeated until the required length (n=1 to 4) of the peptoid was obtained.

Conjugation of Ligand Modules to the Peptoid Scaffold: The following process was employed:

(a) an Ht carboxylate with the following structure was coupled to the end of the peptoid backbone.

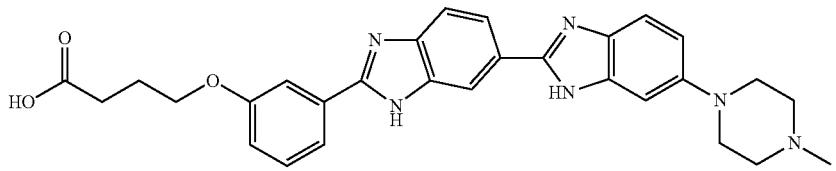 [SMILES: CN1CCN(c2ccc3nc(-c4ccc5nc(-c6cccc(OCCCC(=O)O)c6)[nH]c5c4)[nH]c3c2)CC1]

The peptoid (50 mg, 34.5 μmol) from the previous step was directly treated with a solution of Ht carboxylate (27 mg, 52 μmol), EDC (8 mg, 52 μmol), HOAT (7 mg, 52 μmol) and DIEA (66 μL, 345 μmol) in 2 mL dDMF in a microwave vial in a Biotage Initiator+ at 75° C. for 2 h. The resin was then washed with DMF (3×5 min)

(b) BSH azide was added onto the peptoid from the previous step via Huisgen dipolar cycloaddition reaction (HDCR). The peptoid (50 mg, 34.5 μmol) from previous step was directly treated with a solution of BSH azide (7 mg, 8.6 μmol), Cu(I) catalyst (1.5 mg, 2.6 μmol) and DIEA (66 μL, 345 μmol) in 2 mL dDMF in a microwave vial at 120° C. for 2 h in a Biotage Initiator+. The resin was then washed with DMF (3×5 min) followed by DCM (3×5 min) before cleaving the peptoid off the resin in (1:1) TFA:DCM for 15 min at room temperature. The solvent was removed under vacuum and the crude product was purified via HPLC as described in general methods.

General Methods for Cell Culture: MDA MB 231 cells were cultured in Roswell Park Memorial Institute 1640 medium (RPMI 1640) (Cellgro) supplemented with 10% FBS (Cellgro) and penicillin-streptomycin (MP Biomedicals). MCF-10A cells were cultured in Dulbecco's modified eagle medium/F12 (DMEM/F12) (Cellgro) supplemented with 10% FBS, 20 ng/mL EGF, 0.5 μg/mL hydrocortisone (Pfaltz and Bauer Inc.), 100 ng/mL cholera toxin (Sigma), 10 μg/mL insulin (Gemini Bio-Products) and penicillin-streptomycin.

Annexin V/PI Assays: MDA MB 231 or MCF-10A cells were grown in 6-well plates to 40-50% confluency. The cells were incubated with 50 nM of small molecule for 72 h and then detached from the surface using accutase. They were washed twice each with ice cold 1×DPBS and 1× Annexin Binding Buffer (50 mM Hepes (pH 7.4), 700 mM NaCl and 12.5 mM $CaCl_2$). The cells were resuspended in 100 μL 1× Annexin Binding Buffer, and then 5 μL Annexin V-APC (eBioscience) were added. The solution was incubated for 10 min at room temperature followed by washing with 1× Annexin Binding Buffer. The cells were then stained with 1 μg/mL propidium iodide in 300 μL of 1× Annexin Binding Buffer for 15 min at room temperature. Flow cytometry was performed using a BD LSRII instrument (BD Biosciences). At least 10,000 events were used for analysis.

Results

Figure 16A:
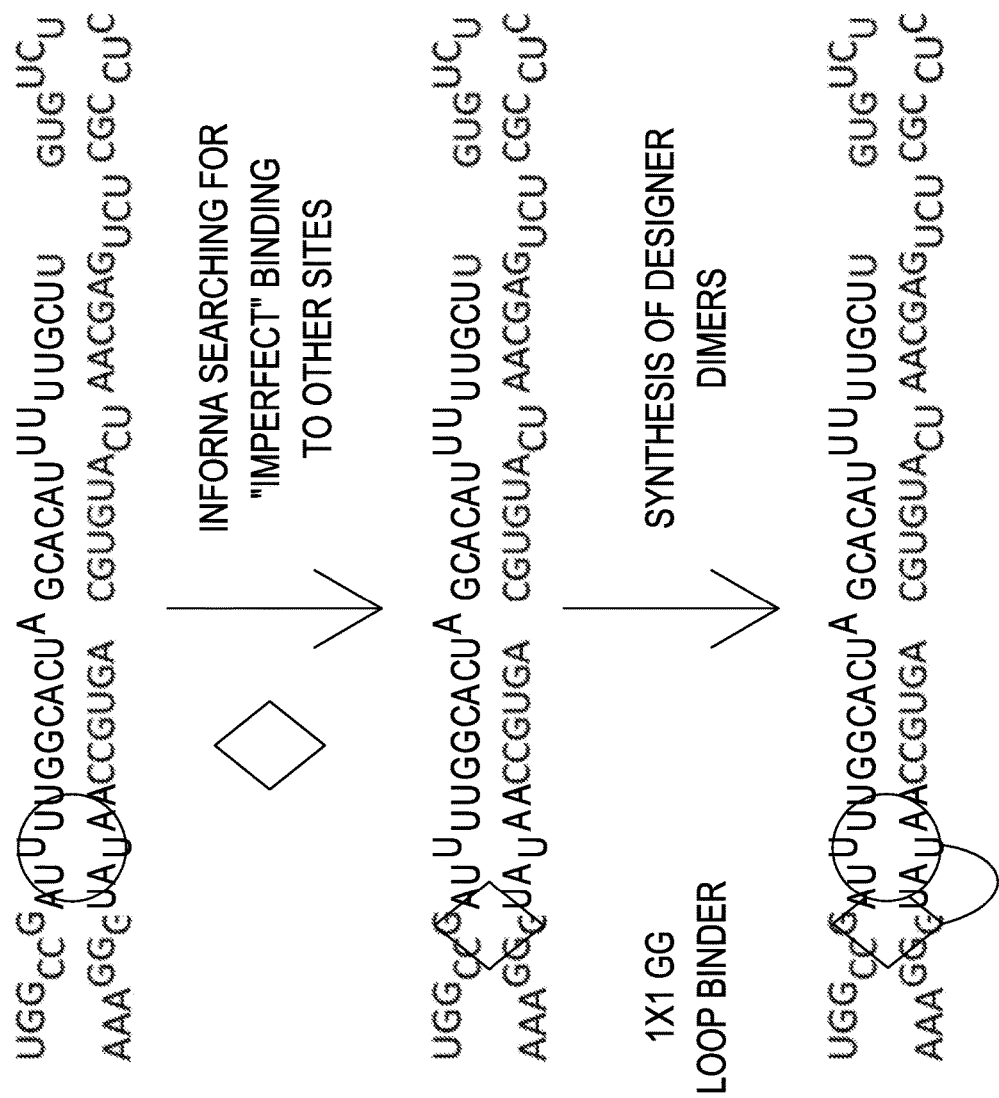
FIG. 16A-16C illustrates design of dimeric molecules that target precursor miRNA-96 (SEQ ID NO:11).
Figure 16B:
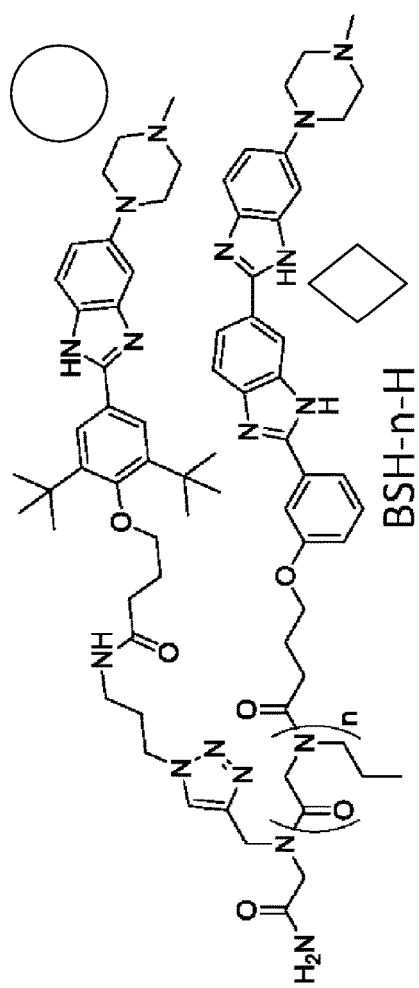
Figure 16C:
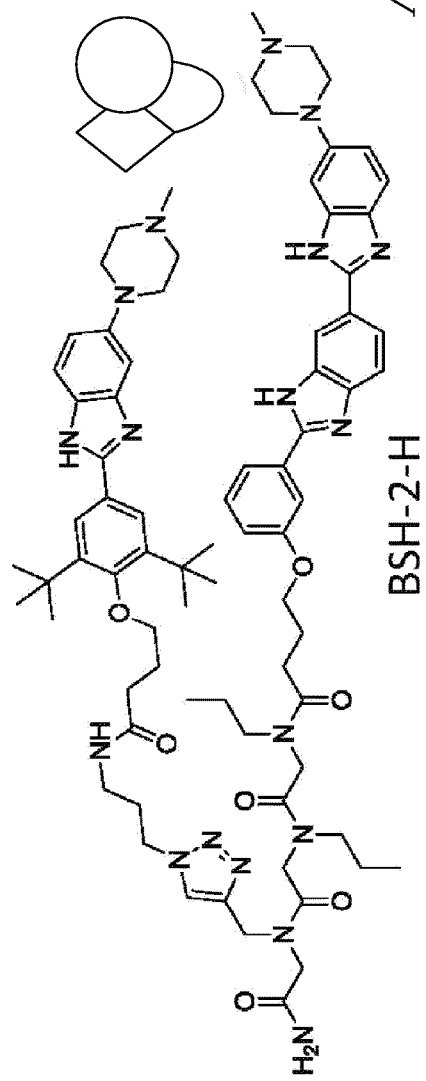

The lead small molecule 1 was optimized by using modular assembly approach enabled by Inforna. Briefly, the secondary structure of the microRNA-96 hairpin precursor was mined using the methods described herein to identify compounds that could bind to target sites in the RNA structure (FIG. 16). This process identified module H (diamond symbol in FIG. 16) as a binding molecule to the 1×1 nucleotide GG internal loop. By synthesizing appropriately spaced dimeric compounds, both the 1×1 nucleotide GG internal loop and the 1×1 nucleotide UU internal loop in the Drosha site (circled loop in FIG. 16) could be bound simultaneously by a single small molecule, resulting in an increase in the binding affinity and also in sufficient cellular potency for triggering apoptosis by the compounds.

The dimeric compounds were synthesized by using a modular assembly approach shown in the synthetic scheme below. A peptoid scaffold was employed where an azide derivative of compound 1 was the first module, and the second module was an acylated derivative of compound H, where the acylation was on an amino site on a peptoid backbone. A peptoid backbone was linked to the H compound, which was then linked to the azide derivative of compound 1 via a Huisgen dipolar cycloaddition reaction between the azide on compound 1 and an alkyne on the H peptoid. The spacing between the two modules was varied by inserting propylamine spacers between the RNA binding modules.

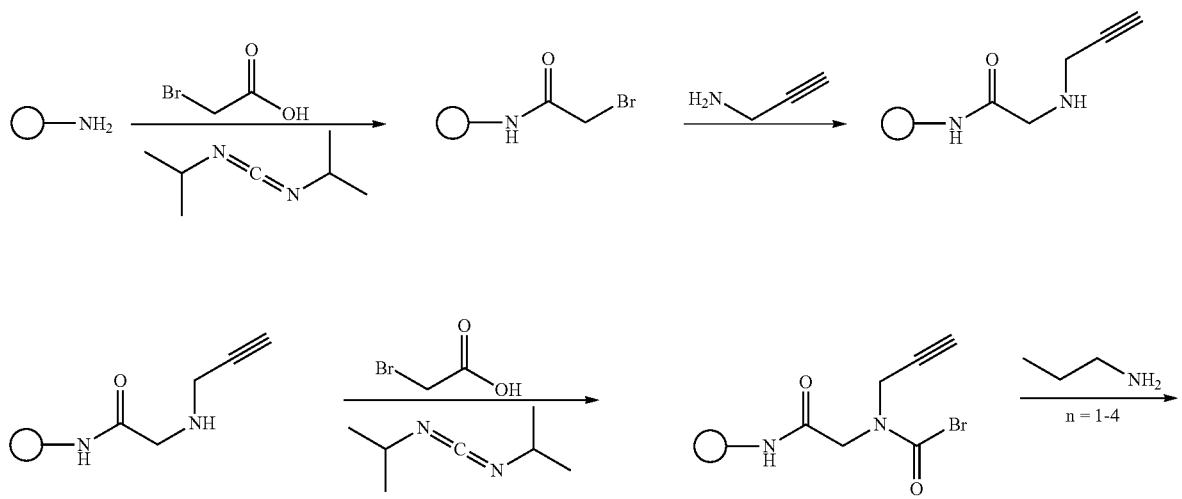

-continued
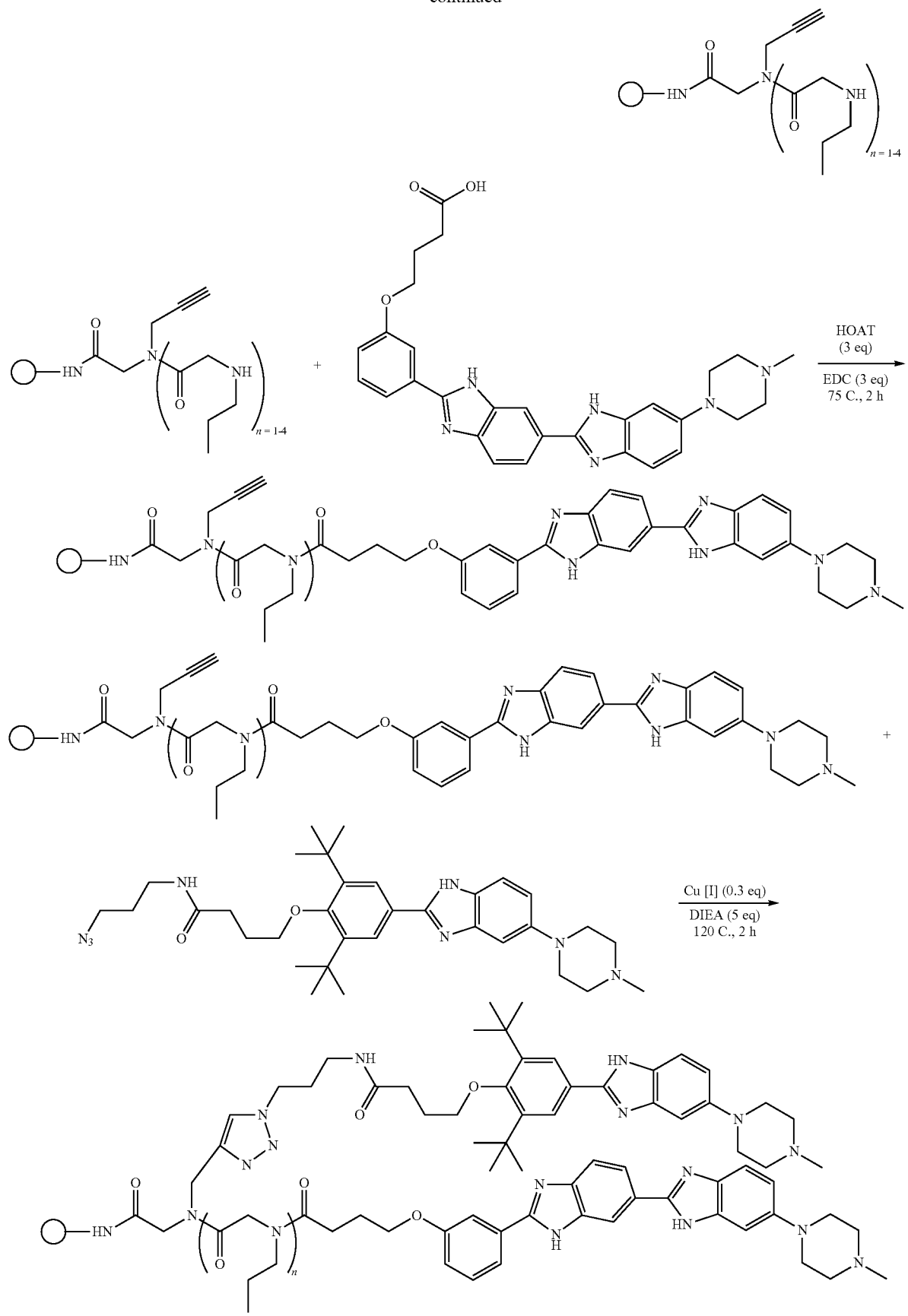

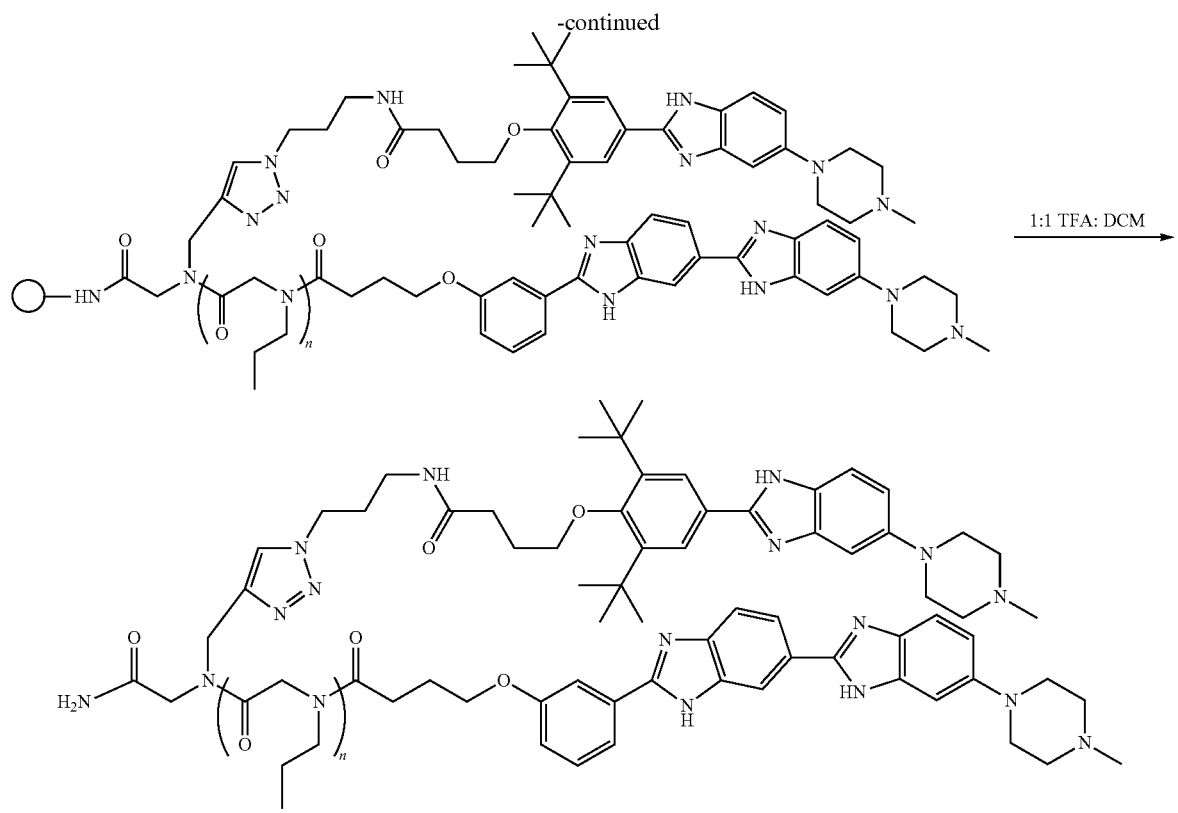

The compounds are called BSH-n-H in which the BSH refers to compound 1 and H refers to module 2, both conjugated onto the backbone. The number between these BSH and H is the number of propylamine spacers between the compound 1 and H RNA binding modules. Thus, BSH-1-H refers to a compound with one propylamine spacer between the two RNA binding modules. The structure of the BSH-n-H genus is shown below.

BSH-n-H

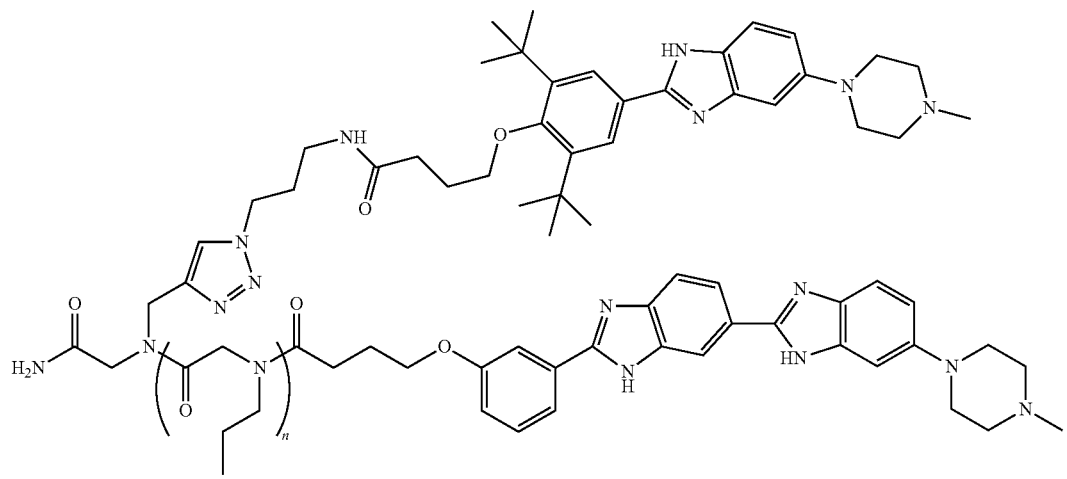

A library of these dimer compounds with varied spacing was synthesized according to the routes shown above. These dimer compounds were characterized using the methods described above. The results are shown in Table 3.

TABLE 3

Characterization of designer dimeric, BSH-n-H, compounds

| Compound Name | Structure | Expected/ Observed Mass (M + H$^+$) | t$_R$ (HPLC retention time) |
|---|---|---|---|
| BSH-1-H | 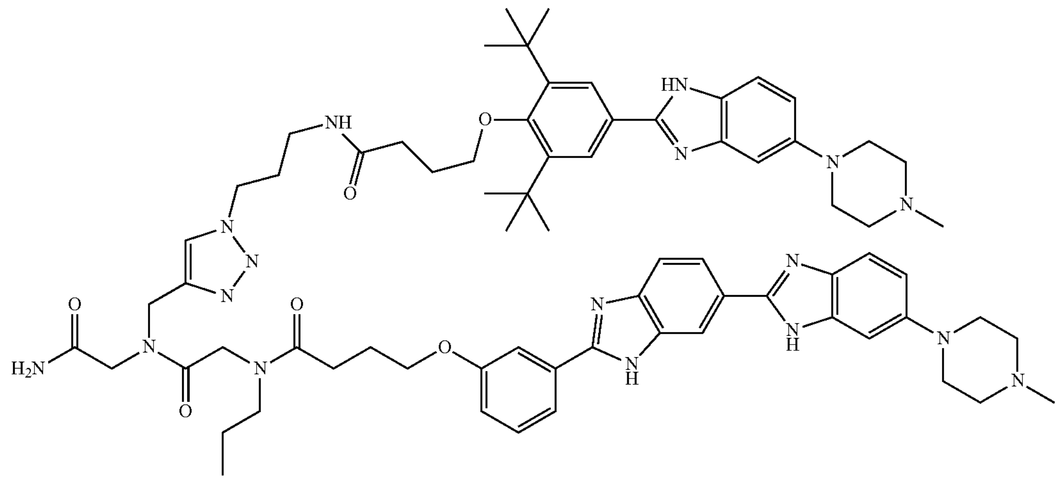 [SMILES: CCCN(CC(=O)N(CC(N)=O)CC1=CN(CCCNC(=O)CCCOc2c(C(C)(C)C)cc(-c3nc4cc(N5CCN(C)CC5)ccc4[nH]3)cc2C(C)(C)C)NN1)C(=O)CCCOc1cccc(-c2nc3ccc(-c4nc5ccc(N6CCN(C)CC6)cc5[nH]4)cc3[nH]2)c1] | 1292/1292 | 33 min (55% methanol) |

TABLE 3-continued
Characterization of designer dimeric, BSH-n-H, compounds
| Compound Name | Structure | Expected/ Observed Mass (M + H+) | $t_R$ (HPLC retention time) |
|---|---|---|---|
| BSH-2-H | 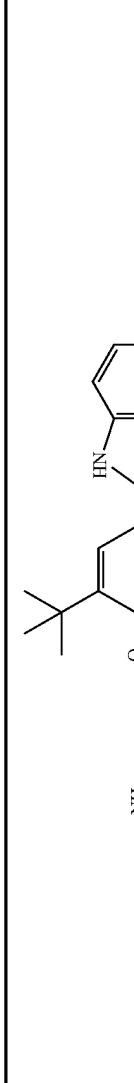 | 1392/1392 | 37 min (61% methanol) |

TABLE 3-continued

Characterization of designer dimeric, BSH-n-H, compounds

| Compound Name | Structure | Expected/ Observed Mass (M + H⁺) | $t_R$ (HPLC retention time) |
|---|---|---|---|
| BSH-3-H | 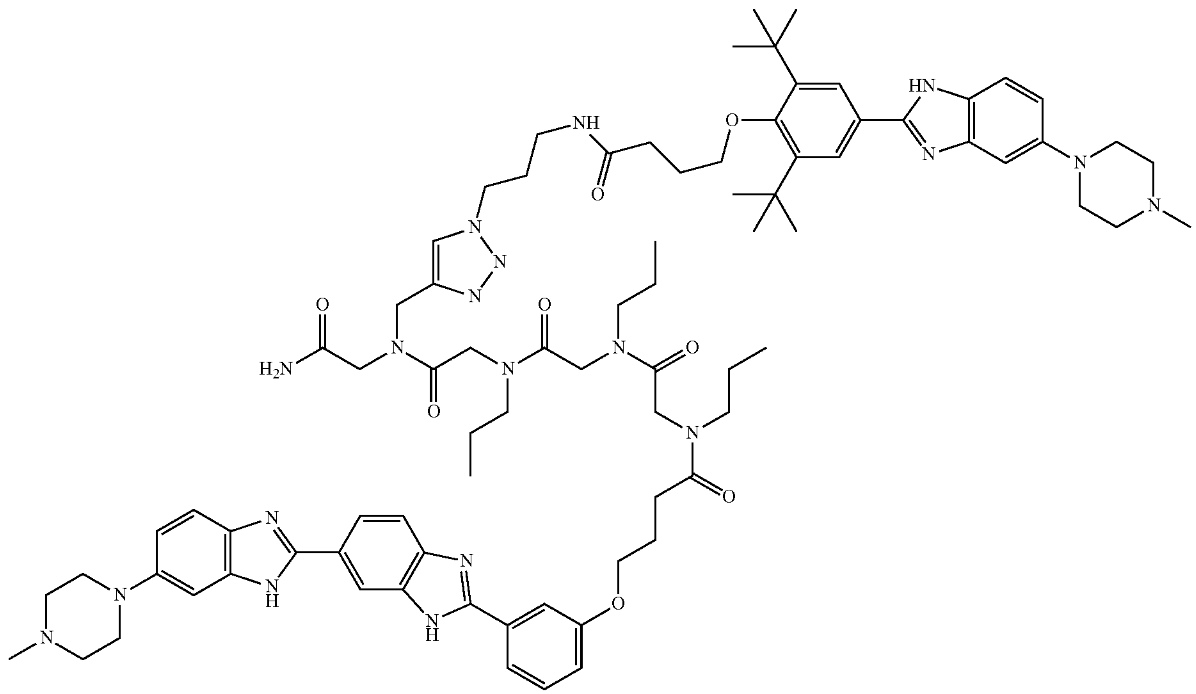 | 1490/1490 | 38 min (63% methanol) |

TABLE 3-continued

Characterization of designer dimeric, BSH-n-H, compounds

| Compound Name | Structure | Expected/ Observed Mass (M + H⁺) | $t_R$ (HPLC retention time) |
|---|---|---|---|
| BSH-4-H | 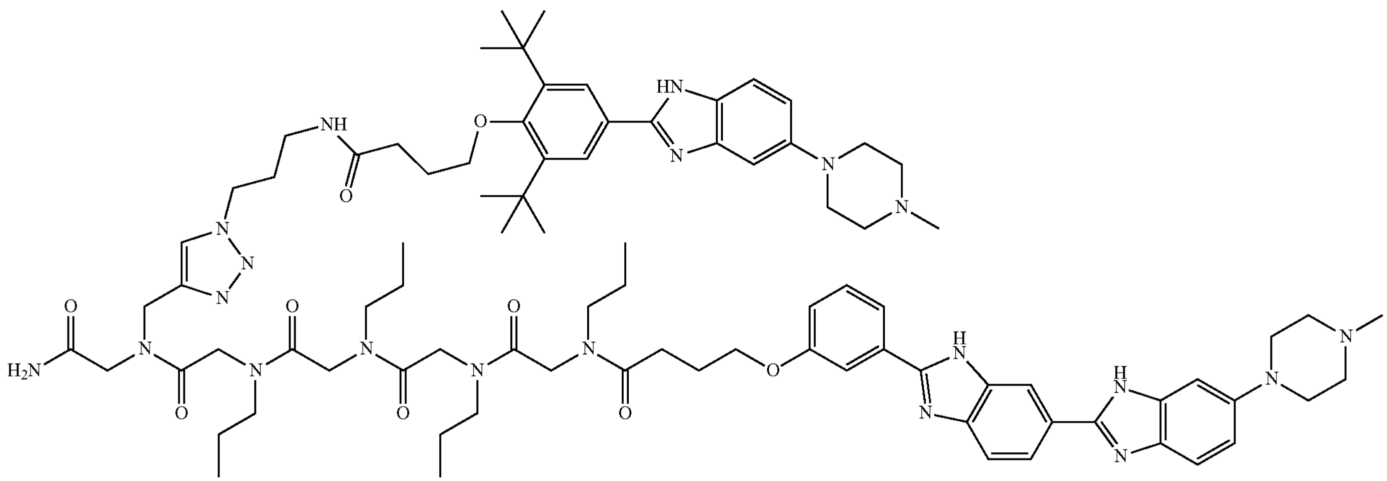 [SMILES: CCCN(CC(=O)N(CCC)CC(=O)N(CCC)CC(=O)N(CCC)CC(=O)N(CC(N)=O)CC1=CN(CCCNC(=O)CCCOc2c(C(C)(C)C)cc(-c3nc4cc(N5CCN(C)CC5)ccc4[nH]3)cc2C(C)(C)C)NN1)C(=O)CCCOc1cccc(-c2nc3ccc(-c4nc5ccc(N6CCN(C)CC6)cc5[nH]4)cc3[nH]2)c1] | 1590/1590 | 40 min (67% methanol) |

Figure 18:
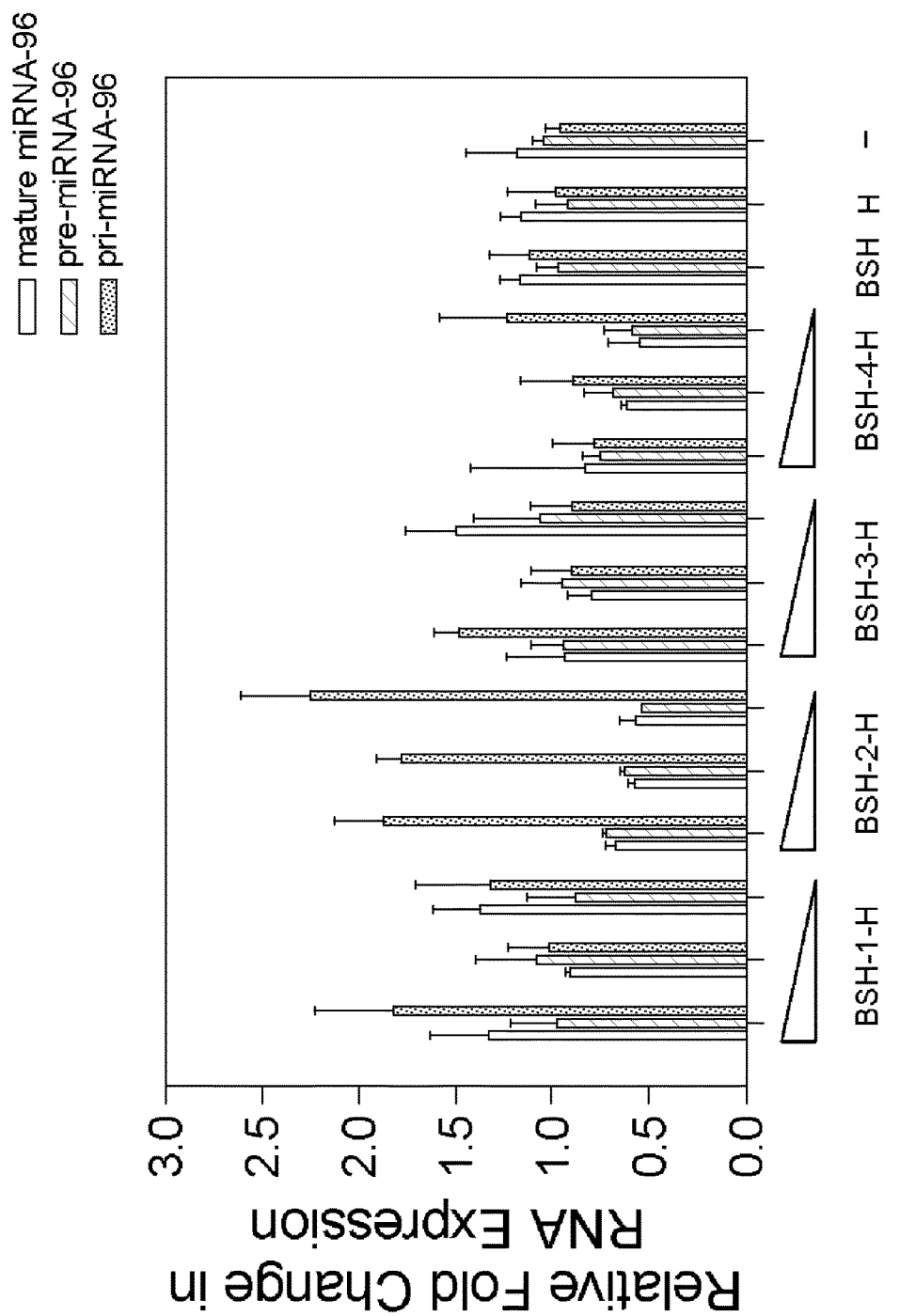
FIG. 18 graphically illustrates the quantities of mature miRNA-96, pre-miRNA-96, and pri-miRNA-96 in the presence of designed dimer molecules as a measure of the ability of these dimer molecules to modulate the microRNA-96 hairpin precursor biogenesis. The amounts of mature miRNA-96 (left bars), pre-miRNA-96 (middle bars), and pri-miRNA-96 (right bars) in MCF7 cells were detected by qRT-PCR after incubating the MCF7 cells with the designed dimer molecules (at 1 µM, 0.5 µM and 0.05 µM) for 24 hours. The BSH-2-H and BSH-4-H dimer compounds reduced mature miRNA-96 levels in a dose-dependent fashion. Compound BSH-2-H had the most significant effect on pri-miRNA 96 (an increase of about 2.3 fold) but the BSH-4-H dimer also increased the levels of pri-miRNA 96. The monomers BSH (compound 1) and H were tested as controls and had no effect at 0.05 µM.
Figure 20A:
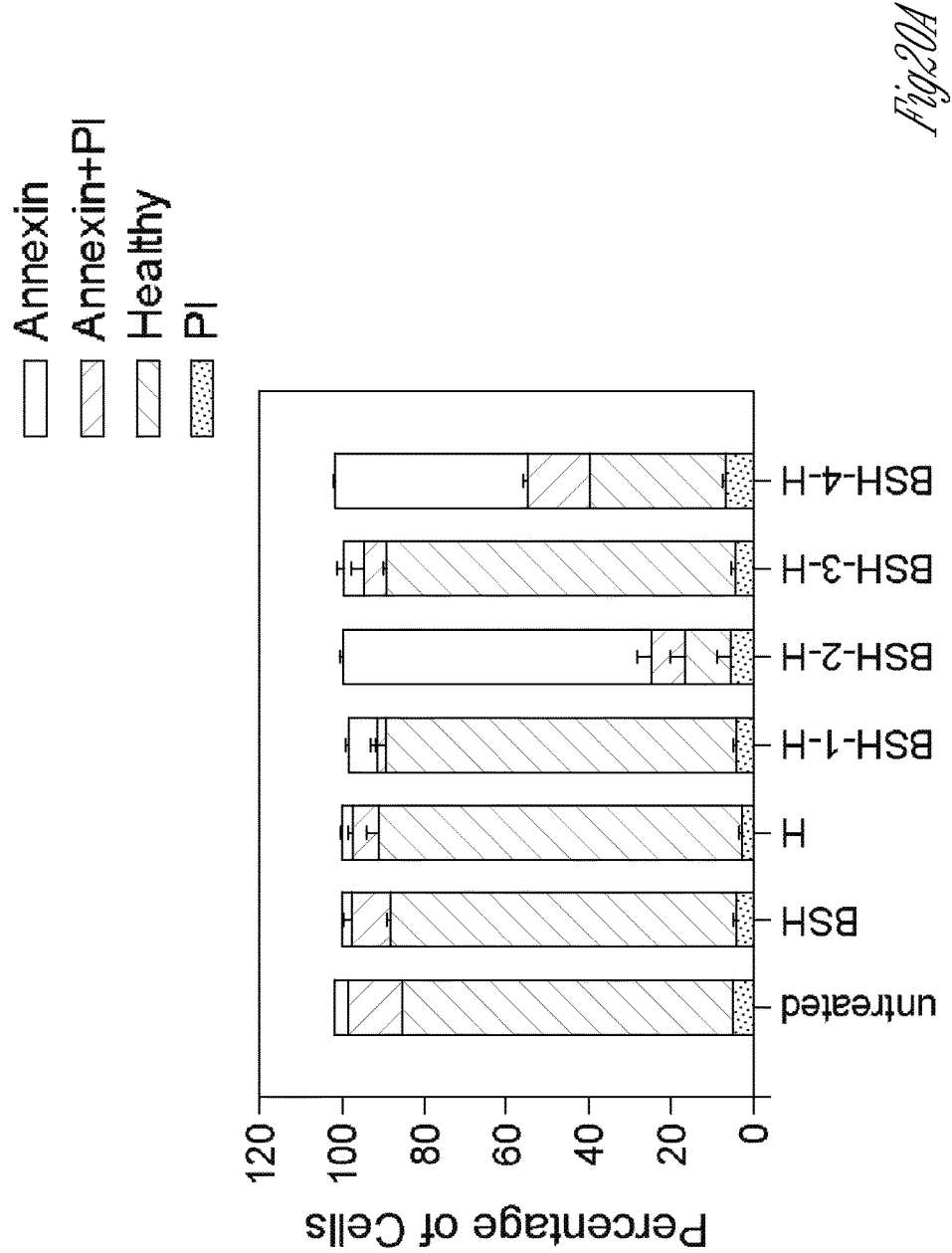
FIG. 20A-C graphically illustrates apoptosis in cancer cell numbers when the cells are incubated with dimer compounds BSH-1-H, BSH-2-H, BSH-3-H, and/or BSH-4-H.
Figure 20B:
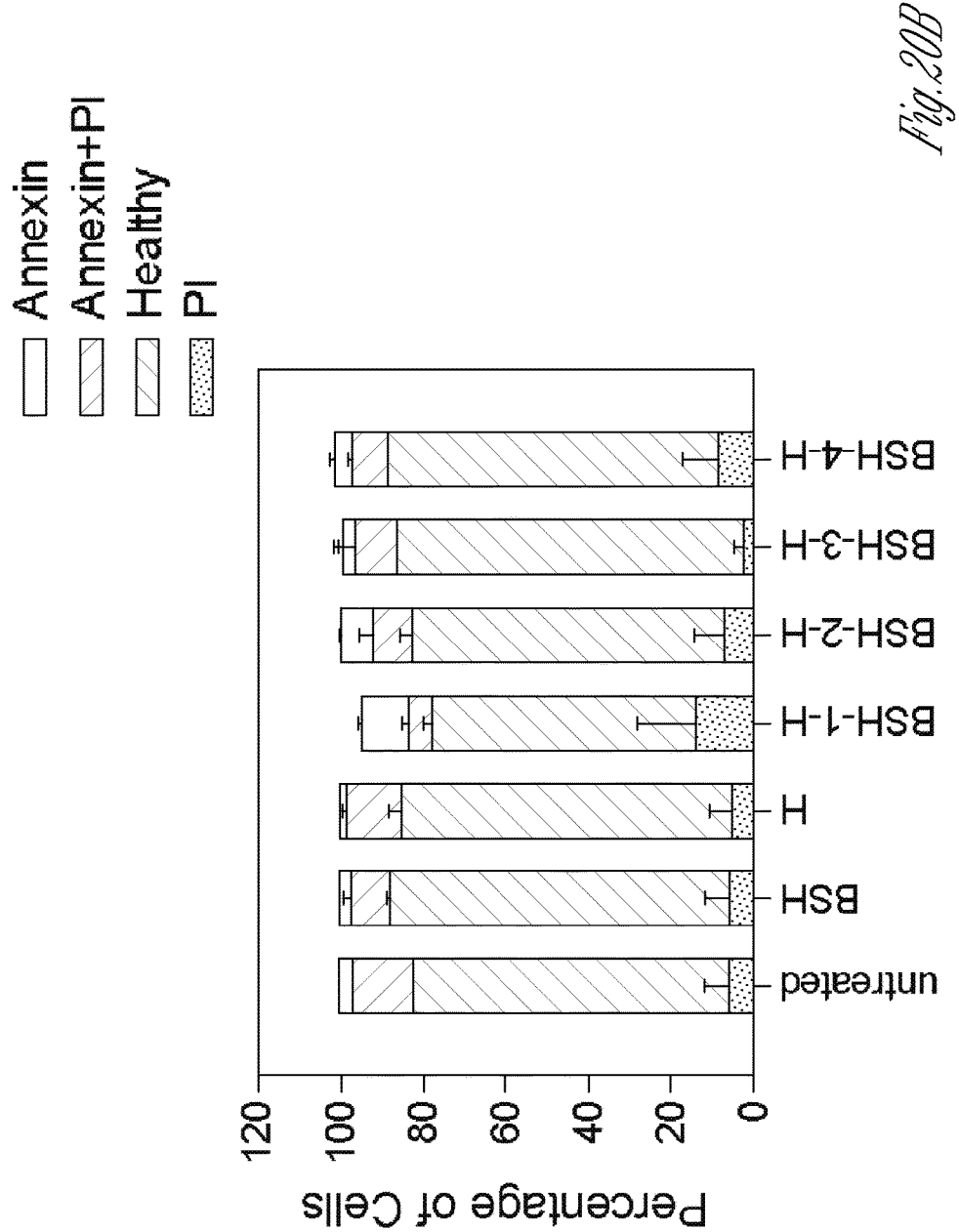
Figure 20C:
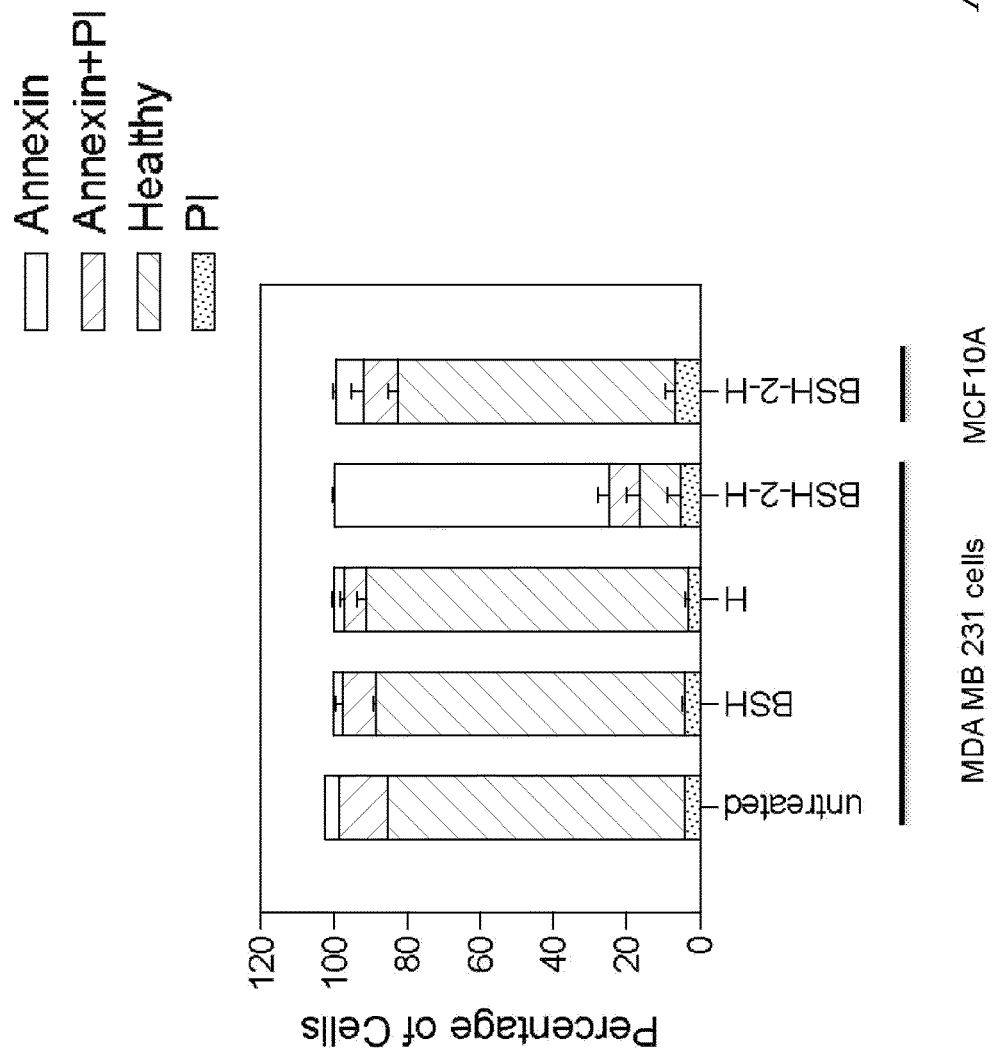

This library of dimers was then screened for processing inhibition of microRNA-96 hairpin precursors by using qRT-PCR to quantify the abundance of the mature, pre-, and pri-microRNAs. The data are shown in FIG. 18. These studies identified BSH-2-H as the most effective compound. The BSH-2-H compound significantly inhibited production of the mature microRNA-96 at 50 nM concentration, while also inhibiting production of the pre-microRNA-96 and boosting production of the pri-microRNA-96. The structure of the optimal dimer, BSH-2-H, is shown below.

in healthy breast tissue (MCF-10A). As shown in FIG. 20A-20C, when BSH-2-H is added to the breast cancer cell lines, significant apoptosis is induced. However, when the BSH-2-H compound is added to healthy breast cells, there is no effect on apoptosis.

REFERENCES

1. Guan, L. & Disney, M. D. Recent advances in developing small molecules targeting RNA. *ACS Chem. Biol.* 7, 73-86 (2012).

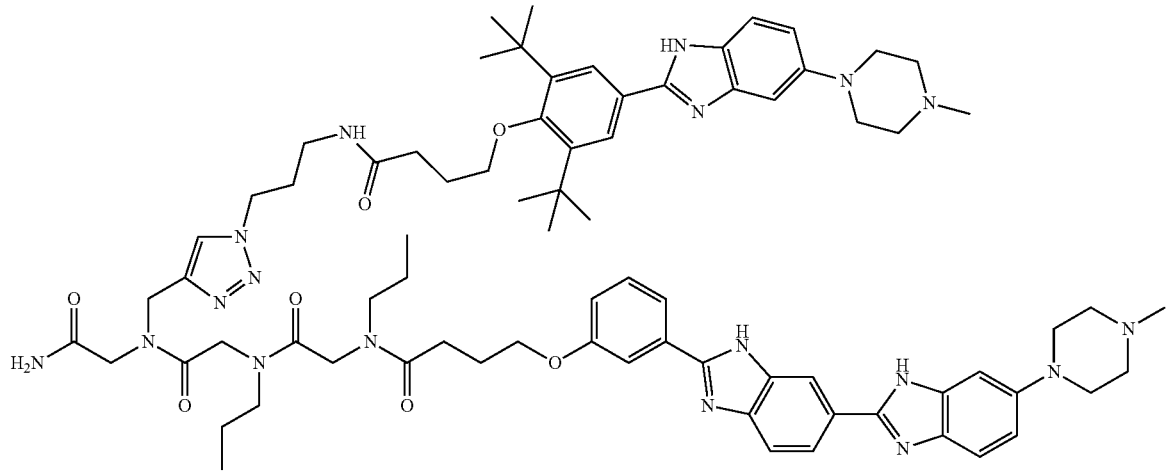

BSH-2-H

Figure 17:
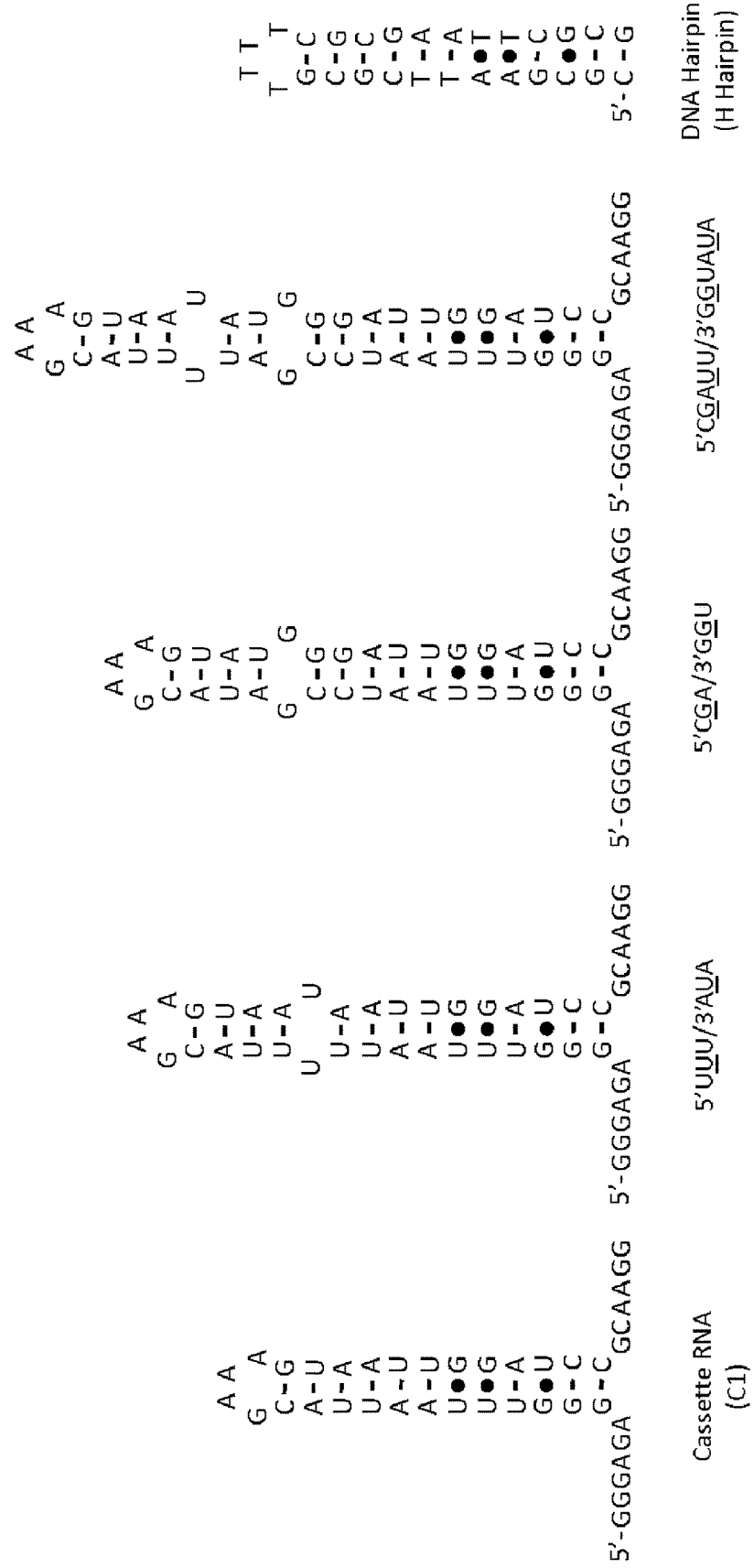
FIG. 17 shows secondary structures of nucleic acids used for evaluating the affinities of small dimer molecules identified in the screen described in Example 10. C1 is the cassette RNA into which loops were embedded to perform binding assays (GGGAGAGGGUUUAAUUAC-GAAAGUAA UUGGAUCCGCAAGG, SEQ ID NO:1). The 5'UUU/3'AUA RNA has the loop and closing base pairs present near the processing site of miRNA-96 precursor. The 5'UUU/3'AUA RNA has a framework for similar to the framework of the 3×3 ILL genus of motifs but with a 5'U UU/3'AUA loop and the following sequence (SEQ ID NO: 227): GGGAGAGGGUUUAAUUUUU ACGAAAGUAAUAAUUGGAUCCGCAAGG. The 5'C GA/3'GGU RNA has a loop near a Drosha processing site separated from 5'UUU/3'AUA by two base pairs. Hence, the 5'CGA/3'GGU RNA has a sequence similar to the 5'U UU/3'AUA RNA but with a 5'CGA/3'GGU loop instead of the 5'UUU/3'AUA loop. The 5'CGA/3'GGU RNA has the following sequence (SEQ ID NO:228): GGGA-GAGGGUUUAAUCCGAUACGAAAGUAU GGGAUUGGAUCCGCAAGG. The 5'CGAUU/3'GGUA UA RNA is dimer RNA molecule containing both of the 5'U UU/3'AUA and 5'CGA/3'GGU loops. The 5'CGAUU/3'G GUAUA RNA has the following sequence (SEQ ID NO:229): GGGAGAGGGUUUAAUCCGAUUUUAC-GAAAGUAAUAU GGGAUUGGAUCCGCAAGG. The DNA hairpin has the following sequence (SEQ ID NO:230): CGCGAATTCGCGTTTTCGCGAATTCGCG. DNA Hairpin (H Hairpin) is the DNA hairpin which has high affinity towards H.

The binding affinity of the optimal BSH-2-H dimer was then tested against a variety of constructs that displace the 1×1 nucleotide GG internal loop binding site, the 1×1 nucleotide UU internal loop binding site, or both. Binding was also evaluated against a DNA hairpin. These studies demonstrated that BSH-2-H has significantly selectivity for the RNA that contains both sites and is >30-fold higher affinity binder than monomeric compounds to the designed RNA substrates, 5'CGAUU/3'GGUAUA (FIG. 17 and Table 4).

2. Thomas, J. R. & Hergenrother, P. J. Targeting RNA with small molecules. *Chem. Rev.* 108, 1171-1224 (2008).
3. Yoshizawa, S., Fourmy, D. & Puglisi, J. D. Recognition of the codon-anticodon helix by ribosomal RNA. *Science* 285, 1722-1725 (1999).
4. Carter, A. P. et al. Functional insights from the structure of the 30S ribosomal subunit and its interactions with antibiotics. *Nature* 407, 340-348. (2000).
5. Mathews, D. H. et al. Incorporating chemical modification constraints into a dynamic programming algorithm

TABLE 4

Dissociation constants of BSH-FL (fluorescein derivative of BSH, compound 1), H and BSH-2-H towards the different nucleic acids with the binding constants are reported in nanomolar.

| Small Molecule | 5'UUU/ 3'AUA | 5'CGA/ 3'GGU | 5'CGAUU/ 3'GGUAUA | C1 | H Hairpin |
|---|---|---|---|---|---|
| BSH-FL | 1270 ± 140 nM | 9400 ± 1400 nM | 3400 ± 100 nM | >30,000 nM | >30,000 nM |
| H | >20,000 nM | 1450 ± 150 nM | 2680 ± 267 nM | >2000 nM | 200 nM |
| BSH-2-H | 1167 ± 279 nM | 900 ± 200 nM | 85 ± 11 nM | >4000 nM | >50,000 nM |

Figure 19:
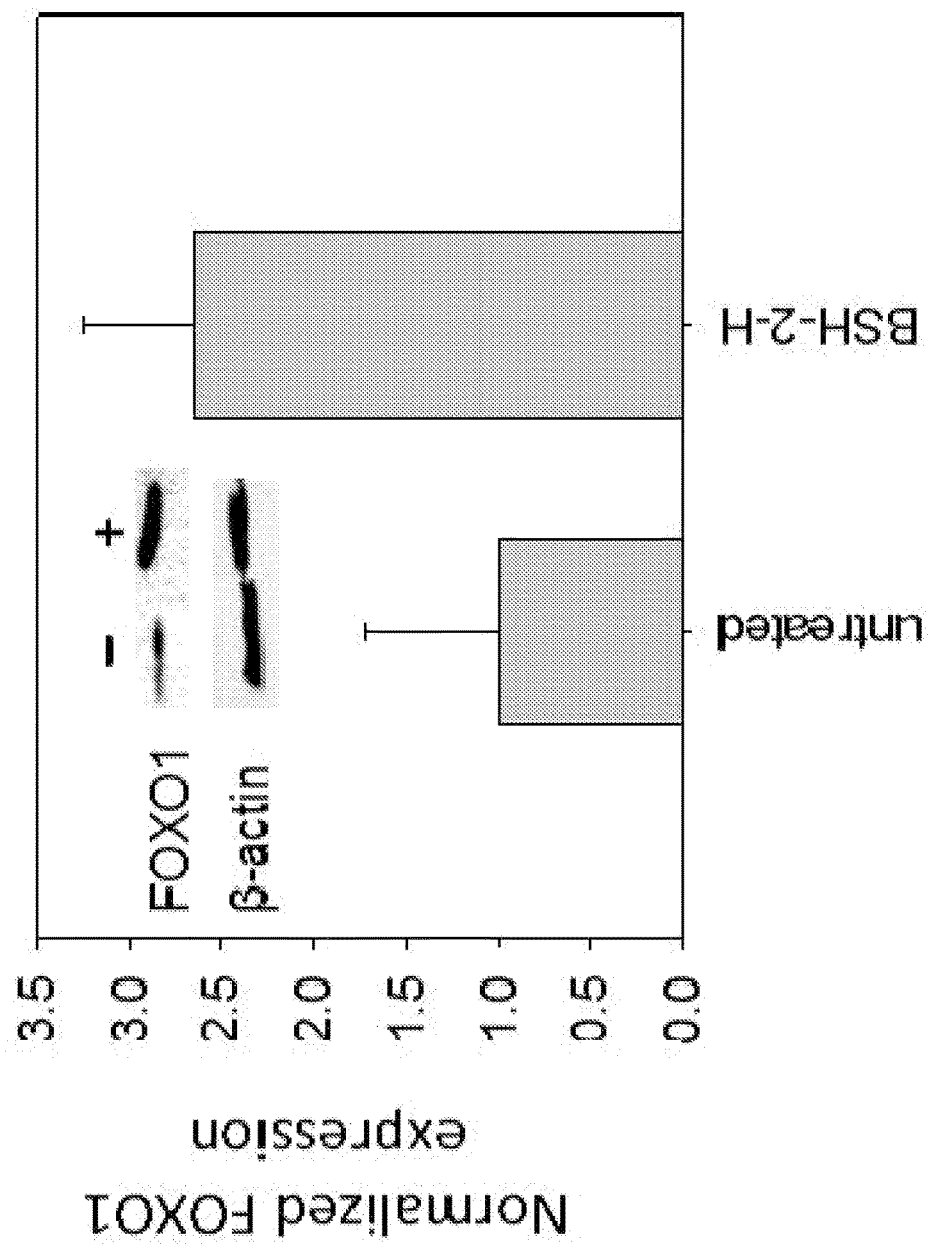
FIG. 19 graphically illustrates the effect of dimer compound BSH-2-H on FOXO1 expression in MCF7 cells as determined by western blot. As shown, BSH-2-H at 50 nM increases the expression level of endogenous FOXO1 by 2.5 fold.

The compound BSH-2-H was then tested to evaluate whether it affected the production of FOXO1 protein in cultured cancer cells. FOXO1 mRNA is targeted by miR-96, and is translationally repressed by it. These studies showed that application of 50 nM of BSH-2-H caused an increase in the amount of FOXO1 protein expressed in cells by 2.5-fold (FIG. 19).

If FOXO1 levels are boosted in cells apoptosis should be triggered. Therefore, the BSH-2-H compound was tested for induction of apoptosis in a variety of breast cancer cell lines (MCF7 and MDA MB 231 triple negative cells) as well as for prediction of RNA secondary structure. *Proc. Natl. Acad. Sci. U.S.A* 101, 7287-7292 (2004).
6. Batey, R. T., Rambo, R. P. & Doudna, J. A. Tertiary Motifs in RNA Structure and Folding. *Angew. Chem. Int. Ed. Engl.* 38, 2326-2343 (1999).
7. Spahn, C. M. et al. Hepatitis C virus IRES RNA-induced changes in the conformation of the 40s ribosomal subunit. *Science* 291, 1959-1962 (2001).
8. Childs-Disney, J. L., Wu, M., Pushechnikov, A., Aminova, 0. & Disney, M. D. A small molecule microarray platform to select RNA internal loop-ligand interactions. *ACS Chem. Biol.* 2, 745-754 (2007).
9. Disney, M. D. et al. Two-dimensional combinatorial screening identifies specific aminoglycoside-RNA internal loop partners. *J. Am. Chem. Soc.* 130, 11185-11194 (2008).
10. Velagapudi, S. P., Seedhouse, S. J. & Disney, M. D. Structure-activity relationships through sequencing (StARTS) defines optimal and suboptimal RNA motif targets for small molecules. *Angew. Chem. Int. Ed. Engl.* 49, 3816-3818 (2010).
11. Velagapudi, S. P., Seedhouse, S. J., French, J. & Disney, M. D. Defining the RNA internal loops preferred by benzimidazole derivatives via 2D combinatorial screening and computational analysis. *J. Am. Chem. Soc.* 133, 10111-10118 (2011).
12. Jiang, Q. et al. miR2Disease: a manually curated database for microRNA deregulation in human disease. *Nucleic Acids Res.* 37, D98-104 (2009).
13. Griffiths-Jones, S., Saini, H. K., van Dongen, S. & Enright, A. J. miRBase: tools for microRNA genomics. *Nucleic Acids Res.* 36, D154-158 (2008).
14. Bartel, D. P. MicroRNAs: target recognition and regulatory functions. Cell 136, 215-233 (2009).
15. Ambros, V. et al. A uniform system for microRNA annotation. *RNA* 9, 277-279 (2003).
16. Wu, M. & Turner, D. H. Solution structure of (rGCGGACGC)2 by two-dimensional NMR and the iterative relaxation matrix approach. *Biochemistry* 35, 9677-9689 (1996).
17. SantaLucia, J., Jr. & Turner, D. H. Structure of (rGGCGAGCC)2 in solution from NMR and restrained molecular dynamics. *Biochemistry* 32, 12612-12623 (1993).
18. Bartel, D. P. MicroRNAs: genomics, biogenesis, mechanism, and function. Cell 116, 281-297 (2004).
19. Krutzfeldt, J. et al. Silencing of microRNAs in vivo with 'antagomirs'. *Nature* 438, 685-689 (2005).
20. Ebert, M. S. & Sharp, P. A. MicroRNA sponges: progress and possibilities. *RNA* 16, 2043-2050 (2010).
21. Obad, S. et al. Silencing of microRNA families by seed-targeting tiny LNAs. *Nat. Genet.* 43, 371-378 (2011).
22. Guttilla, I. K. & White, B. A. Coordinate regulation of FOXO1 by miR-27a, miR-96, and miR-182 in breast cancer cells. *J. Biol. Chem.* 284, 23204-23216 (2009).
23. Redova, M. et al. MiR-210 expression in tumor tissue and in vitro effects of its silencing in renal cell carcinoma. *Tumour Biol.* 34, 481-491 (2013).
24. Childs-Disney, J. L., Hoskins, J., Rzuczek, S. G., Thornton, C. A. & Disney, M. D. Rationally designed small molecules targeting the RNA that causes myotonic dystrophy type 1 are potently bioactive. *ACS Chem. Biol.* 7, 856-862 (2012).
25. Pilch, D. S. et al. Binding of a hairpin polyamide in the minor groove of DNA: sequence-specific enthalpic discrimination. *Proc. Natl. Acad. Sci. U.S.A.* 93, 8306-8311 (1996).
26. Pushechnikov, A. et al. Rational design of ligands targeting triplet repeating transcripts that cause RNA dominant disease: application to myotonic muscular dystrophy type 1 and spinocerebellar ataxia type 3. *J. Am. Chem. Soc.* 131, 9767-9779 (2009).
27. Lee, M. M., Pushechnikov, A. & Disney, M. D. Rational and modular design of potent ligands targeting the RNA that causes myotonic dystrophy 2. *ACS Chem. Biol.* 4, 345-355 (2009).
28. Parkesh, R. et al. Design of a bioactive small molecule that targets the myotonic dystrophy type 1 RNA via an RNA motif-ligand database & chemical similarity searching. *J. Am. Chem. Soc.* 134, 4731-4742 (2012).
29. Kumar, A. et al. Chemical correction of pre-mRNA splicing defects associated with sequestration of muscleblind-like 1 protein by expanded r(CAG)-containing transcripts. *ACS Chem. Biol.* 7, 496-505 (2012).
30. Pinto, I. G., Guilbert, C., Ulyanov, N. B., Stearns, J. & James, T. L. Discovery of ligands for a novel target, the human telomerase RNA, based on flexible-target virtual screening and NMR. *J. Med. Chem.* 51, 7205-7215 (2008).
31. Disney, M. D. et al. A small molecule that targets r(CGG)exp and improves defects in fragile X-associated tremor ataxia syndrome *ACS Chem. Biol.* 7, 1711-1718 (2012).
32. Luzhkov, V. B. et al. Virtual screening and bioassay study of novel inhibitors for dengue virus mRNA cap (nucleoside-2'O)-methyltransferase. *Bioorg. Med. Chem.* 15, 7795-7802 (2007).
33. Xu, S., Witmer, P. D., Lumayag, S., Kovacs, B. & Valle, D. MicroRNA (miRNA) transcriptome of mouse retina and identification of a sensory organ-specific miRNA cluster. *J. Biol. Chem.* 282, 25053-25066 (2007).
34. Stenvang, J., Petri, A., Lindow, M., Obad, S. & Kauppinen, S. Inhibition of microRNA function by antimiR oligonucleotides. *Silence* 3, 1 (2012).
35. Xie, L. et al. FOXO1 is a tumor suppressor in classical Hodgkin lymphoma. *Blood* 119, 3503-3511 (2012).
36. Dansen, T. B. & Burgering, B. M. Unravelling the tumor-suppressive functions of FOXO proteins. *Trends Cell Biol.* 18, 421-429 (2008).
37. Huang, H. & Tindall, D. J. FOXO factors: a matter of life and death. *Future Oncol.* 2, 83-89. (2006).
38. Lewis, B. P., Burge, C. B. & Bartel, D. P. Conserved seed pairing, often flanked by adenosines, indicates that thousands of human genes are microRNA targets. *Cell* 120, 15-20 (2005).
39. Wolkenberg, S. E. & Boger, D. L. Mechanisms of in situ activation for DNA-targeting antitumor agents. *Chem. Rev.* 102, 2477-2495 (2002).
40. Tran, T. & Disney, M. D. Identifying the preferred RNA motifs and chemotypes that interact by probing millions of combinations. *Nat. Commun.* 3, 1125 (2012).
41. Hawkins, P. C., Skillman, A. G. & Nicholls, A. Comparison of shape-matching and docking as virtual screening tools. *J. Med. Chem.* 50, 74-82 (2007).
42. Stelzer, A. C. et al. Discovery of selective bioactive small molecules by targeting an RNA dynamic ensemble. *Nat. Chem. Biol.* 7, 553-559 (2011).
43. Kramer, R. & Cohen, D. Functional genomics to new drug targets. *Nat. Rev. Drug Discov.* 3, 965-972 (2004).
44. Bevilacqua, J. M. & Bevilacqua, P. C. Thermodynamic analysis of an RNA combinatorial library contained in a short hairpin. *Biochemistry* 37, 15877-15884 (1998).
45. McKenna, S. A. et al. Purification and characterization of transcribed RNAs using gel filtration chromatography. *Nat. Protoc.* 2, 3270-3277 (2007).
46. Peyret, N., Seneviratne, P. A., Allawi, H. T. & SantaLucia, J., Jr. Nearest-neighbor thermodynamics and NMR of DNA sequences with internal A. A, C. C, G. G, and T. T mismatches. *Biochemistry* 38, 3468-3477 (1999).
47. SantaLucia, J., Jr. A unified view of polymer, dumbbell, and oligonucleotide DNA nearest-neighbor thermodynamics. *Proc. Natl. Acad. Sci. U.S.A.* 95, 1460-1465 (1998).

48. Puglisi, J. D. & Tinoco, I., Jr. Absorbance melting curves of RNA. *Methods Enzymol.* 180, 304-325 (1989).
49. Wang, Y. & Rando, R. R. Specific binding of aminoglycoside antibiotics to RNA. *Chem. Biol.* 2, 281-290 (1995).
50. Disney, M. D.; Gryaznov, S. M. & Turner, D. H. Contributions of individual nucleotides to tertiary binding of substrate by a *Pneumocystis carinii* group I intron. *Biochemistry* 39, 14269-14278 (2000).
51. Landthaler, M., Yalcin, A. & Tuschl, T. The human DiGeorge syndrome critical region gene 8 and its *D. melanogaster* homolog are required for miRNA biogenesis. *Curr. Biol.* 14, 2162-2167 (2004).
52. Jong, H.; Fafarman, A.; Holub, J. M.; Kirshenbaum, K. *Org Lett,* 7: 1951 (2005).
53. Disney, M. D.; Labuda, L. P.; Paul, D. J.; Poplawski, S. G.; Pushechnikov, A.; Tran, T.; Velagapudi, S. P.; Wu, M.; Childs-Disney, J. L. *J Am Chem Soc* 130: 11185 (2008).

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a compound," "a small molecule," "a nucleic acid" or "an RNA" includes a plurality of such compounds, small molecules, nucleic acids or RNA molecules (for example, a solution of compounds, small molecules, nucleic acids or RNA molecules, or a series of compound, small molecule, nucleic acid or RNA molecule preparations), and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The following statements are intended to describe and summarize various features of the invention according to the foregoing description in the specification.

Statements:

1. A method for identifying a compound that binds to an RNA, comprising comparing a query dataset of RNA secondary structures from the RNA, with a dataset of identified bound RNA motif-small molecule pairs, to thereby identify a compound that binds to the RNA.

2. The method of statement 1, wherein the query dataset of RNA secondary structures comprises one or more RNA sequence for one or more selected secondary structure from the RNA.

3. The method of statement 1 or 2, wherein the query dataset of RNA secondary structures comprises one or more RNA sequence for one or more selected secondary structure, and a description of the secondary structure.

4. The method of any of statements 1-3, wherein the query dataset of RNA secondary structures from the RNA comprises one or more single-stranded segments, one or more double-stranded segments, or a combination thereof that are present in the RNA after folding of the RNA.

5. The method of any of statements 1-4, wherein query dataset of RNA secondary structures comprises one or more single-stranded segments formed by the RNA after folding into a low free energy structure.

6. The method of any of statements 1-5, wherein query dataset of RNA secondary structures comprises one or more single-stranded segments formed by the RNA after folding into a folded structure that is stable under physiological conditions.

7. The method of any of statements 1-6, wherein the query dataset of RNA secondary structures comprises one or more internal loops, hairpin loops, bulges, bubbles, branches, or combinations thereof.

8. The method of any of statements 1-7, wherein the query dataset of RNA secondary structures comprises one or more RNA symmetric internal loop, asymmetric internal loop, 1×1 internal loop, 1×2 internal loop, 1×3 internal loop, 2×2 internal loop, 2×3 internal loop, 2×4 internal loop, 3×3 internal loop, 3×4 internal loop, 4×4 internal loop, 4×5 internal loop, 5×5 internal loop, 1 base bulge, 2 base bulge, 3 base bulge, 4 base bulge, 5 base bulge, 4 base hairpin loop, 5 base hairpin loop, 6 base hairpin loop, 7 base hairpin loop, 8 base hairpin loop, 9 base hairpin loop, 10 base hairpin loop, multibranch loop, pseudoknot, or a combination therefore.

9. The method of any of statements 1-8, wherein the dataset of identified bound RNA motif-small molecule pairs comprises a structural description of each RNA motif, a structural description of each small molecule, and a listing of which RNA motif binds to each small molecule or compound.

10. The method of any of statements 1-9, wherein the dataset of identified bound RNA motif-small molecule pairs comprises one or more RNA sequence for each RNA motif.

11. The method of any of statements 1-10, wherein the dataset of identified bound RNA motif-small molecule pairs comprises one or more RNA sequence for each RNA motif, and a description of each RNA motif's 2-dimensional and/or three-dimensional structure.

12. The method of any of statements 1-10, wherein the dataset of identified bound RNA motif-small molecule pairs comprises a description of each RNA motif as single-stranded or double-stranded. 13. The method of any of statements 1-12, wherein the dataset of identified bound RNA motif-small molecule pairs comprises a description of each RNA motif as an internal loop, hairpin loop, a bulge, a bubble, or a branch.

14. The method of any of statements 1-13, wherein the dataset of identified bound RNA motif-small molecule pairs comprises a description of each RNA motif as an RNA symmetric internal loop, asymmetric internal loop, 1×1 internal loop, 1×2 internal loop, 1×3 internal loop, 2×2 internal loop, 2×3 internal loop, 2×4 internal loop, 3×3 internal loop, 3×4 internal loop, 4×4 internal loop, 4×5 internal loop, 5×5 internal loop, 1 base bulge, 2 base bulge, 3 base bulge, 4 base bulge, 5 base bulge, 4 base hairpin loop, 5 base hairpin loop, 6 base hairpin loop, 7 base hairpin loop, 8 base hairpin loop, 9 base hairpin loop, 10 base hairpin loop, multi-branch loop, or pseudoknot.

15. The method of any of statements 1-14, wherein the dataset of identified bound RNA motif-small molecule pairs comprises a description of each small molecule by chemical formula, chemical name, chemical structure, three-dimensional structure, three-dimensional atomic structure, or a combination thereof.

16. The method of any of statements 1-15, wherein the dataset of identified bound RNA motif-small molecule pairs comprises a description of bonds formed between RNA motifs and small molecules.

17. The method of any of statements 1-16, wherein the dataset of identified bound RNA motif-small molecule pairs comprises a description of alignments for each structural feature of each RNA motif with each small molecule to which the RNA motif binds.

18. The method of any of statements 1-17, wherein the dataset of identified bound RNA motif-small molecule pairs comprises a description of alignments for each structural feature of small molecule with each structural feature of the RNA motif to which the small molecule binds.

19. The method of any of statements 1-18, wherein comparing the query dataset of RNA secondary structures from the RNA, with the dataset of identified bound RNA motif-small molecule pairs comprises aligning one or more structural feature of each RNA secondary structure with one or more structural feature of one or more of the RNA motifs.

20. The method of any of statements 1-19, wherein comparing the query dataset of RNA secondary structures from the RNA, with the dataset of identified bound RNA motif-small molecule pairs comprises a series of alignments for each structural feature of each RNA secondary structure with one or more structural feature of one or more of the RNA motifs.

21. The method of any of statements 1-20, wherein comparing the query dataset of RNA secondary structures from the RNA, with the dataset of identified bound RNA motif-small molecule pairs comprises a series of alignments for each structural feature of each RNA secondary structure with one or more structural feature of one or more of the RNA motifs until a best-fit RNA motif is identified that optimally corresponds with RNA secondary structure.

22. The method of any of statements 1-21, wherein comparing the query dataset of RNA secondary structures from the RNA, with the dataset of identified bound RNA motif-small molecule pairs comprises a series of alignments for each structural feature of each RNA secondary structure with one or more structural feature of one or more of the RNA motifs until a best-fit compound-RNA motif pair is identified, where the RNA motif of the pair has a structure that optimally corresponds with RNA secondary structure.

23. The method of statements 22, wherein the one or more structural feature of each RNA secondary structure is a ribonucleotide, a ribonucleotide sequence, a ribonucleotide position, a ribonucleotide conformation, a ribonucleotide atomic coordinate dataset, a ribonucleotide sequence atomic coordinate dataset, or a combination thereof for each RNA secondary structure.

24. The method of any of statements 1-23, wherein the one or more structural feature of each RNA secondary structure is a ribonucleotide, a ribonucleotide sequence, a ribonucleotide position, a ribonucleotide conformation, a ribonucleotide atomic coordinate dataset, a ribonucleotide sequence atomic coordinate dataset, or a combination thereof for each RNA secondary structure as the RNA secondary structure is optimally positioned to bind a small molecule.

25. The method of any of statements 1-24, wherein the one or more structural feature of one or more of the RNA motifs is a ribonucleotide, a ribonucleotide sequence, a ribonucleotide position, a ribonucleotide conformation, a ribonucleotide atomic coordinate dataset, a ribonucleotide sequence atomic coordinate dataset, or a combination thereof for each RNA motif as the RNA motif is optimally positioned to bind a small molecule.

26. The method of any of statements 1-25, further comprising generating the query dataset of RNA secondary structures from the RNA sequence.

27. The method of any of statements 1-23, further comprising generating the query dataset of RNA secondary structures from the RNA sequence by folding the RNA into a low free energy folded structure.

28. The method of any of statements 1-24, further comprising generating the query dataset of RNA secondary structures from the RNA sequence by folding the RNA into folded structure that is stable under physiological conditions.

29. The method of any of statements 1-25, wherein the method identifies a compound that binds to the RNA by providing an output listing at least one RNA secondary structure from the RNA, and a small molecule that binds to the at least one RNA secondary structure.

30. The method of statement 26, wherein the output listing further comprises each RNA secondary structure and the compound that binds to the at least one RNA secondary structure, by name, sequence, chemical formula, chemical structure, or a combination thereof.

31. The method of any of statements 1-27, wherein the RNA and compound are assayed to determine a binding affinity.

32. The method of any of statements 1-28, wherein a RNA secondary structure identified to bind a compound is further evaluated by StARTS.

33. The method of any of statements 1-29, wherein a RNA secondary structure identified to bind a compound is further evaluated compiling sequence features in the RNA secondary structure and observing an occurrence rate of each sequence feature in the RNA secondary structure compared to an occurrence rate of the same sequence feature in a larger population of RNA motifs.

34. The method of any of statements 1-30, wherein a RNA secondary structure identified to bind a compound is assigned one or more $Z_{obs}$-scores using Equations (I) and (II):

$$\varphi = \frac{n_1 p_1 + n_2 p_2}{n_1 + n_2} \quad \text{I}$$

$$Z_{obs} = \frac{(p_1 - p_2)}{\sqrt{\varphi(1-\varphi)\left(\left(\frac{1}{n_1}\right) + \left(\frac{1}{n_2}\right)\right)}} \quad \text{II}$$

where
$n_1$ is the size of a population of structural features in RNA secondary structure identified to bind a compound (population 1);
$n_2$ is the size of a population of structural features from a larger library of RNA motifs (population 2);
p1 is the observed proportion of Population 1 displaying the feature, and
p2 is the observed proportion for Population 2 displaying the feature.

35. The method of statement 31, wherein $Z_{obs}$-scores are summed to generate at least one $\Sigma Z$ score for an RNA secondary structure when a $Z_{obs}$-score indicates that a structural feature in the RNA secondary structure is distinct from the larger library of structural features (population 2) at a 95% confidence level.

36. The method of statement 32, wherein $\Sigma Z$ scores are plotted against measured binding affinities the RNA to generate a $\Sigma Z$ score-binding affinity plot.

37. The method of statement 33, where and the plot is fitted to an inverse first-order equation.

38. The method of any of statements 1-34, wherein the method predicts the affinity and selectivity of a compound for an RNA.

39. The method of any of statements 1-35, wherein the dataset of identified bound RNA motif-small molecule pairs is or has been generated by two-dimensional combinatorial screening.

40. The method of any of statements 1-36, wherein the dataset of identified bound RNA motif-small molecule pairs is or has been generated by two-dimensional combinatorial screening, which comprises probing a small molecule library with a library of RNA motifs, and identifying which RNA motif(s) bind to which small molecule(s).

41. The method of statement 37, wherein small molecules in the small molecule library are immobilized on a solid support.

42. The method of statement 37 or 38, wherein each small molecule in the small molecule library is immobilized at an identified address on a solid support.

43. The method of any of statements 37-39, wherein identifying which RNA motif(s) bind to which small molecule(s) comprising isolating RNA bound to each small molecule to generate a series of RNA samples, amplifying each RNA sample in the series, sequencing each RNA sample in the series, or combinations thereof.

44. The method of any of statements 1-40, wherein the compound is one of the small molecules listed or identified in the dataset of identified bound RNA motif-small molecule pairs.

45. The method of any of statements 1-41, further comprising simultaneously identifying series of compounds, each binding to a different RNA.

46. The method of any of statements 1-42, wherein the method is a computer-based method.

47. A computer system for performing the method of any of statements 1-43.

48. A computer program product comprising a computer program for performing the method of any of statements 1-43.

49. A compound selected from the group consisting of:

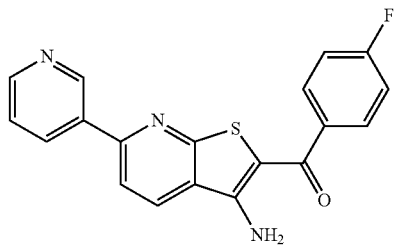

L1

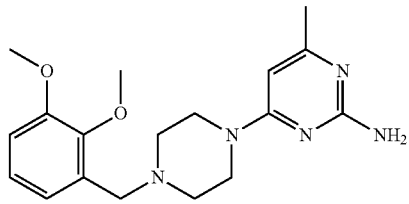

L2

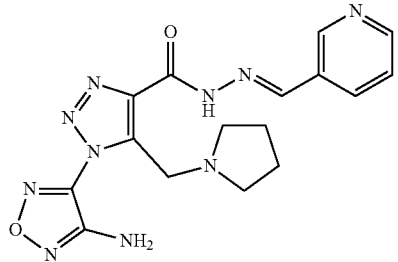

L3

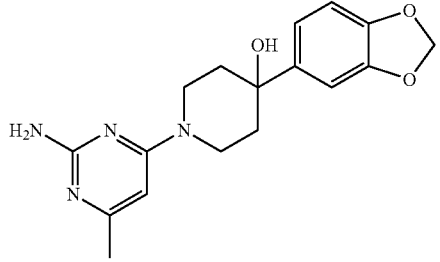

L4

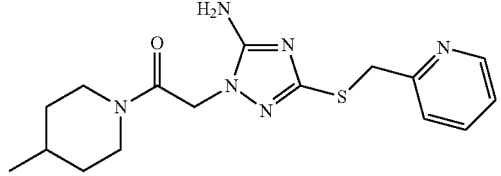

L5

L6
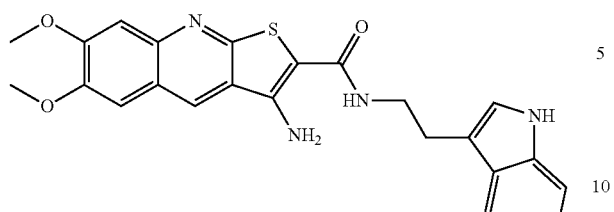
L7
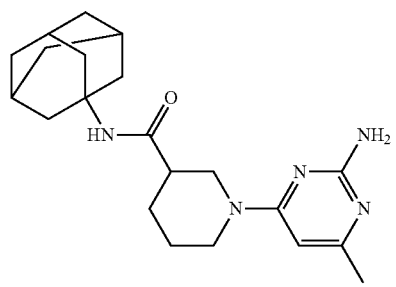
L8
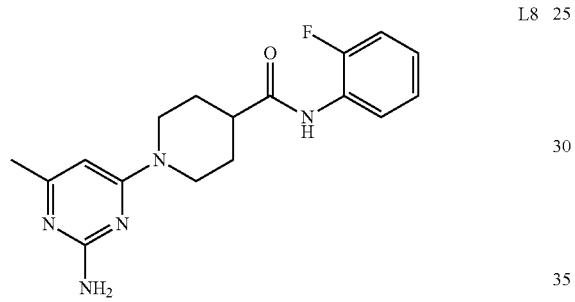
L9
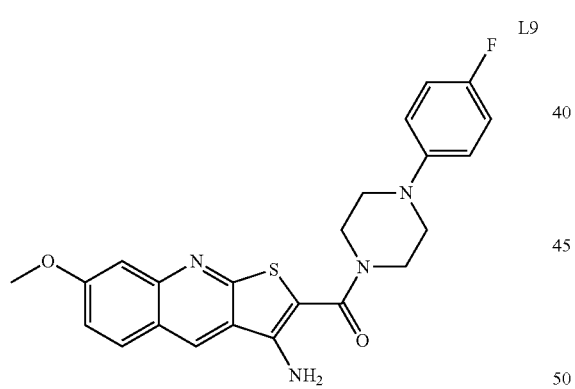
L10
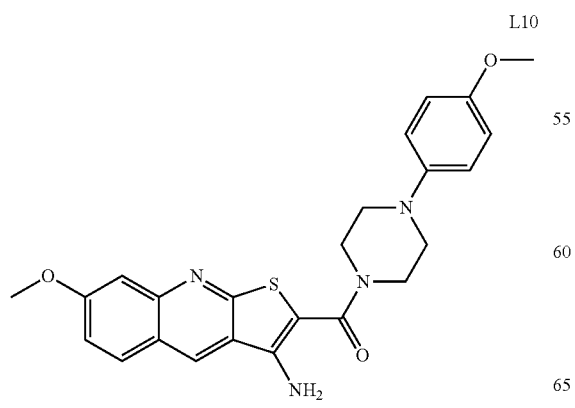
L11
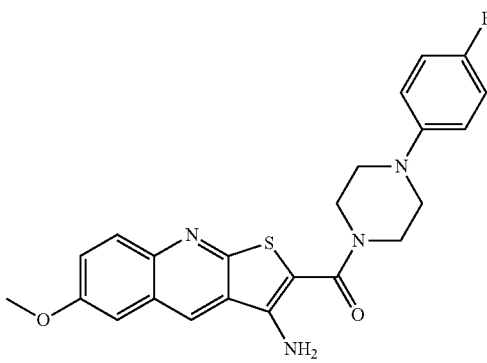
L12
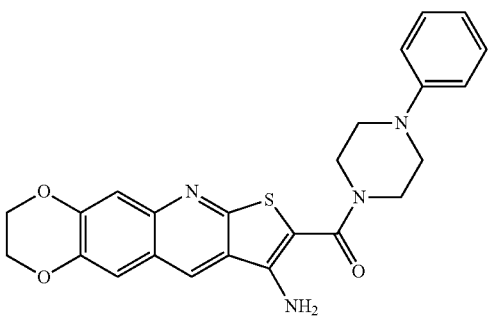
L13
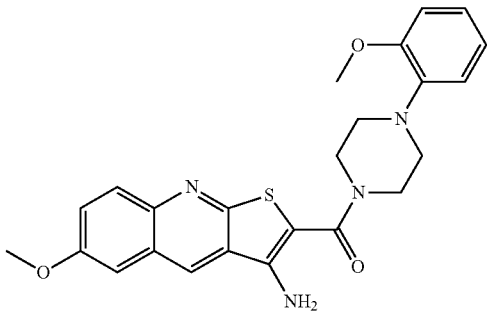
L14
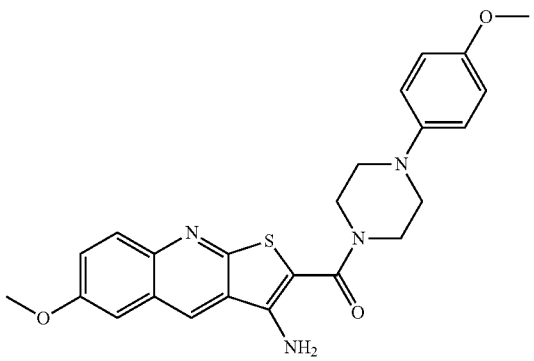

L15 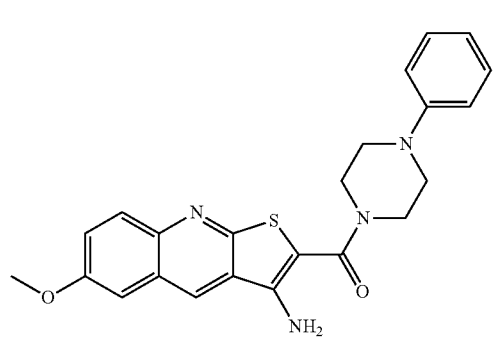
L16 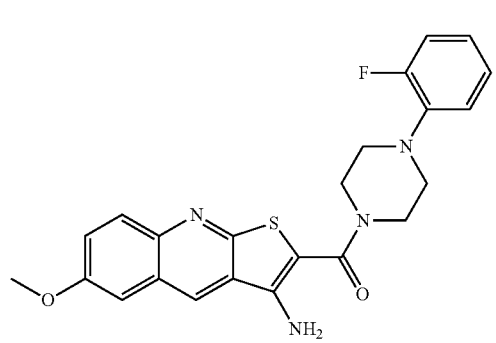
L17 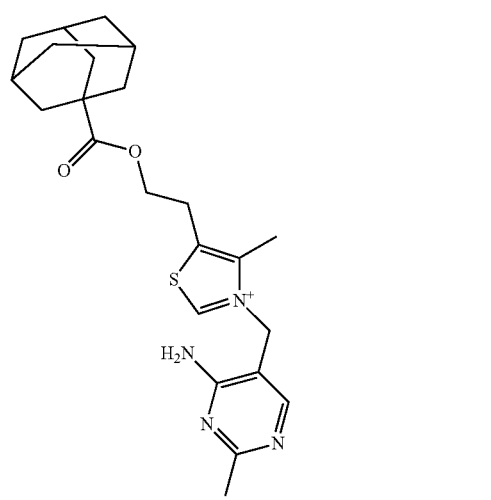
L18 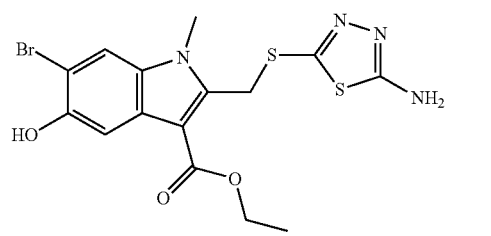
L19 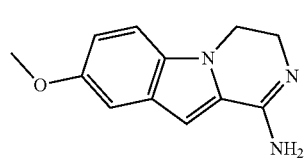
L20 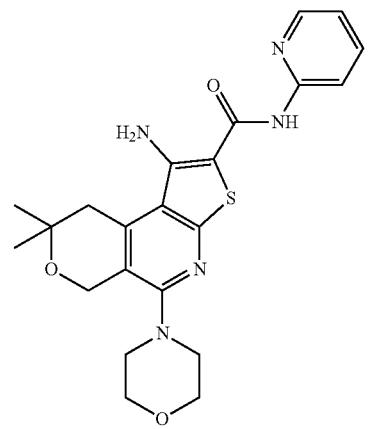
L21 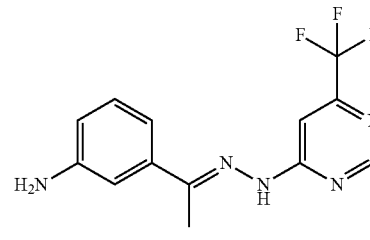
L22 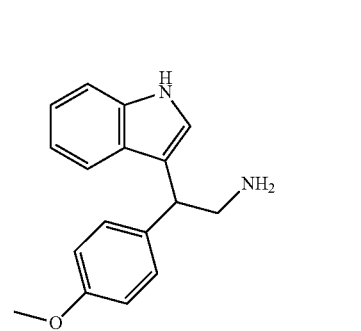
L23 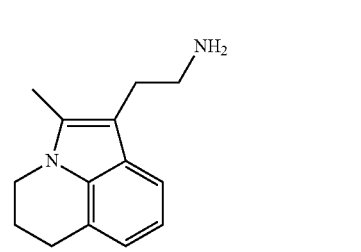
L24 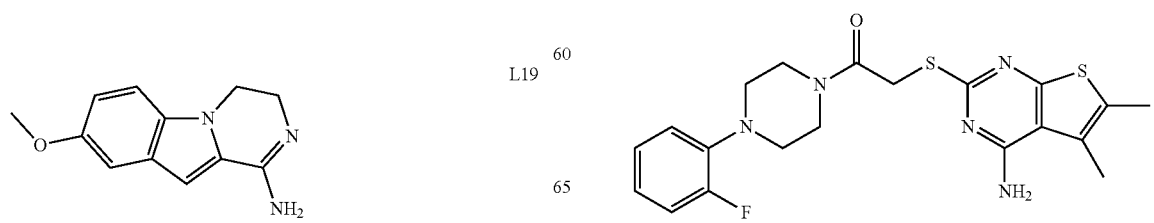

-continued
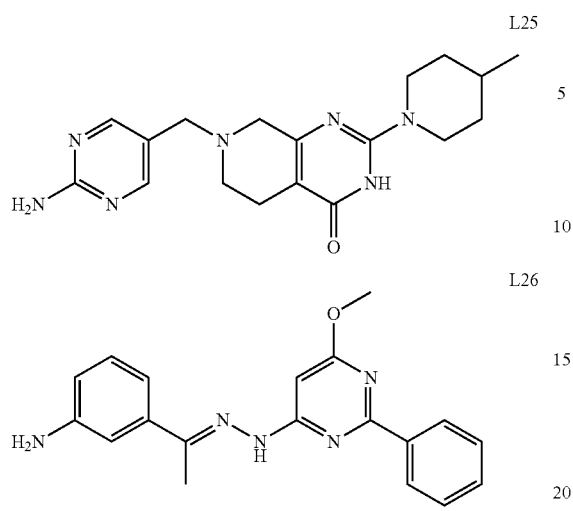
L25
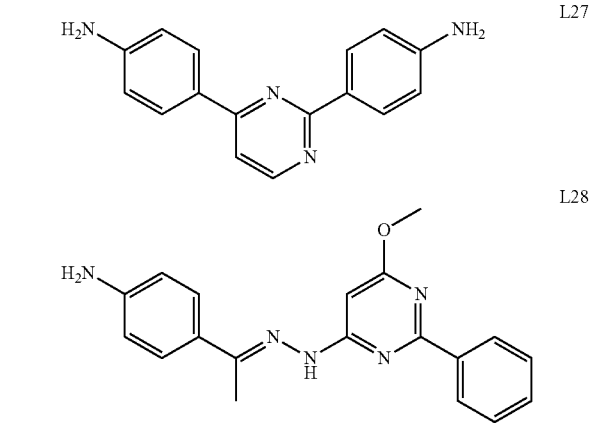
L27
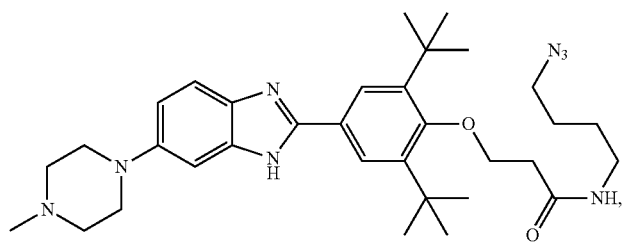
L26
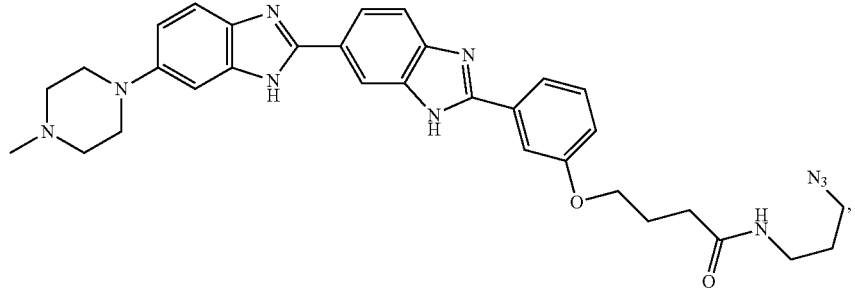
L28
50. An immobilized compound of statement 46.
51. The compound of statement 46 or 47, immobilized to a solid support.
52. A compound selected from the group consisting of:
1
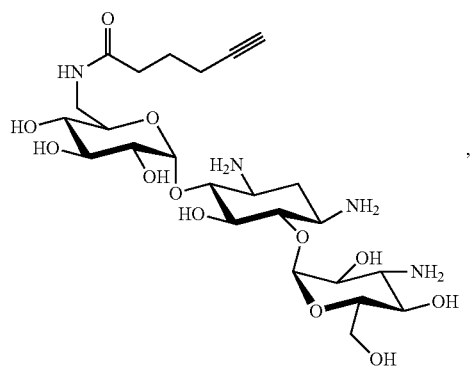
2
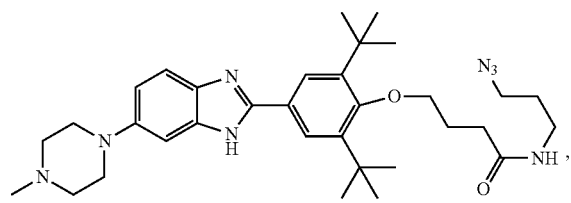
3
4

-continued
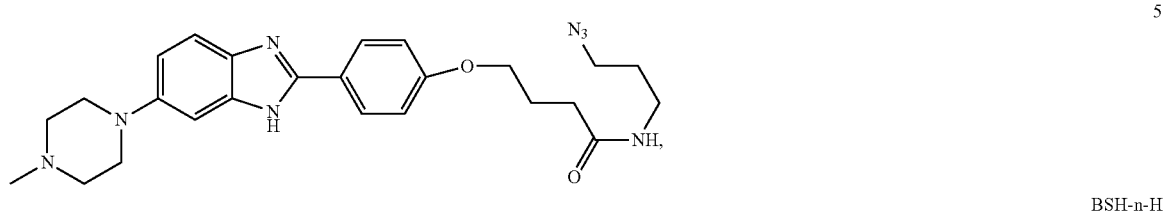
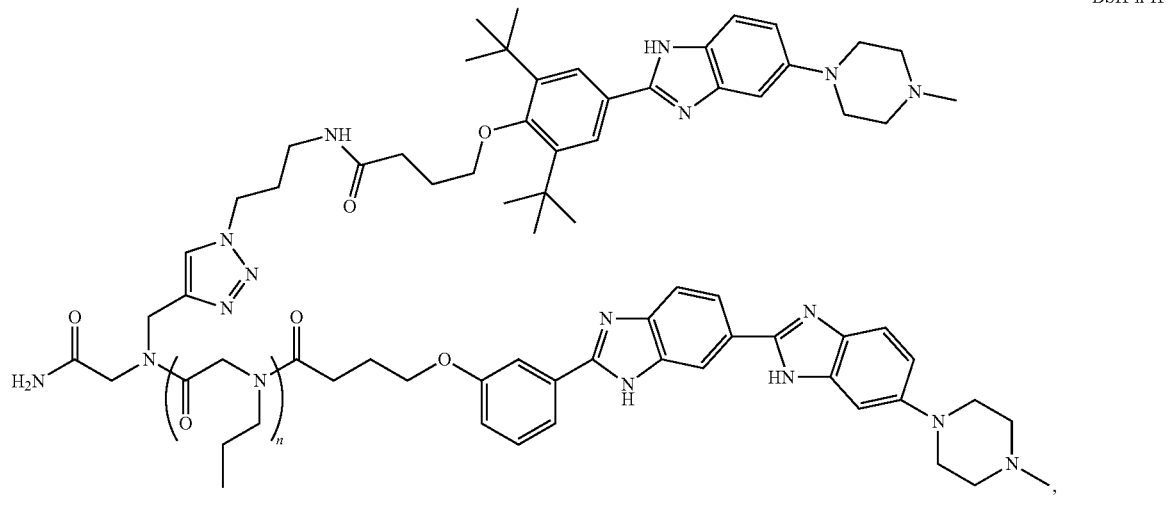
BSH-n-H
BSH-1-H
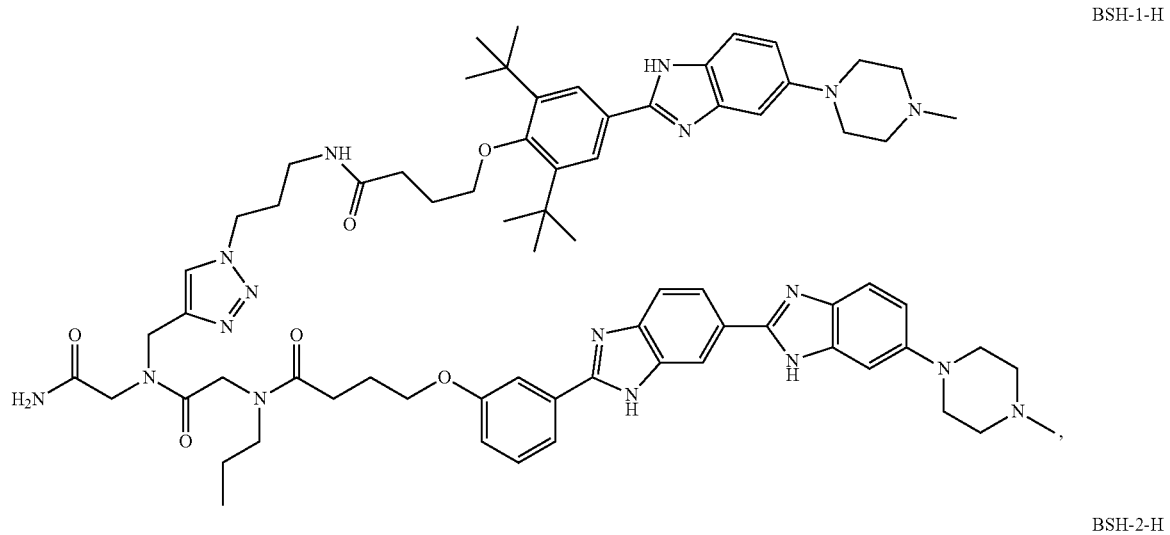
BSH-2-H
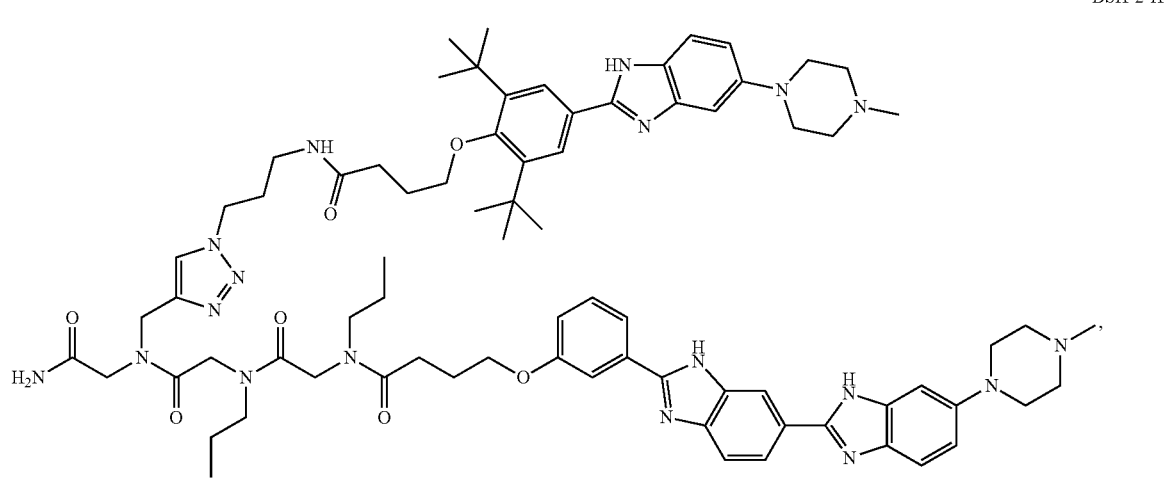

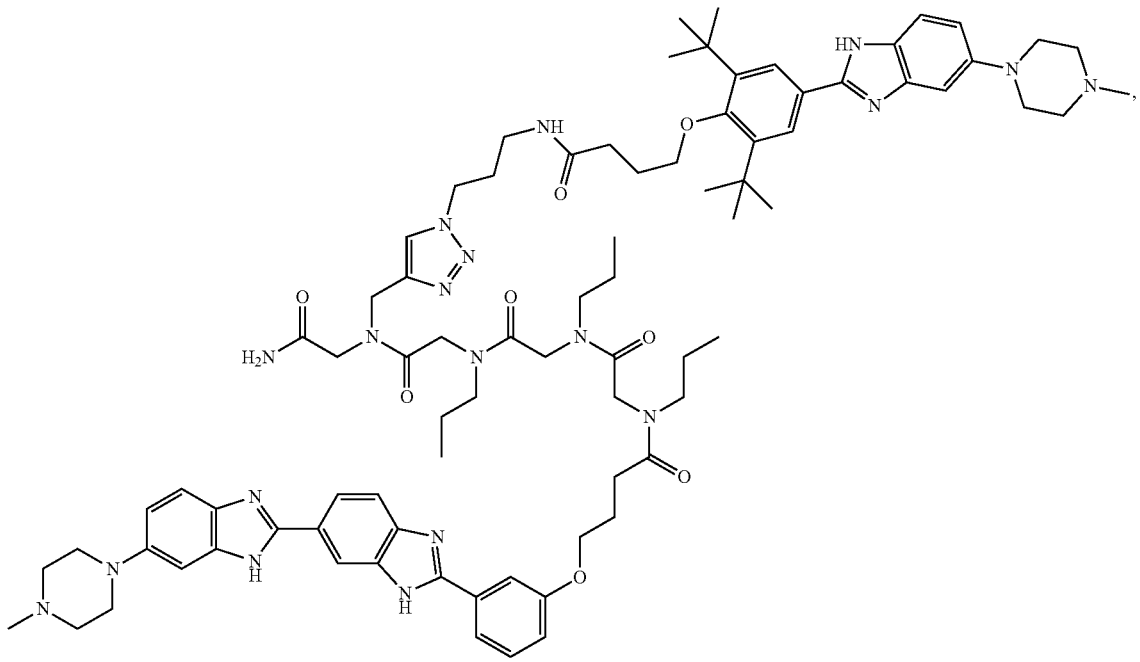

BSH-3-H

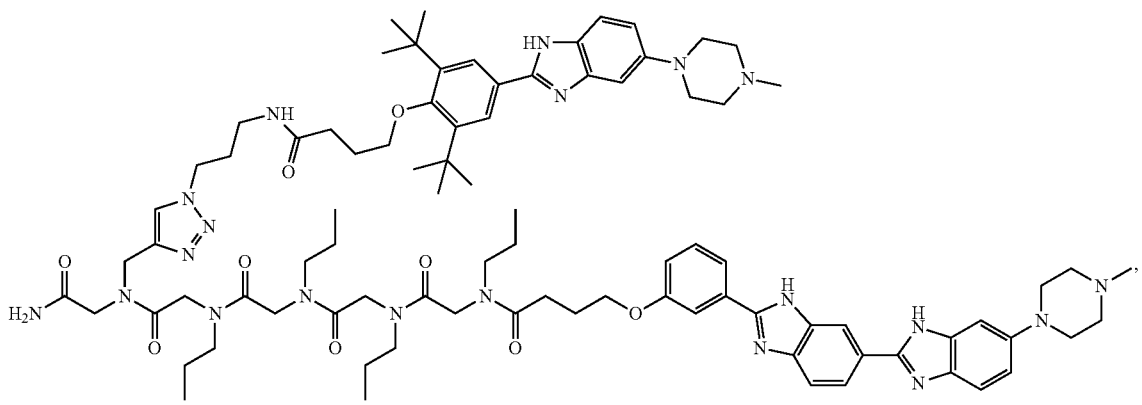

BSH-4-H and any combination thereof.

53. A composition comprising a carrier and one or more the compounds of statement 46 or 49.

54. The composition of statement 50, wherein the carrier is a pharmaceutically acceptable carrier.

55. A method of modulating microRNA function or activity comprising contacting the microRNA with one or more of the compounds of statement 46 or 47, or with the composition of statement 50 or 51, to thereby modulate microRNA function or activity.

56. The method of statement 52, wherein the microRNA function or activity is reduced.

57. The method of statement 52, wherein the microRNA function or activity is increased.

58. A method of treatment comprising administering a compound of statement 46 or 49 to a subject in need thereof, to thereby treat the subject.

59. A method of treatment comprising administering a small molecule identified by the method of any statements 1-42, to a subject in need thereof, to thereby treat the subject.

60. The method of statement 54 or 55, wherein the subject has, or is suspected of having, cancer.

61. The method of any of statements 51-56, wherein the compound binds to a microRNA.

62. The method of any of statements 51-56, wherein the compound binds to a microRNA selected from the group consisting of an miR-96, miR-182, miR-210, and precursors thereof.

63. The method of any of statements 51-56, wherein the compound binds to a microRNA sequence selected from the groups consisting of SEQ ID NO:11; SEQ ID NO:12; SEQ ID NO:13; SEQ ID NO:14; SEQ ID NO: 15; SEQ ID NO:16; and SEQ ID NO:17.

64. The method of any of statements 55-60, wherein the subject has pancreatic cancer, Parkinson's disease, Alzheimer's disease, melanoma, breast cancer, lymphoma, hepatocellular carcinoma, glioblastomas, colorectal neoplasm, breast neoplasm, breast neoplasm, urinary bladder neoplasm, hepatocellular neoplasm, prostatic neoplasm, colorectal neoplasm, stomach neoplasms, chronic myeloid leukemia, acute myeloid leukemia, melanoma, prostatic neoplasms, glioma, breast neoplasm, acute leukemia, endometrial neoplasm, lung cancer, prostatic neoplasm, ovarian neoplasm, ischemic heart disease, renal carcinoma, pancreatic cancer, colorectal cancer, breast cancer, breast cancer, breast cancer, Kaposi's sarcoma, stomach neoplasms, leukemia, melanoma, neoplasms (Myc regulator), non-small cell lung cancer, colorectal neoplasm, Parkinson's disease, stomach neoplasm, squamous cell neoplasm, squamous cell neoplasm, stomach neoplasm, hepatocellular carcinoma, melanoma, breast neoplasm, hepatocellular neoplasm, hepatocellular neoplasm, hepatocellular carcinoma, breast neoplasm, stomach neoplasm, squamous cell neoplasm, or a combination thereof.

65. A computer system for identifying a molecule that binds to an RNA comprising: one or more computer processors and storage configured to compare a structured query dataset describing RNA secondary structures of the RNA, and a structured dataset of identified RNA motif-small molecule pairs, to thereby identify a molecule that binds to the RNA.

66. The computer system of statement 65, wherein the query dataset describing RNA secondary structures comprises one or more RNA sequence for one or more selected secondary structure.

67. The computer system of statement 65 or 66, wherein the query dataset of RNA secondary structures comprises one or more internal loops, hairpin loops, bulges, bubbles, branches, or combinations thereof.

68. The computer system of any of statements 65-67, wherein the query dataset of RNA secondary structures comprises one or more RNA symmetric internal loop, asymmetric internal loop, 1×1 internal loop, 1×2 internal loop, 1×3 internal loop, 2×2 internal loop, 2×3 internal loop, 2×4 internal loop, 3×3 internal loop, 3×4 internal loop, 4×4 internal loop, 4×5 internal loop, 5×5 internal loop, 1 base bulge, 2 base bulge, 3 base bulge, 4 base bulge, 5 base bulge, 4 base hairpin loop, 5 base hairpin loop, 6 base hairpin loop, 7 base hairpin loop, 8 base hairpin loop, 9 base hairpin loop, 10 base hairpin loop, multibranch loop, pseudoknot, or a combination therefore.

69. The computer system of any of statements 65-68, wherein the dataset of identified bound RNA motif-small molecule pairs comprises a structural description of each RNA motif, a structural description of each small molecule, and a listing of which RNA motif binds to each small molecule or compound.

70. The computer system of any of statements 65-69, wherein the dataset of identified bound RNA motif-small molecule pairs comprises a description of each RNA motif as an internal loop, hairpin loop, a bulges, a bubble, or a branch.

71. The computer system of any of statements 65-70, wherein the dataset of identified bound RNA motif-small molecule pairs comprises a description of each RNA motif as an RNA symmetric internal loop, asymmetric internal loop, 1×1 internal loop, 1×2 internal loop, 1×3 internal loop, 2×2 internal loop, 2×3 internal loop, 2×4 internal loop, 3×3 internal loop, 3×4 internal loop, 4×4 internal loop, 4×5 internal loop, 5×5 internal loop, 1 base bulge, 2 base bulge, 3 base bulge, 4 base bulge, 5 base bulge, 4 base hairpin loop, 5 base hairpin loop, 6 base hairpin loop, 7 base hairpin loop, 8 base hairpin loop, 9 base hairpin loop, 10 base hairpin loop, multibranch loop, or pseudoknot.

72. The computer system of any of statements 65-71, wherein the dataset of identified bound RNA motif-small molecule pairs comprises a description of each small molecule by chemical formula, chemical name, chemical structure, three-dimensional structure, or a combination thereof.

73. The computer system of any of statements 65-72, wherein comparison of the structured query dataset describing RNA secondary structures of the RNA, with the structured dataset of identified RNA motif-small molecule pairs comprises a series of alignments for each structural feature of each RNA secondary structure with one or more structural feature of one or more of the RNA motifs in the identified RNA motif-small molecule pairs.

74. The computer system of any of statements 65-73, wherein comparison of the structured query dataset describing RNA secondary structures of the RNA, with the structured dataset of identified RNA motif-small molecule pairs comprises a series of alignments for each structural feature of each RNA secondary structure with one or more structural feature of one or more of the RNA motifs in the identified RNA motif-small molecule pairs until a best-fit RNA motif is identified that optimally corresponds with RNA secondary structure.

75. The computer system of statement 74, wherein the one or more structural feature of each RNA secondary structure is a ribonucleotide, a ribonucleotide sequence, a ribonucleotide position, a ribonucleotide conformation, a ribonucleotide atomic coordinate dataset, a ribonucleotide sequence atomic coordinate dataset, or a combination thereof for each RNA secondary structure.

76. The computer system of statement 74 or 75, wherein the one or more structural feature of one or more of the RNA motifs is a ribonucleotide, a ribonucleotide sequence, a ribonucleotide position, a ribonucleotide conformation, a ribonucleotide atomic coordinate dataset, a ribonucleotide sequence atomic coordinate dataset, or a combination thereof for each RNA motif as the RNA motif is optimally positioned to bind a small molecule.

77. The computer system of any of statements 65-76, wherein the computer system is further configured to generate the query dataset of RNA secondary structures from the RNA sequence.

78. The computer system of any of statements 65-77, wherein the computer system is further configured to generate the query dataset of RNA secondary structures by a computer system that comprises folding the RNA into a low free energy folded structure.

79. The computer system of any of statements 65-78, wherein the computer system is further configured to provide an output listing at least one RNA secondary structure from the RNA, and a small molecule that binds to the at least one RNA secondary structure.

80. The computer system of any of statements 65-79, wherein the computer system is further configured to evaluate a RNA secondary structure identified to bind a small molecule by compiling sequence features in the RNA secondary structure, and comparing the number of sequence features in the RNA secondary structure to the number of the same sequence features in a larger population of RNA motifs.

81. The computer system of any of statements 65-80, wherein the computer system is further configured to assign one or more $Z_{obs}$-scores to a RNA secondary structure identified to bind a small molecule using Equations (I) and (II):

$$\varphi = \frac{n_1 p_1 + n_2 p_2}{n_1 + n_2} \qquad \mathrm{I}$$

-continued $$Z_{obs} = \frac{(p_1 - p_2)}{\sqrt{\varphi(1-\varphi)\left(\left(\frac{1}{n_1}\right)+\left(\frac{1}{n_2}\right)\right)}} \quad \text{II}$$

where
- $n_1$ is the size of a population of structural features in RNA secondary structure identified to bind a compound (population 1);
- $n_2$ is the size of a population of structural features from a larger library of RNA motifs (population 2);
- p1 is the observed proportion of Population 1 displaying the feature, and
- p2 is the observed proportion for Population 2 displaying the feature.

82. The computer system of statement 81, wherein the computer system is further configured to sum the $Z_{obs}$-scores to generate at least one ΣZ score for an RNA secondary structure when a $Z_{obs}$-score indicates that a structural feature in the RNA secondary structure is distinct from the larger library of structural features (population 2) at a 95% confidence level.

83. The computer system of statement 81 or 82, wherein the computer system is further configured to plot the ΣZ scores against measured binding affinities of the small molecule for the RNA to generate a ΣZ score-binding affinity plot.

84. The computer system of statement 82, where and the plot is fitted to an inverse first-order equation.

85. The computer system of any of statements 65-84, wherein the computer system is further configured to generate output that predicts the affinity and selectivity of a small molecule for an RNA.

86. The computer system of any of statements 65-85, wherein the computer system is configured to simultaneously compare a series of RNA secondary structures with a series of RNA motif-small molecule pairs to thereby identify a series of RNA-molecule binding pairs.

87. One or more computer-readable hardware storage having computer-useable instructions embodied thereon for performing a method of comparing a structured query dataset describing RNA secondary structures of the RNA, with a structured dataset of identified RNA motif-small molecule pairs to identify a molecule that binds to the RNA.

88. Use of the compound of claim 52 or the composition of claim 53 or 54 for treatment of cancer.

89. Use of the compound of claim 52 or the composition of claim 53 or 54 as a medicament.

What is claimed:

1. A method for identifying a small molecule that binds to an RNA of the human transcriptome and modulates the amount thereof, said method comprising:
   (a) determining the secondary structure or sequence of the RNA;
   (b) selecting a small molecule from a listing of small molecules capable of binding to the secondary structure or sequence of the RNA;
   (c) measuring the effect of the small molecule on the amount of the RNA and, optionally, measuring the binding affinity between the small molecule and the RNA;
   (d) optionally, repeating steps (b) and (c) with at least one other small molecule from the listing;
   wherein a small molecule is identified, when the small molecule modulates the amount of the RNA.

2. The method of claim 1, further comprising amplifying the RNA, sequencing the RNA, or a combination thereof.

3. The method of claim 1, wherein the secondary structure of the RNA comprises an internal loop, hairpin loop, a bulge, a bubble, or a branch, or any combination thereof.

4. The method of claim 3, wherein the secondary structure of the RNA comprises an RNA motif selected from: an RNA symmetric internal loop, asymmetric internal loop, 1×1 internal loop, 1×2 internal loop, 1×3 internal loop, 2×2 internal loop, 2×3 internal loop, 2×4 internal loop, 3×3 internal loop, 3×4 internal loop, 4×4 internal loop, 4×5 internal loop, 5×5 internal loop, 1 base bulge, 2 base bulge, 3 base bulge, 4 base bulge, 5 base bulge, 4 base hairpin loop, 5 base hairpin loop, 6 base hairpin loop, 7 base hairpin loop, 8 base hairpin loop, 9 base hairpin loop, 10 base hairpin loop, multi-branch loop, or pseudoknot.

5. The method of claim 1, wherein the listing comprises a structural description of each small molecule, a description of each small molecule by chemical formula, chemical name, a description of each small molecule structure, a description of each small molecule three-dimensional structure, a description of each small molecule three-dimensional atomic structure, or a combination thereof.

6. The method of claim 1, wherein the listing comprises a description of bonds formed between RNA motifs and small molecules, a description of alignments for each structural feature of each RNA motif with each small molecule to which the RNA motif binds, a description of alignments for each structural feature of small molecule with each structural feature of the RNA motif to which the small molecule binds, of any combination thereof.

7. The method of claim 1, wherein the RNA is a microRNA (miRNA), a pri-miRNA, an mRNA, a tRNA, a rRNA, or a small interfering RNA (siRNA).

8. The method of claim 7, wherein the RNA is a microRNA (miRNA), a pri-miRNA, an mRNA, or an siRNA.

9. The method of claim 1, wherein the listing is generated by combining a dataset of RNA secondary structures and RNA sequences with a dataset of small molecules and RNA secondary structures to which the small molecules bind.

10. The method of claim 9, wherein the dataset of RNA secondary structures and RNA sequences comprises a dataset of RNA secondary structures and RNA sequences of all human precursor microRNAs (miRNAs).

11. The method of claim 10, wherein the RNA secondary structures are RNA secondary structures predicted using a free energy minimization program.

12. The method of claim 9, wherein the dataset of small molecules and RNA secondary structures to which the small molecules bind comprises a dataset obtained from a 2-Dimensional Combinatorial Screening (2DCS) assay of RNA secondary structures and small molecules.

13. The method of claim 9, wherein the dataset obtained from 2DCS was statistically analyzed using a method called Structure-Activity Relationships Through Sequencing (StARTS) to identify and annotate or score the interactions between the small molecules and the RNA secondary structures.

14. The method of claim 9, wherein the listing identifies about 1668 small molecules that bind to an RNA secondary structure.

15. The method of claim 14, wherein the listing identifies about 26 RNA secondary structures that are located in either a Drosha or Dicer processing site of miRNAs implicated in a disease and that have been validated for modulation of the disease by oligonucleotides.

16. The method of claim 15, wherein the RNA secondary structures that are located within either a Drosha or Dicer processing site are internal loops.

17. The method of claim 16, wherein the listing identifies small molecules that bind to the internal loops.

18. The method of claim 1, wherein the RNA is involved in a disease.

19. The method of claim 9, wherein the listing is generated by a computer system comprising one or more computer processors and storage configured to compare a structured query dataset describing predicted RNA secondary structures based on RNA sequence with a structured dataset of identified RNA motif-small molecule pairs.

20. The method of claim 19, wherein the computer system is further configured to assign one or more $Z_{obs}$-scores to a RNA secondary structure identified to bind a small molecule using Equations (I) and (II):

$$\varphi = \frac{n_1 p_1 + n_2 p_2}{n_1 + n_2} \quad \text{I}$$

$$Z_{obs} = \frac{(p_1 - p_2)}{\sqrt{\varphi(1-\varphi)\left(\left(\frac{1}{n_1}\right)+\left(\frac{1}{n_2}\right)\right)}} \quad \text{II}$$

where
   $n_1$ is the size of a population of structural features in RNA secondary structure identified to bind a compound (population 1);
   $n_2$ is the size of a population of structural features from a larger library of RNA motifs (population 2);
   p1 is the observed proportion of Population 1 displaying the feature, and
   p2 is the observed proportion for Population 2 displaying the feature.

21. The method of claim 20, wherein the computer system is further configured to sum the $Z_{obs}$-scores to generate at least one ΣZ score for an RNA secondary structure when a $Z_{obs}$-score indicates that a structural feature in the RNA secondary structure is distinct from the larger library of structural features (population 2) at a 95% confidence level.

22. The method of claim 21, wherein the computer system is further configured to plot the ΣZ scores against measured binding affinities of the small molecule for the RNA to generate a ΣZ score—binding affinity plot, where the plot is fitted to an inverse first-order equation.

* * * * *

SEQUENCE LISTING

```
<160> NUMBER OF SEQ ID NOS: 232

<210> SEQ ID NO 1
<211> LENGTH: 40
<212> TYPE: RNA
<213> ORGANISM: Artificial Sequence
<220> FEATURE:
<223> OTHER INFORMATION: A synthetic RNA sequence

<400> SEQUENCE: 1
gggagagggu uuaauuacga aaguaauugg auccgcaagg                          40

<210> SEQ ID NO 2
<211> LENGTH: 46
<212> TYPE: RNA
<213> ORGANISM: Artificial Sequence
<220> FEATURE:
<223> OTHER INFORMATION: A synthetic RNA sequence
<221> NAME/KEY: misc_feature
<222> LOCATION: (1)...(46)
<223> OTHER INFORMATION: n = A,U,C or G

<400> SEQUENCE: 2
gggagagggu uuaaunnnua cgaaaguann nauuggaucc gcaagg                   46

<210> SEQ ID NO 3
<211> LENGTH: 12
<212> TYPE: RNA
<213> ORGANISM: Artificial Sequence
<220> FEATURE:
<223> OTHER INFORMATION: A synthetic RNA sequence

<400> SEQUENCE: 3
ggguuuaauu ac                                                        12

<210> SEQ ID NO 4
<211> LENGTH: 12
<212> TYPE: RNA
<213> ORGANISM: Artificial Sequence
<220> FEATURE:
```

<223> OTHER INFORMATION: A synthetic RNA sequence

<400> SEQUENCE: 4
guaauuggau cc                                                         12

<210> SEQ ID NO 5
<211> LENGTH: 10
<212> TYPE: RNA
<213> ORGANISM: Artificial Sequence
<220> FEATURE:
<223> OTHER INFORMATION: A synthetic RNA sequence

<400> SEQUENCE: 5
cgcgaaagcg                                                            10

<210> SEQ ID NO 6
<211> LENGTH: 22
<212> TYPE: DNA
<213> ORGANISM: Artificial Sequence
<220> FEATURE:
<223> OTHER INFORMATION: A synthetic deoxyoligonucleotide sequence

<400> SEQUENCE: 6
atatatatat atatatatat at                                              22

<210> SEQ ID NO 7
<211> LENGTH: 22
<212> TYPE: DNA
<213> ORGANISM: Artificial Sequence
<220> FEATURE:
<223> OTHER INFORMATION: A synthetic deoxyoligonucleotide sequence

<400> SEQUENCE: 7
gcgcgcgcgc gcgcgcgcgc gc                                              22

<210> SEQ ID NO 8
<211> LENGTH: 44
<212> TYPE: RNA
<213> ORGANISM: Artificial Sequence
<220> FEATURE:
<223> OTHER INFORMATION: A synthetic RNA sequence

<400> SEQUENCE: 8
gggagagggu uaauuuuac gaaaguaaua uuggauccgc aagg                       44

<210> SEQ ID NO 9
<211> LENGTH: 54
<212> TYPE: RNA
<213> ORGANISM: Artificial Sequence
<220> FEATURE:
<223> OTHER INFORMATION: A synthetic RNA sequence

<400> SEQUENCE: 9
gggagagggu uaauccgau uuuacgaaag uaauauggga uuggauccgc aagg             54

<210> SEQ ID NO 10
<211> LENGTH: 50
<212> TYPE: RNA
<213> ORGANISM: Artificial Sequence
<220> FEATURE:
<223> OTHER INFORMATION: A synthetic RNA sequence

<400> SEQUENCE: 10
gggagagggu uaauggguag uacgaaagua cucucauugg auccgcaagg                 50

```
<210> SEQ ID NO 11
<211> LENGTH: 78
<212> TYPE: RNA
<213> ORGANISM: Artificial Sequence
<220> FEATURE:
<223> OTHER INFORMATION: A synthetic RNA sequence

<400> SEQUENCE: 11
uggccgauuu uggcacuagc acauuuugc uugugucucu ccgcucugag caaucaugug    60
cagugccaau augggaaa                                                 78

<210> SEQ ID NO 12
<211> LENGTH: 110
<212> TYPE: RNA
<213> ORGANISM: Artificial Sequence
<220> FEATURE:
<223> OTHER INFORMATION: A synthetic RNA sequence

<400> SEQUENCE: 12
gagcugcuug ccuccccccg uuuuuggcaa ugguagaacu cacacuggug agguaacagg    60
auccgguggu ucuagacuug ccaacuaugg ggcgaggacu cagccggcac              110

<210> SEQ ID NO 13
<211> LENGTH: 110
<212> TYPE: RNA
<213> ORGANISM: Artificial Sequence
<220> FEATURE:
<223> OTHER INFORMATION: A synthetic RNA sequence

<400> SEQUENCE: 13
ccgcagagug ugacuccugu ucuguguaug gcacugguag aauucacugu gaacagucuc    60
agucagugaa uuaccgaagg gccauaaaca gagcagagac agauccacga              110

<210> SEQ ID NO 14
<211> LENGTH: 109
<212> TYPE: RNA
<213> ORGANISM: Artificial Sequence
<220> FEATURE:
<223> OTHER INFORMATION: A synthetic RNA sequence

<400> SEQUENCE: 14
acccggcagu gccuccaggc gcagggcagc cccugcccac cgcacacugc gcugcccagg    60
cccacugugc gugugacagc ggcugaucug ugccugggca gcgcagccc               109

<210> SEQ ID NO 15
<211> LENGTH: 23
<212> TYPE: RNA
<213> ORGANISM: Artificial Sequence
<220> FEATURE:
<223> OTHER INFORMATION: A synthetic RNA sequence

<400> SEQUENCE: 15
uuuggcacua gcacauuuuu gcu                                           23

<210> SEQ ID NO 16
<211> LENGTH: 24
<212> TYPE: RNA
<213> ORGANISM: Artificial Sequence
<220> FEATURE:
<223> OTHER INFORMATION: A synthetic RNA sequence

<400> SEQUENCE: 16
uuuggcaaug guagaacuca cacu                                          24
```

-continued

```
<210> SEQ ID NO 17
<211> LENGTH: 22
<212> TYPE: RNA
<213> ORGANISM: Artificial Sequence
<220> FEATURE:
<223> OTHER INFORMATION: A synthetic RNA sequence

<400> SEQUENCE: 17
uauggcacug guagaauuca cu                                             22

<210> SEQ ID NO 18
<211> LENGTH: 42
<212> TYPE: DNA
<213> ORGANISM: Artificial Sequence
<220> FEATURE:
<223> OTHER INFORMATION: A synthetic primer

<400> SEQUENCE: 18
ggccggatcc taatacgact cactataggg agagggttta at                       42

<210> SEQ ID NO 19
<211> LENGTH: 15
<212> TYPE: DNA
<213> ORGANISM: Artificial Sequence
<220> FEATURE:
<223> OTHER INFORMATION: A synthetic primer

<400> SEQUENCE: 19
ccttgcggat ccaat                                                     15

<210> SEQ ID NO 20
<211> LENGTH: 44
<212> TYPE: DNA
<213> ORGANISM: Artificial Sequence
<220> FEATURE:
<223> OTHER INFORMATION: A synthetic primer

<400> SEQUENCE: 20
ggccggatcc taatacgact cactataggg tggccgattt tggc                     44

<210> SEQ ID NO 21
<211> LENGTH: 15
<212> TYPE: DNA
<213> ORGANISM: Artificial Sequence
<220> FEATURE:
<223> OTHER INFORMATION: A synthetic primer

<400> SEQUENCE: 21
tttcccatat tggca                                                     15

<210> SEQ ID NO 22
<211> LENGTH: 81
<212> TYPE: DNA
<213> ORGANISM: Artificial Sequence
<220> FEATURE:
<223> OTHER INFORMATION: A synthetic oligonucleotide sequence

<400> SEQUENCE: 22
gggtggccga ttttggcact agcacatttt tgcttgtgtc tctccgctct gagcaatcat    60
gtgcagtgcc aatatgggaa a                                              81

<210> SEQ ID NO 23
<211> LENGTH: 47
<212> TYPE: DNA
<213> ORGANISM: Artificial Sequence
```

```
<220> FEATURE:
<223> OTHER INFORMATION: A synthetic primer

<400> SEQUENCE: 23
ggccgaattc taatacgact cactataggc accagtgcca tctgctt          47

<210> SEQ ID NO 24
<211> LENGTH: 21
<212> TYPE: DNA
<213> ORGANISM: Artificial Sequence
<220> FEATURE:
<223> OTHER INFORMATION: A synthetic primer

<400> SEQUENCE: 24
taacagtctc cagtcacggc c                                      21

<210> SEQ ID NO 25
<211> LENGTH: 23
<212> TYPE: DNA
<213> ORGANISM: Artificial Sequence
<220> FEATURE:
<223> OTHER INFORMATION: A synthetic primer

<400> SEQUENCE: 25
tgtctgcccg catgcctgcc tct                                    23

<210> SEQ ID NO 26
<211> LENGTH: 22
<212> TYPE: DNA
<213> ORGANISM: Artificial Sequence
<220> FEATURE:
<223> OTHER INFORMATION: A synthetic primer

<400> SEQUENCE: 26
tgtaacagca actccatgtg ga                                     22

<210> SEQ ID NO 27
<211> LENGTH: 22
<212> TYPE: DNA
<213> ORGANISM: Artificial Sequence
<220> FEATURE:
<223> OTHER INFORMATION: A synthetic primer

<400> SEQUENCE: 27
taggtagttt cctgttgttg gg                                     22

<210> SEQ ID NO 28
<211> LENGTH: 22
<212> TYPE: DNA
<213> ORGANISM: Artificial Sequence
<220> FEATURE:
<223> OTHER INFORMATION: A synthetic primer

<400> SEQUENCE: 28
taggtagttt catgttgttg gg                                     22

<210> SEQ ID NO 29
<211> LENGTH: 21
<212> TYPE: PRT
<213> ORGANISM: Artificial Sequence
<220> FEATURE:
<223> OTHER INFORMATION: A synthetic primer

<400> SEQUENCE: 29

Thr Ala Ala Ala Gly Thr Gly Cys Thr Gly Ala Cys Ala Gly Thr Gly
 1               5                  10                  15
```

Cys Ala Gly Ala Thr
            20

<210> SEQ ID NO 30
<211> LENGTH: 22
<212> TYPE: DNA
<213> ORGANISM: Artificial Sequence
<220> FEATURE:
<223> OTHER INFORMATION: A synthetic primer

<400> SEQUENCE: 30
ctgtgcgtgt gacagcggct ga                                          22

<210> SEQ ID NO 31
<211> LENGTH: 22
<212> TYPE: DNA
<213> ORGANISM: Artificial Sequence
<220> FEATURE:
<223> OTHER INFORMATION: A synthetic primer

<400> SEQUENCE: 31
acagcaggca cagacaggca gt                                          22

<210> SEQ ID NO 32
<211> LENGTH: 23
<212> TYPE: DNA
<213> ORGANISM: Artificial Sequence
<220> FEATURE:
<223> OTHER INFORMATION: A synthetic primer

<400> SEQUENCE: 32
caaagtgctt acagtgcagg tag                                         23

<210> SEQ ID NO 33
<211> LENGTH: 21
<212> TYPE: DNA
<213> ORGANISM: Artificial Sequence
<220> FEATURE:
<223> OTHER INFORMATION: A synthetic primer

<400> SEQUENCE: 33
attgacactt ctgtgagtag a                                           21

<210> SEQ ID NO 34
<211> LENGTH: 22
<212> TYPE: DNA
<213> ORGANISM: Artificial Sequence
<220> FEATURE:
<223> OTHER INFORMATION: A synthetic primer

<400> SEQUENCE: 34
tagcaccatt tgaaatcggt ta                                          22

<210> SEQ ID NO 35
<211> LENGTH: 21
<212> TYPE: DNA
<213> ORGANISM: Artificial Sequence
<220> FEATURE:
<223> OTHER INFORMATION: A synthetic primer

<400> SEQUENCE: 35
aatataacac agatggcctg t                                           21

<210> SEQ ID NO 36
<211> LENGTH: 22

```
<212> TYPE: DNA
<213> ORGANISM: Artificial Sequence
<220> FEATURE:
<223> OTHER INFORMATION: A synthetic primer

<400> SEQUENCE: 36
ggtccagagg ggagataggt tc                                              22

<210> SEQ ID NO 37
<211> LENGTH: 22
<212> TYPE: DNA
<213> ORGANISM: Artificial Sequence
<220> FEATURE:
<223> OTHER INFORMATION: A synthetic primer

<400> SEQUENCE: 37
tgaggtagta gtttgtgctg tt                                              22

<210> SEQ ID NO 38
<211> LENGTH: 21
<212> TYPE: DNA
<213> ORGANISM: Artificial Sequence
<220> FEATURE:
<223> OTHER INFORMATION: A synthetic primer

<400> SEQUENCE: 38
catcccttgc atggtggagg g                                               21

<210> SEQ ID NO 39
<211> LENGTH: 22
<212> TYPE: DNA
<213> ORGANISM: Artificial Sequence
<220> FEATURE:
<223> OTHER INFORMATION: A synthetic primer

<400> SEQUENCE: 39
tattgcactt gtcccggcct gt                                              22

<210> SEQ ID NO 40
<211> LENGTH: 22
<212> TYPE: DNA
<213> ORGANISM: Artificial Sequence
<220> FEATURE:
<223> OTHER INFORMATION: A synthetic primer

<400> SEQUENCE: 40
tcgtaccgtg agtaataatg cg                                              22

<210> SEQ ID NO 41
<211> LENGTH: 22
<212> TYPE: DNA
<213> ORGANISM: Artificial Sequence
<220> FEATURE:
<223> OTHER INFORMATION: A synthetic primer

<400> SEQUENCE: 41
aacattcaac ctgtcggtga gt                                              22

<210> SEQ ID NO 42
<211> LENGTH: 22
<212> TYPE: DNA
<213> ORGANISM: Artificial Sequence
<220> FEATURE:
<223> OTHER INFORMATION: A synthetic primer

<400> SEQUENCE: 42
```
tgtaaacatc ctacactcag ct                                               22

<210> SEQ ID NO 43
<211> LENGTH: 22
<212> TYPE: DNA
<213> ORGANISM: Artificial Sequence
<220> FEATURE:
<223> OTHER INFORMATION: A synthetic primer

<400> SEQUENCE: 43
tatggcactg gtagaattca ct                                               22

<210> SEQ ID NO 44
<211> LENGTH: 23
<212> TYPE: DNA
<213> ORGANISM: Artificial Sequence
<220> FEATURE:
<223> OTHER INFORMATION: A synthetic primer

<400> SEQUENCE: 44
tgtaaacatc ctacactctc agc                                              23

<210> SEQ ID NO 45
<211> LENGTH: 23
<212> TYPE: DNA
<213> ORGANISM: Artificial Sequence
<220> FEATURE:
<223> OTHER INFORMATION: A synthetic primer

<400> SEQUENCE: 45
atcaacagac attaattggg cgc                                              23

<210> SEQ ID NO 46
<211> LENGTH: 22
<212> TYPE: DNA
<213> ORGANISM: Artificial Sequence
<220> FEATURE:
<223> OTHER INFORMATION: A synthetic primer

<400> SEQUENCE: 46
aactggccct caaagtcccg ct                                               22

<210> SEQ ID NO 47
<211> LENGTH: 22
<212> TYPE: DNA
<213> ORGANISM: Artificial Sequence
<220> FEATURE:
<223> OTHER INFORMATION: A synthetic primer

<400> SEQUENCE: 47
tttaggataa gcttgacttt tg                                               22

<210> SEQ ID NO 48
<211> LENGTH: 22
<212> TYPE: DNA
<213> ORGANISM: Artificial Sequence
<220> FEATURE:
<223> OTHER INFORMATION: A synthetic primer

<400> SEQUENCE: 48
tagcagcaca taatggtttg tg                                               22

<210> SEQ ID NO 49
<211> LENGTH: 23
<212> TYPE: DNA
<213> ORGANISM: Artificial Sequence
<220> FEATURE:
<223> OTHER INFORMATION: A synthetic primer

<400> SEQUENCE: 49
cagtgcaatg atattgtcaa agc                                    23

<210> SEQ ID NO 50
<211> LENGTH: 23
<212> TYPE: DNA
<213> ORGANISM: Artificial Sequence
<220> FEATURE:
<223> OTHER INFORMATION: A synthetic primer

<400> SEQUENCE: 50
taaggtgcat ctagtgcagt tag                                    23

<210> SEQ ID NO 51
<211> LENGTH: 22
<212> TYPE: DNA
<213> ORGANISM: Artificial Sequence
<220> FEATURE:
<223> OTHER INFORMATION: A synthetic primer

<400> SEQUENCE: 51
tagcagcaca tcatggttta ca                                     22

<210> SEQ ID NO 52
<211> LENGTH: 23
<212> TYPE: DNA
<213> ORGANISM: Artificial Sequence
<220> FEATURE:
<223> OTHER INFORMATION: A synthetic primer

<400> SEQUENCE: 52
taccctgtag atccgaattt gtg                                    23

<210> SEQ ID NO 53
<211> LENGTH: 21
<212> TYPE: DNA
<213> ORGANISM: Artificial Sequence
<220> FEATURE:
<223> OTHER INFORMATION: A synthetic primer

<400> SEQUENCE: 53
ttcaagtaat tcaggatagg t                                      21

<210> SEQ ID NO 54
<211> LENGTH: 22
<212> TYPE: DNA
<213> ORGANISM: Artificial Sequence
<220> FEATURE:
<223> OTHER INFORMATION: A synthetic primer

<400> SEQUENCE: 54
tgaggtagta ggttgtatag tt                                     22

<210> SEQ ID NO 55
<211> LENGTH: 21
<212> TYPE: DNA
<213> ORGANISM: Artificial Sequence
<220> FEATURE:
<223> OTHER INFORMATION: A synthetic primer

<400> SEQUENCE: 55
taaggcaccc ttctgagtag a                                      21

<210> SEQ ID NO 56
<211> LENGTH: 22
<212> TYPE: DNA
<213> ORGANISM: Artificial Sequence
<220> FEATURE:
<223> OTHER INFORMATION: A synthetic primer

<400> SEQUENCE: 56
tgaggtagta gtttgtacag tt                                              22

<210> SEQ ID NO 57
<211> LENGTH: 22
<212> TYPE: DNA
<213> ORGANISM: Artificial Sequence
<220> FEATURE:
<223> OTHER INFORMATION: A synthetic primer

<400> SEQUENCE: 57
cattgcactt gtctcggtct ga                                              22

<210> SEQ ID NO 58
<211> LENGTH: 22
<212> TYPE: DNA
<213> ORGANISM: Artificial Sequence
<220> FEATURE:
<223> OTHER INFORMATION: A synthetic primer

<400> SEQUENCE: 58
atcatgatgg gctcctcggt gt                                              22

<210> SEQ ID NO 59
<211> LENGTH: 20
<212> TYPE: DNA
<213> ORGANISM: Artificial Sequence
<220> FEATURE:
<223> OTHER INFORMATION: A synthetic primer

<400> SEQUENCE: 59
tacagtatag atgatgtact                                                 20

<210> SEQ ID NO 60
<211> LENGTH: 22
<212> TYPE: DNA
<213> ORGANISM: Artificial Sequence
<220> FEATURE:
<223> OTHER INFORMATION: A synthetic primer

<400> SEQUENCE: 60
tattgcacat tactaagttg ca                                              22

<210> SEQ ID NO 61
<211> LENGTH: 23
<212> TYPE: DNA
<213> ORGANISM: Artificial Sequence
<220> FEATURE:
<223> OTHER INFORMATION: A synthetic primer

<400> SEQUENCE: 61
taatactgcc gggtaatgat gga                                             23

<210> SEQ ID NO 62
<211> LENGTH: 22
<212> TYPE: DNA
<213> ORGANISM: Artificial Sequence
<220> FEATURE:
<223> OTHER INFORMATION: A synthetic primer

```
<400> SEQUENCE: 62
tagcaccatc tgaaatcggt ta                                              22

<210> SEQ ID NO 63
<211> LENGTH: 21
<212> TYPE: DNA
<213> ORGANISM: Artificial Sequence
<220> FEATURE:
<223> OTHER INFORMATION: A synthetic primer

<400> SEQUENCE: 63
cagcagcaca ctgtggtttg t                                               21

<210> SEQ ID NO 64
<211> LENGTH: 22
<212> TYPE: DNA
<213> ORGANISM: Artificial Sequence
<220> FEATURE:
<223> OTHER INFORMATION: A synthetic primer

<400> SEQUENCE: 64
caagaacctc agttgctttt gt                                              22

<210> SEQ ID NO 65
<211> LENGTH: 22
<212> TYPE: DNA
<213> ORGANISM: Artificial Sequence
<220> FEATURE:
<223> OTHER INFORMATION: A synthetic primer

<400> SEQUENCE: 65
tggctcagtt cagcaggaac ag                                              22

<210> SEQ ID NO 66
<211> LENGTH: 22
<212> TYPE: DNA
<213> ORGANISM: Artificial Sequence
<220> FEATURE:
<223> OTHER INFORMATION: A synthetic primer

<400> SEQUENCE: 66
tcgtgtcttg tgttgcagcc gg                                              22

<210> SEQ ID NO 67
<211> LENGTH: 23
<212> TYPE: DNA
<213> ORGANISM: Artificial Sequence
<220> FEATURE:
<223> OTHER INFORMATION: A synthetic primer

<400> SEQUENCE: 67
taaggtgcat ctagtgcaga tag                                             23

<210> SEQ ID NO 68
<211> LENGTH: 21
<212> TYPE: DNA
<213> ORGANISM: Artificial Sequence
<220> FEATURE:
<223> OTHER INFORMATION: A synthetic primer

<400> SEQUENCE: 68
agctacatct ggctactggg t                                               21

<210> SEQ ID NO 69
```

```
<211> LENGTH: 23
<212> TYPE: DNA
<213> ORGANISM: Artificial Sequence
<220> FEATURE:
<223> OTHER INFORMATION: A synthetic primer

<400> SEQUENCE: 69
tctttggtta tctagctgta tga                                      23

<210> SEQ ID NO 70
<211> LENGTH: 22
<212> TYPE: DNA
<213> ORGANISM: Artificial Sequence
<220> FEATURE:
<223> OTHER INFORMATION: A synthetic primer

<400> SEQUENCE: 70
tccctgagac cctaacttgt ga                                       22

<210> SEQ ID NO 71
<211> LENGTH: 22
<212> TYPE: DNA
<213> ORGANISM: Artificial Sequence
<220> FEATURE:
<223> OTHER INFORMATION: A synthetic primer

<400> SEQUENCE: 71
taatgcccct aaaaatcctt at                                       22

<210> SEQ ID NO 72
<211> LENGTH: 23
<212> TYPE: DNA
<213> ORGANISM: Artificial Sequence
<220> FEATURE:
<223> OTHER INFORMATION: A synthetic primer

<400> SEQUENCE: 72
taccctgtag aaccgaattt gtg                                      23

<210> SEQ ID NO 73
<211> LENGTH: 22
<212> TYPE: DNA
<213> ORGANISM: Artificial Sequence
<220> FEATURE:
<223> OTHER INFORMATION: A synthetic primer

<400> SEQUENCE: 73
tgaggtagta ggttgtatgg tt                                       22

<210> SEQ ID NO 74
<211> LENGTH: 22
<212> TYPE: DNA
<213> ORGANISM: Artificial Sequence
<220> FEATURE:
<223> OTHER INFORMATION: A synthetic primer

<400> SEQUENCE: 74
tggagagaaa ggcagttcct ga                                       22

<210> SEQ ID NO 75
<211> LENGTH: 19
<212> TYPE: DNA
<213> ORGANISM: Artificial Sequence
<220> FEATURE:
<223> OTHER INFORMATION: A synthetic primer

<400> SEQUENCE: 75
```
aagtgtgcag ggcactggt                                            19

<210> SEQ ID NO 76
<211> LENGTH: 22
<212> TYPE: DNA
<213> ORGANISM: Artificial Sequence
<220> FEATURE:
<223> OTHER INFORMATION: A synthetic primer

<400> SEQUENCE: 76
tggaatgtaa ggaagtgtgt gg                                        22

<210> SEQ ID NO 77
<211> LENGTH: 20
<212> TYPE: DNA
<213> ORGANISM: Artificial Sequence
<220> FEATURE:
<223> OTHER INFORMATION: A synthetic primer

<400> SEQUENCE: 77
taaggcacgc ggtgaatgcc                                           20

<210> SEQ ID NO 78
<211> LENGTH: 22
<212> TYPE: DNA
<213> ORGANISM: Artificial Sequence
<220> FEATURE:
<223> OTHER INFORMATION: A synthetic primer

<400> SEQUENCE: 78
taacagtcta cagccatggt cg                                        22

<210> SEQ ID NO 79
<211> LENGTH: 22
<212> TYPE: DNA
<213> ORGANISM: Artificial Sequence
<220> FEATURE:
<223> OTHER INFORMATION: A synthetic primer

<400> SEQUENCE: 79
ctctagaggg aagcgctttc tg                                        22

<210> SEQ ID NO 80
<211> LENGTH: 22
<212> TYPE: DNA
<213> ORGANISM: Artificial Sequence
<220> FEATURE:
<223> OTHER INFORMATION: A synthetic primer

<400> SEQUENCE: 80
tcagtgcatc acagaacttt gt                                        22

<210> SEQ ID NO 81
<211> LENGTH: 24
<212> TYPE: DNA
<213> ORGANISM: Artificial Sequence
<220> FEATURE:
<223> OTHER INFORMATION: A synthetic primer

<400> SEQUENCE: 81
tccctgagac cctttaacct gtga                                      24

<210> SEQ ID NO 82
<211> LENGTH: 23
<212> TYPE: DNA

```
<213> ORGANISM: Artificial Sequence
<220> FEATURE:
<223> OTHER INFORMATION: A synthetic primer

<400> SEQUENCE: 82
caaagtgctc atagtgcagg tag                                              23

<210> SEQ ID NO 83
<211> LENGTH: 22
<212> TYPE: DNA
<213> ORGANISM: Artificial Sequence
<220> FEATURE:
<223> OTHER INFORMATION: A synthetic primer

<400> SEQUENCE: 83
aagtgctgtc atagctgagg tc                                               22

<210> SEQ ID NO 84
<211> LENGTH: 22
<212> TYPE: DNA
<213> ORGANISM: Artificial Sequence
<220> FEATURE:
<223> OTHER INFORMATION: A synthetic primer

<400> SEQUENCE: 84
caaagaattc tccttttggg ct                                               22

<210> SEQ ID NO 85
<211> LENGTH: 23
<212> TYPE: DNA
<213> ORGANISM: Artificial Sequence
<220> FEATURE:
<223> OTHER INFORMATION: A synthetic primer

<400> SEQUENCE: 85
tctggctccg tgtcttcact ccc                                              23

<210> SEQ ID NO 86
<211> LENGTH: 21
<212> TYPE: DNA
<213> ORGANISM: Artificial Sequence
<220> FEATURE:
<223> OTHER INFORMATION: A synthetic primer

<400> SEQUENCE: 86
acagtctgct gaggttggag c                                                21

<210> SEQ ID NO 87
<211> LENGTH: 22
<212> TYPE: DNA
<213> ORGANISM: Artificial Sequence
<220> FEATURE:
<223> OTHER INFORMATION: A synthetic primer

<400> SEQUENCE: 87
taatactgtc tggtaaaacc gt                                               22

<210> SEQ ID NO 88
<211> LENGTH: 21
<212> TYPE: DNA
<213> ORGANISM: Artificial Sequence
<220> FEATURE:
<223> OTHER INFORMATION: A synthetic primer

<400> SEQUENCE: 88
atcacattgc cagggatttc c                                                21
```

<210> SEQ ID NO 89
<211> LENGTH: 22
<212> TYPE: DNA
<213> ORGANISM: Artificial Sequence
<220> FEATURE:
<223> OTHER INFORMATION: A synthetic primer

<400> SEQUENCE: 89
gtcatacacg gctctcctct ct                                              22

<210> SEQ ID NO 90
<211> LENGTH: 23
<212> TYPE: DNA
<213> ORGANISM: Artificial Sequence
<220> FEATURE:
<223> OTHER INFORMATION: A synthetic primer

<400> SEQUENCE: 90
tgtgcaaatc catgcaaaac tga                                             23

<210> SEQ ID NO 91
<211> LENGTH: 22
<212> TYPE: DNA
<213> ORGANISM: Artificial Sequence
<220> FEATURE:
<223> OTHER INFORMATION: A synthetic primer

<400> SEQUENCE: 91
taacactgtc tggtaaagat gg                                              22

<210> SEQ ID NO 92
<211> LENGTH: 23
<212> TYPE: DNA
<213> ORGANISM: Artificial Sequence
<220> FEATURE:
<223> OTHER INFORMATION: A synthetic primer

<400> SEQUENCE: 92
agcagcattg tacagggcta tga                                             23

<210> SEQ ID NO 93
<211> LENGTH: 23
<212> TYPE: DNA
<213> ORGANISM: Artificial Sequence
<220> FEATURE:
<223> OTHER INFORMATION: A synthetic primer

<400> SEQUENCE: 93
tttggcacta gcacattttt gct                                             23

<210> SEQ ID NO 94
<211> LENGTH: 21
<212> TYPE: DNA
<213> ORGANISM: Artificial Sequence
<220> FEATURE:
<223> OTHER INFORMATION: A synthetic primer

<400> SEQUENCE: 94
atcacattgc cagggattac c                                               21

<210> SEQ ID NO 95
<211> LENGTH: 21
<212> TYPE: DNA
<213> ORGANISM: Artificial Sequence
<220> FEATURE:

<223> OTHER INFORMATION: A synthetic primer

<400> SEQUENCE: 95
tcagtgcatg acagaacttg g                                    21

<210> SEQ ID NO 96
<211> LENGTH: 21
<212> TYPE: DNA
<213> ORGANISM: Artificial Sequence
<220> FEATURE:
<223> OTHER INFORMATION: A synthetic primer

<400> SEQUENCE: 96
tgagctaaat gtgtgctggg a                                    21

<210> SEQ ID NO 97
<211> LENGTH: 22
<212> TYPE: DNA
<213> ORGANISM: Artificial Sequence
<220> FEATURE:
<223> OTHER INFORMATION: A synthetic primer

<400> SEQUENCE: 97
gtgaaatgtt taggaccact ag                                   22

<210> SEQ ID NO 98
<211> LENGTH: 22
<212> TYPE: DNA
<213> ORGANISM: Artificial Sequence
<220> FEATURE:
<223> OTHER INFORMATION: A synthetic primer

<400> SEQUENCE: 98
tcggatccgt ctgagcttgg ct                                   22

<210> SEQ ID NO 99
<211> LENGTH: 22
<212> TYPE: DNA
<213> ORGANISM: Artificial Sequence
<220> FEATURE:
<223> OTHER INFORMATION: A synthetic primer

<400> SEQUENCE: 99
tgtgactggt tgaccagagg gg                                   22

<210> SEQ ID NO 100
<211> LENGTH: 22
<212> TYPE: DNA
<213> ORGANISM: Artificial Sequence
<220> FEATURE:
<223> OTHER INFORMATION: A synthetic primer

<400> SEQUENCE: 100
tgaggtagta gattgtatag tt                                   22

<210> SEQ ID NO 101
<211> LENGTH: 22
<212> TYPE: DNA
<213> ORGANISM: Artificial Sequence
<220> FEATURE:
<223> OTHER INFORMATION: A synthetic primer

<400> SEQUENCE: 101
tggagtgtga caatggtgtt tg                                   22

```
<210> SEQ ID NO 102
<211> LENGTH: 23
<212> TYPE: DNA
<213> ORGANISM: Artificial Sequence
<220> FEATURE:
<223> OTHER INFORMATION: A synthetic primer

<400> SEQUENCE: 102
tgtagtgttt cctactttat gga                                         23

<210> SEQ ID NO 103
<211> LENGTH: 22
<212> TYPE: DNA
<213> ORGANISM: Artificial Sequence
<220> FEATURE:
<223> OTHER INFORMATION: A synthetic primer

<400> SEQUENCE: 103
tggcagtgtc ttagctggtt gt                                          22

<210> SEQ ID NO 104
<211> LENGTH: 22
<212> TYPE: DNA
<213> ORGANISM: Artificial Sequence
<220> FEATURE:
<223> OTHER INFORMATION: A synthetic primer

<400> SEQUENCE: 104
tggctcagtt cagcaggaac ag                                          22

<210> SEQ ID NO 105
<211> LENGTH: 22
<212> TYPE: DNA
<213> ORGANISM: Artificial Sequence
<220> FEATURE:
<223> OTHER INFORMATION: A synthetic primer

<400> SEQUENCE: 105
tcgtgtcttg tgttgcagcc gg                                          22

<210> SEQ ID NO 106
<211> LENGTH: 23
<212> TYPE: DNA
<213> ORGANISM: Artificial Sequence
<220> FEATURE:
<223> OTHER INFORMATION: A synthetic primer

<400> SEQUENCE: 106
taaggtgcat ctagtgcaga tag                                         23

<210> SEQ ID NO 107
<211> LENGTH: 21
<212> TYPE: DNA
<213> ORGANISM: Artificial Sequence
<220> FEATURE:
<223> OTHER INFORMATION: A synthetic primer

<400> SEQUENCE: 107
agctacatct ggctactggg t                                           21

<210> SEQ ID NO 108
<211> LENGTH: 23
<212> TYPE: DNA
<213> ORGANISM: Artificial Sequence
<220> FEATURE:
<223> OTHER INFORMATION: A synthetic primer
```

```
<400> SEQUENCE: 108
tctttggtta tctagctgta tga                                         23

<210> SEQ ID NO 109
<211> LENGTH: 22
<212> TYPE: DNA
<213> ORGANISM: Artificial Sequence
<220> FEATURE:
<223> OTHER INFORMATION: A synthetic primer

<400> SEQUENCE: 109
tccctgagac cctaacttgt ga                                          22

<210> SEQ ID NO 110
<211> LENGTH: 22
<212> TYPE: DNA
<213> ORGANISM: Artificial Sequence
<220> FEATURE:
<223> OTHER INFORMATION: A synthetic primer

<400> SEQUENCE: 110
taatgcccct aaaaatcctt at                                          22

<210> SEQ ID NO 111
<211> LENGTH: 23
<212> TYPE: DNA
<213> ORGANISM: Artificial Sequence
<220> FEATURE:
<223> OTHER INFORMATION: A synthetic primer

<400> SEQUENCE: 111
taccctgtag aaccgaattt gtg                                         23

<210> SEQ ID NO 112
<211> LENGTH: 22
<212> TYPE: DNA
<213> ORGANISM: Artificial Sequence
<220> FEATURE:
<223> OTHER INFORMATION: A synthetic primer

<400> SEQUENCE: 112
tgaggtagta ggttgtatgg tt                                          22

<210> SEQ ID NO 113
<211> LENGTH: 22
<212> TYPE: DNA
<213> ORGANISM: Artificial Sequence
<220> FEATURE:
<223> OTHER INFORMATION: A synthetic primer

<400> SEQUENCE: 113
tggagagaaa ggcagttcct ga                                          22

<210> SEQ ID NO 114
<211> LENGTH: 19
<212> TYPE: DNA
<213> ORGANISM: Artificial Sequence
<220> FEATURE:
<223> OTHER INFORMATION: A synthetic primer

<400> SEQUENCE: 114
aagtgtgcag ggcactggt                                              19

<210> SEQ ID NO 115
<211> LENGTH: 22
```

```
<212> TYPE: DNA
<213> ORGANISM: Artificial Sequence
<220> FEATURE:
<223> OTHER INFORMATION: A synthetic primer

<400> SEQUENCE: 115
tggaatgtaa ggaagtgtgt gg                                              22

<210> SEQ ID NO 116
<211> LENGTH: 20
<212> TYPE: DNA
<213> ORGANISM: Artificial Sequence
<220> FEATURE:
<223> OTHER INFORMATION: A synthetic primer

<400> SEQUENCE: 116
taaggcacgc ggtgaatgcc                                                 20

<210> SEQ ID NO 117
<211> LENGTH: 22
<212> TYPE: DNA
<213> ORGANISM: Artificial Sequence
<220> FEATURE:
<223> OTHER INFORMATION: A synthetic primer

<400> SEQUENCE: 117
taacagtcta cagccatggt cg                                              22

<210> SEQ ID NO 118
<211> LENGTH: 22
<212> TYPE: DNA
<213> ORGANISM: Artificial Sequence
<220> FEATURE:
<223> OTHER INFORMATION: A synthetic primer

<400> SEQUENCE: 118
ctctagaggg aagcgctttc tg                                              22

<210> SEQ ID NO 119
<211> LENGTH: 22
<212> TYPE: DNA
<213> ORGANISM: Artificial Sequence
<220> FEATURE:
<223> OTHER INFORMATION: A synthetic primer

<400> SEQUENCE: 119
tcagtgcatc acagaacttt gt                                              22

<210> SEQ ID NO 120
<211> LENGTH: 24
<212> TYPE: DNA
<213> ORGANISM: Artificial Sequence
<220> FEATURE:
<223> OTHER INFORMATION: A synthetic primer

<400> SEQUENCE: 120
tccctgagac cctttaacct gtga                                            24

<210> SEQ ID NO 121
<211> LENGTH: 23
<212> TYPE: DNA
<213> ORGANISM: Artificial Sequence
<220> FEATURE:
<223> OTHER INFORMATION: A synthetic primer

<400> SEQUENCE: 121
```
caaagtgctc atagtgcagg tag                                       23

<210> SEQ ID NO 122
<211> LENGTH: 22
<212> TYPE: DNA
<213> ORGANISM: Artificial Sequence
<220> FEATURE:
<223> OTHER INFORMATION: A synthetic primer

<400> SEQUENCE: 122
aagtgctgtc atagctgagg tc                                        22

<210> SEQ ID NO 123
<211> LENGTH: 22
<212> TYPE: DNA
<213> ORGANISM: Artificial Sequence
<220> FEATURE:
<223> OTHER INFORMATION: A synthetic primer

<400> SEQUENCE: 123
caaagaattc tcctttgggg ct                                        22

<210> SEQ ID NO 124
<211> LENGTH: 23
<212> TYPE: DNA
<213> ORGANISM: Artificial Sequence
<220> FEATURE:
<223> OTHER INFORMATION: A synthetic primer

<400> SEQUENCE: 124
tctggctccg tgtcttcact ccc                                       23

<210> SEQ ID NO 125
<211> LENGTH: 21
<212> TYPE: DNA
<213> ORGANISM: Artificial Sequence
<220> FEATURE:
<223> OTHER INFORMATION: A synthetic primer

<400> SEQUENCE: 125
acagtctgct gaggttggag c                                         21

<210> SEQ ID NO 126
<211> LENGTH: 22
<212> TYPE: DNA
<213> ORGANISM: Artificial Sequence
<220> FEATURE:
<223> OTHER INFORMATION: A synthetic primer

<400> SEQUENCE: 126
taatactgtc tggtaaaacc gt                                        22

<210> SEQ ID NO 127
<211> LENGTH: 21
<212> TYPE: DNA
<213> ORGANISM: Artificial Sequence
<220> FEATURE:
<223> OTHER INFORMATION: A synthetic primer

<400> SEQUENCE: 127
atcacattgc cagggatttc c                                         21

<210> SEQ ID NO 128
<211> LENGTH: 22
<212> TYPE: DNA
<213> ORGANISM: Artificial Sequence

```
<220> FEATURE:
<223> OTHER INFORMATION: A synthetic primer

<400> SEQUENCE: 128
gtcatacacg gctctcctct ct                                           22

<210> SEQ ID NO 129
<211> LENGTH: 23
<212> TYPE: DNA
<213> ORGANISM: Artificial Sequence
<220> FEATURE:
<223> OTHER INFORMATION: A synthetic primer

<400> SEQUENCE: 129
tgtgcaaatc catgcaaaac tga                                          23

<210> SEQ ID NO 130
<211> LENGTH: 22
<212> TYPE: DNA
<213> ORGANISM: Artificial Sequence
<220> FEATURE:
<223> OTHER INFORMATION: A synthetic primer

<400> SEQUENCE: 130
taacactgtc tggtaaagat gg                                           22

<210> SEQ ID NO 131
<211> LENGTH: 23
<212> TYPE: DNA
<213> ORGANISM: Artificial Sequence
<220> FEATURE:
<223> OTHER INFORMATION: A synthetic primer

<400> SEQUENCE: 131
agcagcattg tacagggcta tga                                          23

<210> SEQ ID NO 132
<211> LENGTH: 23
<212> TYPE: DNA
<213> ORGANISM: Artificial Sequence
<220> FEATURE:
<223> OTHER INFORMATION: A synthetic primer

<400> SEQUENCE: 132
tttggcacta gcacattttt gct                                          23

<210> SEQ ID NO 133
<211> LENGTH: 21
<212> TYPE: DNA
<213> ORGANISM: Artificial Sequence
<220> FEATURE:
<223> OTHER INFORMATION: A synthetic primer

<400> SEQUENCE: 133
atcacattgc cagggattac c                                            21

<210> SEQ ID NO 134
<211> LENGTH: 21
<212> TYPE: DNA
<213> ORGANISM: Artificial Sequence
<220> FEATURE:
<223> OTHER INFORMATION: A synthetic primer

<400> SEQUENCE: 134
tcagtgcatg acagaacttg g                                            21
```

<210> SEQ ID NO 135
<211> LENGTH: 21
<212> TYPE: DNA
<213> ORGANISM: Artificial Sequence
<220> FEATURE:
<223> OTHER INFORMATION: A synthetic primer

<400> SEQUENCE: 135
tgagctaaat gtgtgctggg a                                              21

<210> SEQ ID NO 136
<211> LENGTH: 22
<212> TYPE: DNA
<213> ORGANISM: Artificial Sequence
<220> FEATURE:
<223> OTHER INFORMATION: A synthetic primer

<400> SEQUENCE: 136
gtgaaatgtt taggaccact ag                                             22

<210> SEQ ID NO 137
<211> LENGTH: 22
<212> TYPE: DNA
<213> ORGANISM: Artificial Sequence
<220> FEATURE:
<223> OTHER INFORMATION: A synthetic primer

<400> SEQUENCE: 137
tcggatccgt ctgagcttgg ct                                             22

<210> SEQ ID NO 138
<211> LENGTH: 22
<212> TYPE: DNA
<213> ORGANISM: Artificial Sequence
<220> FEATURE:
<223> OTHER INFORMATION: A synthetic primer

<400> SEQUENCE: 138
tgtgactggt tgaccagagg gg                                             22

<210> SEQ ID NO 139
<211> LENGTH: 22
<212> TYPE: DNA
<213> ORGANISM: Artificial Sequence
<220> FEATURE:
<223> OTHER INFORMATION: A synthetic primer

<400> SEQUENCE: 139
tgaggtagta gattgtatag tt                                             22

<210> SEQ ID NO 140
<211> LENGTH: 22
<212> TYPE: DNA
<213> ORGANISM: Artificial Sequence
<220> FEATURE:
<223> OTHER INFORMATION: A synthetic primer

<400> SEQUENCE: 140
tggagtgtga caatggtgtt tg                                             22

<210> SEQ ID NO 141
<211> LENGTH: 23
<212> TYPE: DNA
<213> ORGANISM: Artificial Sequence
<220> FEATURE:
<223> OTHER INFORMATION: A synthetic primer

<400> SEQUENCE: 141
tgtagtgttt cctactttat gga                                       23

<210> SEQ ID NO 142
<211> LENGTH: 22
<212> TYPE: DNA
<213> ORGANISM: Artificial Sequence
<220> FEATURE:
<223> OTHER INFORMATION: A synthetic primer

<400> SEQUENCE: 142
tggcagtgtc ttagctggtt gt                                        22

<210> SEQ ID NO 143
<211> LENGTH: 23
<212> TYPE: DNA
<213> ORGANISM: Artificial Sequence
<220> FEATURE:
<223> OTHER INFORMATION: A synthetic primer

<400> SEQUENCE: 143
tgtgcaaatc tatgcaaaac tga                                       23

<210> SEQ ID NO 144
<211> LENGTH: 22
<212> TYPE: DNA
<213> ORGANISM: Artificial Sequence
<220> FEATURE:
<223> OTHER INFORMATION: A synthetic primer

<400> SEQUENCE: 144
cagtgcaatg atgaaagggc at                                        22

<210> SEQ ID NO 145
<211> LENGTH: 21
<212> TYPE: DNA
<213> ORGANISM: Artificial Sequence
<220> FEATURE:
<223> OTHER INFORMATION: A synthetic primer

<400> SEQUENCE: 145
tcacagtgaa ccggtctctt t                                         21

<210> SEQ ID NO 146
<211> LENGTH: 24
<212> TYPE: DNA
<213> ORGANISM: Artificial Sequence
<220> FEATURE:
<223> OTHER INFORMATION: A synthetic primer

<400> SEQUENCE: 146
tttggcaatg gtagaactca cact                                      24

<210> SEQ ID NO 147
<211> LENGTH: 23
<212> TYPE: DNA
<213> ORGANISM: Artificial Sequence
<220> FEATURE:
<223> OTHER INFORMATION: A synthetic primer

<400> SEQUENCE: 147
tatggctttt cattcctatg tga                                       23

<210> SEQ ID NO 148

```
<211> LENGTH: 23
<212> TYPE: DNA
<213> ORGANISM: Artificial Sequence
<220> FEATURE:
<223> OTHER INFORMATION: A synthetic primer

<400> SEQUENCE: 148
aggcagtgta gttagctgat tgc                                           23

<210> SEQ ID NO 149
<211> LENGTH: 22
<212> TYPE: DNA
<213> ORGANISM: Artificial Sequence
<220> FEATURE:
<223> OTHER INFORMATION: A synthetic primer

<400> SEQUENCE: 149
tggaatgtaa agaagtatgt at                                            22

<210> SEQ ID NO 150
<211> LENGTH: 21
<212> TYPE: DNA
<213> ORGANISM: Artificial Sequence
<220> FEATURE:
<223> OTHER INFORMATION: A synthetic primer

<400> SEQUENCE: 150
tgagatgaag cactgtagct c                                             21

<210> SEQ ID NO 151
<211> LENGTH: 22
<212> TYPE: DNA
<213> ORGANISM: Artificial Sequence
<220> FEATURE:
<223> OTHER INFORMATION: A synthetic primer

<400> SEQUENCE: 151
tccagcatca gtgattttgt tg                                            22

<210> SEQ ID NO 152
<211> LENGTH: 23
<212> TYPE: DNA
<213> ORGANISM: Artificial Sequence
<220> FEATURE:
<223> OTHER INFORMATION: A synthetic primer

<400> SEQUENCE: 152
agctggtgtt gtgaatcagg ccg                                           23

<210> SEQ ID NO 153
<211> LENGTH: 21
<212> TYPE: DNA
<213> ORGANISM: Artificial Sequence
<220> FEATURE:
<223> OTHER INFORMATION: A synthetic primer

<400> SEQUENCE: 153
ttcacagtgg ctaagttccg c                                             21

<210> SEQ ID NO 154
<211> LENGTH: 21
<212> TYPE: DNA
<213> ORGANISM: Artificial Sequence
<220> FEATURE:
<223> OTHER INFORMATION: A synthetic primer

<400> SEQUENCE: 154
```
ttcacagtgg ctaagttctg c                                              21

<210> SEQ ID NO 155
<211> LENGTH: 22
<212> TYPE: DNA
<213> ORGANISM: Artificial Sequence
<220> FEATURE:
<223> OTHER INFORMATION: A synthetic primer

<400> SEQUENCE: 155
aaaagctggg ttgagagggc ga                                             22

<210> SEQ ID NO 156
<211> LENGTH: 22
<212> TYPE: DNA
<213> ORGANISM: Artificial Sequence
<220> FEATURE:
<223> OTHER INFORMATION: A synthetic primer

<400> SEQUENCE: 156
tagcagcacg taaatattgg cg                                             22

<210> SEQ ID NO 157
<211> LENGTH: 22
<212> TYPE: DNA
<213> ORGANISM: Artificial Sequence
<220> FEATURE:
<223> OTHER INFORMATION: A synthetic primer

<400> SEQUENCE: 157
aacccgtaga tccgaacttg tg                                             22

<210> SEQ ID NO 158
<211> LENGTH: 21
<212> TYPE: DNA
<213> ORGANISM: Artificial Sequence
<220> FEATURE:
<223> OTHER INFORMATION: A synthetic primer

<400> SEQUENCE: 158
taccacaggg tagaaccacg g                                              21

<210> SEQ ID NO 159
<211> LENGTH: 22
<212> TYPE: DNA
<213> ORGANISM: Artificial Sequence
<220> FEATURE:
<223> OTHER INFORMATION: A synthetic primer

<400> SEQUENCE: 159
gagcttattc ataaaagtgc ag                                             22

<210> SEQ ID NO 160
<211> LENGTH: 23
<212> TYPE: DNA
<213> ORGANISM: Artificial Sequence
<220> FEATURE:
<223> OTHER INFORMATION: A synthetic primer

<400> SEQUENCE: 160
tatggctttt tattcctatg tga                                            23

<210> SEQ ID NO 161
<211> LENGTH: 21
<212> TYPE: DNA

<213> ORGANISM: Artificial Sequence
<220> FEATURE:
<223> OTHER INFORMATION: A synthetic primer

<400> SEQUENCE: 161
actggacttg gagtcagaag g                                              21

<210> SEQ ID NO 162
<211> LENGTH: 22
<212> TYPE: DNA
<213> ORGANISM: Artificial Sequence
<220> FEATURE:
<223> OTHER INFORMATION: A synthetic primer

<400> SEQUENCE: 162
tctacagtgc acgtgtctcc ag                                             22

<210> SEQ ID NO 163
<211> LENGTH: 22
<212> TYPE: DNA
<213> ORGANISM: Artificial Sequence
<220> FEATURE:
<223> OTHER INFORMATION: A synthetic primer

<400> SEQUENCE: 163
ctaggtatgg tcccagggat cc                                             22

<210> SEQ ID NO 164
<211> LENGTH: 23
<212> TYPE: DNA
<213> ORGANISM: Artificial Sequence
<220> FEATURE:
<223> OTHER INFORMATION: A synthetic primer

<400> SEQUENCE: 164
tctcacacag aaatcgcacc cgt                                            23

<210> SEQ ID NO 165
<211> LENGTH: 22
<212> TYPE: DNA
<213> ORGANISM: Artificial Sequence
<220> FEATURE:
<223> OTHER INFORMATION: A synthetic primer

<400> SEQUENCE: 165
aacccgtaga tccgatcttg tg                                             22

<210> SEQ ID NO 166
<211> LENGTH: 22
<212> TYPE: DNA
<213> ORGANISM: Artificial Sequence
<220> FEATURE:
<223> OTHER INFORMATION: A synthetic primer

<400> SEQUENCE: 166
atcgtgcatc cctttagagt gt                                             22

<210> SEQ ID NO 167
<211> LENGTH: 22
<212> TYPE: DNA
<213> ORGANISM: Artificial Sequence
<220> FEATURE:
<223> OTHER INFORMATION: A synthetic primer

<400> SEQUENCE: 167
gtgacatcac atatacggca gc                                             22

<210> SEQ ID NO 168
<211> LENGTH: 23
<212> TYPE: DNA
<213> ORGANISM: Artificial Sequence
<220> FEATURE:
<223> OTHER INFORMATION: A synthetic primer

<400> SEQUENCE: 168
taaagtgctt atagtgcagg tag                                          23

<210> SEQ ID NO 169
<211> LENGTH: 21
<212> TYPE: DNA
<213> ORGANISM: Artificial Sequence
<220> FEATURE:
<223> OTHER INFORMATION: A synthetic primer

<400> SEQUENCE: 169
ttgtgcttga tctaaccatg t                                            21

<210> SEQ ID NO 170
<211> LENGTH: 21
<212> TYPE: DNA
<213> ORGANISM: Artificial Sequence
<220> FEATURE:
<223> OTHER INFORMATION: A synthetic primer

<400> SEQUENCE: 170
tacagtactg tgataactga a                                            21

<210> SEQ ID NO 171
<211> LENGTH: 22
<212> TYPE: DNA
<213> ORGANISM: Artificial Sequence
<220> FEATURE:
<223> OTHER INFORMATION: A synthetic primer

<400> SEQUENCE: 171
tccttcattc caccggagtc tg                                           22

<210> SEQ ID NO 172
<211> LENGTH: 22
<212> TYPE: DNA
<213> ORGANISM: Artificial Sequence
<220> FEATURE:
<223> OTHER INFORMATION: A synthetic primer

<400> SEQUENCE: 172
tgaggtagta agttgtattg tt                                           22

<210> SEQ ID NO 173
<211> LENGTH: 22
<212> TYPE: DNA
<213> ORGANISM: Artificial Sequence
<220> FEATURE:
<223> OTHER INFORMATION: A synthetic primer

<400> SEQUENCE: 173
tgaggtagta ggttgtgtgg tt                                           22

<210> SEQ ID NO 174
<211> LENGTH: 23
<212> TYPE: DNA
<213> ORGANISM: Artificial Sequence
<220> FEATURE:

<223> OTHER INFORMATION: A synthetic primer

<400> SEQUENCE: 174
aacattcatt gctgtcggtg ggt                                              23

<210> SEQ ID NO 175
<211> LENGTH: 22
<212> TYPE: DNA
<213> ORGANISM: Artificial Sequence
<220> FEATURE:
<223> OTHER INFORMATION: A synthetic primer

<400> SEQUENCE: 175
tgtaaacatc ctcgactgga ag                                               22

<210> SEQ ID NO 176
<211> LENGTH: 22
<212> TYPE: DNA
<213> ORGANISM: Artificial Sequence
<220> FEATURE:
<223> OTHER INFORMATION: A synthetic primer

<400> SEQUENCE: 176
tagcttatca gactgatgtt ga                                               22

<210> SEQ ID NO 177
<211> LENGTH: 22
<212> TYPE: DNA
<213> ORGANISM: Artificial Sequence
<220> FEATURE:
<223> OTHER INFORMATION: A synthetic primer

<400> SEQUENCE: 177
cagtggtttt accctatggt ag                                               22

<210> SEQ ID NO 178
<211> LENGTH: 23
<212> TYPE: DNA
<213> ORGANISM: Artificial Sequence
<220> FEATURE:
<223> OTHER INFORMATION: A synthetic primer

<400> SEQUENCE: 178
taagtgcttc catgttttgg tga                                              23

<210> SEQ ID NO 179
<211> LENGTH: 23
<212> TYPE: DNA
<213> ORGANISM: Artificial Sequence
<220> FEATURE:
<223> OTHER INFORMATION: A synthetic primer

<400> SEQUENCE: 179
tagcaccatt tgaaatcagt gtt                                              23

<210> SEQ ID NO 180
<211> LENGTH: 21
<212> TYPE: DNA
<213> ORGANISM: Artificial Sequence
<220> FEATURE:
<223> OTHER INFORMATION: A synthetic primer

<400> SEQUENCE: 180
taattttatg tataagctag t                                                21

```
<210> SEQ ID NO 181
<211> LENGTH: 22
<212> TYPE: DNA
<213> ORGANISM: Artificial Sequence
<220> FEATURE:
<223> OTHER INFORMATION: A synthetic primer

<400> SEQUENCE: 181
agaggtagta ggttgcatag tt                                              22

<210> SEQ ID NO 182
<211> LENGTH: 22
<212> TYPE: DNA
<213> ORGANISM: Artificial Sequence
<220> FEATURE:
<223> OTHER INFORMATION: A synthetic primer

<400> SEQUENCE: 182
aaagtgcatc tttttagagg at                                              22

<210> SEQ ID NO 183
<211> LENGTH: 23
<212> TYPE: DNA
<213> ORGANISM: Artificial Sequence
<220> FEATURE:
<223> OTHER INFORMATION: A synthetic primer

<400> SEQUENCE: 183
aacattcaac gctgtcggtg agt                                             23

<210> SEQ ID NO 184
<211> LENGTH: 23
<212> TYPE: DNA
<213> ORGANISM: Artificial Sequence
<220> FEATURE:
<223> OTHER INFORMATION: A synthetic primer

<400> SEQUENCE: 184
aacattcatt gttgtcggtg ggt                                             23

<210> SEQ ID NO 185
<211> LENGTH: 23
<212> TYPE: DNA
<213> ORGANISM: Artificial Sequence
<220> FEATURE:
<223> OTHER INFORMATION: A synthetic primer

<400> SEQUENCE: 185
cagtgcaata gtattgtcaa agc                                             23

<210> SEQ ID NO 186
<211> LENGTH: 22
<212> TYPE: DNA
<213> ORGANISM: Artificial Sequence
<220> FEATURE:
<223> OTHER INFORMATION: A synthetic primer

<400> SEQUENCE: 186
tctcccaacc cttgtaccag tg                                              22

<210> SEQ ID NO 187
<211> LENGTH: 24
<212> TYPE: DNA
<213> ORGANISM: Artificial Sequence
<220> FEATURE:
<223> OTHER INFORMATION: A synthetic primer
```

```
<400> SEQUENCE: 187
agcagaagca gggaggttct ccca                                      24

<210> SEQ ID NO 188
<211> LENGTH: 23
<212> TYPE: DNA
<213> ORGANISM: Artificial Sequence
<220> FEATURE:
<223> OTHER INFORMATION: A synthetic primer

<400> SEQUENCE: 188
ttattgctta agaatacgcg tag                                       23

<210> SEQ ID NO 189
<211> LENGTH: 22
<212> TYPE: DNA
<213> ORGANISM: Artificial Sequence
<220> FEATURE:
<223> OTHER INFORMATION: A synthetic primer

<400> SEQUENCE: 189
ctgaagctca gagggctctg at                                        22

<210> SEQ ID NO 190
<211> LENGTH: 24
<212> TYPE: DNA
<213> ORGANISM: Artificial Sequence
<220> FEATURE:
<223> OTHER INFORMATION: A synthetic primer

<400> SEQUENCE: 190
tttggtcccc ttcaaccagc tgaa                                      24

<210> SEQ ID NO 191
<211> LENGTH: 22
<212> TYPE: DNA
<213> ORGANISM: Artificial Sequence
<220> FEATURE:
<223> OTHER INFORMATION: A synthetic primer

<400> SEQUENCE: 191
ttgcatagtc acaaaagtga tc                                        22

<210> SEQ ID NO 192
<211> LENGTH: 24
<212> TYPE: DNA
<213> ORGANISM: Artificial Sequence
<220> FEATURE:
<223> OTHER INFORMATION: A synthetic primer

<400> SEQUENCE: 192
aactggccta caaagtccca gtaa                                      24

<210> SEQ ID NO 193
<211> LENGTH: 24
<212> TYPE: DNA
<213> ORGANISM: Artificial Sequence
<220> FEATURE:
<223> OTHER INFORMATION: A synthetic primer

<400> SEQUENCE: 193
taatctcagc tggcaactgt gaaa                                      24

<210> SEQ ID NO 194
<211> LENGTH: 25
```

```
<212> TYPE: DNA
<213> ORGANISM: Artificial Sequence
<220> FEATURE:
<223> OTHER INFORMATION: A synthetic primer

<400> SEQUENCE: 194
tactgcatca ggaactgatt ggaaa                                          25

<210> SEQ ID NO 195
<211> LENGTH: 21
<212> TYPE: DNA
<213> ORGANISM: Artificial Sequence
<220> FEATURE:
<223> OTHER INFORMATION: A synthetic primer

<400> SEQUENCE: 195
caagtcacta gtggttccgt t                                              21

<210> SEQ ID NO 196
<211> LENGTH: 23
<212> TYPE: DNA
<213> ORGANISM: Artificial Sequence
<220> FEATURE:
<223> OTHER INFORMATION: A synthetic primer

<400> SEQUENCE: 196
cccagtgttc aggctacctg ttc                                            23

<210> SEQ ID NO 197
<211> LENGTH: 24
<212> TYPE: DNA
<213> ORGANISM: Artificial Sequence
<220> FEATURE:
<223> OTHER INFORMATION: A synthetic primer

<400> SEQUENCE: 197
taacactgtc tggtaacgat gtaa                                           24

<210> SEQ ID NO 198
<211> LENGTH: 20
<212> TYPE: DNA
<213> ORGANISM: Artificial Sequence
<220> FEATURE:
<223> OTHER INFORMATION: A synthetic primer

<400> SEQUENCE: 198
taaacgtgga tgtacttgct                                                20

<210> SEQ ID NO 199
<211> LENGTH: 18
<212> TYPE: DNA
<213> ORGANISM: Artificial Sequence
<220> FEATURE:
<223> OTHER INFORMATION: A synthetic primer

<400> SEQUENCE: 199
tgggcccttc ctccagaa                                                  18

<210> SEQ ID NO 200
<211> LENGTH: 20
<212> TYPE: DNA
<213> ORGANISM: Artificial Sequence
<220> FEATURE:
<223> OTHER INFORMATION: A synthetic primer

<400> SEQUENCE: 200
```
gtgcattgct gttgcattgc                                                  20

<210> SEQ ID NO 201
<211> LENGTH: 22
<212> TYPE: DNA
<213> ORGANISM: Artificial Sequence
<220> FEATURE:
<223> OTHER INFORMATION: A synthetic primer

<400> SEQUENCE: 201
ggagacgcgg ccctgttgga gt                                               22

<210> SEQ ID NO 202
<211> LENGTH: 21
<212> TYPE: DNA
<213> ORGANISM: Artificial Sequence
<220> FEATURE:
<223> OTHER INFORMATION: A synthetic primer

<400> SEQUENCE: 202
ccgttaccat tactgagtta a                                                21

<210> SEQ ID NO 203
<211> LENGTH: 20
<212> TYPE: DNA
<213> ORGANISM: Artificial Sequence
<220> FEATURE:
<223> OTHER INFORMATION: A synthetic primer

<400> SEQUENCE: 203
actgccccag gtgctgctgg                                                  20

<210> SEQ ID NO 204
<211> LENGTH: 25
<212> TYPE: DNA
<213> ORGANISM: Artificial Sequence
<220> FEATURE:
<223> OTHER INFORMATION: A synthetic primer

<400> SEQUENCE: 204
gggtactgca gacgtggcaa tcatg                                            25

<210> SEQ ID NO 205
<211> LENGTH: 21
<212> TYPE: DNA
<213> ORGANISM: Artificial Sequence
<220> FEATURE:
<223> OTHER INFORMATION: A synthetic primer

<400> SEQUENCE: 205
tcactcctct cctcccgtct t                                                21

<210> SEQ ID NO 206
<211> LENGTH: 20
<212> TYPE: DNA
<213> ORGANISM: Artificial Sequence
<220> FEATURE:
<223> OTHER INFORMATION: A synthetic primer

<400> SEQUENCE: 206
ctgtggactc agttctggaa                                                  20

<210> SEQ ID NO 207
<211> LENGTH: 22
<212> TYPE: DNA
<213> ORGANISM: Artificial Sequence

```
<220> FEATURE:
<223> OTHER INFORMATION: A synthetic primer

<400> SEQUENCE: 207
aatcactaac tccactgcca tc                                              22

<210> SEQ ID NO 208
<211> LENGTH: 19
<212> TYPE: DNA
<213> ORGANISM: Artificial Sequence
<220> FEATURE:
<223> OTHER INFORMATION: A synthetic primer

<400> SEQUENCE: 208
caaactgtgg gggcactaa                                                  19

<210> SEQ ID NO 209
<211> LENGTH: 16
<212> TYPE: DNA
<213> ORGANISM: Artificial Sequence
<220> FEATURE:
<223> OTHER INFORMATION: A synthetic primer

<400> SEQUENCE: 209
cccagataat ggcact                                                     16

<210> SEQ ID NO 210
<211> LENGTH: 21
<212> TYPE: DNA
<213> ORGANISM: Artificial Sequence
<220> FEATURE:
<223> OTHER INFORMATION: A synthetic primer

<400> SEQUENCE: 210
tttcaccttt ctgagaagga a                                               21

<210> SEQ ID NO 211
<211> LENGTH: 22
<212> TYPE: DNA
<213> ORGANISM: Artificial Sequence
<220> FEATURE:
<223> OTHER INFORMATION: A synthetic primer

<400> SEQUENCE: 211
ttcacaagga ggtgtcattt at                                              22

<210> SEQ ID NO 212
<211> LENGTH: 28
<212> TYPE: DNA
<213> ORGANISM: Artificial Sequence
<220> FEATURE:
<223> OTHER INFORMATION: A synthetic primer

<400> SEQUENCE: 212
gccagcaggc agtgtattgt tagctggc                                        28

<210> SEQ ID NO 213
<211> LENGTH: 22
<212> TYPE: DNA
<213> ORGANISM: Artificial Sequence
<220> FEATURE:
<223> OTHER INFORMATION: A synthetic primer

<400> SEQUENCE: 213
tcctgtactg agctgccccg ag                                              22
```

<210> SEQ ID NO 214
<211> LENGTH: 19
<212> TYPE: DNA
<213> ORGANISM: Artificial Sequence
<220> FEATURE:
<223> OTHER INFORMATION: A synthetic primer

<400> SEQUENCE: 214 aatggattttt tggagcagg                                               19

<210> SEQ ID NO 215
<211> LENGTH: 21
<212> TYPE: DNA
<213> ORGANISM: Artificial Sequence
<220> FEATURE:
<223> OTHER INFORMATION: A synthetic primer

<400> SEQUENCE: 215
aagtgatcta aaggcctaca t                                             21

<210> SEQ ID NO 216
<211> LENGTH: 21
<212> TYPE: DNA
<213> ORGANISM: Artificial Sequence
<220> FEATURE:
<223> OTHER INFORMATION: A synthetic primer

<400> SEQUENCE: 216
ccccaggtaa ctcttgagtg t                                             21

<210> SEQ ID NO 217
<211> LENGTH: 21
<212> TYPE: DNA
<213> ORGANISM: Artificial Sequence
<220> FEATURE:
<223> OTHER INFORMATION: A synthetic primer

<400> SEQUENCE: 217
taatgatatc actgtaaaac c                                             21

<210> SEQ ID NO 218
<211> LENGTH: 22
<212> TYPE: DNA
<213> ORGANISM: Artificial Sequence
<220> FEATURE:
<223> OTHER INFORMATION: A synthetic primer

<400> SEQUENCE: 218
atgctgactg aacatgaagg tc                                            22

<210> SEQ ID NO 219
<211> LENGTH: 23
<212> TYPE: DNA
<213> ORGANISM: Artificial Sequence
<220> FEATURE:
<223> OTHER INFORMATION: A synthetic primer

<400> SEQUENCE: 219
acacgcaaat tcgtgaagcg ttc                                           23

<210> SEQ ID NO 220
<211> LENGTH: 20
<212> TYPE: DNA
<213> ORGANISM: Artificial Sequence
<220> FEATURE:
<223> OTHER INFORMATION: A synthetic primer -continued

```
<400> SEQUENCE: 220
gaatcgagca ccagttacgc                                          20

<210> SEQ ID NO 221
<211> LENGTH: 25
<212> TYPE: DNA
<213> ORGANISM: Artificial Sequence
<220> FEATURE:
<223> OTHER INFORMATION: A synthetic primer

<400> SEQUENCE: 221
attttggcac tagcacattt ttgct                                    25

<210> SEQ ID NO 222
<211> LENGTH: 23
<212> TYPE: DNA
<213> ORGANISM: Artificial Sequence
<220> FEATURE:
<223> OTHER INFORMATION: A synthetic primer

<400> SEQUENCE: 222
ccatattggc actgcacatg att                                      23

<210> SEQ ID NO 223
<211> LENGTH: 17
<212> TYPE: DNA
<213> ORGANISM: Artificial Sequence
<220> FEATURE:
<223> OTHER INFORMATION: A synthetic primer

<400> SEQUENCE: 223
agagagcccg caccagt                                             17

<210> SEQ ID NO 224
<211> LENGTH: 18
<212> TYPE: DNA
<213> ORGANISM: Artificial Sequence
<220> FEATURE:
<223> OTHER INFORMATION: A synthetic primer

<400> SEQUENCE: 224
cttgaggagg agcaggct                                            18

<210> SEQ ID NO 225
<211> LENGTH: 20
<212> TYPE: DNA
<213> ORGANISM: Artificial Sequence
<220> FEATURE:
<223> OTHER INFORMATION: A synthetic primer

<400> SEQUENCE: 225
aaggtgaagg tcggagtcaa                                          20

<210> SEQ ID NO 226
<211> LENGTH: 20
<212> TYPE: DNA
<213> ORGANISM: Artificial Sequence
<220> FEATURE:
<223> OTHER INFORMATION: A synthetic primer

<400> SEQUENCE: 226
aatgaagggg tcattgatgg                                          20

<210> SEQ ID NO 227
```

```
<211> LENGTH: 46
<212> TYPE: RNA
<213> ORGANISM: Artificial Sequence
<220> FEATURE:
<223> OTHER INFORMATION: A synthetic RNA sequence

<400> SEQUENCE: 227
gggagagggu uuaauuuuua cgaaaguaau aauuggaucc gcaagg              46

<210> SEQ ID NO 228
<211> LENGTH: 48
<212> TYPE: RNA
<213> ORGANISM: Artificial Sequence
<220> FEATURE:
<223> OTHER INFORMATION: A synthetic RNA sequence

<400> SEQUENCE: 228
gggagagggu uuaauccgau acgaaaguau gggauuggau ccgcaagg            48

<210> SEQ ID NO 229
<211> LENGTH: 54
<212> TYPE: RNA
<213> ORGANISM: Artificial Sequence
<220> FEATURE:
<223> OTHER INFORMATION: A synthetic RNA sequence

<400> SEQUENCE: 229
gggagagggu uuaauccgau uuuacgaaag uaauauggga uuggauccgc aagg    54

<210> SEQ ID NO 230
<211> LENGTH: 28
<212> TYPE: DNA
<213> ORGANISM: Artificial Sequence
<220> FEATURE:
<223> OTHER INFORMATION: A synthetic DNA Hairpin sequence

<400> SEQUENCE: 230
cgcgaattcg cgttttcgcg aattcgcg                                  28

<210> SEQ ID NO 231
<211> LENGTH: 81
<212> TYPE: RNA
<213> ORGANISM: Artificial Sequence
<220> FEATURE:
<223> OTHER INFORMATION: A synthetic RNA sequence

<400> SEQUENCE: 231
ggguggccga uuuuggcacu agcacauuuu ugcuuguguc ucuccgcucu gagcaaucau  60
gugcagugcc aauagggaa a                                           81

<210> SEQ ID NO 232
<211> LENGTH: 16
<212> TYPE: DNA
<213> ORGANISM: Artificial Sequence
<220> FEATURE:
<223> OTHER INFORMATION: A synthetic primer

<400> SEQUENCE: 232
cgcagctgcg ggtcct                                               16
```